(12) United States Patent
Iwata et al.

(10) Patent No.: US 10,570,117 B2
(45) Date of Patent: Feb. 25, 2020

(54) PHENYLIMIDAZOLE COMPOUND

(71) Applicant: Otsuka Pharmaceutical Factory, Inc., Tokushima (JP)

(72) Inventors: Koushi Iwata, Tokushima (JP); Tadao Shibutani, Tokushima (JP); Satoshi Kido, Tokushima (JP); Daisuke Mori, Tokushima (JP); Hidenori Yoshioka, Tokushima (JP); Hikaru Nakata, Tokushima (JP); Akiko Ishimaru, Tokushima (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 15/780,436

(22) PCT Filed: Oct. 25, 2016

(86) PCT No.: PCT/JP2016/081633
§ 371 (c)(1),
(2) Date: May 31, 2018

(87) PCT Pub. No.: WO2017/110237
PCT Pub. Date: Jun. 29, 2017

(65) Prior Publication Data
US 2018/0354930 A1 Dec. 13, 2018

(30) Foreign Application Priority Data
Dec. 25, 2015 (JP) ................. 2015-254016

(51) Int. Cl.
| C07D 401/04 | (2006.01) |
| C07D 401/12 | (2006.01) |
| C07D 401/14 | (2006.01) |
| C07D 233/64 | (2006.01) |
| C07D 403/12 | (2006.01) |
| C07D 413/12 | (2006.01) |
| C07D 417/14 | (2006.01) |
| A61P 3/06 | (2006.01) |
| C07D 413/14 | (2006.01) |
| A61K 31/422 | (2006.01) |
| A61K 31/506 | (2006.01) |
| A61K 31/4164 | (2006.01) |
| A61P 3/04 | (2006.01) |
| A61K 31/444 | (2006.01) |
| A61K 31/4439 | (2006.01) |
| A61K 31/497 | (2006.01) |
| A61P 9/10 | (2006.01) |
| A61K 31/4178 | (2006.01) |

(52) U.S. Cl.
CPC ........ *C07D 401/14* (2013.01); *A61K 31/4164* (2013.01); *A61K 31/4178* (2013.01); *A61K 31/422* (2013.01); *A61K 31/444* (2013.01); *A61K 31/4439* (2013.01); *A61K 31/497* (2013.01); *A61K 31/506* (2013.01); *A61P 3/04* (2018.01); *A61P 3/06* (2018.01); *A61P 9/10* (2018.01); *C07D 233/64* (2013.01); *C07D 401/04* (2013.01); *C07D 401/12* (2013.01); *C07D 403/12* (2013.01); *C07D 413/12* (2013.01); *C07D 413/14* (2013.01); *C07D 417/14* (2013.01)

(58) Field of Classification Search
CPC .. C07D 401/04; C07D 401/12; C07D 401/14; C07D 233/64; C07D 403/12; C07D 413/12; C07D 413/14; C07D 417/14
See application file for complete search history.

(56) References Cited

U.S. PATENT DOCUMENTS

| 4,134,983 A * | 1/1979 | Baldwin ................. C07C 45/00 514/326 |
| 4,443,446 A | 4/1984 | Karjalainen et al. |
| 4,443,466 A | 4/1984 | Karjalainen et al. |
| 4,642,311 A | 2/1987 | Baldwin et al. |
| 5,861,359 A | 1/1999 | Theodoridis |
| 2011/0275823 A1 | 11/2011 | Shibutani et al. |

FOREIGN PATENT DOCUMENTS

| CA | 1075689 A | 4/1980 |
| SU | 997607 A3 | 2/1983 |
| WO | WO-2009/139076 A1 | 11/2009 |
| WO | WO-2010/090200 A1 | 8/2010 |

OTHER PUBLICATIONS

Mao et al "Fluorescent Labeling of Oleanolic Acid Using 'Click' Chemistry" Heterocyclic Communications vol. 19, pp. 239-243, 2013.
CAS Registry No. 1785300-90-4, 1784342-46-6, 1782331-14-9, 1556637-00-3, 2014, 2015, pp. 1-12.
Office Action dated Apr. 15, 2019 in Corresponding Russian Patent Application No. 2018127016/04(043074).

* cited by examiner

Primary Examiner — Rebecca L Anderson
(74) Attorney, Agent, or Firm — Cesari & McKenna, LLP

(57) ABSTRACT

Phenylimidazole compounds of formula (1) shown below and pharmaceutically acceptable salts thereof:

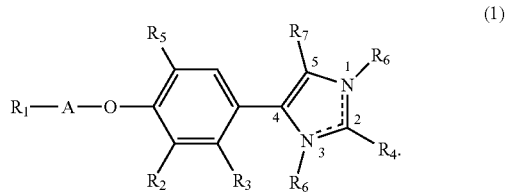

(1)

Also disclosed are a pharmaceutical composition and a lipoprotein lipase activator, each containing one of the phenylimidazole compounds.

19 Claims, No Drawings

PHENYLIMIDAZOLE COMPOUND

CROSS-REFERENCE TO RELATED APPLICATIONS

This application is the National Stage of International Application No. PCT/JP2016/081633, filed on Oct. 25, 2016, which claims the benefit of Japanese Application No. 2015-254016, filed on Dec. 25, 2015.

TECHNICAL FIELD

The present invention relates to a novel phenylimidazole compound.

BACKGROUND ART

Today's society is called a society of gluttony, and the number of people diagnosed with hyperlipidemia, obesity, or the like, has been sharply rising. Conditions such as hyperlipidemia or obesity can lead to diabetes and cause arteriosclerosis or other diseases due to arteriosclerosis, such as cardiac infarction and cerebral infarction.

Accordingly, various studies have been conducted on, for example, pharmaceutical products and chemotherapy for preventing or treating hyperlipidemia, obesity, or the like. Chemotherapy for activating lipoprotein lipase (LPL) is an example of such studies. LPL activation is considered to be effective in the prevention and treatment of hyperlipidemia, obesity, or the like. Compounds having a phenylimidazole skeleton have been reported as compounds having LPL-activating action (for example, Patent Literature 1 and 2).

CITATION LIST

Patent Literature

PTL 1: WO2009/139076
PTL 2: WO2010/090200

SUMMARY OF INVENTION

Technical Problem

A primary object of the present invention is to provide a compound (chemotherapeutic agent) that is effective in the prevention and treatment of hyperlipidemia, obesity, or the like.

Solution to Problem

For the purpose of providing a compound (chemotherapeutic agent) that is effective in the prevention and treatment of hyperlipidemia, obesity, or the like, the present inventors conducted extensive research to develop a compound having LPL-activating action, particularly LPL-activating action that is specific to skeletal muscle. In the course of the research, the inventors succeeded in synthesizing a phenylimidazole compound represented by formula (1) described below, and found that the compound has desired properties superior to those of known compounds having a phenylimidazole skeleton. Based on this and further findings, the invention represented by the following is provided.
(Reclaims)
Item 1.
A phenylimidazole compound represented by the following formula (1) or a pharmaceutically acceptable salt thereof

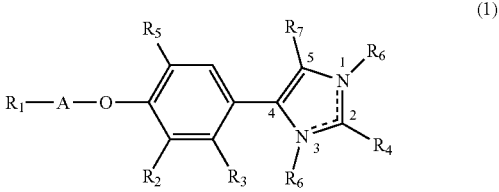

wherein $R^1$ is
(1-1) hydrogen,
(1-2) pyrazolyl,
(1-3) pyrimidinyl,
(1-4) pyridyl having one or two substituents each independently selected from the group consisting of halogen, cyano, $C_1$-$C_6$ alkyl, $C_1$-$C_6$ alkylsulfonyl, and halogen-substituted $C_1$-$C_6$ alkyl,
(1-5) oxazolyl having one or more $C_1$-$C_6$ alkyl groups,
(1-6) pyrazinyl optionally substituted with at least one group selected from the group consisting of halogen and $C_1$-$C_6$ alkyl,
(1-7) phenyl having one or two substituents each independently selected from the group consisting of halogen and halogen-substituted $C_1$-$C_6$ alkyl,
(1-8) (pyridine 1-oxide)yl having one or two substituents each independently selected from the group consisting of halogen and halogen-substituted $C_1$-$C_6$ alkyl,
(1-9) halogen-substituted thiazolyl,
(1-10) $C_1$-$C_6$ alkyl-substituted isoxazolyl,
(1-11) $C_3$-$C_8$ cycloalkyl-substituted 1,2,4-oxadiazolyl, or
(1-12) phenyl;
$R^2$ represents hydrogen or $C_1$-$C_6$ alkoxy;
$R^3$ is
(3-1) hydrogen,
(3-2) $C_1$-$C_6$ alkoxy,
(3-3) $C_1$-$C_6$ alkoxy $C_1$-$C_6$ alkoxy,
(3-4) $C_1$-$C_6$ alkyl,
(3-5) halogen,
(3-6) benzyloxy, or
(3-7) hydroxy;
$R^4$ is
(4-1) pyridyl optionally having at least one substituent selected from the group consisting of halogen, cyano, hydroxy, pyrrolidinyl, $C_1$-$C_6$ alkyl, $C_1$-$C_6$ alkylthio, $C_1$-$C_6$ alkylsulfonyl, $C_1$-$C_6$ alkoxy, and halogen-substituted $C_1$-$C_6$ alkyl,
(4-2) $C_3$-$C_{10}$ cycloalkyl optionally having one or two substituents each independently selected from the group consisting of halogen and $C_1$-$C_6$ alkyl, or
(4-3) lower alkyl;
$R^5$ is
(5-1) hydrogen,
(5-2) $C_1$-$C_6$ alkyl, or
(5-3) $C_1$-$C_6$ alkoxy;
$R^6$ is
(6-1) hydrogen,
(6-2) $C_1$-$C_6$ alkoxy $C_1$-$C_6$ alkyl, or
(6-3) $C_1$-$C_6$ alkyl optionally substituted with one or more $C_3$-$C_{10}$ cycloalkyl groups,
wherein $R^6$ is attached to only one of N at the 1-position and N at the 3-position of the imidazole skeleton, $R^6$ is attached to N at the 1-position when the bond between N at the 3-position and C at the 2-position of the imidazole skeleton is a double bond, and $R^6$ is attached to N at the 3-position when the bond between N at the 3-position and C at the 2-position of the imidazole skeleton is a single bond;

$R^7$ is (7-1) hydrogen,
(7-2) halogen,
(7-3) $C_1$-$C_6$ alkyl,
(7-4) hydroxymethyl,
(7-5) halogen-substituted $C_1$-$C_6$ alkyl, or
(7-6) cyano;

A is a single bond when $R^1$ is hydrogen, and A is $C_1$-$C_6$ alkylene when $R^1$ is a group other than hydrogen;

in the imidazole skeleton, the bond between C at the 2-position and N at the 1-position is a single bond when the bond between N at the 3-position and C at the 2-position is a double bond, and the bond between C at the 2-position and N at the 1-position is a double bond when the bond between N at the 3-position and C at the 2-position is a single bond;

with the proviso that the compound represented by formula (1) wherein $R^1$ is a group of (1-7) or (1-12) and $R^4$ is a group of (4-3) is excluded.

Item 2.

The phenylimidazole compound according to Item 1 or a pharmaceutically acceptable salt thereof, wherein $R^4$ is a group of (4-1).

Item 3.

The phenylimidazole compound according to Item 1 or a pharmaceutically acceptable salt thereof, wherein $R^4$ is pyridyl optionally having at least one substituent selected from the group consisting of halogen, cyano, hydroxy, pyrrolidinyl, $C_1$-$C_6$ alkyl, $C_1$-$C_6$ alkoxy, and halogen-substituted $C_1$-$C_6$ alkyl, or a group of (4-2).

Item 4.

The phenylimidazole compound according to any one of Items 1 to 3 or a pharmaceutically acceptable salt thereof, wherein $R^1$ is a group of (1-4).

Item 5.

The phenylimidazole compound according to any one of Items 1 to 4 or a pharmaceutically acceptable salt thereof, wherein $R^3$ is hydrogen or $C_1$-$C_6$ alkoxy, and $R^5$ is hydrogen or $C_1$-$C_6$ alkoxy.

Item 6.

The phenylimidazole compound according to any one of Items 1 to 5 or a pharmaceutically acceptable salt thereof, wherein $R^4$ is halogen-substituted pyridyl.

Item 7.

The phenylimidazole compound according to any one of Items 1 to 6 or a pharmaceutically acceptable salt thereof, wherein $R^1$ is pyridyl having one or two substituents each independently selected from the group consisting of halogen and halogen-substituted $C_1$-$C_6$ alkyl.

Item 8.

The phenylimidazole compound according to any one of Items 1 to 7 or a pharmaceutically acceptable salt thereof, wherein $R^2$ and $R^5$ each represent hydrogen, and $R^3$ is $C_1$-$C_6$ alkoxy.

Item 9.

The phenylimidazole compound according to any one of Items 1 to 8 or a pharmaceutically acceptable salt thereof, wherein $R^6$ is hydrogen, and $R^7$ is halogen.

Item 10.

The phenylimidazole compound according to any one of Items 1 to 8 or a pharmaceutically acceptable salt thereof, selected from the following compounds:

5-[[4-(5-chloro-2-(6-fluoropyridin-3-yl)-1H-imidazol-4-yl)-3-methoxyphenoxy]methyl]-2-(trifluoromethyl)pyridine 2-[[4-(5-chloro-2-(6-fluoropyridin-3-yl)-1H-imidazol-4-yl)-3-methoxyphenoxy]methyl]-3-fluoro-5-(trifluoromethyl)pyridine 2-[[4-(5-bromo-2-(6-fluoropyridin-3-yl)-1H-imidazol-4-yl)-3-methoxyphenoxy]methyl]-3-fluoro-5-(trifluoromethyl)pyridine 3-chloro-2-[[4-(5-chloro-2-(6-fluoropyridin-3-yl)-1H-imidazol-4-yl)-3-methoxyphenoxy]methyl]-5-(trifluoromethyl)pyridine 2-[[4-(5-bromo-2-(6-chloropyridin-3-yl)-1H-imidazol-4-yl)-3-methoxyphenoxy]methyl]-5-(trifluoromethyl)pyridine 5-bromo-2-[[4-(4-chloro-2-(6-fluoropyridin-3-yl)-1H-imidazol-5-yl)-3-methoxyphenoxy]methyl]-3-fluoropyridine 5-[4-chloro-5-[2-methoxy-4-((6-(trifluoromethyl)pyridin-2-yl)methoxy)phenyl]-1H-imidazol-2-yl]-2-fluoropyridine.

Item 11.

A pharmaceutical composition comprising the compound according to any one of Items 1 to 10 or a pharmaceutically acceptable salt thereof.

Item 12.

An LPL activator comprising the compound according to any one of Items 1 to 10 or a pharmaceutically acceptable salt thereof.

Item 13.

The pharmaceutical composition according to Item 11 for use in the prevention or treatment of hyperlipidemia, arteriosclerosis, or obesity.

Item 14.

A method for activating LPL activity, comprising administering the compound according to any one of Items 1 to 10 or a pharmaceutically acceptable salt thereof to a subject in need of activation of LPL activity.

Item 15.

A method for preventing or treating hyperlipidemia, arteriosclerosis, or obesity, comprising administering the compound according to any one of Items 1 to 10 or a pharmaceutically acceptable salt thereof to a subject in need of the prevention or treatment of hyperlipidemia, arteriosclerosis, or obesity.

Item 16.

Use of the compound according to any one of Items 1 to 10 or a pharmaceutically acceptable salt thereof for the production of an LPL activator.

Item 17.

Use of the compound according to any one of Items 1 to 10 or a pharmaceutically acceptable salt thereof for the production of a pharmaceutical composition for preventing or treating hyperlipidemia, arteriosclerosis, or obesity.

Advantageous Effects of Invention

The phenylimidazole compound of the present invention has lipoprotein lipase (LPL)-activating action and is useful as an LPL activator for the prevention and/or treatment of hyperlipidemia, arteriosclerosis, obesity, etc. The phenylimidazole compound of the present invention also has excellent solubility in water (e.g., water with a pH of 1.2 and water with a pH of 6.8). In an embodiment, the solubility of the phenylimidazole compound of the present invention in water with a pH of 1.2 and/or water with a pH of 6.8 is preferably 0.3 μg/mL or more.

DESCRIPTION OF EMBODIMENTS

1. Definition of Substituents

Examples of pyrazolyl groups include 1H-pyrazol-3-yl, 1H-pyrazol-4-yl, and 1H-pyrazol-1-yl.

Examples of pyrimidinyl groups include 2-pyrimidinyl, 4-pyrimidinyl, and 5-pyrimidinyl.

Examples of halogen atoms include fluorine, chlorine, bromine, iodine, and the like.

Examples of $C_1$-$C_6$ alkyl groups include linear or branched alkyl groups having 1 to 6 carbon atoms, such as methyl, ethyl, n-propyl, n-butyl, n-pentyl, n-hexyl, 1-methylethyl, tert-butyl, and 2-methylbutyl.

Examples of $C_1$-$C_6$ alkylsulfonyl groups include linear or branched alkylsulfonyl groups having 1 to 6 carbon atoms, such as methylsulfonyl, ethylsulfonyl, n-propylsulfonyl, n-butylsulfonyl, n-pentylsulfonyl, n-hexylsulfonyl, 1-methylethylsulfonyl, tert-butylsulfonyl, and 2-methylbutylsulfonyl.

Examples of halogen-substituted $C_1$-$C_6$ alkyl groups include halogenoalkyl groups that are linear or branched $C_{1-6}$ alkyl groups substituted with one or more halogen atoms selected from the group consisting of fluorine, chlorine, bromine, and iodine. A preferable example of halogen-substituted $C_1$-$C_6$ alkyl groups is a perhalogenoalkyl group, and a more preferable example is a perfluoroalkyl group. Specific examples of halogen-substituted $C_1$-$C_6$ alkyl groups include trifluoromethyl, pentafluoroethyl, heptafluoropropyl, nonafluorobutyl, undecafluoropentyl, tridecafluorohexyl, 2,2,2-trifluoroethyl, 3,3,3-trifluoropropyl, 4,4,4-trifluorobutyl, 5,5,5-trifluoropentyl, 6,6,6-trifluorohexyl, and the like.

Examples of pyridyl groups having one or two substituents each independently selected from the group consisting of halogen, cyano, $C_1$-$C_6$ alkyl, $C_1$-$C_6$ alkylsulfonyl, and halogen-substituted $C_1$-$C_6$ alkyl include 3-fluoropyridin-2-yl, 4-fluoropyridin-2-yl, 5-fluoropyridin-2-yl, 6-fluoropyridin-2-yl, 2-fluoropyridin-3-yl, 4-fluoropyridin-3-yl, 5-fluoropyridin-3-yl, 6-fluoropyridin-3-yl, 2-fluoropyridin-4-yl, 3-fluoropyridin-4-yl, 3-chloropyridin-2-yl, 3-bromopyridin-2-yl, 3-iodopyridin-2-yl, 3,5-difluoropyridin-2-yl, 4,5-difluoropyridin-2-yl, 3,5-dichloropyridin-2-yl, 3,5-dibromopyridin-2-yl, 5-bromo-3-fluoropyridin-2-yl, 3-bromo-5-chloropyridin-2-yl, 5-chloro-3-fluoropyridin-2-yl, 3-cyanopyridin-2-yl, 4-cyanopyridin-2-yl, 5-cyanopyridin-2-yl, 6-cyanopyridin-2-yl, 2-cyanopyridin-3-yl, 4-cyanopyridin-3-yl, 5-cyanopyridin-3-yl, 6-cyanopyridin-3-yl, 2-cyanopyridin-4-yl, 3-cyanopyridin-4-yl, 3,5-dicyanopyridin-2-yl, 4,5-dicyanopyridin-2-yl, 3-methylpyridin-2-yl, 4-methylpyridin-2-yl, 5-methylpyridin-2-yl, 6-methylpyridin-2-yl, 2-methylpyridin-3-yl, 4-methylpyridin-3-yl, 5-methylpyridin-3-yl, 6-methylpyridin-3-yl, 2-methylpyridin-4-yl, 3-methylpyridin-4-yl, 3-ethylpyridin-2-yl, 3-n-propylpyridin-2-yl, 3-n-butylpyridin-2-yl, 3-n-pentylpyridin-2-yl, 3-n-hexylpyridin-2-yl, 3,5-dimethylpyridin-2-yl, 4,5-dimethylpyridin-2-yl, 3,5-diethylpyridin-2-yl, 3-methylsulfonylpyridin-2-yl, 4-methylsulfonylpyridin-2-yl, 5-methylsulfonylpyridin-2-yl, 6-methylsulfonylpyridin-2-yl, 2-methylsulfonylpyridin-3-yl, 4-methylsulfonylpyridin-3-yl, 5-methylsulfonylpyridin-3-yl, 6-methylsulfonylpyridin-3-yl, 2-methylsulfonylpyridin-4-yl, 3-methylsulfonylpyridin-4-yl, 5-ethylsulfonylpyridin-2-yl, 5-n-propylsulfonylpyridin-2-yl, 5-n-butylsulfonylpyridin-2-yl, 5-n-pentylsulfonylpyridin-2-yl, 5-n-hexylsulfonylpyridin-2-yl, 3,5-dimethylsulfonylpyridin-2-yl, 4,5-dimethylsulfonylpyridin-2-yl, 3,5-diethylsulfonylpyridin-2-yl, 3-trifluoromethylpyridin-2-yl, 4-trifluoromethylpyridin-2-yl, 5-trifluoromethylpyridin-2-yl, 6-trifluoromethylpyridin-2-yl, 2-trifluoromethylpyridin-3-yl, 4-trifluoromethylpyridin-3-yl, 5-trifluoromethylpyridin-3-yl, 6-trifluoromethylpyridin-3-yl, 2-trifluoromethylpyridin-4-yl, 3-trifluoromethylpyridin-4-yl, 6-pentafluoroethylpyridin-3-yl, 6-n-heptafluoropentylpyridin-3-yl, 6-n-nonafluorobutylpyridin-3-yl, 6-n-undecafluoropentylpyridin-3-yl, 6-n-tridecafluorohexylpyridin-3-yl, 3,5-bistrifluoromethylpyridin-2-yl, 4,5-bistrifluoromethylpyridin-2-yl, 3-fluoro-5-trifluoromethylpyridin-2-yl, 3-chloro-5-trifluoromethylpyridin-2-yl, 3-bromo-5-trifluoromethylpyridin-2-yl, 3-iodo-5-trifluoromethylpyridin-2-yl, 5-fluoro-3-trifluoromethylpyridin-2-yl, 5-chloro-3-trifluoromethylpyridin-2-yl, 5-bromo-3-trifluoromethylpyridin-2-yl, 5-iodo-3-trifluoromethylpyridin-2-yl, 3-fluoro-5-methylpyridin-2-yl, 3-chloro-5-methylpyridin-2-yl, 3-bromo-5-methylpyridin-2-yl, 3-iodo-5-methylpyridin-2-yl, 5-fluoro-3-methylpyridin-2-yl, 5-chloro-3-methylpyridin-2-yl, 5-bromo-3-methylpyridin-2-yl, 5-iodo-3-methylpyridin-2-yl, 3-fluoro-5-methylsulfonylpyridin-2-yl, 3-chloro-5-methylsulfonylpyridin-2-yl, 3-bromo-5-methylsulfonylpyridin-2-yl, 3-iodo-5-methylsulfonylpyridin-2-yl, 5-fluoro-3-methylsulfonylpyridin-2-yl, 5-chloro-3-methylsulfonylpyridin-2-yl, 5-bromo-3-methylsulfonylpyridin-2-yl, 5-iodo-3-methylsulfonylpyridin-2-yl, 5-cyano-3-fluoropyridin-2-yl, 3-chloro-5-cyanopyridin-2-yl, 3-bromo-5-cyanopyridin-2-yl, 5-cyano-3-iodopyridin-2-yl, 3-cyano-5-fluoropyridin-2-yl, 5-chloro-3-cyanopyridin-2-yl, 5-bromo-3-cyanopyridin-2-yl, 3-cyano-5-iodopyridin-2-yl, 5-cyano-3-trifluoromethylpyridin-2-yl, 3-cyano-5-trifluoromethylpyridin-2-yl, 5-cyano-3-methylpyridin-2-yl, 3-cyano-5-methylpyridin-2-yl, 5-cyano-3-methylsulfonylpyridin-2-yl, 3-cyano-5-methylsulfonylpyridin-2-yl, 5-methyl-3-methylsulfonylpyridin-2-yl, 3-methyl-5-methylsulfonylpyridin-2-yl, 5-methyl-3-trifluoromethylpyridin-2-yl, 3-methyl-5-trifluoromethylpyridin-2-yl, 5-methylsulfonyl-3-trifluoromethylpyridin-2-yl, 3-methylsulfonyl-5-trifluoromethylpyridin-2-yl, and the like.

Examples of oxazolyl groups having one or more $C_1$-$C_6$ alkyl groups include oxazolyl groups substituted with one or more linear or branched alkyl groups having 1 to 6 carbon atoms, such as 2-methyloxazol-4-yl, 2-methyloxazol-5-yl, 4-methyloxazol-2-yl, 4-methyloxazol-5-yl, 5-methyloxazol-2-yl, 5-methyloxazol-4-yl, 2-ethyloxazol-4-yl, 2-n-propyloxazol-4-yl, 2-n-butyloxazol-4-yl, 2-n-pentyloxazol-4-yl, 2-n-hexyloxazol-4-yl, and 2-tert-butyloxazol-4-yl. The oxazolyl group having one or more $C_1$-$C_6$ alkyl groups is an oxazolyl group having one or more $C_1$-$C_6$ alkyl groups, and preferably one $C_1$-$C_6$ alkyl group.

Examples of pyrazinyl groups optionally substituted with at least one group selected from the group consisting of halogen and $C_1$-$C_6$ alkyl include pyrazin-2-yl, pyrazin-3-yl, 5-fluoropyrazin-2-yl, 5-chloropyrazin-2-yl, 5-bromopyrazin-2-yl, 5-iodopyrazin-2-yl, 6-chloropyrazin-2-yl, 5-methylpyrazin-2-yl, 5-ethylpyrazin-2-yl, 5-n-propylpyrazin-2-yl, 5-n-butylpyrazin-2-yl, 5-n-pentylpyrazin-2-yl, 5-n-hexylpyrazin-2-yl, 5-tert-butylpyrazin-2-yl, 6-methylpyrazin-2-yl, and the like. The pyrazinyl group optionally substituted with at least one group selected from the group consisting of halogen and $C_1$-$C_6$ alkyl is a pyrazinyl group optionally having one or more substituents, and preferably having one substituent, each independently selected from the group consisting of halogen and $C_1$-$C_6$ alkyl.

Examples of phenyl groups having one or two substituents each independently selected from the group consisting of halogen and halogen-substituted $C_1$-$C_6$ alkyl include 2-trifluoromethylphenyl, 3-trifluoromethylphenyl, 4-trifluoromethylphenyl, 4-pentafluoroethylphenyl, 4-n-heptafluoropropylphenyl, 4-n-nonafluorobutylphenyl, 4-n-undecafluoropentylphenyl, 4-tridecafluorohexylphenyl, 2,3-bis(trifluoromethyl)phenyl, 2,4-bis(trifluoromethyl)phenyl, 3,4-bis(trifluoromethyl)phenyl, 2,5-bis(trifluoromethyl)phenyl, 3,5-bis(trifluoromethyl)phenyl, 2-fluorophenyl, 3-fluorophenyl, 4-fluorophenyl, 4-chlorophenyl, 4-bromophenyl, 4-iodophenyl, 2,3-difluorophenyl, 2,4-difluorophenyl, 3,4-difluorophenyl, 2,5-difluorophenyl, 2,6-difluorophenyl, 2,4-dichlorophenyl, 2,4-dibromophenyl, 2,4-diiodophenyl, 4-bromo-2-fluorophenyl, 4-chloro-2-fluorophenyl, 2-fluoro-4-iodophenyl, 2-bromo-4-fluorophenyl, 2-bromo-4-chlorophenyl, 4-bromo-2-chlorophenyl, and the like.

Examples of $C_1$-$C_6$ alkoxy groups include linear or branched alkoxy groups having 1 to 6 carbon atoms, such as methoxy, ethoxy, n-propoxy, n-butoxy, n-pentyloxy, n-hexyloxy, 1-methylethoxy, tert-butoxy, and 2-methylbutoxy.

Examples of $C_1$-$C_6$ alkoxy $C_1$-$C_6$ alkoxy groups include linear or branched alkoxy groups having 1 to 6 carbon atoms and substituted with one or more linear or branched alkoxy groups having 1 to 6 carbon atoms, such as methoxymethoxy, 2-methoxyethoxy, 3-methoxypropoxy, 4-methoxybutoxy, 5-methoxypentyloxy, 6-methoxyhexyloxy, 2-methoxy-1-methylethoxy, ethoxymethoxy, n-propoxymethoxy, n-butoxymethoxy, n-pentyloxymethoxy, n-hexyloxymethoxy, and 1-methylethoxymethoxy.

Examples of pyrrolidinyl groups include 1-pyrrolidinyl, 2-pyrrolidinyl, and 3-pyrrolidinyl.

Examples of $C_1$-$C_6$ alkylthio groups include linear or branched alkylthio groups having 1 to 6 carbon atoms, such as methylthio, ethylthio, n-propylthio, n-butylthio, n-pentylthio, n-hexylthio, 1-methylethylthio, tert-butylthio, and 2-methylbutylthio.

Examples of pyridyl groups optionally having at least one substituent selected from the group consisting of halogen, cyano, hydroxy, pyrrolidinyl, $C_1$-$C_6$ alkyl, $C_1$-$C_6$ alkylthio, $C_1$-$C_6$ alkylsulfonyl, $C_1$-$C_6$ alkoxy, and halogen-substituted $C_1$-$C_6$ alkyl include 2-pyridyl, 3-pyridyl, 4-pyridyl, 3-fluoropyridin-2-yl, 4-fluoropyridin-2-yl, 5-fluoropyridin-2-yl, 6-fluoropyridin-2-yl, 2-fluoropyridin-3-yl, 4-fluoropyridin-3-yl, 5-fluoropyridin-3-yl, 6-fluoropyridin-3-yl, 2-fluoropyridin-4-yl, 3-fluoropyridin-4-yl, 6-chloropyridin-3-yl, 6-bromopyridin-3-yl, 6-iodopyridin-3-yl, 5-chloropyridin-2-yl, 5-bromopyridin-2-yl, 5-iodopyridin-2-yl, 3-methylpyridin-2-yl, 4-methylpyridin-2-yl, 5-methylpyridin-2-yl, 6-methylpyridin-2-yl, 2-methylpyridin-3-yl, 4-methylpyridin-3-yl, 5-methylpyridin-3-yl, 6-methylpyridin-3-yl, 2-methylpyridin-4-yl, 3-methylpyridin-4-yl, 6-ethylpyridin-3-yl, 6-n-propylpyridin-3-yl, 6-n-butylpyridin-3-yl, 6-n-pentylpyridin-3-yl, 6-n-hexylpyridin-3-yl, 6-tert-butylpyridin-3-yl, 3-cyanopyridin-2-yl, 4-cyanopyridin-2-yl, 5-cyanopyridin-2-yl, 6-cyanopyridin-2-yl, 2-cyanopyridin-3-yl, 4-cyanopyridin-3-yl, 5-cyanopyridin-3-yl, 6-cyanopyridin-3-yl, 2-cyanopyridin-4-yl, 3-cyanopyridin-4-yl, 3-hydroxypyridin-2-yl, 4-hydroxypyridin-2-yl, 5-hydroxypyridin-2-yl, 6-hydroxypyridin-2-yl, 2-hydroxypyridin-3-yl, 4-hydroxypyridin-3-yl, 5-hydroxypyridin-3-yl, 6-hydroxypyridin-3-yl, 2-hydroxypyridin-4-yl, 3-hydroxypyridin-4-yl, 3-methoxypyridin-2-yl, 4-methoxypyridin-2-yl, 5-methoxypyridin-2-yl, 6-methoxypyridin-2-yl, 2-methoxypyridin-3-yl, 4-methoxypyridin-3-yl, 5-methoxypyridin-3-yl, 6-methoxypyridin-3-yl, 2-methoxypyridin-4-yl, 3-methoxypyridin-4-yl, 6-ethoxypyridin-3-yl, 6-n-propoxypyridin-3-yl, 6-n-butoxypyridin-3-yl, 6-n-pentyloxypyridin-3-yl, 6-n-hexyloxypyridin-3-yl, 6-tert-butoxypyridin-3-yl, 3-methylthiopyridin-2-yl, 4-methylthiopyridin-2-yl, 5-methylthiopyridin-2-yl, 6-methylthiopyridin-2-yl, 2-methylthiopyridin-3-yl, 4-methylthiopyridin-3-yl, 5-methylthiopyridin-3-yl, 6-methylthiopyridin-3-yl, 2-methylthiopyridin-4-yl, 3-methylthiopyridin-4-yl, 5-ethylthiopyridin-2-yl, 2-ethylthiopyridin-5-yl, 5-n-propylthiopyridin-2-yl, 5-n-butylthiopyridin-2-yl, 5-n-pentylthiopyridin-2-yl, 5-n-hexylthiopyridin-2-yl, 5-tert-butylthiopyridin-2-yl, 3-methylsulfonylpyridin-2-yl, 4-methylsulfonylpyridin-2-yl, 5-methylsulfonylpyridin-2-yl, 6-methylsulfonylpyridin-2-yl, 2-methylsulfonylpyridin-3-yl, 4-methylsulfonylpyridin-3-yl, 5-methylsulfonylpyridin-3-yl, 6-methylsulfonylpyridin-3-yl, 2-methylsulfonylpyridin-4-yl, 2-methylsulfonylpyridin-5-yl, 3-methylsulfonylpyridin-4-yl, 5-ethylsulfonylpyridin-2-yl, 5-n-propylsulfonylpyridin-2-yl, 5-n-butylsulfonylpyridin-2-yl, 5-n-pentylsulfonylpyridin-2-yl, 5-n-hexylsulfonylpyridin-2-yl, 3,5-dimethylsulfonylpyridin-2-yl, 4,5-dimethylsulfonylpyridin-2-yl, 3,5-diethylsulfonylpyridin-2-yl, 3-trifluoromethylpyridin-2-yl, 4-trifluoromethylpyridin-2-yl, 5-trifluoromethylpyridin-2-yl, 6-trifluoromethylpyridin-2-yl, 2-trifluoromethylpyridin-3-yl, 4-trifluoromethylpyridin-3-yl, 5-trifluoromethylpyridin-3-yl, 6-trifluoromethylpyridin-3-yl, 2-trifluoromethylpyridin-4-yl, 3-trifluoromethylpyridin-4-yl, 6-pentafluoroethylpyridin-3-yl, 6-n-heptafluoropropylpyridin-3-yl, 6-n-nonafluorobutylpyridin-3-yl, 6-n-undecafluoropentylpyridin-3-yl, 6-n-tridecafluorohexylpyridin-3-yl, 3-(1-pyrrolidinyl)pyridin-2-yl, 4-(1-pyrrolidinyl)pyridin-2-yl, 5-(1-pyrrolidinyl)pyridin-2-yl, 6-(1-pyrrolidinyl)pyridin-2-yl, 2-(1-pyrrolidinyl)pyridin-3-yl, 4-(1-pyrrolidinyl)pyridin-3-yl, 5-(1-pyrrolidinyl)pyridin-3-yl, 6-(1-pyrrolidinyl)pyridin-3-yl, 2-(1-pyrrolidinyl)pyridin-4-yl, 3-(1-pyrrolidinyl)pyridin-4-yl, 6-(2-pyrrolidinyl)pyridin-2-yl, 6-(3-pyrrolidinyl)pyridin-2-yl, and the like. The pyridyl group is a pyridyl group optionally having one or more substituents, and preferably having one substituent, each independently selected from the group consisting of halogen, cyano, hydroxy, pyrrolidinyl, $C_1$-$C_6$ alkyl, $C_1$-$C_6$ alkylthio, $C_1$-$C_6$ alkylsulfonyl, $C_1$-$C_6$ alkoxy, and halogen-substituted $C_1$-$C_6$ alkyl.

Examples of $C_3$-$C_{10}$ cycloalkyl groups include cycloalkyl groups having 3 to 10 carbon atoms, such as cyclopropyl, cyclobutyl, cyclopentyl, cyclohexyl, cycloheptyl, cyclooctyl, cyclononyl, cyclodecanyl, norbornan-2-yl, adamantan-1-yl, and adamantan-2-yl.

Examples of $C_3$-$C_{10}$ cycloalkyl groups optionally having one or two substituents each independently selected from the group consisting of halogen and $C_1$-$C_6$ alkyl include the $C_3$-$C_{10}$ cycloalkyl groups described above, and cycloalkyl groups substituted with one or more halogen atoms and/or one or more linear or branched alkyl groups having 1 to 6 carbon atoms, such as 1-fluorocyclopropyl, 2-chlorocyclopropyl, 2-fluorocyclopropyl, 2-bromocyclopropyl, 2-iodocyclopropyl, 2,2-difluorocyclopropyl, 2,3-difluorocyclopropyl, 2,2-difluorocyclobutyl, 3,3-difluorocyclobutyl, 2,2-difluorocyclopentyl, 3,3-difluorocyclopentyl, 3,3-difluorocyclohexyl, 4,4-difluorocyclohexyl, 4,4-difluorocycloheptyl, 4,4-difluorocyclooctyl, 4-methylcyclohexyl, 4,4-dimethylcyclohexyl, 4-ethylcyclohexyl, 4-n-propylcyclohexyl, 4-n-butylcyclohexyl, 4-n-pentylcyclohexyl, 4-n-hexylcyclohexyl, and 4-tert-butylcyclohexyl.

Examples of $C_1$-$C_6$ alkoxy $C_1$-$C_6$ alkyl groups include linear or branched alkyl groups having 1 to 6 carbon atoms and substituted with one or more linear or branched alkoxy groups having 1 to 6 carbon atoms, such as methoxymethyl, 2-methoxyethyl, 3-methoxypropyl, 4-methoxybutyl, 5-methoxypentyl, 6-methoxyhexyl, 2-methoxy-1-methylethyl, ethoxymethyl, n-propoxymethyl, n-butoxymethyl, n-pentyloxymethyl, n-hexyloxymethyl, 1-methoxyethyl, 1-ethoxyethyl, 1-n-propoxyethyl, 1-n-butoxyethyl, 1-n-pentyloxyethyl, 1-n-hexyloxyethyl, and 1-methylethoxymethyl.

Examples of $C_1$-$C_6$ alkyl groups optionally substituted with one or more $C_3$-$C_{10}$ cycloalkyl groups include the $C_1$-$C_6$ alkyl groups described above, cyclopropylmethyl, 2-cyclopropylethyl, 1-cyclopropylethyl, 3-cyclopropylpropyl, 4-cyclopropylbutyl, 5-cyclopropylpentyl, 6-cyclopropylhexyl, 2-cyclopropyl-1-methylethyl, cyclobutylmethyl, cyclopentylmethyl, cyclohexylmethyl, cycloheptylmethyl, cyclooctylmethyl, cyclononylmethyl, cyclodecanylmethyl, norbornan-2-ylmethyl, adamantan-1-ylmethyl, adamantan-2-ylmethyl, and the like.

Examples of $C_1$-$C_6$ alkylene groups include linear or branched alkylene groups having 1 to 6 carbon atoms, such as methylene, ethylene, ethylidene, trimethylene, tetramethylene, pentamethylene, and hexamethylene.

Examples of (pyridine 1-oxide)yl groups having one or two substituents each independently selected from the group consisting of halogen and halogen-substituted $C_1$-$C_6$ alkyl include 3-fluoro(pyridine 1-oxide)-2-yl, 4-fluoro(pyridine 1-oxide)-2-yl, 5-fluoro(pyridine 1-oxide)-2-yl, 6-fluoro(pyridine 1-oxide)-2-yl, 2-fluoro(pyridine 1-oxide)-3-yl, 4-fluoro(pyridine 1-oxide)-3-yl, 5-fluoro(pyridine 1-oxide)-3-yl, 6-fluoro(pyridine 1-oxide)-3-yl, 2-fluoro(pyridine 1-oxide)-4-yl, 3-fluoro(pyridine 1-oxide)-4-yl, 3-chloro(pyridine 1-oxide)-2-yl, 3-bromo(pyridine 1-oxide)-2-yl, 3-iodo(pyridine 1-oxide)-2-yl, 3,5-difluoro(pyridine 1-oxide)-2-yl, 4,5-difluoro(pyridine 1-oxide)-2-yl, 3,5-dichloro(pyridine 1-oxide)-2-yl, 3,5-dibromo(pyridine 1-oxide)-2-yl, 5-bromo-3-fluoro(pyridine 1-oxide)-2-yl, 3-bromo-5-chloro(pyridine 1-oxide)-2-yl, 5-chloro-3-fluoro(pyridine 1-oxide)-2-yl, 3-trifluoromethyl(pyridine 1-oxide)-2-yl, 4-trifluoromethyl(pyridine 1-oxide)-2-yl, 5-trifluoromethyl(pyridine 1-oxide)-2-yl, 6-trifluoromethyl(pyridine 1-oxide)-2-yl, 2-trifluoromethyl(pyridine 1-oxide)-3-yl, 2-trifluoromethyl(pyridine 1-oxide)-4-yl, 2-trifluoromethyl(pyridine 1-oxide)-5-yl, 4-trifluoromethyl(pyridine 1-oxide)-3-yl, 5-trifluoromethyl(pyridine 1-oxide)-3-yl, 6-trifluoromethyl(pyridine 1-oxide)-3-yl, 2-trifluoromethyl(pyridine 1-oxide)-4-yl, 3-trifluoromethyl(pyridine 1-oxide)-4-yl, 6-pentafluoroethyl(pyridine 1-oxide)-3-yl, 6-n-heptafluoropentyl(pyridine 1-oxide)-3-yl, 6-n-nonafluorobutyl(pyridine 1-oxide)-3-yl, 6-n-undecafluoropentyl(pyridine 1-oxide)-3-yl, 6-n-tridecafluorohexyl(pyridine 1-oxide)-3-yl, 3,5-bistrifluoromethyl(pyridine 1-oxide)-2-yl, 4,5-bistrifluoromethyl(pyridine 1-oxide)-2-yl, 3-fluoro-5-trifluoromethyl(pyridine 1-oxide)-2-yl, 3-chloro-5-trifluoromethyl(pyridine 1-oxide)-2-yl, 3-bromo-5-trifluoromethyl(pyridine 1-oxide)-2-yl, 3-iodo-5-trifluoromethyl(pyridine 1-oxide)-2-yl, 5-fluoro-3-trifluoromethyl(pyridine 1-oxide)-2-yl, 5-chloro-3-trifluoromethyl(pyridine 1-oxide)-2-yl, 5-bromo-3-trifluoromethyl(pyridine 1-oxide)-2-yl, 5-iodo-3-trifluoromethyl(pyridine 1-oxide)-2-yl, and the like.

Examples of halogen-substituted thiazolyl groups include 2-chlorothiazol-5-yl, 2-chlorothiazol-4-yl, 2-fluorothiazol-5-yl, 2-bromothiazol-5-yl, and the like. The thiazolyl group is a thiazolyl group having one or more halogen atoms, and preferably one halogen atom.

Examples of $C_1$-$C_6$ alkyl-substituted isoxazolyl groups include 3-methylisoxazol-5-yl, 3-ethylisoxazol-5-yl, 3-n-propylisoxazol-5-yl, 3-n-butylisoxazol-5-yl, 3-n-pentylisoxazol-5-yl, 3-n-hexylisoxazol-5-yl, 3-(1-methylethyl)isoxazol-5-yl, and the like. The isoxazolyl group is an isoxazolyl group having one or more $C_1$-$C_6$ alkyl groups, and preferably one $C_1$-$C_6$ alkyl group.

Examples of $C_3$-$C_8$ cycloalkyl-substituted 1,2,4-oxadiazolyl groups include 5-cyclopropyl-1,2,4-oxadiazol-3-yl, 5-cyclobutyl-1,2,4-oxadiazol-3-yl, 5-cyclopentyl-1,2,4-oxadiazol-3-yl, 5-cyclohexyl-1,2,4-oxadiazol-3-yl, 5-cycloheptyl-1,2,4-oxadiazol-3-yl, 5-cyclooctyl-1,2,4-oxadiazol-3-yl, and the like. The 1,2,4-oxadiazolyl group is a 1,2,4-oxadiazolyl group having one or more $C_3$-$C_8$ cycloalkyl groups, and preferably one $C_3$-$C_5$ cycloalkyl group.

2. Phenylimidazole Compound Represented by Formula (1)

In an embodiment, $R^1$ in formula (1) is preferably pyridyl having one or two substituents each independently selected from the group consisting of halogen, cyano, $C_1$-$C_6$ alkyl, $C_1$-$C_6$ alkylsulfonyl, and halogen-substituted $C_1$-$C_6$ alkyl. The pyridyl having one or two substituents each independently selected from the group consisting of halogen, cyano, $C_1$-$C_6$ alkyl, $C_1$-$C_6$ alkylsulfonyl, and halogen-substituted $C_1$-$C_6$ alkyl is preferably pyridyl having one or two halogen-substituted $C_1$-$C_6$ alkyl groups, or pyridyl having one or two substituents each independently selected from the group consisting of halogen-substituted $C_1$-$C_6$ alkyl and halogen, and more preferably pyridyl having one or two substituents each independently selected from the group consisting of halogen and halogen-substituted $C_1$-$C_6$ alkyl.

In an embodiment, $R^2$ in formula (1) is preferably hydrogen.

In an embodiment, $R^3$ in formula (1) is preferably hydrogen or $C_1$-$C_6$ alkoxy.

In an embodiment, $R^4$ in formula (1) is preferably pyridyl optionally having at least one substituent selected from the group consisting of halogen, cyano, hydroxy, pyrrolidinyl, $C_1$-$C_6$ alkyl, $C_1$-$C_6$ alkylthio, $C_1$-$C_6$ alkylsulfonyl, $C_1$-$C_6$ alkoxy, and halogen-substituted $C_1$-$C_6$ alkyl. The pyridyl optionally having at least one substituent selected from the group consisting of halogen, cyano, hydroxy, pyrrolidinyl, $C_1$-$C_6$ alkyl, $C_1$-$C_6$ alkylthio, $C_1$-$C_6$ alkylsulfonyl, $C_1$-$C_6$ alkoxy, and halogen-substituted $C_1$-$C_6$ alkyl is preferably halogen-substituted pyridyl.

In an embodiment, $R^5$ in formula (1) is preferably hydrogen or $C_1$-$C_6$ alkoxy.

In an embodiment, $R^6$ in formula (1) is preferably hydrogen.

In an embodiment, $R^7$ in formula (1) is preferably hydrogen or $C_1$-$C_6$ alkyl, and more preferably hydrogen.

In a preferred embodiment, $R^3$ in formula (1) is hydrogen or $C_1$-$C_6$ alkoxy, and $R^5$ is hydrogen or $C_1$-$C_6$ alkoxy.

In a preferred embodiment, $R^2$ and $R^5$ in formula (1) each represent hydrogen, and $R^3$ is $C_1$-$C_6$ alkoxy.

In a preferred embodiment, $R^6$ in formula (1) is hydrogen, and $R^7$ is halogen.

In an embodiment, the bond between N at the 3-position and C at the 2-position of the imidazole skeleton in formula (1) is a double bond, and the bond between C at the 2-position and N at the 1-position of the imidazole skeleton in formula (1) is a single bond. In this case, $R^6$ is attached to only N at the 1-position, as shown in formula 1-1 below. In another embodiment, the bond between N at the 3-position and C at the 2-position of the imidazole skeleton in formula (1) is a single bond, and the bond between C at the 2-position and N at the 1-position of the imidazole skeleton in formula (1) is a double bond. In this case, $R^6$ is attached to only N at the 3-position, as shown in formula (1-2) below.

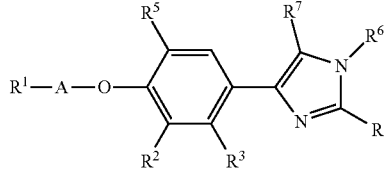

(1-1)

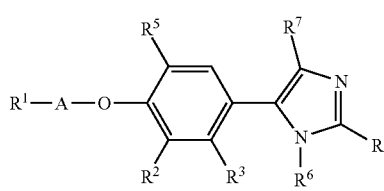

(1-2)

Preferable examples of phenylimidazole compounds represented by formula (1) include the following compounds:

5-[[4-(5-chloro-2-(6-fluoropyridin-3-yl)-1H-imidazol-4-yl)-3-methoxyphenoxy]methyl]-2-(trifluoromethyl)pyridine 2-[[4-(5-chloro-2-(6-fluoropyridin-3-yl)-1H-imidazol-4-yl)-3-methoxyphenoxy]methyl]-3-fluoro-5-(trifluoromethyl)pyridine 2-[[4-(5-bromo-2-(6-fluoropyridin-3-yl)-1H-imidazol-4-yl)-3-methoxyphenoxy]methyl]-3-fluoro-5-(trifluoromethyl)pyridine 3-chloro-2-[[4-(5-chloro-2-(6-fluoropyridin-3-yl)-1H-imidazol-4-yl)-3-methoxyphenoxy]methyl]-5-(trifluoromethyl)pyridine 2-[[4-(5-bromo-2-(6-chloropyridin-3-yl)-1H-imidazol-4-yl)-3-methoxyphenoxy]methyl]-5-(trifluoromethyl)pyridine 5-bromo-2-[[4-(4-chloro-2-(6-fluoropyridin-3-yl)-1H-imidazol-5-yl)-3-methoxyphenoxy]methyl]-3-fluoropyridine 5-[4-chloro-5-[2-methoxy-4-((6-(trifluoromethyl)pyridin-2-yl)methoxy)phenyl]-1H-imidazol-2-yl]-2-fluoropyridine.

3. Production Method

The phenylimidazole compound represented by formula (1) can be produced by various methods. In an embodiment, the phenylimidazole compound represented by formula (1) can be produced according to a synthesis scheme shown in the following Reaction Scheme-1.

Reaction Scheme-1

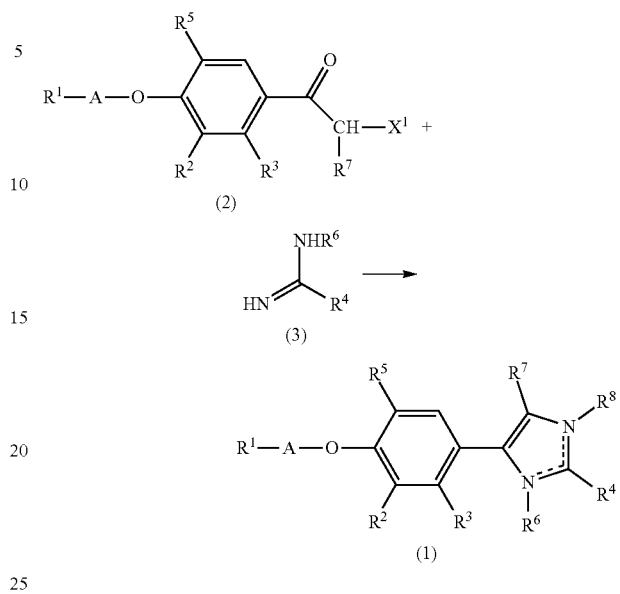

wherein A, $R^1$, $R^2$, $R^3$, $R^4$, $R^5$, $R^6$, $R^7$, and dashed lines are as defined above, and $X^1$ represents halogen.

As shown in Reaction Scheme-1 described above, compound (1) of the present invention can be produced through cyclization of compound (2) and compound (3).

The cyclization reaction can be performed by reacting substantially equimolar amounts of compound (2) and compound (3) in an inert solvent such as tetrahydrofuran (THF), 1,4-dioxane, water, or a mixture of these, in the presence of at least one alkali selected from the group consisting of sodium hydrogen carbonate, potassium hydrogen carbonate, sodium carbonate, and the like at room temperature to 100° C. for 0.5 to 10 hours. The alkali can be used in an amount of 1 to 5 moles per mole of compound (2).

In Reaction Scheme-1, compound (la), wherein $R^6$ is hydrogen, can take the form of tautomerism as shown below and can be represented by either of these forms.

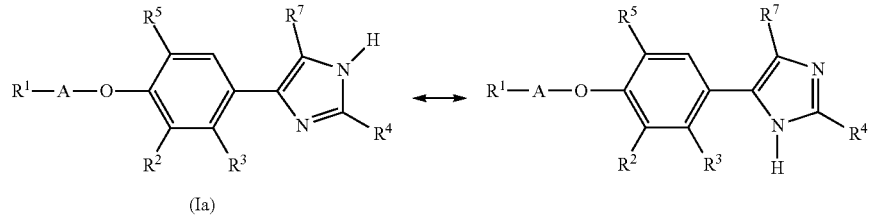

(Ia)

In Reaction Scheme-1, compound (2), which is used as a starting material, can be obtained by reacting compound (4) and trimethylphenylammonium trihalide (5) as shown in Reaction Scheme-2 below. This reaction can be performed, for example, in at least one inert solvent selected from the group consisting of tetrahydrofuran (THF), 1,4-dioxane, and the like at 0 to 50° C. for 5 to 20 hours. Trimethylphenylammonium trihalide (5) can be used in an amount of 1 to 1.3 moles per mole of compound (4).

Reaction Scheme-2

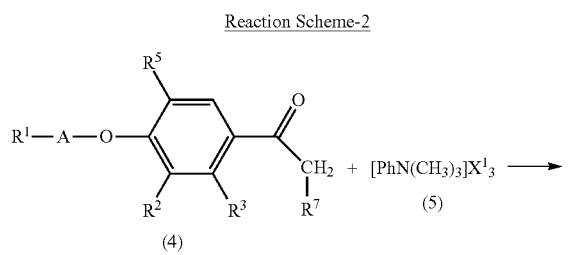

wherein A, $R^1$, $R^2$, $R^3$, $R^5$, $R^7$, and $X^1$ are as defined above.

In Reaction Scheme-2, compound (4a) included in compound (4) used as a starting material is a compound wherein $R^1$ is not hydrogen, and can be obtained by the method shown in Reaction Scheme-3 below.

Reaction Scheme-3

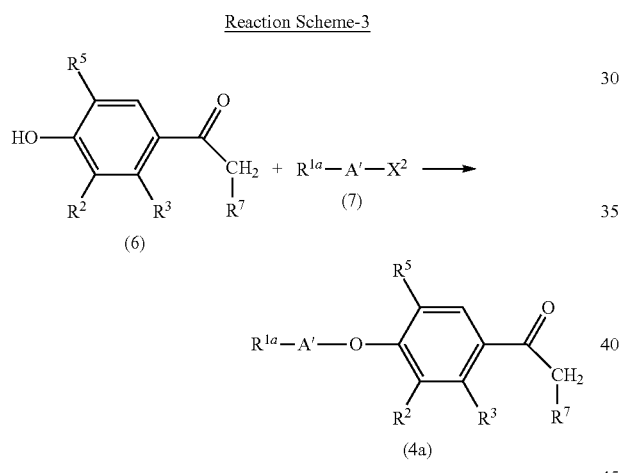

wherein $R^{1a}$ is any of groups (1-2) to (1-12) described above; A' is $C_1$-$C_6$ alkylene; $R^2$, $R^3$, $R^5$, and $R^7$ are as defined above; and $X^2$ is halogen.

The known compound (6) mentioned above can be converted to compound (4a) by reacting it with halide (7). The reaction can be performed in at least one inert solvent selected from the group consisting of N,N-dimethylformamide (DMF), N,N-dimethylacetamide (DMA), dimethyl sulfoxide (DMSO), and the like in the presence of at least one alkali selected from the group consisting of potassium carbonate, sodium carbonate, and the like at room temperature to temperature around the boiling point of the solvent for about 2 to 30 hours. Halide (7) can be used in an amount of 1 to 2 moles per mole of compound (6), and the alkali can be used in an amount of 1 to 3 moles per mole of compound (6).

Phenylimidazole compound (1b), which is a compound represented by formula (1) wherein $R^1$ is hydrogen, can be synthesized by the method shown in Reaction Scheme-4 below. Compound (1b) can be obtained by synthesizing compound (8) according to the method shown in Reaction Scheme-1 described above and then performing catalytic reduction. The catalytic reduction can be carried out under a hydrogen atmosphere in the presence of at least one catalyst selected from the group consisting of palladium-carbon, platinum oxide, and the like using, if necessary, acetic acid or like acid, in at least one solvent selected from the group consisting of methanol, ethanol, water, and the like at about room temperature for about 10 minutes to 12 hours.

Reaction Scheme-4

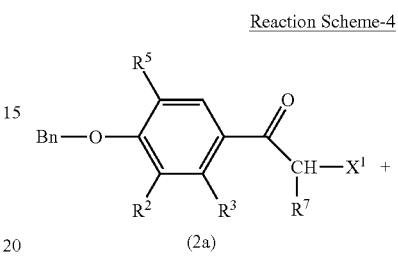

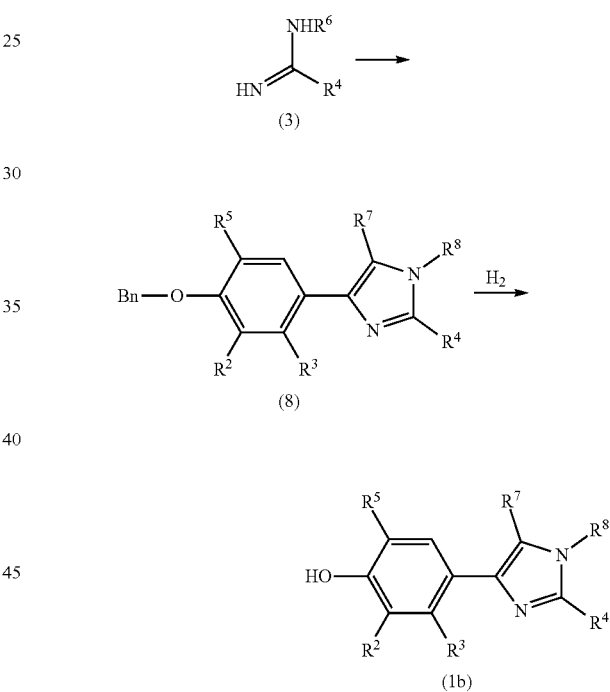

wherein $R^2$, $R^3$, $R^4$, $R^5$, $R^6$, $R^7$, and $X^1$ are as defined above, and Bn represents benzyl.

As shown in Reaction Scheme-5 below, phenylimidazole compounds represented by formula (1) wherein $R^7$ is hydrogen ((1c-1) and (1c-2)) can be converted to compounds (1d-1) and (1d-2), wherein $R^7$ is halogen, by halogenation. The halogenation reaction can be performed using at least one halogenating agent selected from the group consisting of N-bromosuccinimide, N-chlorosuccinimide, N-iodosuccinimide, and the like in at least one inert solvent selected from the group consisting of N,N-dimethylformamide, dimethyl sulfoxide, tetrahydrofuran, and the like at 0 to 70° C. for 0.5 to 6 hours. The halogenating agent is used in an equimolar to 1.3-fold molar amount, relative to phenylimidazole compound (1c-1) or (1c-2).

Reaction Scheme-5

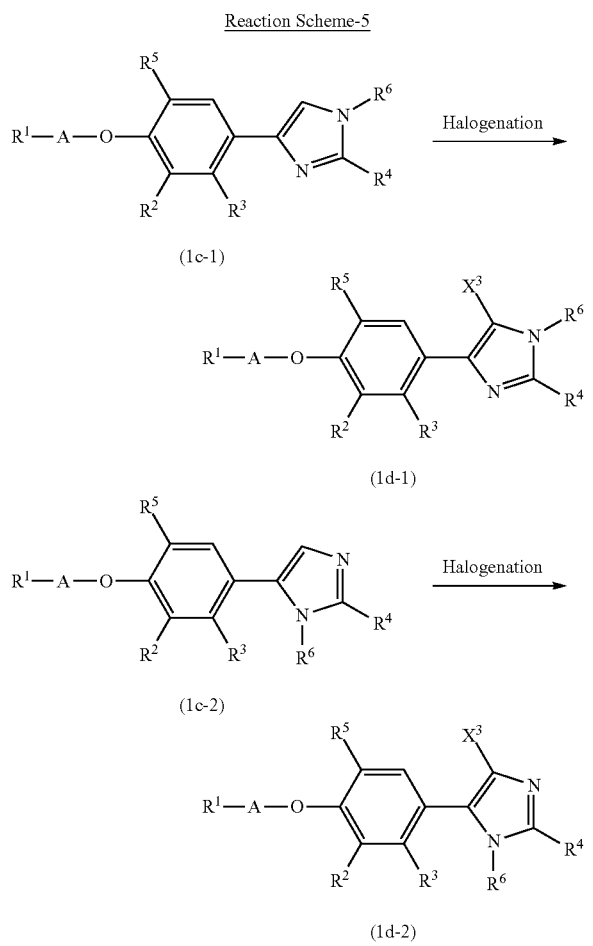

wherein A, $R^1$, $R^2$, $R^3$, $R^4$, $R^5$, and $R^6$ are as defined above, and $X^3$ represents halogen.

Phenylimidazole compound (1b) obtained in Reaction Scheme-4, which is a compound represented by formula (1) wherein $R^1$ is hydrogen, can be converted to compound (1e) by reacting it with halide (7) as shown in Reaction Scheme-6 below. This reaction can be performed under conditions similar to those of Reaction Scheme-3 described above.

Reaction Scheme-6

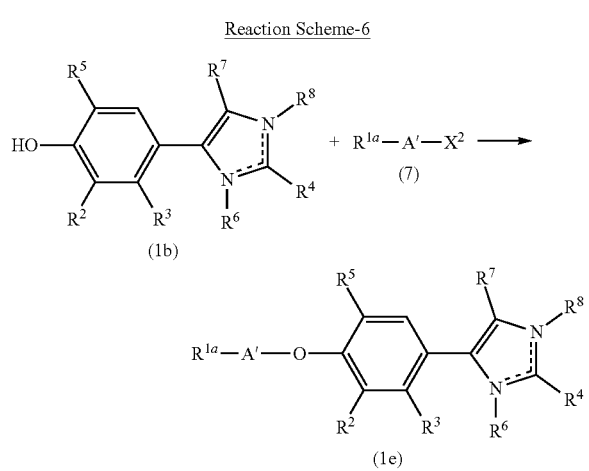

wherein A', $R^{1a}$, $R^2$, $R^3$, $R^4$, $R^5$, $R^6$, $R^7$, $X^2$, and dashed lines are as defined above.

As shown in Reaction Scheme-7 below, phenylimidazole compound (1f), which is a compound represented by formula (1) wherein $R^6$ is hydrogen, can be converted to compounds (1g) and (1h), wherein $R^6$ is a group other than hydrogen, by reacting it with compound (9). This reaction can be performed using compound (9) in an 1- to 2-fold molar amount, relative to phenylimidazole compound (1f), in at least one inert solvent selected from the group consisting of N,N-dimethylformamide, dimethyl sulfoxide, and the like in the presence of at least one alkali selected from the group consisting of anhydrous potassium carbonate, anhydrous sodium carbonate, and the like. The amount of the alkali is not particularly limited and is generally 1- to 5-fold molar amount, relative to phenylimidazole compound (if). This reaction can be performed at 0° C. to about room temperature for 2 to 24 hours.

Reaction Scheme-7

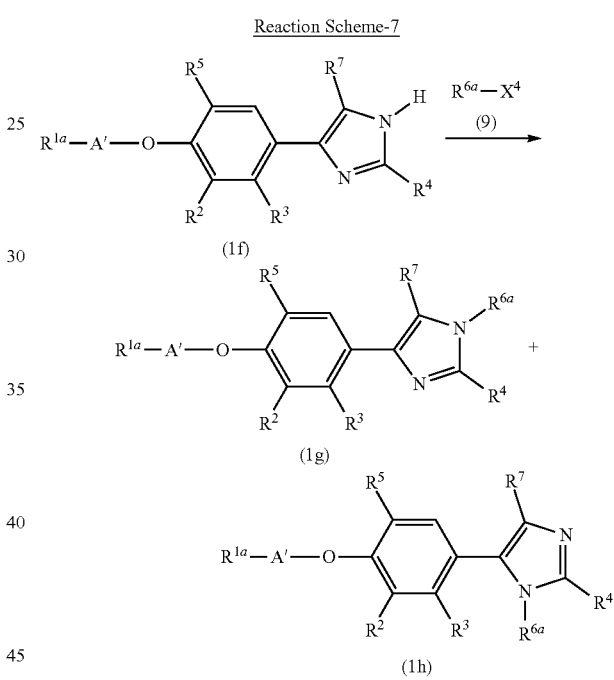

wherein A', $R^{1a}$, $R^2$, $R^3$, $R^4$, $R^5$, and $R^7$ are as defined above, $R^{6a}$ represents $C_1$-$C_6$ alkoxy $C_1$-$C_6$ alkyl or $C_1$-$C_6$ alkyl optionally substituted with one or more $C_3$-$C_{10}$ cycloalkyl groups, and $X^4$ represents halogen.

When $R^7$ in compound (1f) is hydrogen, compound (1h) may hardly be obtained. On the other hand, when $R^7$ in compound (1f) is not hydrogen, compound (1g) may hardly be obtained.

As shown in Reaction Scheme-8 below, phenylimidazole compounds (1j-1) and (1j-2), wherein $R^{4a}$ is halogen-substituted pyridyl, can be converted to compounds (1k-1) and (1k-2), wherein the halogen is replaced by cyano. This reaction can be performed in at least one inert solvent selected from the group consisting of N,N-dimethylformamide, dimethyl sulfoxide, N-methylpyrrolidone, toluene, and the like by using 1- to 2-fold molar amount of at least one cyanide selected from the group consisting of zinc cyanide, copper cyanide, sodium cyanide, copper thiocyanate, and the like and suitably adding, as a catalyst, at least one member selected from the group consisting of tetrakis triphenylphosphine palladium, tetrakis triphenylphosphine platinum, [1,2-bis(diphenylphosphino)ethane]palladium(II) dichloride, and the like. This reaction can be performed at 50 to 150° C. for about 0.5 to 15 hours.

Reaction Scheme-8

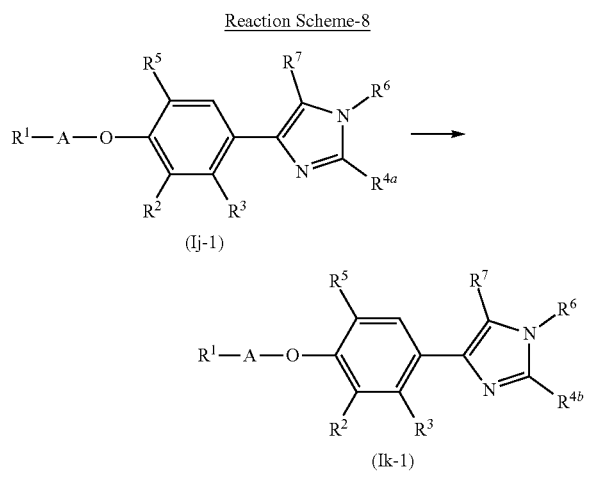

wherein A, $R^1$, $R^2$, $R^3$, $R^5$, $R^6$, and $R^7$ are as defined above, $R^{4a}$ represents halogen-substituted pyridyl, and $R^{4b}$ represents cyano-substituted pyridyl.

As shown in Reaction Scheme-9 below, compounds (1d-1) and (1d-2), wherein $R^7$ is halogen, can be converted to compounds (1m-1) and (1m-2), wherein the halogen is replaced by cyano. This reaction can be performed according to the method shown in Reaction Scheme-8 described above.

Reaction Scheme-9

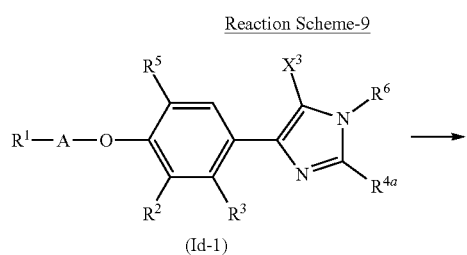

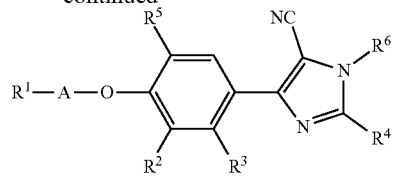

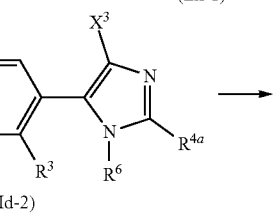

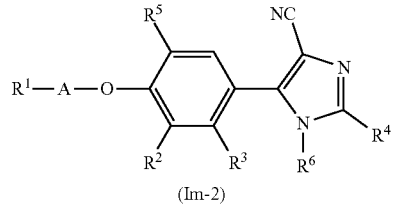

wherein A, $R^1$, $R^2$, $R^3$, $R^4$, $R^5$, $R^6$, and $X^3$ are as defined above.

As shown in Reaction Scheme-10 below, compound (in), wherein $R^3$ is benzyloxy, can be converted to compound (1P), wherein $R^3$ is hydroxy. This reaction can be performed according to the catalytic reduction method shown in Reaction Scheme-4 described above.

Reaction Scheme-10

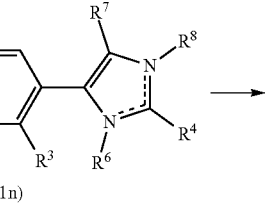

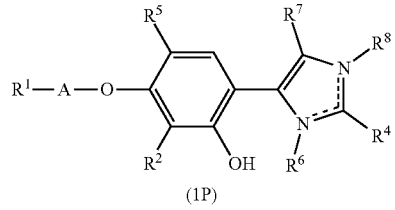

wherein A, $R^1$, $R^2$, $R^3$, $R^4$, $R^5$, $R^6$, $R^7$, and Bn are as defined above.

As shown in Reaction Scheme-11 below, compound (1Q), wherein $R^7$ is hydrogen, can be converted to compound (1R), wherein $R^7$ is hydroxymethyl. This reaction can be performed by reacting compound (1Q) with formaldehyde in an 1- to 5-fold molar amount, relative to compound (1Q), in at least one inert solvent selected from the group consisting of methanol, ethanol, tetrahydrofuran, 1,4-dioxane, and the like in the presence of an alkali. Examples of alkalis include potassium hydroxide, sodium hydroxide, and the like. The alkali is generally added as an aqueous solution. Formaldehyde is also used in the form of an aqueous solution. The reaction is performed at room temperature to 100° C. for about 2 to 15 hours.

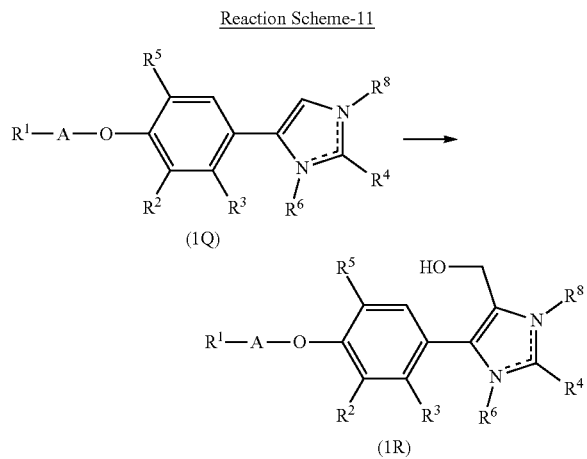

Reaction Scheme-11 wherein A, $R^1$, $R^2$, $R^3$, $R^4$, $R^5$, and $R^6$ are as defined above.

As shown in Reaction Scheme-12 below, compound (1Q), wherein $R^7$ is hydrogen, can be converted to compound (1S), wherein $R^7$ is halogen-substituted $C_1$-$C_6$ alkyl. For this reaction, the method found by Umemoto et al. (Tetrahedron Lett., 31, 3579-3582 (1990)) can suitably be used. Specifically, the reaction is performed by reacting compound (1Q) with a halogen-substituted $C_1$-$C_6$ alkylating agent such as a trifluoromethylating agent (S-(trifluoromethyl)dibenzothiophenium tetrafluoroborate) in an 1- to 3-fold molar amount, relative to compound (1Q), in an inert solvent such as N,N-dimethylformamide, N,N-dimethylacetamide, or dimethyl sulfoxide. In this reaction, it is preferred that an organic base such as 1,4-diazabicyclo[2.2.2]octane, diazabicycloundecene, triethylamine, or N,N-dimethylaminopyridine be added to the reaction system in an 1- to 3-fold molar amount, relative to compound (1Q). This reaction is generally performed at 0 to 50° C. for about 0.5 to 10 hours.

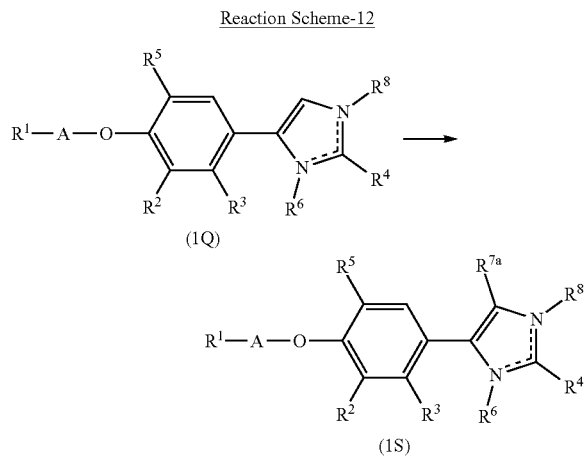

Reaction Scheme-12 wherein A, $R^1$, $R^2$, $R^3$, $R^4$, $R^5$, and $R^6$ are as defined above, and $R^{7a}$ represents halogen-substituted $C_1$-$C_6$ alkyl.

The phenylimidazole compound represented by formula (1) may be a pharmaceutically acceptable salt thereof. The pharmaceutically acceptable salt is not particularly limited and, for example, can be at least one member selected from the group consisting of hydrochloride, nitrate, sulfate, hydrobromide, phosphate, carbonate, sulfonate, acetate, lactate, and citrate. These acid addition salts can be produced according to usual methods.

The phenylimidazole compound represented by formula (1) may include optical isomers having a carbon atom as an asymmetric center. The phenylimidazole compound represented by formula (1) includes all racemates that are mixtures of such optical isomers, and optically active forms (i.e., optical isomers). The optical isomers can be separated using various known separation methods.

The desired compound in each process shown in each Reaction Scheme described above can be easily isolated and purified by usual separation means. Examples of such separation means include adsorption chromatography, preparative thin-layer chromatography, recrystallization, solvent extraction, and the like.

The phenylimidazole compound represented by formula (1) and a pharmaceutically acceptable salt thereof have lipoprotein lipase (LPL)-activating action, and are useful as LPL activators in the prevention and treatment of hyperlipidemia, arteriosclerosis, obesity, etc. Accordingly, the phenylimidazole compound represented by formula (1) or a pharmaceutically acceptable salt thereof can be used as an agent for preventing and treating hyperlipidemia, an anti-arteriosclerotic agent, and/or an anti-obesity agent.

The present invention provides a pharmaceutical composition containing the phenylimidazole compound represented by formula (1) or a pharmaceutically acceptable salt thereof. The pharmaceutical composition can be in the form of a general pharmaceutical preparation. The pharmaceutical composition may contain any pharmaceutically acceptable carriers in addition to the phenylimidazole compound represented by formula (1) or a pharmaceutically acceptable salt thereof. Examples of pharmaceutically acceptable carriers include fillers, extenders, binders, humectants, disintegrators, surfactants, lubricants, and like diluents and excipients that are usually used according to the usage of the pharmaceutical preparations. These carriers are suitably selected according to the unit dosage form of the resulting pharmaceutical preparations.

A variety of unit dosage forms can be selected for the pharmaceutical preparation mentioned above, depending on the therapeutic purpose. Typical examples include tablets, pills, powders, solutions, suspensions, emulsions, granules, capsules, suppositories, injections (solutions, suspensions, etc.), ointments, and the like.

To form tablets, at least one member selected from the group consisting of the following carriers, for example, may be used as the pharmaceutically acceptable carrier mentioned above: lactose, sucrose, sodium chloride, glucose, urea, starch, calcium carbonate, kaolin, crystalline cellulose, silicic acid, potassium phosphate, and like excipients; water, ethanol, propanol, simple syrup, glucose solutions, starch solutions, gelatin solutions, carboxymethylcellulose, hydroxypropyl cellulose, methylcellulose, polyvinylpyrrolidone, and like binders; carboxymethylcellulose sodium, carboxymethylcellulose calcium, low-substituted hydroxypropyl cellulose, dry starch, sodium alginate, agar powder, laminarin powder, sodium hydrogen carbonate, calcium carbonate, and like disintegrators; polyoxyethylene sorbitan fatty acid esters, sodium lauryl sulfate, stearic acid monoglyceride, and like surfactants; sucrose, stearin, cacao butter, hydrogenated oils, and like disintegration inhibitors; quaternary ammonium bases, sodium lauryl sulfate, and like absorption promoters; glycerin, starch, and like humectants; starch, lactose, kaolin, bentonite, colloidal silicic acid, and like adsorbents; purified talc, stearate, boric acid powder, polyethylene glycol, and like lubricants; and the like. Further, such tablets may be coated with typical coating materials as required, to prepare, for example, sugar-coated tablets, gelatin-coated tablets, enteric-coated tablets, film-coated tablets, and double- or multi-layered tablets.

To form pills, at least one member selected from the group consisting of the following carriers, for example, may be used as the pharmaceutically acceptable carrier: glucose, lactose, starch, cacao butter, hydrogenated vegetable oils, kaolin, talc and like excipients; gum arabic powder, tragacanth powder, gelatin, ethanol, and like binders; laminarin, agar and like disintegrators; and the like.

To form suppositories, at least one member selected from the group consisting of the following carriers, for example, may be used as the pharmaceutically acceptable carrier: polyethylene glycol, cacao butter, higher alcohols, esters of higher alcohols, gelatin, semi synthetic glycerides, and the like.

Capsules are prepared according to usual methods, by mixing the phenylimidazole compound represented by formula (1) or a pharmaceutically acceptable salt thereof with the pharmaceutically acceptable carriers mentioned above and loading the mixture into a hard gelatin capsule, soft gelatin capsule, or the like.

To prepare injections such as solutions, emulsions, or suspensions, the injections are sterilized and preferably made isotonic to blood. To form such injections, at least one member selected from the group consisting of the following, for example, may be used as a diluent: water, ethanol, macrogol, propylene glycol, ethoxylated isostearyl alcohol, polyoxylated isostearyl alcohol, polyoxyethylene sorbitan fatty acid esters, and the like. In this case, the pharmaceutical preparation may contain sodium chloride, glucose, or glycerin in an amount sufficient to prepare an isotonic solution, and may also contain typical solubilizers, buffers, soothing agents, etc.

To form ointments such as pastes, creams, or gels, at least one member selected from the group consisting of the following, for example, may be used as a diluent: white petrolatum, paraffin, glycerin, cellulose derivatives, polyethylene glycol, silicone, bentonite, and the like.

The pharmaceutical composition may contain, if necessary, coloring agents, preservatives, fragrances, flavors, sweetening agents, etc., and/or other medicines.

The amount of the phenylimidazole compound represented by formula (1) or a pharmaceutically acceptable salt thereof to be contained in the pharmaceutical composition is not particularly limited, and is suitably selected from a wide range. Generally, the proportion in the pharmaceutical composition is about 0.5 to 90 wt. %, and preferably about 1 to 85 wt. %.

The route of administration of the pharmaceutical composition is not particularly limited, and is determined by, for example, the form of the preparation, the patient's age and sex, the severity of the disease, and other conditions. For example, tablets, pills, solutions, suspensions, emulsions, granules, and capsules are orally administered. Injections are administered intravenously, intramuscularly, intracutaneously, subcutaneously, or intraperitoneally, singly or as mixed with usual injection transfusions, such as glucose solutions or amino acid solutions. Suppositories are administered intrarectally.

The dosage of the pharmaceutical composition is suitably selected according to the method of use, the patient's age, sex and other conditions, the severity of the disease, etc. For example, the amount of the phenylimidazole compound represented by formula (1) or a pharmaceutically acceptable salt thereof can be about 0.5 to 20 mg, and preferably about 1 to 10 mg, per kg body weight per human adult per day. The pharmaceutical composition can be administered once a day, or in two to four portions a day.

The present invention provides a method for activating LPL, the method comprising administering an effective amount of the phenylimidazole compound represented by formula (1) or a pharmaceutically acceptable salt thereof to a patient in need of LPL activation treatment.

The present invention provides a method for preventing or treating hyperlipidemia, the method comprising administering an effective amount of the phenylimidazole compound represented by formula (1) or a pharmaceutically acceptable salt thereof to a patient in need of the prevention or treatment of hyperlipidemia.

The present invention provides a method for preventing or treating arteriosclerosis, the method comprising administering an effective amount of the phenylimidazole compound represented by formula (1) or a pharmaceutically acceptable salt thereof to a patient in need of the prevention or treatment of arteriosclerosis.

The present invention provides a method for treating obesity, the method comprising administering an effective amount of the phenylimidazole compound represented by formula (1) or a pharmaceutically acceptable salt thereof to a patient in need of the treatment of obesity.

The present invention provides the use of the phenylimidazole compound represented by formula (1) or a pharmaceutically acceptable salt thereof for the production of an LPL-activating composition, the use of the phenylimidazole compound represented by formula (1) or a pharmaceutically acceptable salt thereof for the production of a composition for preventing or treating hyperlipidemia, and the use of the phenylimidazole compound represented by formula (1) or a pharmaceutically acceptable salt thereof for the production of an anti-obesity composition.

EXAMPLES

The present invention is described in more detail below with reference to Reference Examples and Examples but is not limited to these Examples.

Reference Example 1

Production of 2-bromo-1-[4-(4-bromo-2-fluorobenzyloxy)-3-methoxyphenyl]ethanone 2-bromo-1-[4-(4-bromo-2-fluorobenzyloxy)-3-methoxyphenyl]ethanone having a melting point of 139 to 141° C. was obtained in the same manner as in Reference Example 1 of WO2010/090200.

Reference Example 2

Production of 2-bromo-1-[4-(4-bromo-2-fluorobenzyloxy)-2-methoxyphenyl]ethanone 2-bromo-1-[4-(4-bromo-2-fluorobenzyloxy)-2-methoxyphenyl]ethanone having a melting point of 122 to 123° C. was obtained in the same manner as in Reference Example 8 of WO2010/090200.

Reference Examples 3 to 30

The compounds of Reference Examples 3 to 30, which have the structures and melting points shown in Table 1 below, were synthesized in the same manner as in Reference Example 1 or 2.

TABLE 1
| Reference Example No. | Structure | Melting point (° C.) |
|---|---|---|
| 1 | 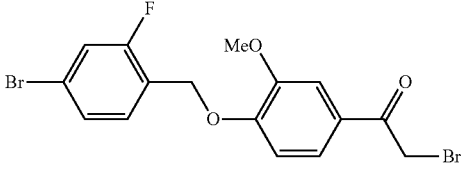 [SMILES: COc1cc(C(=O)CBr)ccc1OCc1ccc(Br)cc1F] | 139-141 |
| 2 | 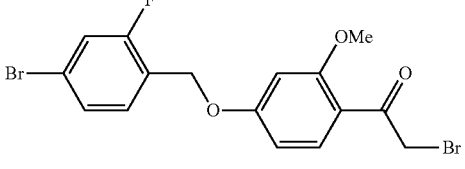 | 122-123 |
| 3 | 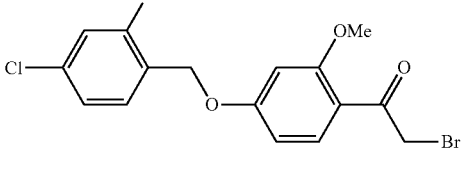 | 118-121 |
| 4 | 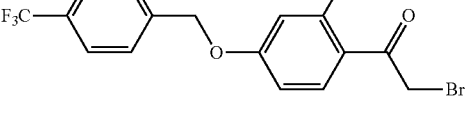 | 125-128 |
| 5 | 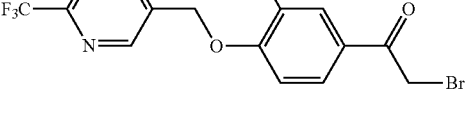 | 138-142 |
| 6 | 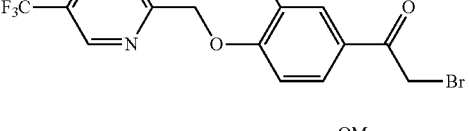 | 145-148 |
| 7 | 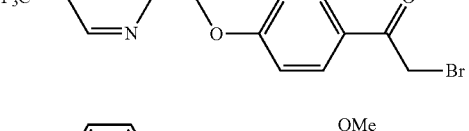 | 144-148 |
| 8 | 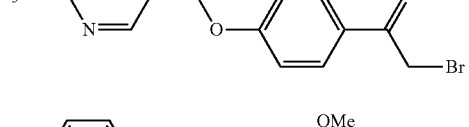 | 126-131 |
| 9 | 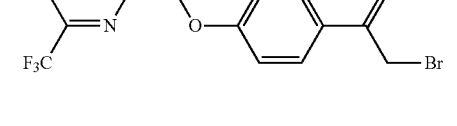 | 111-112 |

TABLE 1-continued

| Reference Example No. | Structure | Melting point (° C.) |
|---|---|---|
| 10 | 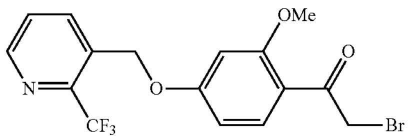 [SMILES: COc1cc(OCc2cccnc2C(F)(F)F)ccc1C(=O)CBr] | 101-105 |
| 11 | 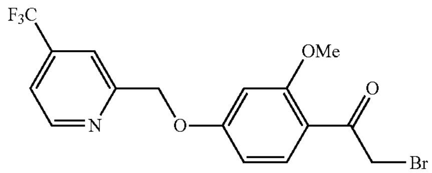 [SMILES: COc1cc(OCc2cc(C(F)(F)F)ccn2)ccc1C(=O)CBr] | 112-116 |
| 12 | 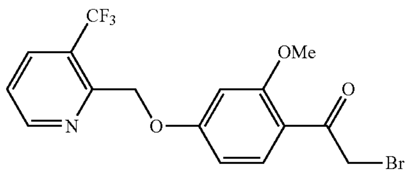 | 101-103 |
| 13 | 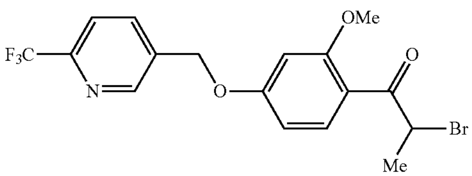 [SMILES: COc1cc(OCc2ccc(C(F)(F)F)nc2)ccc1C(=O)C(C)Br] | 88-90 |
| 14 | 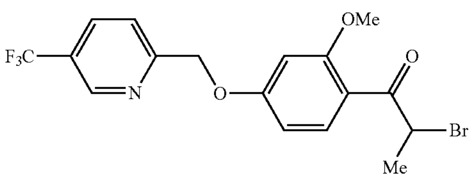 [SMILES: COc1cc(OCc2ccc(C(F)(F)F)cn2)ccc1C(=O)C(C)Br] | 86-88 |
| 15 | 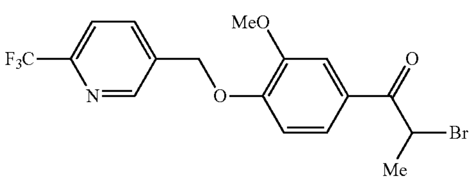 [SMILES: COc1cc(C(=O)C(C)Br)ccc1OCc1ccc(C(F)(F)F)nc1] | 115-117 |
| 16 | 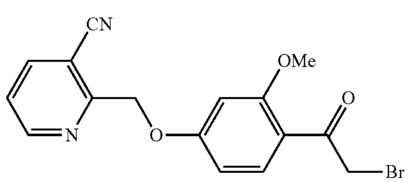 [SMILES: COc1cc(OCc2ncccc2C#N)ccc1C(=O)CBr] | 124-126 |
| 17 | 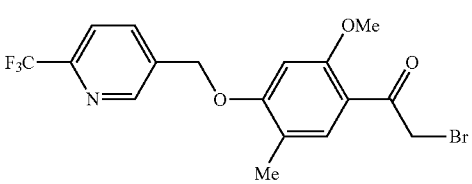 [SMILES: COc1cc(OCc2ccc(C(F)(F)F)nc2)c(C)cc1C(=O)CBr] | 163-165 |
| 18 | 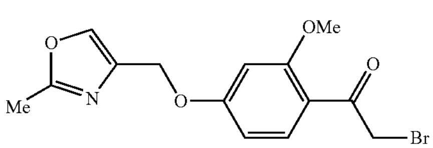 [SMILES: COc1cc(OCc2coc(C)n2)ccc1C(=O)CBr] | 127-129 |

TABLE 1-continued

| Reference Example No. | Structure | Melting point (° C.) |
|---|---|---|
| 19 | 6-(trifluoromethyl)pyridin-3-yl-CH2-O-(2,3-dimethoxyphenyl)-C(O)CH2Br | 109-113 |
| 20 | 5-(trifluoromethyl)pyridin-2-yl-CH2-O-(2,3-dimethoxyphenyl)-C(O)CH2Br | 146-153 |
| 21 | 4-hydroxy-2-methoxyphenyl-C(O)CH2Br | 129-134 |
| 22 | 4-hydroxy-3-methoxyphenyl-C(O)CH2Br | 78-79 |
| 23 | (3-fluoropyridin-2-yl)-CH2-O-(3-methoxyphenyl)-C(O)CH2Br | 124-126 |
| 24 | (3-trifluoromethylpyridin-2-yl)-CH2-O-(3-methoxyphenyl)-C(O)CH2Br | 101-103 |
| 25 | (5-methylpyrazin-2-yl)-CH2-O-(3-methoxyphenyl)-C(O)CH2Br | 106-110 |
| 26 | (pyrazin-2-yl)-CH2-O-(3-methoxyphenyl)-C(O)CH2Br | 92-97 |
| 27 | (5-methylsulfonylpyridin-2-yl)-CH2-O-(3-methoxyphenyl)-C(O)CH2Br | 160-163 |

TABLE 1-continued

| Reference Example No. | Structure | Melting point (° C.) |
|---|---|---|
| 28 | F₃C-pyridine-CH₂-O-(3,5-dimethoxyphenyl)-C(O)-CH₂-Br | 72-75 |
| 29 | 6-fluoropyridine-CH₂-O-(3-methoxyphenyl)-C(O)-CH₂-Br | 140-141 |
| 30 | F₃C-pyridine-CH₂-O-(2,5-dimethoxyphenyl)-C(O)-CH₂-Br | 105-109 |

Reference Examples 31 to 37

Further, the compounds of Reference Examples 31 to 37, which have the structures and melting points shown in Table 2 below, were synthesized in the same manner as in Reference Example 1 or 2.

TABLE 2

| Reference Example No. | Structure | Melting point (° C.) |
|---|---|---|
| 31 | PhCH₂-O-(2-methoxyphenyl)-C(O)-CH(Me)-Br | 70-72 |
| 32 | HO-(2-methylphenyl)-C(O)-CH₂-Br | 128-130 |
| 33 | 5-CF₃-3-F-pyridine-CH₂-O-(2-methylphenyl)-C(O)-CH₂-Br | Oil |
| 34 | HO-(2-chlorophenyl)-C(O)-CH₂-Br | 90-93 |

TABLE 2-continued

| Reference Example No. | Structure | Melting point (° C.) |
|---|---|---|
| 35 | (3-fluoro-5-(trifluoromethyl)pyridin-2-yl)methyl linked via O to 4-(2-bromoacetyl)-3-ethylphenyl | Oil |
| 36 | (3-fluoro-5-(trifluoromethyl)pyridin-2-yl)methyl linked via O to 4-(2-bromoacetyl)-3-fluorophenyl | 71-73 |
| 37 | (3-fluoro-5-(trifluoromethyl)pyridin-2-yl)methyl linked via O to 4-(2-bromoacetyl)-3-(benzyloxy)phenyl | 108-110 |

Example 1

Production of 2-fluoro-5-[5-[2-methoxy-4-((6-(trifluoromethyl)pyridin-3-yl)methoxy)phenyl]-1H-imidazol-2-yl]pyridine The compound obtained in Reference Example 8 (6.0 g, 14.8 mmol), 6-fluoronicotineimidamide acetic acid salt (3.0 g, 14.8 mmol), and potassium hydrogen carbonate (5.9 g, 59.4 mmol) were added to a mixed solvent of water (25 mL) and tetrahydrofuran (75 mL), and the mixture was stirred at 80° C. for 8 hours. Ethyl acetate (200 mL) was then added thereto, and the mixture was subsequently washed with water and saturated saline and dried over magnesium sulfate. After the solvent was distilled off under reduced pressure, the obtained crystals were washed with methanol. The crystals were filtered and vacuum-dried at 40° C. for 1 hour to yield the desired compound (4.6 g, yield: 70%).

Examples 2 to 108

The compounds of Examples 2 to 108, which have the structures and melting points shown in Table 3 below, were produced in the same manner as in Example 1.

Example 109

Production of 4-[2-(6-fluoropyridin-3-yl)-1H-imidazol-5-yl]-3-methoxyphenol

5-[(5-(4-benzyloxy-2-methoxyphenyl)-1H-imidazol-2-yl)]-2-fluoropyridine was obtained in the same manner as in Example 1, using 2-bromo-1-(4-benzyloxy-3-methoxyphenyl)ethanone and 6-fluoropyridin-3-ylamidine. Methanol (150 mL) and acetic acid (7.5 mL) were then added to the obtained compound (6.0 g, 16 mmol). Palladium/carbon (600 mg) was added to this solution, and the atmosphere was replaced with hydrogen. The mixture was stirred at room temperature for 6 hours. After palladium/carbon was filtered, the solvents were distilled off under reduced pressure. The crystals were washed with cold methanol and vacuum-dried at 50° C. for 1 hour to yield the desired compound (3.7 g, yield: 82%).

Example 110

Production of 4-[2-(6-fluoropyridin-3-yl)-1H-imidazol-5-yl]-2-methoxyphenol

The compound of Example 110, which has the structure and melting point shown in Table 3 below, was produced in the same manner as in Example 109.

Example 111

Production of 5-bromo-3-fluoro-2-[[4-(2-(6-fluoro-pyridin-3-yl)-1H-imidazol-5-yl)-3-methoxyphenoxy]methyl]pyridine The compound obtained in Example 109 (2.0 g, 7.0 mmol) and anhydrous potassium carbonate (0.58 g, 4.2 mmol) were added to N,N-dimethylformamide (15 mL), and the mixture was stirred at room temperature for 10 minutes. 5-bromo-2-(chloromethyl)-3-fluoropyridine (2.6 g, 12 mmol) was added to this mixture, and the mixture was stirred at 100° C. for 3 hours. After the reaction, ethyl acetate (100 mL) was added thereto, and the mixture was subsequently washed with water and saturated saline and dried over magnesium sulfate. After the solvents were distilled off under reduced pressure, the residue was separated and purified using a silica gel column (eluent: chloroform/ethyl acetate), and the fractions of the desired product were combined. The solvent was distilled off under reduced pressure, and the obtained crystals were washed with hexane and vacuum-dried at 50° C. for 1 hour to yield the desired product (2.1 g, yield: 64%).

Examples 112 to 149

The compounds of Examples 112 to 149, which have the structures and melting points shown in Table 3 below were produced in the same manner as in Example 111.

Example 150

Production of 5-[5-[2-methoxy-4-((5-(trifluoromethyl)pyridin-2-yl)methoxy)phenyl]-1H-imidazol-2-yl]picolinonitrile N,N-dimethylformamide (9 mL) was added to the compound obtained in Example 94 (450 mg, 0.98 mmol) and zinc cyanide (172 mg, 1.47 mmol), and the inside of the vessel was replaced with argon. Tetrakis triphenylphosphine palladium (339 mg, 0.29 mmol) was then added thereto, and the mixture was stirred at 80° C. for 1.5 hours. Thereafter, ethyl acetate (50 mL) was added thereto, and the mixture was subsequently washed with water and saturated saline and dried over magnesium sulfate. After the solvents were distilled off under reduced pressure, the residue was washed with heptane. The crude product was recrystallized from methanol to yield the desired compound (264 mg, yield: 60%).

Example 151

Production of 2-fluoro-5-[4-[2-methoxy-4-((5-(trifluoromethyl)pyridin-2-yl)methoxy)phenyl]-1-methyl-1H-imidazol-2-yl]pyridine Anhydrous potassium carbonate (0.68 g, 5.0 mmol) and the compound obtained in Example 124 (1.0 g, 2.3 mmol) were added to N,N-dimethylformamide (10 mL), and the mixture was stirred at room temperature for 10 minutes. Iodomethane (0.18 mL, 2.9 mmol) was added to the mixture, and the mixture was stirred at room temperature overnight. Water was added to the reaction solution. The precipitated crystals were filtered and vacuum-dried at 40° C. for 3 hours to yield the desired compound (0.97 g, yield 94%).

Examples 152 and 153

Production of 2-chloro-5-[4-[2-methoxy-4-((6-(trifluoromethyl)pyridin-3-yl)methoxy)phenyl]-1,5-dimethyl-1H-imidazol-2-yl]pyridine (Example 152) and 2-chloro-5-[5-[2-methoxy-4-((6-(trifluoromethyl)pyridin-3-yl)methoxy)phenyl]-1,4-dimethyl-1H-imidazol-2-yl]pyridine (Example 153)

A reaction was performed according to the method of Example 151, using the compound obtained in Example 49 (250 mg, 0.53 mmol). After the reaction, ethyl acetate (150 mL) was added thereto, and the mixture was subsequently washed with water and saturated saline and dried over magnesium sulfate. After the solvents were distilled off under reduced pressure, the residue was separated and purified using a silica gel column (eluent: chloroform/ethyl acetate) to obtain two fractions. The solvent in each fraction was distilled off under reduced pressure, and the obtained crystals were washed with hexane and vacuum-dried at 40° C. for 1 hour to yield the compound of Example 152 (90 mg, yield: 35%) and the compound of Example 153 (120 mg, yield: 47%).

Examples 154 to 168

The compounds of Examples 154 to 168, which have the structures and melting points shown in Table 3 below, were produced in the same manner as in Examples 151 to 153.

Example 169

Production of 2-[[4-(5-chloro-2-(6-fluoropyridin-3-yl)-1-methyl-1H-imidazol-4-yl)-3-methoxyphenoxy]methyl]-5-(trifluoromethyl)pyridine The compound obtained in Example 151 (0.50 g, 1.0 mmol) and N-chlorosuccinimide (0.16 g, 1.2 mmol) were added to N,N-dimethylformamide (10 mL), and the mixture was stirred at 50° C. for 4 hours. After N,N-dimethylformamide was distilled off under reduced pressure, the residue was separated and purified using a silica gel column (eluent: chloroform/ethyl acetate). The desired fractions were combined, and the solvent was distilled off under reduced pressure. The obtained crystals were washed with n-hexane and vacuum-dried at 40° C. for 1 hour to yield the desired compound (0.32 g, yield: 60%).

Examples 170 to 291

The compounds of Examples 170 to 291, which have the structures and melting points shown in Table 3 below, were produced in the same manner as in Example 169.

Examples 292 to 312

The compounds of Examples 292 to 312, which have the structures and melting points shown in Table 3 below, were produced in the same manner as in Examples 151 to 153.

TABLE 3

| Example No. | Structure | Melting point (° C.) | 1H-NMR (δ:ppm) |
|---|---|---|---|
| 1 | 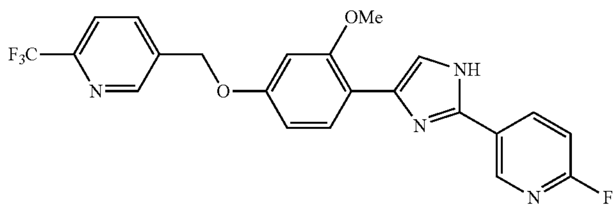 [SMILES: COc1cc(OCc2ccc(C(F)(F)F)nc2)ccc1-c1c[nH]c(-c2ccc(F)nc2)n1] | 165-166 | 1H-NMR (DMSO) δ 3.91 (s, 3H), 5.33 (s, 2H), 6.64-6.88 (m, 2H), 7.30 (dd, J = 8.5, 2.7 Hz, 1H), 7.58 (s, 1H), 7.95 (d, J = 7.8 Hz, 1H), 8.10 (s, 0H), 8.19 (dd, J = 7.8, 1.5 Hz, 1H), 8.50 (ddd, J = 7.8, 7.8, 1.5 Hz, 1H), 8.82 (s, 1H), 8.89 (d, J = 1.5 Hz, 1H), 12.70 (s, 1H) |
| 2 | 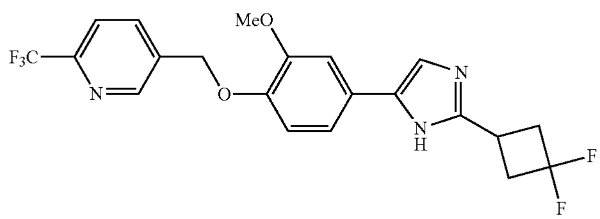 [SMILES: COc1cc(-c2cnc(C3CC(F)(F)C3)[nH]2)ccc1OCc1ccc(C(F)(F)F)nc1] | Oil | 1H-NMR (CDCL3) δ 2.90-3.09 (m, 4H), 3.35-3.54 (m, 1H), 3.95 (s, 3H), 5.23 (s, 2H), 6.89 (d, J = 8.3 Hz, 1H), 7.13-7.19 (m, 1H), 7.22 (dd, J = 8.3, 1.5 Hz, 1H), 7.41 (d, J = 1.5 Hz, 1H), 7.70 (d, J = 8.3 Hz, 1H), 8.00 (dd, J = 8.3, 1.5 Hz, 1H), 8.80 (d, J = 1.5 Hz, 1H), 9.04 (s, 1H) |
| 3 | 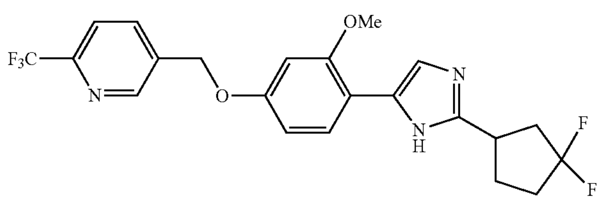 [SMILES: COc1cc(OCc2ccc(C(F)(F)F)nc2)ccc1-c1cnc(C2CCC(F)(F)C2)[nH]1] | Amorphous | 1H-NMR (DMSO) δ 1.92-2.48 (m, 6H), 3.87 (s, 3H), 5.29 (s, 2H), 6.64 (dd, J = 8.3, 2.4 Hz, 1H), 6.71 (d, J = 2.4 Hz, 1H), 7.32 (d, J = 2.0 Hz, 1H), 7.86-8.06 (m, 2H), 8.17 (dd, J = 8.3, 1.5 Hz, 1H), 8.87 (s, 1H), 11.78 (s, 1H) |
| 4 | 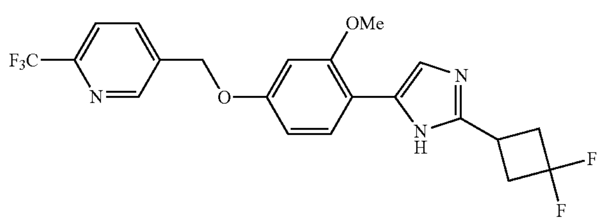 [SMILES: COc1cc(OCc2ccc(C(F)(F)F)nc2)ccc1-c1cnc(C2CC(F)(F)C2)[nH]1] | 167-169 | 1H-NMR (CDCL3) δ 2.87-3.09 (m, 4H), 3.39-3.54 (m, 1H), 3.94 (s, 3H), 5.19 (s, 2H), 6.58-6.68 (m, 2H), 7.19-7.34 (m, 1H), 7.39-7.65 (m, 1H), 7.72 (d, J = 8.0 Hz, 1H), 7.99 (dd, J = 8.0, 1.5 Hz, 1H), 8.81 (d, J = 1.5 Hz, 1H), 10.06 (s, 1H) |
| 5 | 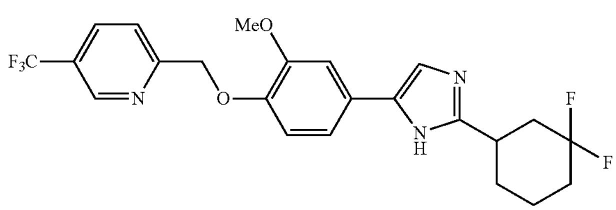 [SMILES: COc1cc(-c2cnc(C3CCCC(F)(F)C3)[nH]2)ccc1OCc1ccc(C(F)(F)F)cn1] | Oil | 1H-NMR (DMSO) δ 1.42-1.62 (m, 2H), 1.67-2.20 (m, 5H), 2.25-2.39 (m, 1H), 2.82-3.04 (m, 1H), 3.86 (s, 3H), 5.22-5.36 (2H), 6.97 (d, J = 8.3 Hz, 1H), 7.22 (dd, J = 8.3, 2.0 Hz, 1H), 7.36 (d, J = 2.0 Hz, 1H), 7.43 (s, 1H), 7.75 (d, J = 8.3 Hz, 1H), 8.27 (d, J = 8.3 Hz, 1H), 8.97 (s, 1H), 11.82 (s, 1H) |
| 6 | 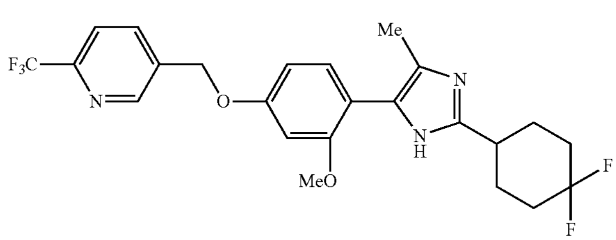 [SMILES: COc1cc(OCc2ccc(C(F)(F)F)nc2)ccc1-c1[nH]c(C2CCC(F)(F)CC2)nc1C] | 167-169 | 1H-NMR (DMSO) δ 1.69-2.15 (m, 11H), 2.00 (s, 3H), 2.78 (t, J = 10.0 Hz, 1H), 3.75 (s, 3H), 5.32 (s, 2H), 6.55-6.84 (m, 2H), 7.14 (d, J = 8.3 Hz, 1H), 7.96 (d, J = 7.8 Hz, 1H), 8.17 (d, J = 7.8 Hz, 1H), 8.88 (s, 1H), 11.33 (s, 1H) |

TABLE 3-continued

| Example No | Structure | Melting point (° C.) | 1H-NMR (δ:ppm) |
|---|---|---|---|
| 7 | 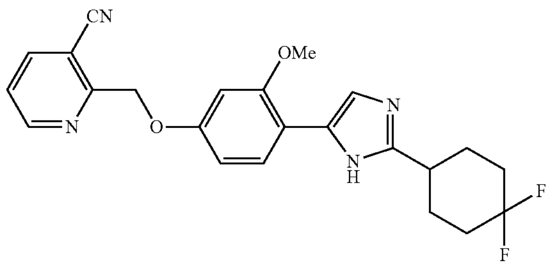 [SMILES: COc1cc(OCc2ncccc2C#N)ccc1-c1cnc(C2CCC(F)(F)CC2)[nH]1] | 69-89 | 1H-NMR (DMSO) δ 1.73-2.18 (m, J = 33.3 Hz, 8H), 2.81-2.95 (m, 1H), 3.85 (s, 3H), 5.32 (s, 2H), 6.66 (dd, J = 8.3, 2.4 Hz, 1H), 6.70 (d, J = 2.4 Hz, 1H), 7.29 (d, J = 1.5 Hz, 1H), 7.63 (dd, J = 7.8, 4.9 Hz, 1H), 7.93 (d, J = 8.3 Hz, 1H), 8.39 (dd, J = 7.8, 1.5 Hz, 1H), 8.86 (dd, J = 4.9, 1.5 Hz, 1H), 11.71 (s, 1H) |
| 8 | 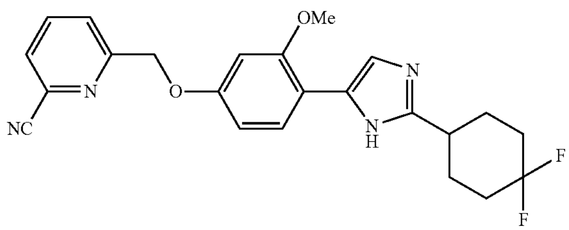 [SMILES: COc1cc(OCc2cccc(C#N)n2)ccc1-c1cnc(C2CCC(F)(F)CC2)[nH]1] | 195-197 | 1H-NMR (DMSO) δ 1.73-2.17 (m, 8H), 2.81-2.94 (m, 1H), 3.86 (s, 3H), 5.25 (s, 2H), 6.65 (dd, J = 8.3, 2.4 Hz, 1H), 6.72 (d, J = 2.4 Hz, 1H), 7.28 (d, J = 2.0 Hz, 1H), 7.87 (d, J = 8.3 Hz, 1H), 7.93 (d, J = 8.3 Hz, 1H), 8.00 (d, J = 8.3 Hz, 1H), 8.11 (dd, J = 8.3, 8.3 Hz, 1H), 11.70 (s, 1H) |
| 9 | 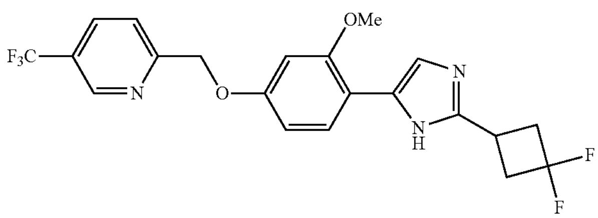 [SMILES: COc1cc(OCc2ccc(C(F)(F)F)cn2)ccc1-c1cnc(C2CC(F)(F)C2)[nH]1] | | 1H-NMR (CDCL3) δ 2.88-3.11 (m, 4H), 3.39-3.55 (m, 1H), 3.95 (s, 3H), 5.29 (s, 2H), 6.62 (dd, J = 8.8, 2.4 Hz, 1H), 6.64-6.71 (m, 1H), 7.18-7.33 (m, 1H), 7.46-7.62 (m, 1H), 7.69 (d, J = 8.3 Hz, 1H), 7.96 (dd, J = 8.3, 1.0 Hz, 1H), 8.80-8.95 (m, 1H), 10.03 (s, 1H) |
| 10 | 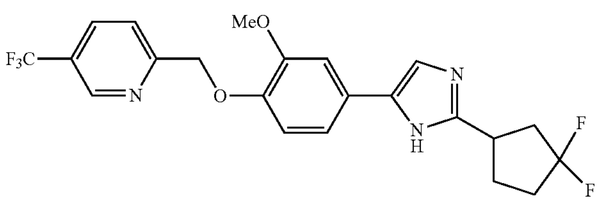 [SMILES: COc1cc(-c2cnc(C3CCC(F)(F)C3)[nH]2)ccc1OCc1ccc(C(F)(F)F)cn1] | | 1H-NMR (CDCL3) δ 1.98-2.69 (m, 6H), 3.39-3.58 (m, 1H), 3.97 (s, 3H), 5.34 (s, 2H), 6.85 (d, J = 8.3 Hz, 1H), 7.08-7.24 (m, 2H), 7.36-7.48 (m, 1H), 7.73 (d, J = 8.3 Hz, 1H), 7.88-8.00 (m, 1H), 8.76-8.95 (m, 1H), 9.03 (s, 1H) |
| 11 | 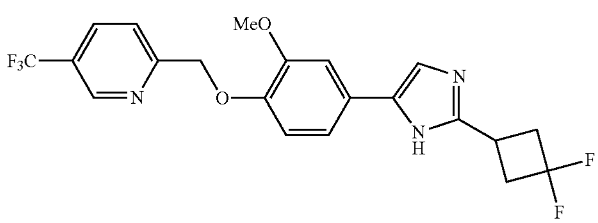 [SMILES: COc1cc(-c2cnc(C3CC(F)(F)C3)[nH]2)ccc1OCc1ccc(C(F)(F)F)cn1] | | 1H-NMR (CDCL3) δ 2.89-3.07 (m, 4H), 3.35-3.53 (m, 1H), 3.98 (s, 3H), 5.34 (s, 2H), 6.84 (d, J = 8.3 Hz, 1H), 7.08-7.24 (m, 2H), 7.35-7.49 (m, 1H), 7.73 (d, J = 8.3 Hz, 1H), 7.94 (d, J = 6.8 Hz, 1H), 8.77-8.94 (m, 1H), 9.08 (s, 1H) |
| 12 | 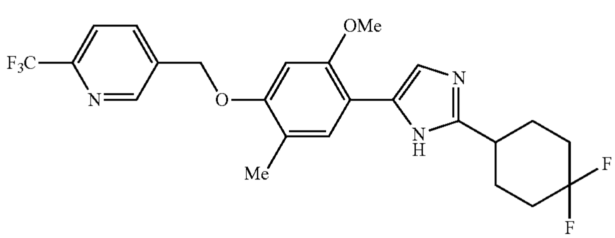 [SMILES: COc1cc(OCc2ccc(C(F)(F)F)nc2)c(C)cc1-c1cnc(C2CCC(F)(F)CC2)[nH]1] | Amorphous | 1H-NMR (DMSO) δ 1.72-2.14 (m, 8H), 2.16 (s, 3H), 2.77-2.98 (m, 1H), 3.86 (s, 3H), 5.33 (s, 2H), 6.76 (s, 1H), 7.28 (d, J = 1.5 Hz, 1H), 7.81 (s, 1H), 7.96 (d, J = 8.3 Hz, 1H), 8.18 (d, J = 8.3 Hz, 1H), 8.89 (s, 1H), 11.69 (s, 1H) |

TABLE 3-continued

| Example No. | Structure | Melting point (° C.) | 1H-NMR (δ:ppm) |
|---|---|---|---|
| 13 | 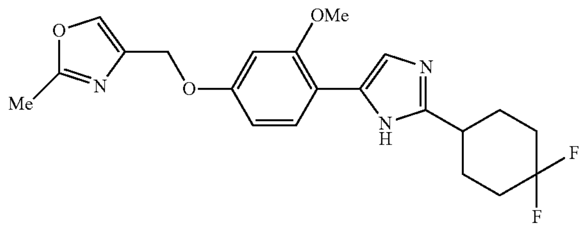 [SMILES: COc1cc(OCc2coc(C)n2)ccc1-c1cnc(C2CCC(F)(F)CC2)[nH]1] | 52-63 | 1H-NMR (DMSO) δ 1.73-2.17 (m, 8H), 2.40 (s. 3H), 2.77-2. 98 (m, 1H), 3.85 (s, 3H) , 4.92 (s, 2H), 6.58-6.72 (m, 2H) 7.27 (d, J = 1.5 Hz, 1H), 7.92 (d, J = 8.8 Hz, 1H), 8.04 (s, 1H), 11.69 (s, 1H) |
| 14 | 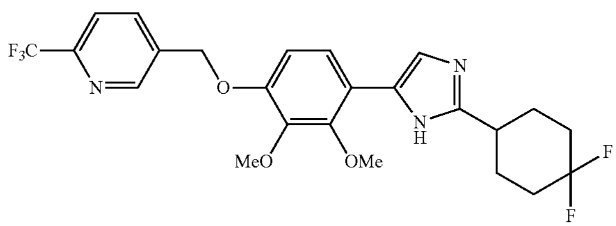 [SMILES: COc1c(OCc2ccc(C(F)(F)F)nc2)ccc(-c2cnc(C3CCC(F)(F)CC3)[nH]2)c1OC] | Amorphous | 1H-NMR (DMSO) δ 1.73-2.17 (m, 8H), 2.77-2.99 (m, 1H), 3.77 (s, 3H), 3.80 (s, 3H), 5.29 (s, 2H), 6.92 (d, J = 8.8 Hz, 1H), 7.31 (d, J = 2.0 Hz, 1H), 7.69 (d, J = 8.8 Hz, 1H), 7.96 (d, J = 8.3 Hz, 1H), 8.18 (d, J = 8.3 Hz, 1H), 8.88 (s, 1H), 11.79 (s, 1H) |
| 15 | 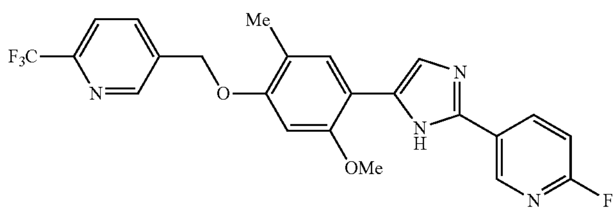 [SMILES: COc1cc(OCc2ccc(C(F)(F)F)nc2)c(C)cc1-c1cnc(-c2ccc(F)nc2)[nH]1] | 199-201 Decomposition | 1H-NMR (DMSO) δ 2.21 (s, 3H), 3.91 (s, 3H), 5.37 (s, 2H), 6.82 (s, 1H), 7.29 (dd, J = 8.3, 2.4 Hz, 1H), 7.58 (s, 1H), 7.91-8.06 (m, 2H), 8.20 (dd, J = 8.3, 1.5 Hz, 1H), 8.51 (ddd, J = 8.3, 8.3, 1.5 Hz, 1H), 8.82 (s, 1H), 8.90 (d, J = 1.5 Hz, 1H), 12.69 (s, 1H) |
| 16 | 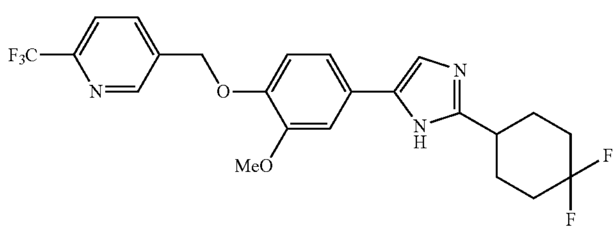 [SMILES: COc1cc(-c2cnc(C3CCC(F)(F)CC3)[nH]2)ccc1OCc1ccc(C(F)(F)F)nc1] | 162-167 | 1H-NMR (CDCL3) δ 1.70-2.00 (m, 4H), 2.07-2.32 (m, 4H), 2.83-2.98 (m, 1H), 3.92 (s, 3H), 5.22 (s, 2H), 6.88 (d, J = 8.3 Hz, 1H), 7.08-7.49 (m, 3H), 7.70 (d, J = 8.3 Hz, 1H), 7.99 (d, J = 8.3 Hz, 1H), 8.71-8.90 (m, 1H), 9.30 (s, 1H) |
| 17 | 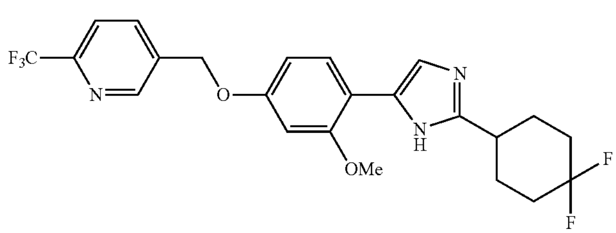 [SMILES: COc1cc(OCc2ccc(C(F)(F)F)nc2)ccc1-c1cnc(C2CCC(F)(F)CC2)[nH]1] | 62-72 | 1H-NMR (CDCL3) δ 1.77-2.02 (m, 4H), 2.11-2.32 (m, 4H), 2.91 (s, 1H), 3.95 (s, 3H), 5.19 (s, 2H), 6.61 (S, 2H), 7.26 (s, 1H), 7.53 (s, 1H), 7.73 (d, J = 7.8 Hz, 1H), 7.98 (d, J = 7.8 Hz, 1H), 8.81 (s, 1H), 9.87 (s, 1H) |
| 18 | 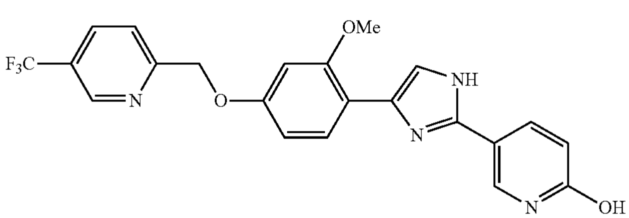 [SMILES: COc1cc(OCc2ccc(C(F)(F)F)cn2)ccc1-c1c[nH]c(-c2ccc(O)nc2)n1] | >250 | 1H-NMR (DMSO) δ 3.90 (s, 3H), 5.29 (s, 2H), 6.71 (dd, J = 8.7, 2.1 Hz, 1H), 6.78 (d, J = 2.1 Hz, 1H), 7.54 (s, 1H), 7.60 (d, J = 8.7 Hz, 1H), 7.67 (d, J = 8.1 Hz, 1H), 7.97 (d, J = 8.3 Hz, 1H), 8.32 (dd, J = 8.1, 2.1 Hz, 1H), 8.36 (dd, J = 8.3, 2.5 Hz, 1H), 8.99 (d, J = 2.5 Hz, 1H), 9.07 (d, J = 2.1 Hz, 1H) |

TABLE 3-continued

| Example No. | Structure | Melting point (° C.) | 1H-NMR (δ:ppm) |
|---|---|---|---|
| 19 | 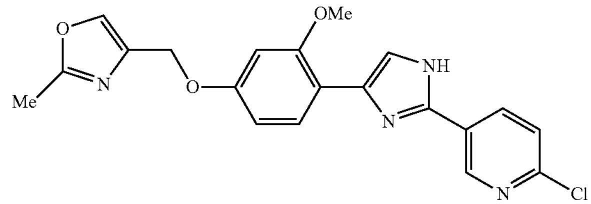 [SMILES: COc1cc(OCc2coc(C)n2)ccc1-c1c[nH]c(-c2ccc(Cl)nc2)n1] | 168-171 | 1H-NMR (DMSO) δ 2.42 (s, 3H), 3.91 (s, 3H), 4.98 (s, 2H), 6.69-6.77 (m, 2H), 7.57 (s, 1H), 7.63 (d, J = 8.3 Hz, 1H), 8.00 (s, 1H), 8.07 (s, 1H), 8.39 (dd, J = 8.3, 2.4 Hz, 1H), 9.01 (d, J = 2.4 Hz, 1H), 12.80 (s, 1H) |
| 20 | 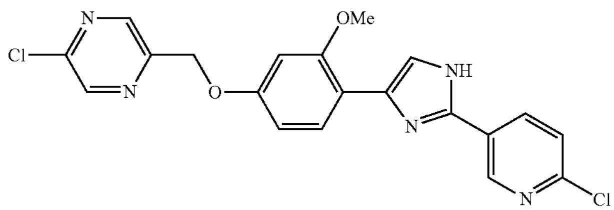 [SMILES: COc1cc(OCc2cnc(Cl)cn2)ccc1-c1c[nH]c(-c2ccc(Cl)nc2)n1] | 219-221 | 1H-NMR (DMSO) δ 3.91 (s, 3H), 5.31 (s, 2H), 6.75 (dd, J = 8.5, 2.4 Hz, 1H), 6.79 (d, J = 2.4 Hz, 1H), 7.57 (s, 1H), 7.61 (d, J = 8.5 Hz, 1H), 8.00 (d, J = 8.5 Hz, 1H), 8.37 (dd, J = 8.5, 2.4 Hz, 1H), 8.70 (d, J = 1.5 Hz, 1H), 8.84 (d, J = 1.5 Hz, 1H), 8.99 (d, J = 2.4 Hz, 1H) |
| 21 | 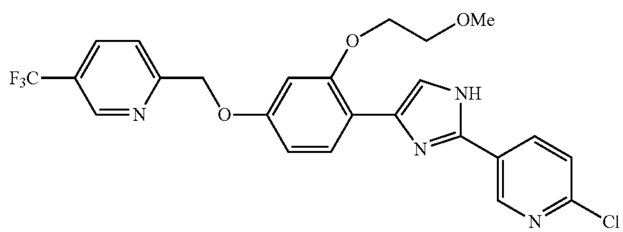 [SMILES: COCCOc1cc(OCc2ccc(C(F)(F)F)cn2)ccc1-c1c[nH]c(-c2ccc(Cl)nc2)n1] | 162-167 | 1H-NMR (DMSO) δ 3.37 (s, 3H), 3.78 (t, J = 4.1 Hz, 2H), 4.22 (t, J = 4.1 Hz, 2H), 5.34 (s, 2H), 6.72 (d, J = 8.3 Hz, 1H), 6.80 (s, 1H), 7.54-7.71 (m, 2H), 7.77 (d, J = 8.3 Hz, 1H), 8.02 (s, 1H), 8.26 (d, J = 8.3 Hz, 1H), 8.35 (dd, J = 8.9, 1.9 Hz, 1H), 8.92-9.02 (m, 2H) |
| 22 | 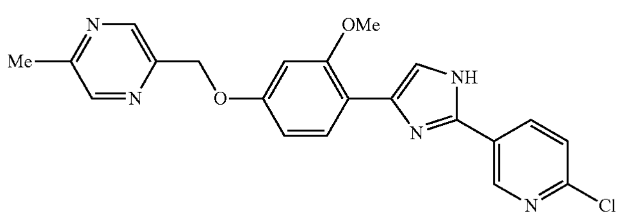 | 199-201 | 1H-NMR (DMSO) δ 2.49 (s, 3H), 3.89 (s, 3H), 5.23 (s, 2H), 6.71 (dd, J = 8.7, 2.1 Hz, 1H), 6.76 (d, J = 2.1 Hz, 1H), 7.43-7.69 (m, 2H), 7.99 (s, 1H), 8.35 (dd, J = 8.3, 2.5 Hz, 1H), 8.54 (s, 1H), 8.67 (d, J = 1.2 Hz, 1H), 8.98 (d, J = 2.5 Hz, 1H) |
| 23 | 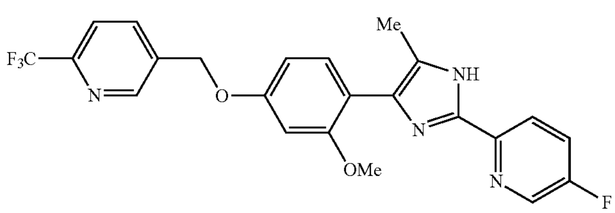 | 140-142 | 1H-NMR (DMSO) δ 2.13 (s, 3H), 3.78 (s, 3H), 5.33 (s, 2H), 6.58-6.89 (m, 2H), 7.33 (d, J = 8.3 Hz, 1H), 7.65-7.88 (m, 1H), 7.94 (d, J = 7.8 Hz, 1H), 7.99-8.09 (m, 1H), 8.18 (d, J = 7.8 Hz, 1H), 8.45-8.66 (m, 1H), 8.89 (s, 1H), 12.57 (s, 1H) |
| 24 | 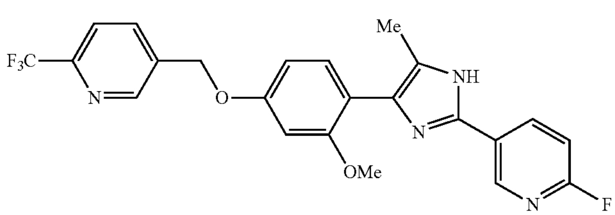 | 169-171 | 1H-NMR (DMSO) δ 2.10 (s, 3H), 3.80 (s, 3H), 5.36 (s, 2H), 6.60-6.91 (m, 2H), 7.15-7.43 (m, 2H), 7.86-8.06 (m, 1H), 8.19 (d, J = 7.8 Hz, 1H), 8.29-8.53 (m, 1H), 8.75 (s, 1H), 8.89 (s, 1H), 12.30 (s, 1H) |

TABLE 3-continued

| Example No. | Structure | Melting point (° C.) | 1H-NMR (δ:ppm) |
|---|---|---|---|
| 25 | 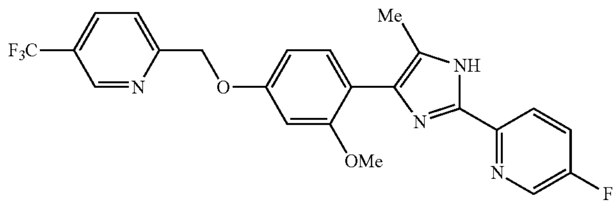 [SMILES: COc1cc(OCc2ccc(C(F)(F)F)cn2)ccc1-c1nc(-c2ccc(F)cn2)[nH]c1C] | 180-182 | 1H-NMR (DMSO) δ 2.13 (s, 3H), 3.78 (s, 3H), 5.35 (s, 2H), 6.67 (dd, J = 8.3, 2.4 Hz, 1H), 6.80 (d, J = 2.4 Hz, 1H), 7.28 (d, J = 8.3 Hz, 1H), 7.68-7.89 (m, 2H), 7.94-8.13 (m, 1H), 8.28 (dd, J = 8.4, 2.3 Hz, 1H), 8.56 (d, J = 2.9 Hz, 1H), 8.91-9.08 (m, 1H), 12.72 (s, 1H) |
| 26 | 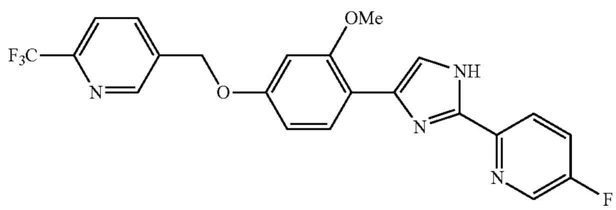 | 176-178 | 1H-NMR (DMSO) δ 3.92 (s, 3H), 5.34 (s, 2H), 6.75 (dd, J = 8.3, 2.0 Hz, 1H), 6.78 (d, J = 2.0 Hz, 1H), 7.53 (s, 1H), 7.84 (ddd, J = 8.8, 8.8, 2.4 Hz, 1H), 7.97 (d, J = 8.3 Hz, 1H), 8.11 (d, J = 8.3 Hz, 1H), 8.15-8.27 (m, 2H), 8.61 (d, J = 2.4 Hz, 1H), 8.90 (s, 1H), 12.78 (s, 1H) |
| 27 | 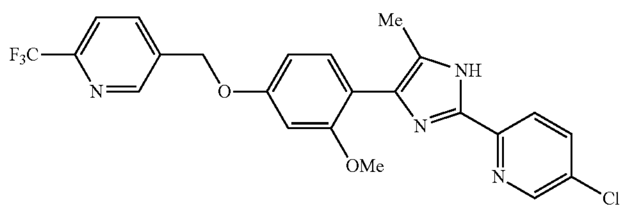 [SMILES: COc1cc(OCc2ccc(C(F)(F)F)nc2)ccc1-c1nc(-c2ccc(Cl)cn2)[nH]c1C] | 157-159 | 1H-NMR (DMSO) δ 2.13 (s, 3H), 3.77 (s, 3H), 5.35 (s, 2H), 6.60-6.86 (m, 2H), 7.33 (d, J = 8.3 Hz, 1H), 7.85-8.10 (m, 3H), 8.19 (d, J = 8.3 Hz, 1H), 8.50-8.67 (m, 1H), 8.89 (s, 1H), 12.68 (s, 1H) |
| 28 | 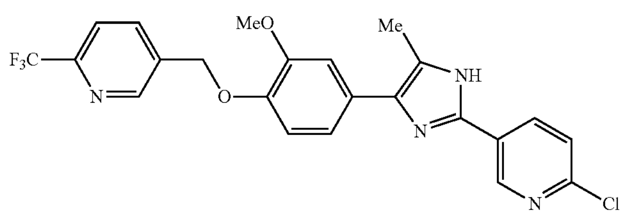 [SMILES: COc1cc(-c2nc(-c3ccc(Cl)nc3)[nH]c2C)ccc1OCc1ccc(C(F)(F)F)nc1] | 209-211 | 1H-NMR (DMSO) δ 2.44 (s, 3H), 3.85 (s, 3H), 5.29 (s, 2H), 6.98-7.28 (m, 2H), 7.51-7.78 (m, 2H), 7.95 (d, J = 7.8 Hz, 1H), 8.11-8.36 (m, 2H), 8.76-9.05 (m, 2H), 12.61 (s, 1H) |
| 29 | 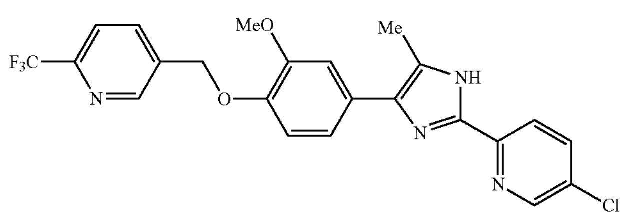 [SMILES: COc1cc(-c2nc(-c3ccc(Cl)cn3)[nH]c2C)ccc1OCc1ccc(C(F)(F)F)nc1] | 267-269 | 1H-NMR (DMSO) δ 2.48 (s, 3H), 3.89 (s, 3H), 5.34 (s, 2H), 7.13-7.32 (m, 2H), 7.46 (d, J = 1.0 Hz, 1H), 7.96 (d, J = 8.5 Hz, 1H), 8.16 (d, J = 8.8 Hz, 1H), 8.29 (dd, J = 8.5, 2.2 Hz, 1H), 8.70 (d, J = 8.8 Hz, 1H), 8.77-8.94 (m, 2H) |
| 30 | 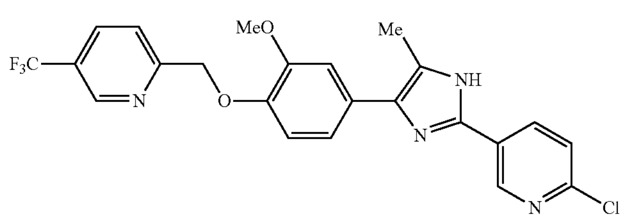 [SMILES: COc1cc(-c2nc(-c3ccc(Cl)nc3)[nH]c2C)ccc1OCc1ccc(C(F)(F)F)cn1] | 228-230 Decomposition | 1H-NMR (DMSO) δ 2.43 (s, 3H), 3.87 (s, 3H), 5.31 (s, 2H), 6.96-7.43 (m, 3H), 7.60 (d, J = 8.8 Hz, 1H), 7.77 (d, J = 8.3 Hz, 1H), 8.20-8.43 (m, 2H), 8.84-9.08 (m, 2H), 12.61 (s, 1H) |

TABLE 3-continued

| Example No. | Structure | Melting point (° C.) | 1H-NMR (δ:ppm) |
|---|---|---|---|
| 31 | 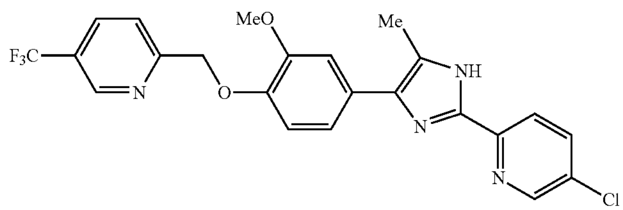 [SMILES: COc1cc(-c2nc(-c3ccc(Cl)cn3)[nH]c2C)ccc1OCc1ccc(C(F)(F)F)cn1] | 168-171 | 1H-NMR (DMSO) δ 2.45 (s, 3H), 3.87 (s, 3H), 5.30 (s, 2H), 7.05 (d, J = 8.3 Hz, 1H), 7.16 (dd, J = 8.3, 2.0 Hz, 1H), 7.39 (d, J = 2.0 Hz, 1H), 7.77 (d, J = 8.3 Hz, 1H), 7.89-8.13 (m, 2H), 8.28 (dd, J = 8.3, 2.0 Hz, 1H), 8.61 (d, J = 2.4 Hz, 1H), 8.98 (s, 1H), 12.79 (s, 1H) |
| 32 | 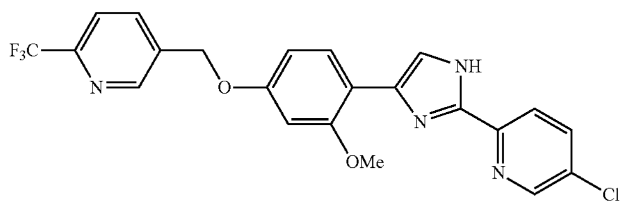 [SMILES: COc1cc(OCc2ccc(C(F)(F)F)nc2)ccc1-c1c[nH]c(-c2ccc(Cl)cn2)n1] | 186-189 | 1H-NMR (CDCL3) δ 4.02 (s, 3H), 5.21 (s, 2H), 6.55-6.79 (m, 2H), 7.47 (d, J = 1.5 Hz, 1H), 7.58-7.68 (m, 1H), 7.69-7.79 (m, 2H), 7.91-8.32 (m, 2H), 8.43-8.55 (m, 1H), 8.83 (s, 1H), 11.06 (s, 1H) |
| 33 | 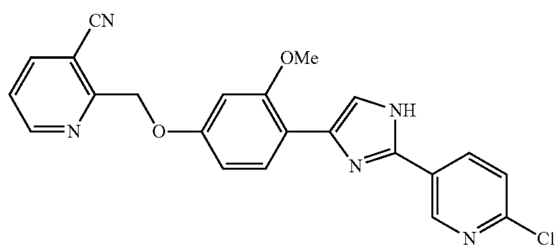 [SMILES: COc1cc(OCc2ncccc2C#N)ccc1-c1c[nH]c(-c2ccc(Cl)nc2)n1] | 193-195 | 1H-NMR (DMSO) δ 3.90 (s, 3H), 5.37 (s, 2H), 6.67-6.85 (m, 2H), 7.43-7.81 (m, 3H), 8.04 (s, 1H), 8.24-8.53 (m, 2H), 8.86 (dd, J = 4.9, 1.5 Hz, 1H), 9.00 (d, J = 2.4 Hz, 1H), 12.73 (s, 1H) |
| 34 | 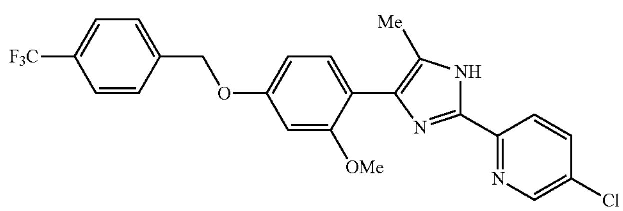 [SMILES: COc1cc(OCc2ccc(C(F)(F)F)cc2)ccc1-c1nc(-c2ccc(Cl)cn2)[nH]c1C] | 170-173 | 1H-NMR (DMSO) δ 2.13 (s, 3H), 3.77 (s, 3H), 5.35 (s, 2H), 6.57-6.88 (m, 2H), 7.31 (d, J = 8.3 Hz, 1H), 7.71-8.07 (m, 3H), 8.19-8.37 (m, 1H) 8.50-8.67 (m, 1H), 8.99 (s, 1H), 12.68 (s, 1H) |
| 35 | 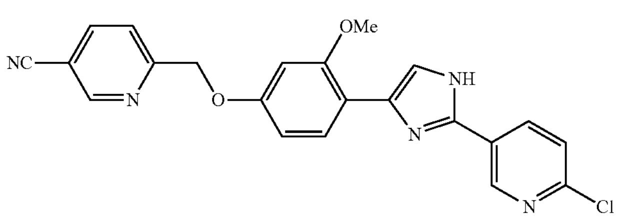 [SMILES: COc1cc(OCc2ccc(C#N)cn2)ccc1-c1c[nH]c(-c2ccc(Cl)nc2)n1] | 233-237 Decomposition | 1H-NMR (CDCL3) δ 4.02 (s, 3H), 5.21 (s, 2H), 6.55-6.79 (d, 2H), 7.47 (d, J = 1.5 Hz, 1H), 7.58-7.68 (m, 1H), 7.69-7.79 (m, 2H), 7.91-8.32 (m, 2H), 8.43-8.55 (m, 1H), 8.83 (s, 1H), 11.06 (s, 1H) |
| 36 | 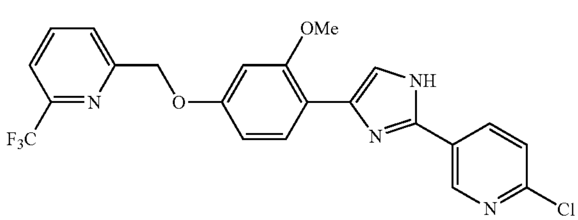 [SMILES: COc1cc(OCc2cccc(C(F)(F)F)n2)ccc1-c1c[nH]c(-c2ccc(Cl)nc2)n1] | 222-224 | 1H-NMR (DMSO) δ 3.90 (s, 3H), 5.37 (s, 2H), 6.67-6.85 (m, 2H), 7.43-7.81 (m, 3H), 8.04 (s, 1H), 8.24-8.53 (m, 2H), 8.86 (dd, J = 4.9, 1.5 Hz, 1H), 9.00 (d, J = 2.4 Hz, 1H), 12.73 (s, 1H) |

TABLE 3-continued

| Example No. | Structure | Melting point (° C.) | 1H-NMR (δ:ppm) |
|---|---|---|---|
| 37 | 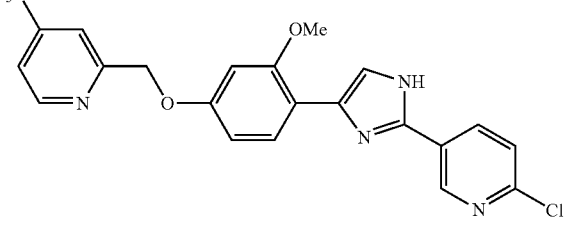 | 216-217 | 1H-NMR (DMSO) δ 3.93 (s, 3H), 5.34 (s, 2H), 6.75 (dd, J = 8.8, 2.4 Hz, 1H), 6.82 (d, J = 2.4 Hz, 1H), 7.60-7.71 (m, 2H), 7.77 (d, J = 4.9 Hz, 1H), 7.91 (s, 1H), 8.10 (d, J = 8.8 Hz, 1H), 8.38 (dd, J = 8.3, 2.4 Hz, 1H), 8.90 (d, J = 4.9 Hz, 1H), 9.01 (d, J = 2.4 Hz, 1H), 12.80 (s, 1H) |
| 38 | 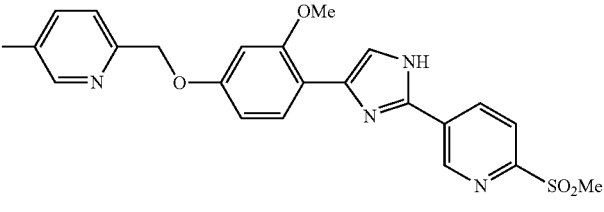 | 213-214 | 1H-NMR (CDCL3) δ 3.25 (s, 3H), 4.01 (s, 3H), 5.31 (s, 2H), 6.55-6.81 (m, 2H), 7.24-7.28 (m, 1H), 7.47-7.79 (m, 2H), 7.98 (dd, J = 8.3, 2.0 Hz, 1H), 8.11 (d, J = 8.3 Hz, 1H), 8.26-8.51 (m, 1H), 8.80-8.97 (m, 1H), 9.16 (d, J = 2.0 Hz, 1H), 10.80 (s, 1H) |
| 39 | 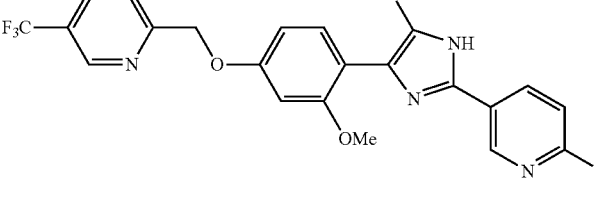 | 141-150 | 1H-NMR (DMSO) δ 2.31 (s, 3H), 3.86 (s, 3H), 5.43 (s, 2H), 6.82 (dd, J = 8.8, 2.4 Hz, 1H), 6.94 (d, J = 2.4 Hz, 1H), 7.43 (d, J = 8.8 Hz, 1H), 7.55 (dd, J = 8.5, 2.7 Hz, 1H), 7.82 (dd, J = 8.3, 2.9 Hz, 1H), 8.32 (dd, J = 8.3, 2.2 Hz, 1H), 8.78 (ddd, J = 8.5, 8.5, 2.4 Hz, 1H), 9.02 (d, J = 2.2 Hz, 1H), 9.06 (d, J = 2.4 Hz, 1H) |
| 40 | 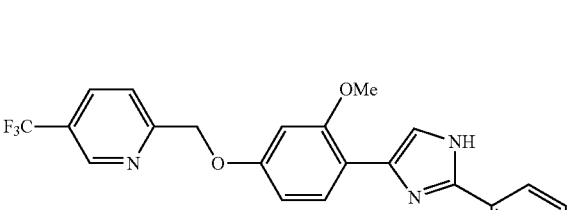 | 100-108 | 1H-NMR (DMSO) δ 1.89-2.06 (m, 4H), 3.43-3.58 (m, 4H), 3.92 (s, 3H), 5.35 (s, 2H), 6.39 (d, J = 7.3 Hz, 1H), 6.71 (dd, J = 8.3, 2.2 Hz, 1H), 6.79 (d, J = 2.2 Hz, 1H), 7.29 (d, J = 7.3 Hz, 1H), 7.48 (d, J = 1.5 Hz, 1H), 7.55 (dd, J = 7.3, 7.3 Hz, 1H), 7.80 (d, J = 8.3 Hz, 1H), 8.09 (d, J = 8.3 Hz, 1H), 8.28 (d, J = 8.3 Hz, 1H), 9.00 (s, 1H), 12.11 (s, 1H) |
| 41 | 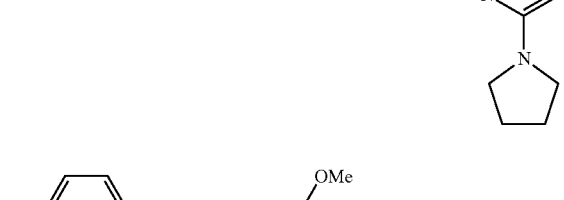 | 152-154 | 1H-NMR (DMSO) δ 3.92 (s, 3H), 5.36 (s, 2H), 6.72 (dd, J = 8.3, 2.2 Hz, 1H), 6.80 (d, J = 2.2 Hz, 1H), 7.52 (s, 1H), 7.77-7.93 (m, 2H), 8.10 (d, J = 8.3 Hz, 1H), 8.17 (dd, J = 8.8, 4.9 Hz, 1H), 8.28 (dd, J = 8.3, 2.0 Hz, 1H), 8.61 (d, J = 2.9 Hz, 1H), 9.00 (d, J = 2.0 Hz, 1H), 12.78 (s, 1H) |

TABLE 3-continued

| Example No. | Structure | Melting point (° C.) | 1H-NMR (δ:ppm) |
|---|---|---|---|
| 42 | 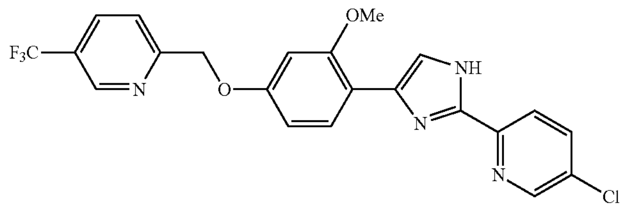 | 147-150 | 1H-NMR (DMSO) δ 3.92 (s, 3H), 5.36 (s, 2H), 6.72 (dd, J = 8.3, 2.2 Hz, 1H), 6.80 (d, J = 2.2 Hz, 1H), 7.55 (s, 1H), 7.80 (d, J = 8.3 Hz, 1H), 8.02 (dd, J = 8.3, 2.4 Hz, 1H), 8.07-8.16 (m, 2H), 8.28 (dd, J = 8.3, 2.0 Hz, 1H), 8.65 (d, J = 2.4 Hz, 1H), 9.01 (s, 1H), 12.89 (s, 1H) |
| 43 | 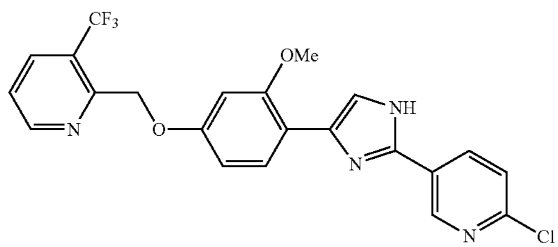 | 185-187 | 1H-NMR (DMSO) δ 3.88 (s, 3H), 5.32 (s, 2H), 6.62-6.80 (m, 2H), 7.56 (s, 1H), 7.62 (d, J = 8.3 Hz, 1H), 7.67 (dd, J = 8.0, 4.9 Hz, 1H), 8.02 (s, 1H), 8.28 (dd, J = 8.0, 1.2 Hz, 1H), 8.37 (dd, J = 8.3, 2.4 Hz, 1H), 8.89 (d, J = 4.9 Hz, 1H), 9.00 (d, J = 2.4 Hz, 1H), 12.72 (s, 1H) |
| 44 | 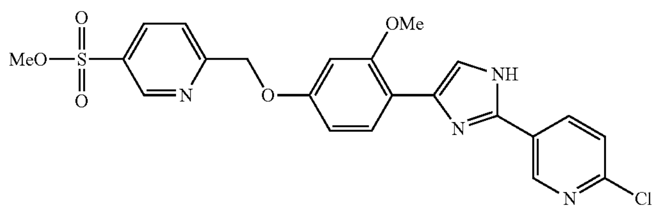 [SMILES: COc1cc(OCc2ccc(S(=O)(=O)OC)cn2)ccc1-c1c[nH]c(-c2ccc(Cl)nc2)n1] | 232-235 Decomposition | 1H-NNR (DMSO) δ 3.35 (s, 3H), 3.93 (s, 3H), 5.38 (s, 2H), 6.73 (dd, J = 8.5, 2.2 Hz, 1H), 6.82 (d, J = 2.2 Hz, 1H), 7.51-7.70 (m, 2H), 7.84 (d, J = 8.3 Hz, 1H), 8.06 (s, 1H), 8.34-8.46 (m, 2H), 9.01 (d, J = 2.4 Hz, 1H), 9.10 (d, J = 2.4 Hz, 1H), 12.79 (s, 1H) |
| 45 | 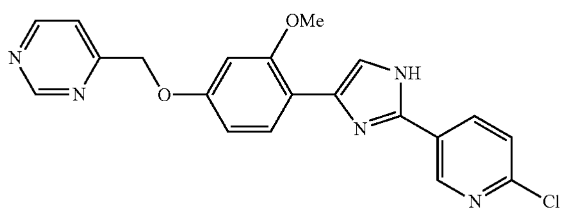 [SMILES: COc1cc(OCc2ccncn2)ccc1-c1c[nH]c(-c2ccc(Cl)nc2)n1] | 221-224 | 1H-NMR (DMSO) δ 3.91 (s, 3H), 5.26 (s, 2H), 6.71 (d, J = 7.8 Hz, 1H), 6.80 (s, 1H), 7.52-7.72 (m, 3H), 8.07 (s, 1H), 8.37 (dd, J = 8.3, 2.0 Hz, 1H), 8.84 (d, J = 4.9 Hz, 1H), 8.99 (d, J = 2.0 Hz, 1H), 9.19 (d, J = 1.0 Hz, 1H), 12.79 (s, 1H) |
| 46 | 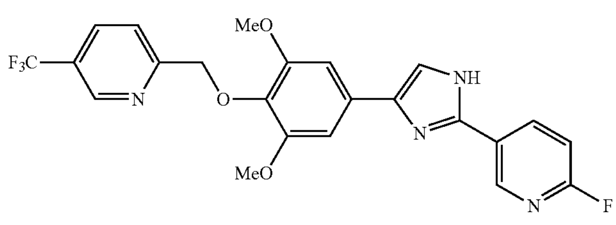 [SMILES: COc1cc(-c2c[nH]c(-c3ccc(F)nc3)n2)cc(OC)c1OCc1ccc(C(F)(F)F)cn1] | 107-110 | 1H-NMR (DMSO) δ 3.84 (s, 3H), 3.84 (s, 3H), 5.09 (s, 2H), 7.22-7.10 (m, 2H), 7.31 (dd, J = 8.3, 2.2 Hz, 1H), 7.81 (s, 1H), 7.96 (d, J = 8.3 Hz, 1H), 8.28 (dd, J = 8.3, 2.2 Hz, 1H), 8.50 (ddd, J = 8.3, 8.3, 2.2 Hz, 1H), 8.81 (d, J = 2.2 Hz, 1H), 8.90 (s, 1H) |
| 47 | 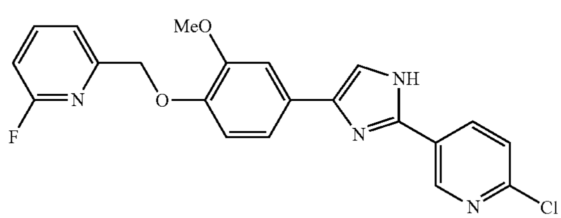 [SMILES: COc1cc(-c2c[nH]c(-c3ccc(Cl)nc3)n2)ccc1OCc1cccc(F)n1] | 185-187 | 1H-NMR (DMSO) δ 3.88 (s, 3H), 5.15 (s, 2H), 6.62-6.83 (m, 2H), 7.30 (dd, J = 8.5, 2.7 Hz, 1H), 7.48 (d, J = 8.3 Hz, 1H), 7.51-7.68 (m, 3H), 8.08 (d, J = 8.3 Hz, 1H), 8.50 (dd, J = 8.5, 8.5 Hz, 1H), 8.82 (s, 1H), 12.70 (s, 1H) |

TABLE 3-continued

| Example No. | Structure | Melting point (° C.) | 1H-NMR (δ:ppm) |
|---|---|---|---|
| 48 | 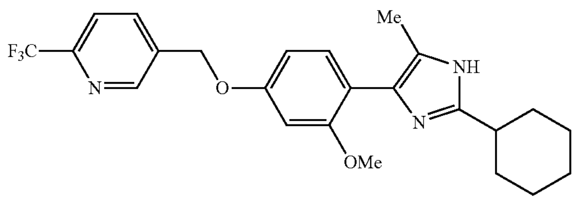 [SMILES: COc1cc(OCc2ccc(C(F)(F)F)nc2)ccc1-c1nc(C2CCCCC2)[nH]c1C] | | 1H-NMR (DMSO) δ 1.12-1.46 (m, 3H), 1.52-2.07 (m, 7H), 2.17 (s, 3H), 2.89-3.05 (m, 1H), 3.82 (s, 3H), 5.38 (s, 2H), 6.78 (dd, J = 8.8, 2.4 Hz, 1H), 6.87 (d, J = 2.4 Hz, 1H), 7.31 (d, J = 8.8 Hz, 1H), 7.98 (d, J = 7.8 Hz, 1H), 8.20 (dd, J = 7.8, 1.5 Hz, 1H), 8.90 (s, 1H), 13.97 (s, 1H) |
| 49 | 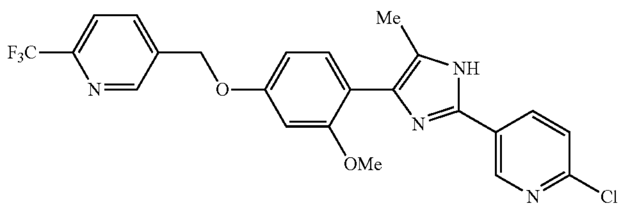 [SMILES: COc1cc(OCc2ccc(C(F)(F)F)nc2)ccc1-c1nc(-c2ccc(Cl)nc2)[nH]c1C] | 196-199 | 1H-NMR (DMSO) δ 2.12 (s, 3H), 3.78 (s, 3H), 5.35 (s, 2H), 6.62-6.89 (m, 2H), 7.28 (s, 1H), 7.56 (d, J = 8.3 Hz, 1H), 7.96 (d, J = 8.3 Hz, 1H), 8.10-8.37 (m, 2H), 8.81-9.00 (m, 2H), 12.40 (s, 1H) |
| 50 | 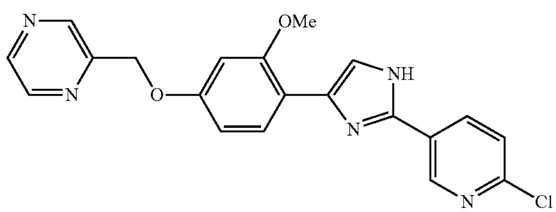 [SMILES: COc1cc(OCc2cnccn2)ccc1-c1c[nH]c(-c2ccc(Cl)nc2)n1] | 210-213 Decomposition | 1H-NMR (DMSO) δ 3.93 (s, 3H), 5.32 (s, 2H), 6.71-6.87 (m, 2H), 7.57-7.70 (m, 2H), 8.11 (d, J = 7.9 Hz, 1H), 8.39 (d, J = 7.5 Hz, 1H), 8.63-8.74 (m, 2H), 8.86 (s, 1H), 9.02 (s, 1H), 12.80 (s, 1H) |
| 51 | 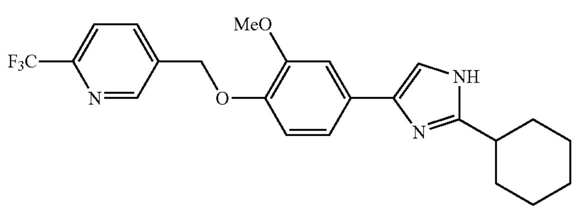 | 89-187 | 1H-NMR (DMSO) δ 1.12-1.48 (m, 3H), 1.55-2.10 (m, 7H), 2.97-3.18 (m, 1H), 3.87 (s, 3H), 5.32 (s, 2H), 7.19 (d, J = 8.3 Hz, 1H), 7.42 (dd, J = 8.3, 1.5 Hz, 1H), 7.59 (d, J = 1.5 Hz, 1H), 7.87-8.05 (m, 2H), 8.15 (d, J = 8.3 Hz, 1H), 8.85 (s, 1H), 14.56 (s, 1H) |
| 52 | 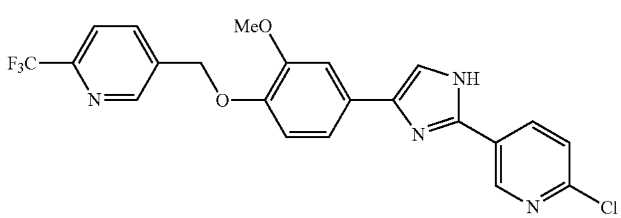 [SMILES: COc1cc(-c2c[nH]c(-c3ccc(Cl)nc3)n2)ccc1OCc1ccc(C(F)(F)F)nc1] | 179-181 | 1H-NMR (DMSO) δ 3.86 (s, 3H), 5.28 (s, 2H), 7.10 (d, J = 8.3 Hz, 1H), 7.38 (d, J = 8.3 Hz, 1H), 7.47 (s, 1H), 7.63 (d, J = 8.3 Hz, 1H), 7.76 (s, 1H), 7.96 (d, J = 8.3 Hz, 1H), 8.16 (d, J = 8.3 Hz, 1H), 8.36 (d, J = 8.3 Hz, 1H), 8.86 (s, 1H), 8.99 (s, 1H), 12.87 (s, 1H) |
| 53 | 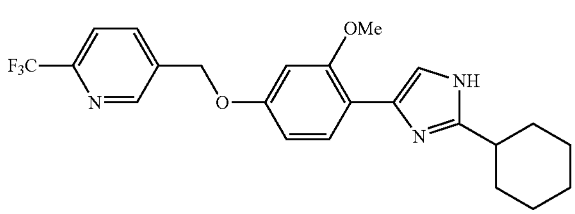 [SMILES: COc1cc(OCc2ccc(C(F)(F)F)nc2)ccc1-c1c[nH]c(C2CCCCC2)n1] | 62-73 | 1H-NMR (DMSO) δ 1.13-2.01 (m, 10H), 2.55-2.75 (m, 1H), 3.86 (s, 3H), 5.29 (s, 2H), 6.66 (dd, J = 8.5, 2.0 Hz, 1H), 6.70 (d, J = 2.0 Hz, 1H), 7.86-8.04 (m, 2H), 8.17 (d, J = 7.8 Hz, 1H), 8.88 (s, 1H), 11.55 (s, 1H) |

TABLE 3-continued

| Example No. | Structure | Melting point (° C.) | 1H-NMR (δ:ppm) |
|---|---|---|---|
| 54 | 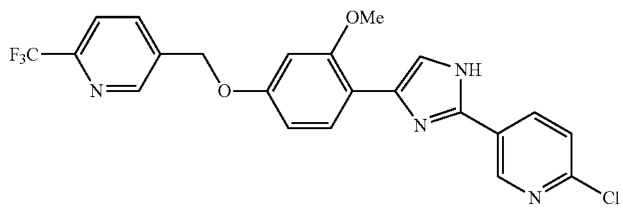 [SMILES: COc1cc(OCc2ccc(C(F)(F)F)nc2)ccc1-c1c[nH]c(-c2ccc(Cl)nc2)n1] | 218-220 | 1H-NMR (DMSO) δ 3.91 (s, 3H), 5.33 (s, 2H), 6.75 (t, J = 8.8 Hz, 2H), 7.45-7.74 (m, 2H), 8.18 (d, J = 8.3 Hz, 1H), 8.37 (dd, J = 8.3, 2.0 Hz, 1H), 8.79-9.11 (m, 2H), 12.79 (s, 1H) |
| 55 | 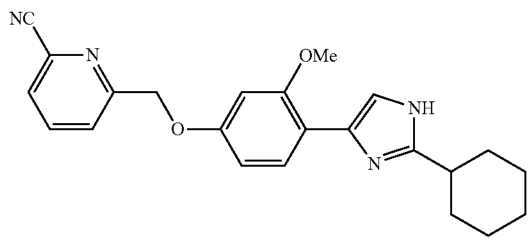 [SMILES: COc1cc(OCc2cccc(C#N)n2)ccc1-c1c[nH]c(C2CCCCC2)n1] | 182-187 | 1H-NMR (CDCL3) δ 1.17-2.19 (m, 11H), 2.66-2.88 (m, 1H), 3.93 (s, 3H), 5.24 (S, 2H), 6.58 (dd, J = 8.5, 2.3 Hz, 1H), 6.60-6.69 (m, 1H), 7.16-7.38 (m, 1H), 7.40-7.68 (m, 2H), 7.78 (d, J = 7.9 Hz, 1H), 7.87 (dd. J = 7.9, 7.9 Hz, 1H), 9.90 (s, 1H) |
| 56 | 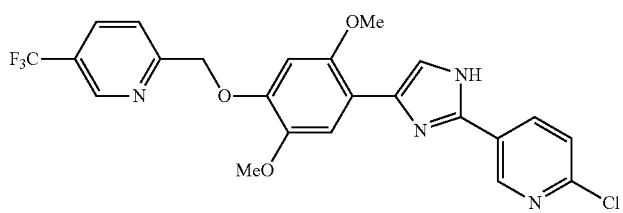 [SMILES: COc1cc(-c2c[nH]c(-c3ccc(Cl)nc3)n2)c(OC)cc1OCc1ccc(C(F)(F)F)cn1] | 204-206 | 1H-KMR (DMSO) δ 3.84 (s, 3H), 3.85 (s, 3H), 5.36 (s, 2H), 6.88 (s, 1H), 7.52-7.72 (m, 2H), 7.72-7.92 (m, 2H), 8.30 (dd, J = 8.3, 2.0 Hz, 1H), 8.39 (dd, J = 8.3, 2.4 Hz, 1H), 8.95-9.00 (m, 1H), 9.01 (d, J = 2.4 Hz, 1H), 12.81 (s, 1H) |
| 57 | 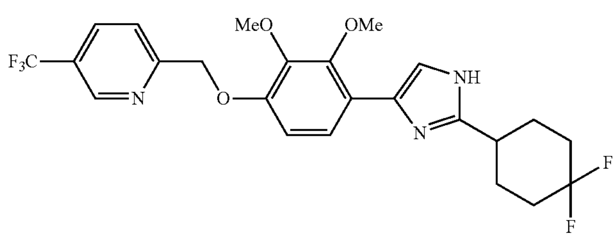 [SMILES: COc1c(OCc2ccc(C(F)(F)F)cn2)ccc(-c2c[nH]c(C3CCC(F)(F)CC3)n2)c1OC] | 155-157 | 1H-NMR (DMSO) δ 1.72-2.18 (m, 8H), 2.79-2.95 (m, 1H), 3.80 (s, 3H), 3.84 (s, 3H), 5.31 (s, 2H), 6.88 (d, J = 8.8 Hz, 1H), 7.33 (d, J = 1.5 Hz, 1H), 7.66 (d, J = 8.8 Hz, 1H), 7.78 (d, J = 8.3 Hz, 1H), 8.29 (dd, J = 8.3, 2.4 Hz, 1H), 8.99 (d, J = 2.4 Hz, 1H), 11.79 (s, 1H) |
| 58 | 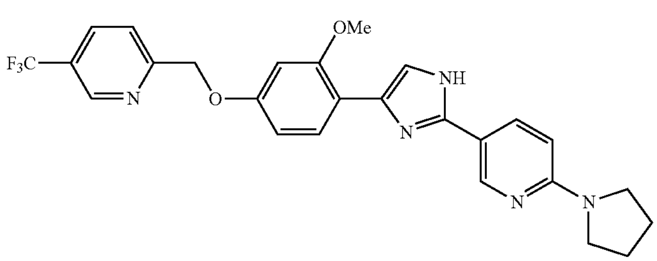 [SMILES: COc1cc(OCc2ccc(C(F)(F)F)cn2)ccc1-c1c[nH]c(-c2ccc(N3CCCC3)nc2)n1] | 227-231 Decomposition | 1H-NMR (DMSO) δ 1.90-1.99 (m, 4H), 2.46-2.51 (m, 4H), 3.90 (s, 3H), 5.33 (s, 2H), 6.51 (d, J = 8.3 Hz, 1H), 6.70 (dd, J = 8.5, 2.2 Hz, 1H), 6.76 (d, J = 2.2 Hz, 1H), 7.36-7.50 (J = 2.0 Hz, 1H), 7.78 (d, J = 8.3 Hz, 1H), 7.94-8.14 (m, 2H), 8.27 (dd, J = 8.3, 2.4 Hz, 1H), 8.66 (d, J = 2.0 Hz, 1H), 8.99 (s, 1H), 12.20 (s, 1H) |
| 59 | 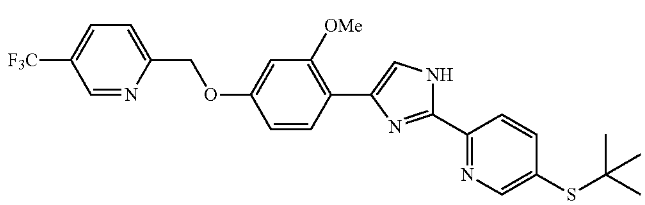 [SMILES: COc1cc(OCc2ccc(C(F)(F)F)cn2)ccc1-c1c[nH]c(-c2ccc(SC(C)(C)C)cn2)n1] | 159-160 | 1H-NMR (DMSO) δ 1.27 (s, 9H), 3.91 (s, 3H), 5.35 (s, 2H), 6.71 (dd, J = 8.5, 1.9 Hz, 1H), 6.79 {s, 1H), 7.54 (s, 1H), 7.78 (d, J = 8.5 Hz, 1H), 7.99 (dd, J = 8.1, 1.9 Hz, 1H), 8.03-8.18 (m, 2H), 8.27 (dd, J = 8.3, 1.7 Hz, 1H), 8.61 (d, J = 1.9 Hz, 1H), 8.99 (s, 1H), 12.91 (s, 1H) |

TABLE 3-continued

| Example No. | Structure | Melting point (° C.) | 1H-NMR (δ:ppm) |
|---|---|---|---|
| 60 | 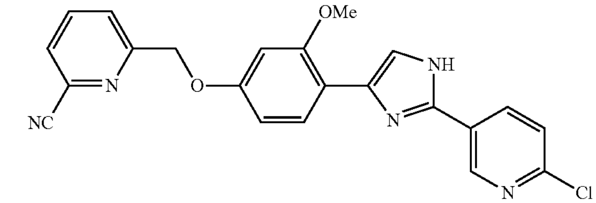 [SMILES: COc1cc(OCc2cccc(C#N)n2)ccc1-c1c[nH]c(-c2ccc(Cl)nc2)n1] | 235-239 Decomposition | 1H-NMR (DMSO) δ 3.90 (s, 3H), 5.28 (s, 2H), 6.71 (dd, J = 8.7, 1.2 Hz, 1H), 6.78 (s, 1H), 7.44-7.69 (m, 2H), 7.88 (d, J = 7.9 Hz, 1H), 7.95-8.14 (m, 3H), 8.36 (dd, J = 8.5, 2.3 Hz, 1H), 8.99 (d, J = 2.3 Hz, 1H), 12.70 (s, 1H) |
| 61 | 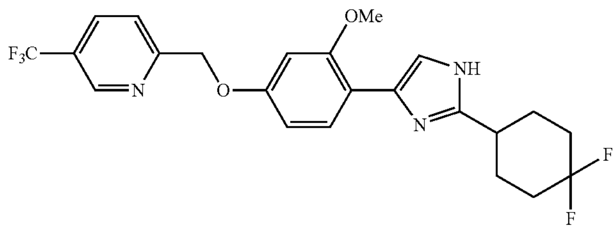 [SMILES: COc1cc(OCc2ccc(C(F)(F)F)cn2)ccc1-c1c[nH]c(C2CCC(F)(F)CC2)n1] | 232-237 | 1H-NMR (CDCL3) δ 1.69-2.01 (m, 4H), 2.03-2.31 (m, 4H), 2.78-2.99 (m, 1H), 3.93 (s, 3H), 5.28 (s, 2H), 6.60 (dd, J = 8.6, 2.2 Hz, 1H), 6.65 (s, 1H), 7.14-7.34 (m, 1H), 7.54 (s, 1H), 7.69 (d, J = 8.2 Hz, 1H), 7.96 (dd, J = 8.2, 1.0 Hz, 1H), 8.87 (s, 1H). 10.05 (s, 1H) |
| 62 | 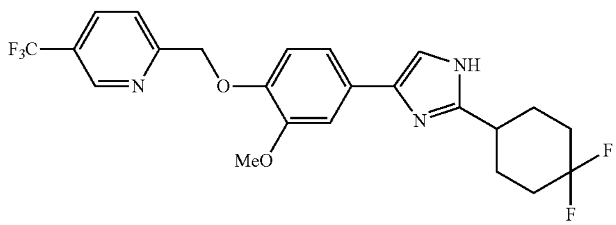 [SMILES: COc1cc(-c2c[nH]c(C3CCC(F)(F)CC3)n2)ccc1OCc1ccc(C(F)(F)F)cn1] | >250 | 1H-NMR (CDCL3) δ 1.70-2.31 (m, 8H), 2.79-2.99 (m, 1H), 3.94 (s, 3H), 5.33 (s, 2H), 6.84 (d, J = 8.5 Hz, 1H), 7.10-7.24 (m, 2H), 7.39 (s, 1H), 7.73 (d, J = 8.2 Hz, 1H), 7.94 (dd, J = 8.2, 1.0 Hz, 1H), 8.84 (s, 1H), 9.42 (s, 1H) |
| 63 | 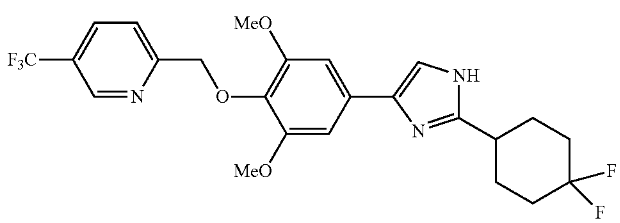 [SMILES: COc1cc(-c2c[nH]c(C3CCC(F)(F)CC3)n2)cc(OC)c1OCc1ccc(C(F)(F)F)cn1] | 155-168 Decomposition | 1H-NMR (CDCL3) δ 1.65-2.41 (m, 8H), 2.75-3.00 (m, 1H), 3.83 (s, 6H), 5.21 (s, 2H), 6.73-7.12 (m, 2H), 7.17 (s, 1H), 7.93-8.05 (m, 2H), 8.80 (s, 1H), 10.00 (s, 1H) |
| 64 | 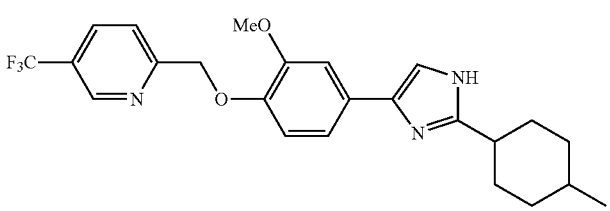 [SMILES: COc1cc(-c2c[nH]c(C3CCC(C)CC3)n2)ccc1OCc1ccc(C(F)(F)F)cn1] | 147-150 | 1H-NMR (DMSO) δ 0.90 (d, J = 6.3 Hz, 3H), 0.94-1.11 (m, 2H), 1.20-2.07 (m, 7H), 2.52-2.64 (m, 1H), 3.84 (s, 3H), 5.26 (s, 2H), 6.98 (d, J = 8.3 Hz, 1H), 7.18 (d, J = 8.3 Hz, 1H), 7.26-7.41 (m, 2H), 7.75 (d, J = 8.3 Hz, 1H), 8.27 (dd, J = 8.3, 2.0 Hz, 1H), 8.96 (d, J = 2.0 Hz, 1H) |
| 65 | 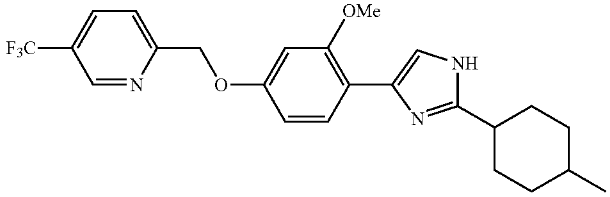 [SMILES: COc1cc(OCc2ccc(C(F)(F)F)cn2)ccc1-c1c[nH]c(C2CCC(C)CC2)n1] | 137-142 | 1H-NMR (DMSO) δ 0.89 (d, J = 6.8 Hz, 3H), 0.93-1.13 (m, 2H), 1.26-2.05 (m, 7H), 2.51-2.63 (m, 1H), 3.85 (s, 3H), 5.30 (s, 2H), 6.54-6.80 (m, 2H), 7.24 (s, 1H), 7.77 (d, J = 8.3 Hz, 1H), 7.93 (d, J = 8.3 Hz, 1H), 8.26 (dd, J = 8.3, 2.0 Hz, 1H), 8.98 (s, 1H), 11.53 (s, 1H) |

TABLE 3-continued

| Example No. | Structure | Melting point (° C.) | 1H-NMR (δ:ppm) |
|---|---|---|---|
| 66 | 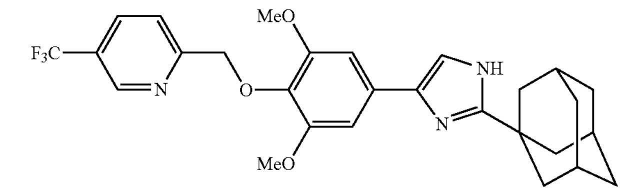 [SMILES: COc1cc(-c2c[nH]c(C34CC5CC(CC(C5)C3)C4)n2)cc(OC)c1OCc1ccc(C(F)(F)F)cn1] | 144-168 | 1H-nMR (DMSO) δ 1.66-1.85 (m, 6H), 2.01-2.24 (m, 9H), 3.89 (s, 6H), 5.12 (s, 2H), 7.38-7.49 (m, 2H), 7.96 (d, J = 8.3 Hz, 1H), 8.10 (s, 1H), 8.31 (d, J = 8.3 Hz, 1H), 8.90 (s, 1H), 14.27 (s, 1H), 14.73 (s, 1H) |
| 67 | 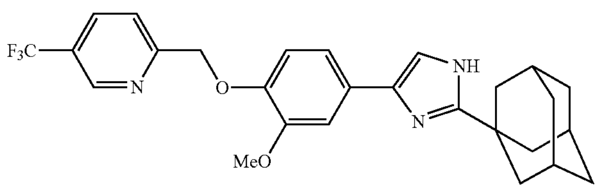 [SMILES: COc1cc(-c2c[nH]c(C34CC5CC(CC(C5)C3)C4)n2)ccc1OCc1ccc(C(F)(F)F)cn1] | 209-217 | 1H-NMR (CDCL3) δ 1.69-1.85 (m, 6H), 1.97-2.12 (m, 9H), 3.96 (s, 3H), 5.32 (s, 2H), 6.83 (d, J = 8.3 Hz, 1H), 7.02-7.20 (m, 2H), 7.22-7.45 (m, 1H), 7.72 (d, J = 8.3 Hz, 1H), 7.93 (dd, J = 8.3, 2.1 Hz, 1H), 8.84 (s, 1H) |
| 68 | 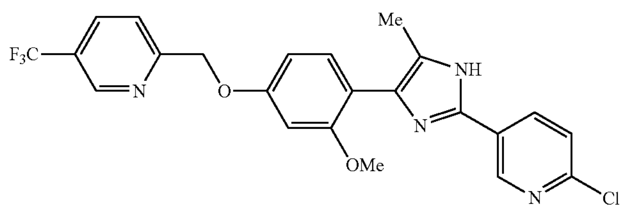 [SMILES: COc1cc(OCc2ccc(C(F)(F)F)cn2)ccc1-c1nc(-c2ccc(Cl)nc2)[nH]c1C] | 129-132 | 1H-NMR (DMSO) δ 2.10 (s, 3H), 3.79 (s, 3H), 5.36 (s, 2H), 6.59-6.89 (m, 2H), 7.29 (d, J = 8.3 Hz, 1H), 7.56 (d, J = 8.8 Hz, 1H), 7.79 (d, J = 8.3 Hz, 1H), 8.15-8.40 (m, 2H), 8.90 (s, 1H), 9.00 (s, 1H), 12.39 (s, 1H) |
| 69 | 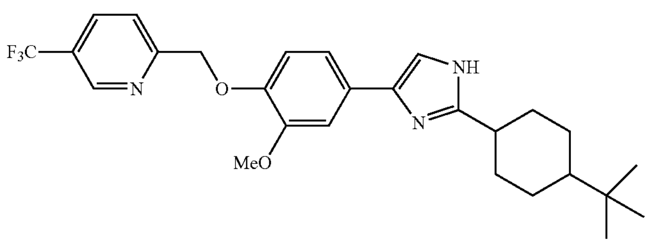 [SMILES: COc1cc(-c2c[nH]c(C3CCC(C(C)(C)C)CC3)n2)ccc1OCc1ccc(C(F)(F)F)cn1] | 159-161 | 1H-NMR (CDCL3) δ 0.83-0.91 (m, 9H), 0.99-1.19 (m, 3H), 1.37-1.61 (m, 2H), 1.77-1.99 (m, 2H), 2.06-2.27 (m, 2H), 2.72 (tt, J = 12.4, 3.6 Hz, 1H), 3.96 (s, 3H), 5.33 (s, 2H), 6.84 (d, J = 8.8 Hz, 1H), 7.07-7.17 (m, 2H), 7.34 (s, 1H), 7.73 (d, J = 8.3 Hz, 1H), 7.93 (dd, J = 8.3, 2.2 Hz, 1H), 8.84 (d, J = 2.2 Hz, 1H) |
| 70 | 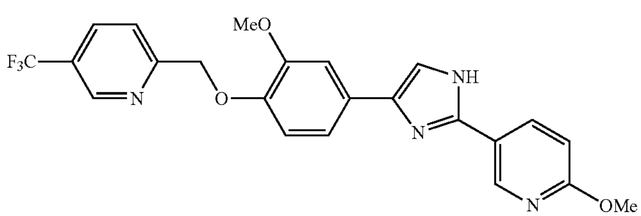 [SMILES: COc1ccc(-c2nc(-c3ccc(OCc4ccc(C(F)(F)F)cn4)c(OC)c3)c[nH]2)cn1] | 217-218 Decomposition | 1H-NMR (CDCL3) δ 3.96 (s, 6H), 5.35 (s, 2H), 6.72-7.01 (m, 2H), 7.06-7.65 (m, 3H), 7.74 (d, J = 8.3 Hz, 1H), 7.94 (d, J = 8.3 Hz, 1H), 8.14 (d, J = 8.3 Hz, 1H), 8.59 (d, J = 2.0 Hz, 1H), 8.85 (s, 1H), 9.86 (s, 1H) |
| 71 | 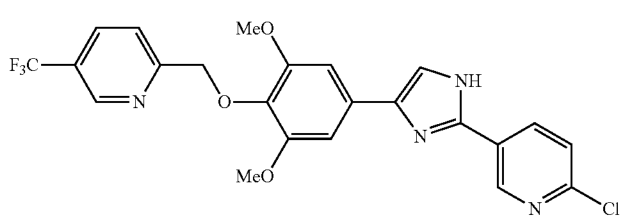 [SMILES: COc1cc(-c2c[nH]c(-c3ccc(Cl)nc3)n2)cc(OC)c1OCc1ccc(C(F)(F)F)cn1] | 171-173 Decomposition | 1H-NMR (CDCL3) δ 3.85 (s, 6H), 5.21 (s, 2H), 6.69-7.14 (m, 2H), 7.29-7.47 (m, 2H), 7.89-8.04 (m, 2H), 8.14-8.36 (m, 1H), 8.79 (s, 1H), 8.81-8.92 (m, 1H), 11.35 (s, 1H) |
| 72 | 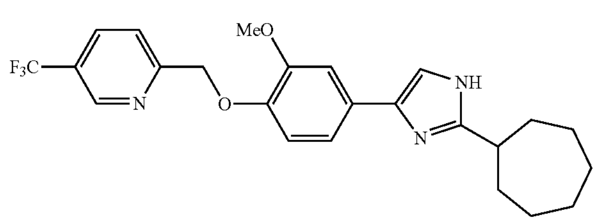 [SMILES: COc1cc(-c2c[nH]c(C3CCCCCC3)n2)ccc1OCc1ccc(C(F)(F)F)cn1] | | 1H-NMR (CDCL3) δ 1.41-2.20 (m, 12H), 2.85-3.08 (m, 1H), 3.93 (s, 3H), 5.33 (s, 2H), 6.83 (d, J = 8.2 Hz, 1H), 7.10 (s, 1H), 7.13-7.22 (m, 1H), 7.41 (s, 1H), 7.73 (d, J = 8.2 Hz, 1H), 7.93 (dd, J = 8.3, 1.5 Hz, 1H), 8.84 (s, 1H), 9.26 (s, 1H) |

TABLE 3-continued

| Example No. | Structure | Melting point (° C.) | 1H-NMR (δ:ppm) |
|---|---|---|---|
| 73 | 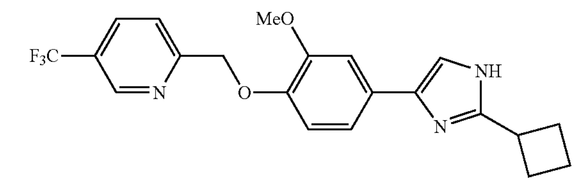 [SMILES: COc1cc(-c2c[nH]c(C3CCC3)n2)ccc1OCc1ccc(C(F)(F)F)cn1] | 210-213 Decomposition | 1H-NMR (DMSO) δ 1.83-1.97 (m, 1H), 2.00-2.14 (m, 1H), 2.28-2.61 (m, 4H), 3.82-3.99 (m, 4H), 5.33 (s, 2H), 7.15 (d, J = 8.3 Hz, 1H), 7.39 (d, J = 8.3 Hz, 1H), 7.53-7.67 (1H), 7.75 (d, J = 8.3 Hz, 1H), 7.97 (d, J = 2.0 Hz, 1H), 8.28 (dd, J = 8.3, 1.0 Hz, 1H), 8.98 (s, J = 1.0 Hz, 1H), 14.61 (s, 1H) |
| 74 | 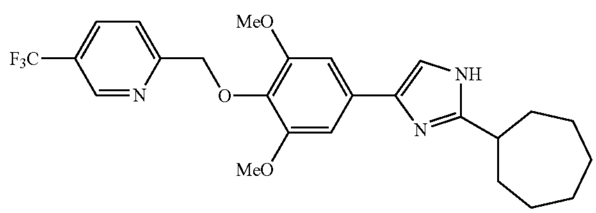 [SMILES: COc1cc(-c2c[nH]c(C3CCCCCC3)n2)cc(OC)c1OCc1ccc(C(F)(F)F)cn1] | 177-179 | 1H-NMR (DMSO) δ 1.46-2.07 (m, 13H), 3.18-3.28 (m, 1H), 3.85 (s, 6H), 5.12 (s, 2H), 7.20-7.30 (m, 2H), 7.93 (d, J = 8.3 Hz, 1H), 8.05 (s, 1H), 8.29 (dd, J = 8.3, 2.2 Hz, 1H), 8.90 (d, J = 2.2 Hz, 1H) |
| 75 | 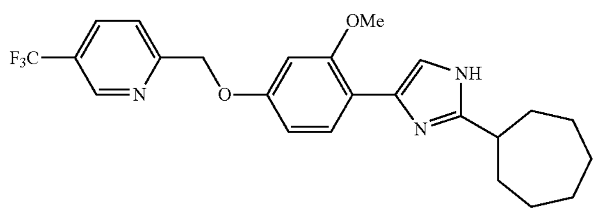 [SMILES: COc1cc(OCc2ccc(C(F)(F)F)cn2)ccc1-c1c[nH]c(C2CCCCCC2)n1] | 202-204 Decomposition | 1H-KMR (DMSO) δ 1.44-2.03 (m, 12H), 3.19-3.29 (m, 1H), 3.91 (s, 3H), 5.39 (s, 2H), 6.79 (dd, J = 8.5, 2.4 Hz, 1H), 6.89 (d, J = 2.4 Hz, 1H), 7.65 (s, 1H), 7.67-7.87 (m, 2H), 8.29 (dd, J = 8.4, 2.1 Hz, 1H), 9.00 (d, J = 2.1 Hz, 1H), 14.09 (s, 1H) |
| 76 | 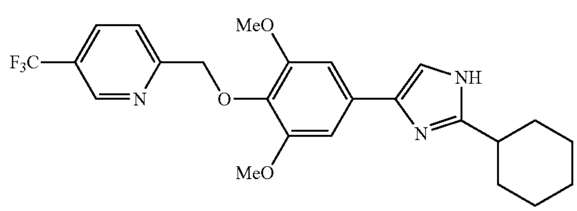 [SMILES: COc1cc(-c2c[nH]c(C3CCCCC3)n2)cc(OC)c1OCc1ccc(C(F)(F)F)cn1] | 183-186 | 1H-NMR (DMSO) δ 1.17-1.46 (m, 3H), 1.57-1.89 (m, 5H), 1.93-2.11 (m, 2H), 3.01-3.14 (m, 1H), 3.85 (s, 6H), 5.12 (s, 2H), 7.25 (s, 2H), 7.93 (d, J = 8.3 Hz, 1H), 8.08 (s, 1H), 8.29 (dd, J = 8.3, 2.1 Hz, 1H), 8.90 (d, J = 2.1 Hz, 1H) |
| 77 | 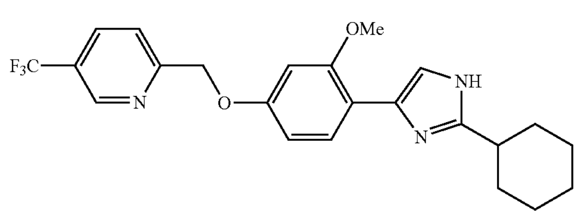 [SMILES: COc1cc(OCc2ccc(C(F)(F)F)cn2)ccc1-c1c[nH]c(C2CCCCC2)n1] | 226-228 | 1H-KMR (DMSO) δ 1.15-1.43 (m, 3H), 1.57-2.03 (m, 7H), 3.08 (tt, J = 12.2, 3.5 Hz, 1H), 3.91 (s, 3H), 5.39 (s, 2H), 6.79 (dd, J = 8.7, 2.3 Hz, 1H), 6.89 (d, J = 2.3 Hz, 1H), 7.66 (S, 1H), 7.73-7.83 (m, 2H), 8.29 (dd, J = 8.4, 2.3 Hz, 1H), 9.00 (d, J = 2.3 Hz, 1H), 14.12 (s, 1H) |
| 78 | 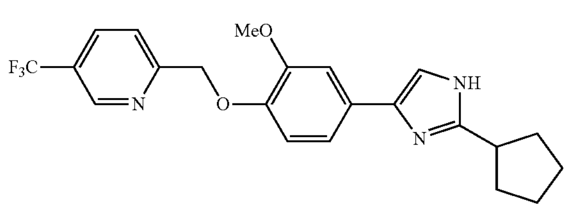 [SMILES: COc1cc(-c2c[nH]c(C3CCCC3)n2)ccc1OCc1ccc(C(F)(F)F)cn1] | 207-210 | 1H-NMR (DMSO) δ 1.39-2.03 (m, 8H), 2.98-3.17 (m, 1H), 3.83 (s, 3H), 5.26 (s, 2H), 6.96 (d, J = 8.3 Hz, 1H), 7.05-7.44 (m, 3H), 7.76 (d, J = 8.3 Hz, 1H), 8.27 (d, J = 8.3 Hz, 1H), 8.97 (s, 1H), 11.66 (s, 1H) |

TABLE 3-continued

| Example No. | Structure | Melting point (° C.) | 1H-NMR (δ:ppm) |
|---|---|---|---|
| 79 | 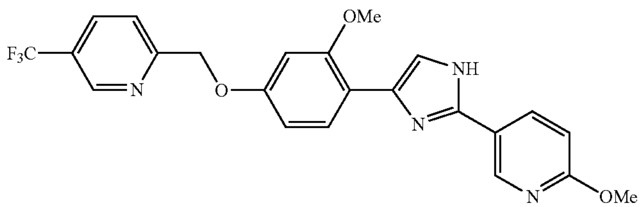 [SMILES: COc1ccc(-c2nc(-c3ccc(OCc4ccc(C(F)(F)F)cn4)cc3OC)c[nH]2)cn1] | 187-189 | 1H-NMR (DMSO) δ 3.89 (s, 3H), 3.92 (s, 3H), 5.34 (s, 2H), 6.70 (dd, J = 8.8, 2.4 Hz, 1H), 6.77 (d, J = 2.4 Hz, 1H), 6.92 (d, J = 8.3 Hz, 1H), 7.52 (s, 1H), 7.78 (d, J = 8.3 Hz, 1H), 8.06 (d, J = 8.8 Hz, 1H), 8.20-8.31 (m, 2H), 8.75 (d, J = 1.5 Hz, 1H), 8.90-9.07 (m, 1H), 12.47 (s, 1H) |
| 80 | 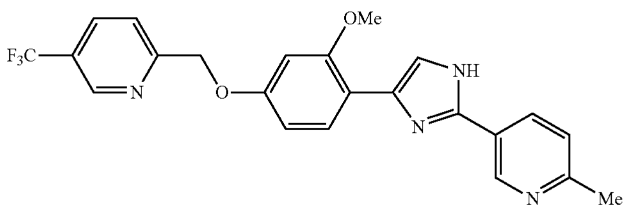 [SMILES: COc1cc(OCc2ccc(C(F)(F)F)cn2)ccc1-c1c[nH]c(-c2ccc(C)nc2)n1] | 203-205 | 1H-NMR (DMSO) δ 2.48 (s, 3H), 3.90 (s, 3H), 5.33 (s, 2H), 6.70 (dd, J = 8.8, 2.4 Hz, 1H), 6.77 (d, J = 2.4 Hz, 1H), 7.33 (d, J = 8.3 Hz, 1H), 7.54 (s, 1H), 7.78 (d, J = 8.3 Hz, 1H), 8.08 (d, J = 8.8 Hz, 1H), 8.19 (dd, J = 8.3, 2.2 Hz, 1H), 8.27 (dd, J = 8.3, 2.0 Hz, 1H), 8.99 (s, 1H), 9.04 (d, J = 2.0 Hz, 1H), 12.60 (s, 1H) |
| 81 | 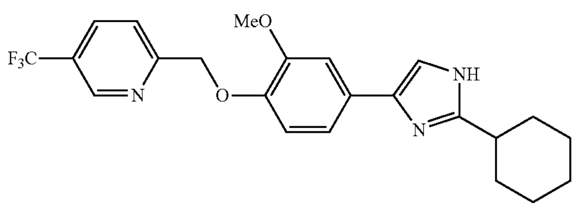 [SMILES: COc1cc(-c2c[nH]c(C3CCCCC3)n2)ccc1OCc1ccc(C(F)(F)F)cn1] | 135-145 | 1H-NMR (CDCL3) δ 1.14-1.59 (m, 5H), 1.64-2.18 (m, 5H), 2.64-2.90 (m, 1H), 3.91 (s, 3H), 5.33 (s, 2H), 6.83 (d, J = 8.3 Hz, 1H), 7.04-7.22 (m, 2H), 7.36 (s, 1H), 7.72 (d, J = 8.3 Hz, 1H), 7.93 (dd, J = 8.3, 2.0 Hz, 1H), 8.84 (s, 1H), 9.50 (s, 1H) |
| 82 | 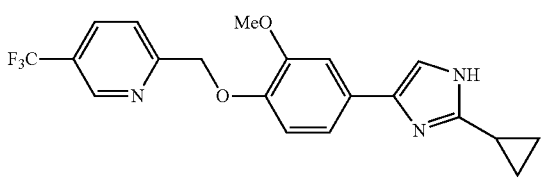 [SMILES: COc1cc(-c2c[nH]c(C3CC3)n2)ccc1OCc1ccc(C(F)(F)F)cn1] | 153-155 | 1H-NMR (DMSO) δ 0.77-0.92 (m, 4H), 1.87-1.99 (m, 1H), 3.83 (s, 3H), 5.25 (s, 2H), 6.91-7.26 (m, 2H), 7.25-7.42 (m, 2H), 7.75 (d, J = 8.3 Hz, 1H), 8.27 (d, J = 8.3 Hz, 1H), 8.96 (s, 1H), 11.67 (s, 1H) |
| 83 | 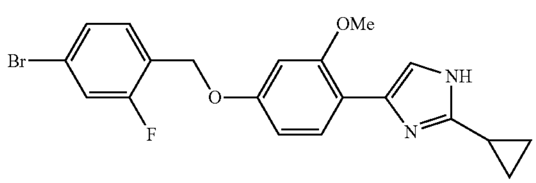 [SMILES: COc1cc(OCc2ccc(Br)cc2F)ccc1-c1c[nH]c(C2CC2)n1] | 157-160 | 1H-NMR (DMSO) δ 0.73-0.99 (m, 4H), 1.87-2.05 (m, 1H), 3.84 (s, 3H), 5.10 (s, 2H), 6.58-6.76 (m, 2H), 7.21 (s, 1H), 7.46 (d, J = 8.0 Hz, 1H), 7.54 (dd, J = 8.0, 8.0 Hz, 1H), 7.60 (d, J = 9.8 Hz, 1H), 7.88 (d, J = 8.8 Hz, 1H), 11.60 (s, 1H) |
| 84 | 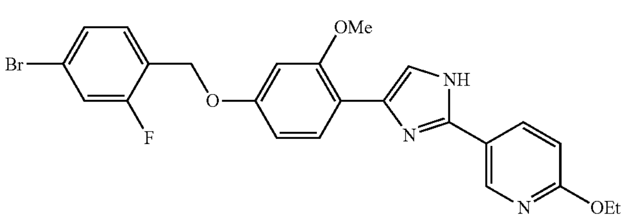 [SMILES: CCOc1ccc(-c2nc(-c3ccc(OCc4ccc(Br)cc4F)cc3OC)c[nH]2)cn1] | 181-184 | 1H-NMR (DMSO) δ 1.33 (t, J = 7.0 Hz, 3H), 3.89 (s, 3H), 4.34 (q, J = 7.0 Hz, 2H), 5.14 (s, 2H), 6.64-6.80 (m, 2H), 6.88 (d, J = 8.3 Hz, 1H), 7.43-7.69 (m, 4H), 8.07 (d, J = 8.3 Hz, 1H), 8.23 (dd, J = 8.3, 2.0 Hz, 1H), 8.73 (d, J = 2.0 Hz, 1H), 12.47 (s, 1H) |

TABLE 3-continued

| Example No. | Structure | Melting point (° C.) | 1H-NMR (δ:ppm) |
|---|---|---|---|
| 85 | F₃C-pyridine-CH₂-O-(3-MeO-phenyl)-imidazole-NH, imidazole-2-(6-Me-pyridin-3-yl) | 201-203 Decomposition | 1H-NMR (DMSO) δ 3.88 (s, 3H), 5.29 (s, 2H), 7.04 (d, J = 7.8 Hz, 1H), 7.27-7.37 (m, 2H), 7.47 (s, 1H), 7.60-7.84 (m, 2H), 8.19 (dd, J = 7.8, 2.0 Hz, 1H), 8.27 (dd, J = 8.3, 2.0 Hz, 1H), 8.97 (d, J = 2.0 Hz, 1H), 9.03 (S, 1H) |
| 86 | Br-(2-F-phenyl)-CH₂-O-(2-OMe-phenyl)-imidazole-NH, imidazole-2-(6-Me-pyridin-3-yl) | 218-220 Decomposition | 1H-NMR (DMSO) δ 2.66 (s, 3H), 3.94 (s, 3H), 5.21 (s, 2H), 6.77-6.90 (m, 2H), 7.49 (d, J = 8.3 Hz, 1H), 7.57 (dd, J = 8.3, 8.3 Hz, 1H), 7.63 (dd, J = 9.5, 1.2 Hz, 1H), 7.73 (d, J = 8.3 Hz, 1H), 7.93 (s, 1H), 8.02 (d, J = 8.8 Hz, 1H), 8.75 (d, J = 8.3 Hz, 1H), 9.38 (s, 1H) |
| 87 | F₃C-pyridine-CH₂-O-(3-MeO-phenyl)-imidazole-NH, imidazole-2-(pyridin-2-yl) | 217-220 | 1H-NMR (CDCL3) δ 4.03 (s, 3H), 5.37 (s, 2H), 6.89 (d, J = 8.3 Hz, 1H), 7.04-7.43 (m, 3H), 7.55 (d, J = 2.0 Hz, 1H), 7.68-7.84 (m, 2H), 7.84-8.04 (m, 1H), 8.23 (d, J = 7.8 Hz, 1H), 8.53 (dd, J = 4.9, 1.0 Hz, 1H), 8.86 (s, 1H), 10.66 (s, 1H) |
| 88 | F₃C-pyridine-CH₂-O-(2-OMe-phenyl)-imidazole-NH, imidazole-2-(pyridin-2-yl) | 214-216 | 1H-NMR (DMSO) δ 3.95 (s, 3H), 5.43 (s, 2H), 6.83 (dd, J = 8.3, 2.0 Hz, 1H), 6.93 (d, J = 2.0 Hz, 1H), 7.68 (dd, J = 7.3, 4.9 Hz, 1H), 7.81 (d, J = 8.3 Hz, 1H), 7.91 (s, 1H), 8.06 (d, J = 8.3 Hz, 1H), 8.16 (ddd, J = 7.8, 7.3, 1.0 Hz, 1H), 8.31 (dd, J = 8.3, 2.4 Hz, 1H), 8.66 (d, J = 7.8 Hz, 1H), 8.84 (dd, J = 4.9, 1.0 Hz, 1H), 9.02 (d, J = 2.4 Hz, 1H) |
| 89 | F₃C-pyridine-CH₂-O-(2-OMe-phenyl)-imidazole-NH, imidazole-2-(pyridin-3-yl) | 240-242 | 1H-NMR (DMSO) δ 3.96 (s, 3H), 5.43 (s, 2H), 6.84 (dd, J = 8.5, 2.0 Hz, 1H), 6.93 (d, J = 2.0 Hz, 1H), 7.73-7.86 (m, 2H), 7.97 (s, 1H), 8.03 (d, J = 8.3 Hz, 1H), 8.31 (dd, J = 8.3, 2.4 Hz, 1H), 8.75 (d, J = 7.8 Hz, 1H), 8.83 (d, J = 4.9 Hz, 1H), 9.02 (d, J = 1.0 Hz, 1H), 9.44 (d, J = 2.4 Hz, 1H) |
| 90 | Br-(2-F-phenyl)-CH₂-O-(2-OMe-phenyl)-imidazole-NH, imidazole-2-(pyridin-2-yl) | 219-222 | 1H-NMR (DMSO) δ 3.94 (s, 3H), 5.23 (s, 2H), 6.82 (dd, J = 8.3, 2.2 Hz, 1H), 6.86 (d, J = 2.0 Hz, 1H), 7.50 (dd, J = 8.0, 1.7 Hz, 1H), 7.58 (dd, J = 8.0, 8.0 Hz, 1H), 7.61-7.75 (m, J = 3.7 Hz, 2H), 7.87 (s, 1H), 8.03 (d, J = 8.3 Hz, 1H), 8.14 (ddd, J = 7.8, 7.8, 1.5 Hz, 1H), 8.56 (d, J = 7.8 Hz, 1H), 8.82 (d, J = 4.9 Hz, 1H) |

TABLE 3-continued

| Example No. | Structure | Melting point (° C.) | 1H-NMR (δ:ppm) |
|---|---|---|---|
| 91 | 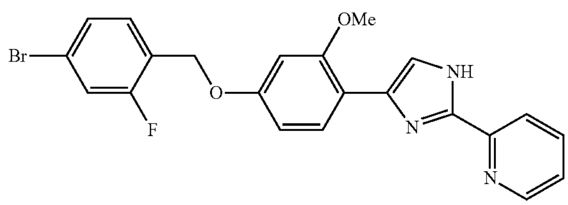 [SMILES: COc1cc(OCc2ccc(Br)cc2F)ccc1-c1c[nH]c(-c2ccccn2)n1] | 143-146 | 1H-NMR (CDCL3) δ 4.01 (s, 3H), 5.12 (s, 2H), 6.59-6.76 (m, 2H), 7.21-7.47 (m, 4H), 7.51 (s, 1H), 7.76 (s, 1H), 8.24 (ddd, J = 6.1, 2.0, 1.5 Hz, 1H), 8.57 (dd, J = 4.9, 1.5 Hz, 1H), 9.06 (d, J = 2.0 Hz, 1H) |
| 92 | 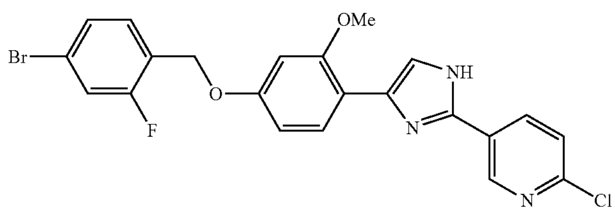 [SMILES: COc1cc(OCc2ccc(Br)cc2F)ccc1-c1c[nH]c(-c2ccc(Cl)nc2)n1] | 220-222 | 1H-NMR (DMSO) δ 3.91 (s, 3H), 5.17 (s, 2H), 6.67-6.91 (m, 2H), 7.44-7.86 (m, 5H), 8.09 (d, J = 7.3 Hz, 1H), 8.38 (d, J = 7.8 Hz, 1H), 9.01 (s, 1H), 12.80 (s, 1H) |
| 93 | 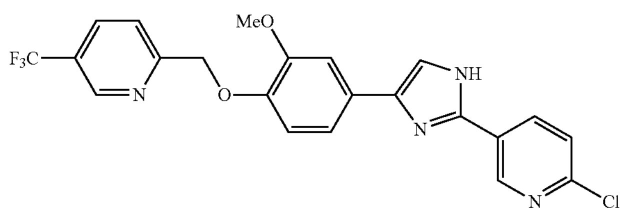 [SMILES: COc1cc(-c2c[nH]c(-c3ccc(Cl)nc3)n2)ccc1OCc1ccc(C(F)(F)F)cn1] | >280 | 1H-NMR (DMSO) δ 3.94 (s, 3H), 5.38 (s, 2H), 7.19 (d, J = 8.3 Hz, 1H), 7.51 (dd, J = 8.3, 1.5 Hz, 1H), 7.71 (s, 1H), 7.77 (d, J = 8.3 Hz, 1H), 7.84 (d, J = 8.3 Hz, 1H), 8.21 (s, 1H), 8.30 (dd, J = 8.3, 2.0 Hz, 1H), 8.65 (dd, J = 8.3, 1.7 Hz, 1H), 9.00 (s, 1H), 9.22 (d, J = 2.0 Hz, 1H) |
| 94 | 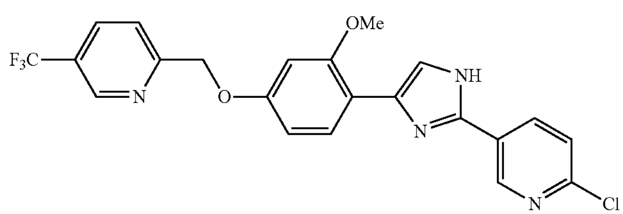 [SMILES: COc1cc(OCc2ccc(C(F)(F)F)cn2)ccc1-c1c[nH]c(-c2ccc(Cl)nc2)n1] | 215-217 | 1H-NMR (DMSO) δ 3.91 (s, 3H), 5.35 (s, 2H), 6.72 (dd, J = 8.3, 2.0 Hz, 1H), 6.79 (d, J = 2.0 Hz, 1H), 7.48-7.68 (m, 2H), 7.78 (d, J = 8.3 Hz, 1H), 8.04 (s, 1H), 8.27 (dd, J = 8.3, 2.0 Hz, 1H), 8.37 (dd, J = 8.3, 2.4 Hz, 1H), 8.90-9.09 (m, 2H), 12.75 (s, 1H) |
| 95 | 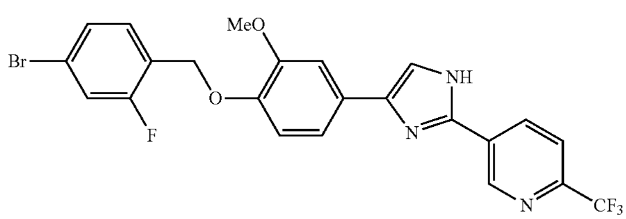 [SMILES: COc1cc(-c2c[nH]c(-c3ccc(C(F)(F)F)nc3)n2)ccc1OCc1ccc(Br)cc1F] | 175-177 | 1H-NMR (DMSO) δ 3.84 (s, 3H), 5.11 (s, 2H), 7.09 (d, J = 8.3 Hz, 1H), 7.39 (dd, J = 8.3, 1.5 Hz, 1H), 7.43-7.56 (m, 3H), 7.61 (dd, J = 9.8, 2.0 Hz, 1H), 7.81 (s, 1H), 8.01 (d, J = 8.3 Hz, 1H), 8.56 (dd, J = 8.3, 1.5 Hz, 1H), 9.33 (d, J = 1.5 Hz, 1H), 13.04 (s, 1H) |
| 96 | 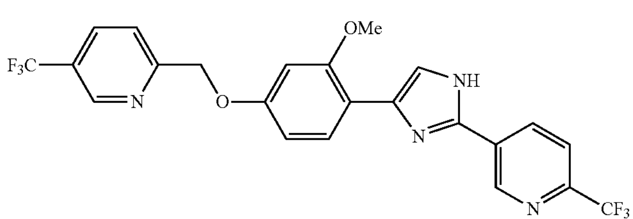 [SMILES: COc1cc(OCc2ccc(C(F)(F)F)cn2)ccc1-c1c[nH]c(-c2ccc(C(F)(F)F)nc2)n1] | 209-211 | 1H-NMR (DMSO) δ 3.92 (s, 3H), 5.35 (s, 2H), 6.73 (dd, J = 8.7, 1.7 Hz, 1H), 6.81 (s, 1H), 7.63 (s, 1H), 7.79 (d, J = 8.3 Hz, 1H), 7.93-8.14 (m, 2H), 8.27 (dd, J = 8.3, 1.9 Hz, 1H), 8.57 (d, J = 8.7 Hz, 1H), 8.99 (d, J = 0.8 Hz, 1H), 9.34 (s, 1H), 12.93 (s, 1H) |

TABLE 3-continued

| Example No. | Structure | Melting point (° C.) | 1H-NMR (δ:ppm) |
|---|---|---|---|
| 97 | 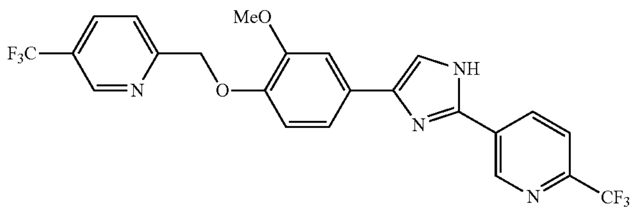 [SMILES: COc1cc(-c2c[nH]c(-c3ccc(C(F)(F)F)nc3)n2)ccc1OCc1ccc(C(F)(F)F)cn1] | 201-203 | 1H-NMR (DMSO) δ 3.89 (s, 3H), 5.30 (s, 2H), 7.07 (d, J = 7.9 Hz, 1H), 7.38 (d, J =7.9 Hz, 1H), 7.50 (s, 1H), 7.77 (d, J = 8.3 Hz, 1H), 7.87 (s, 1H), 8.01 (d, J = 8.3 Hz, 1H), 8.28 (dd, J = 7.9, 0.8 Hz, 1H), 8.56 (d, J = 7.9 Hz, 1H), 8.98 (s, 1H), 9.33 (s, 1H) |
| 98 | 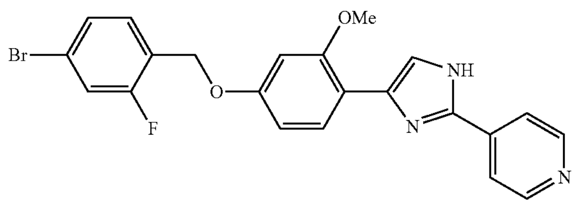 [SMILES: COc1cc(OCc2ccc(Br)cc2F)ccc1-c1c[nH]c(-c2ccncc2)n1] | 226-230 | 1H-NMR (DMSO) δ 3.92 (s, 3H), 5.18 (s, 2H), 6.74-6.87 (m, 2H), 7.48 (d, J = 8.3 Hz, 1H), 7.56 (dd, J = 8.3, 8.3 Hz, 1H), 7.62 (d, J = 9.5 Hz, 1H), 7.87 (s, 1H), 8.03 (d, J = 8.3 Hz, 1H), 8.46 (d, J = 5.4 Hz, 2H), 8.87 (d, J = 5.4 Hz, 2H) |
| 99 | 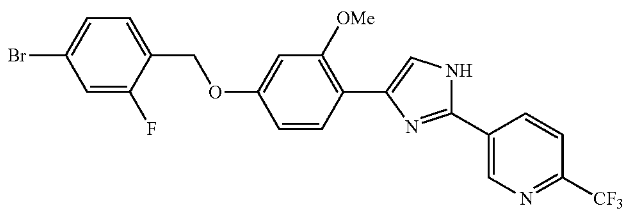 [SMILES: COc1cc(OCc2ccc(Br)cc2F)ccc1-c1c[nH]c(-c2ccc(C(F)(F)F)nc2)n1] | 183-185 | 1H-NMR (DMSO) δ 3.91 (s, 3H), 5.16 (s, 2H), 6.68-6.81 (m, 2H), 7.47 (dd, J = 8.3, 1.2 Hz, 1H), 7.50-7.73 (m, 3H), 7.95-8.20 (m, 2H), 8.57 (d, J = 7.9 Hz, 1H), 9.34 (s, 1H), 12.97 (s, 1H) |
| 100 | 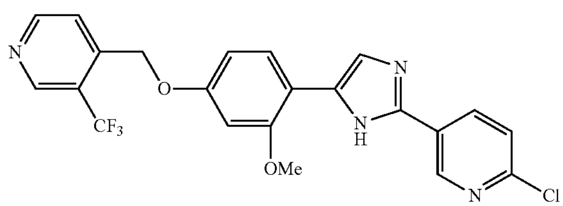 [SMILES: COc1cc(OCc2ccncc2C(F)(F)F)ccc1-c1cnc(-c2ccc(Cl)nc2)[nH]1] | 220-228 | 1H-NMR (CDCL3) δ 4.00 (s, 3H), 5.34 (s, 2H), 6.61 (dd, J = 8.3, 2.4 Hz, 1H), 6.66 (d, J = 2.4 Hz, 1H), 7.20-7.34 (m, 1H), 7.41 (d, J = 8.3 Hz, 1H), 7.45-7.59 (m, 1H), 7.75 (d, J = 5.4 Hz, 1H), 8.12-8.28 (m, 1H), 8.77-8.87 (m, 2H), 8.92 (s, 1H) |
| 101 | 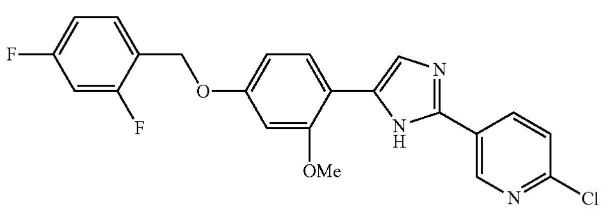 [SMILES: COc1cc(OCc2ccc(F)cc2F)ccc1-c1cnc(-c2ccc(Cl)nc2)[nH]1] | 213-218 | 1H-NMR (DMSO) δ 3.90 (s, 3H), 5.13 (s, 2H), 6.67-6.82 (m, 2H), 7.13 (ddd, J = 8.5, 8.5, 2.3 Hz, 1H), 7.30 (ddd, J = 9.8, 9.8, 2.3 Hz, 1H), 7.57-7.72 (m, 3H), 8.08 (d, J = 9.3 Hz, 1H), 8.36 (dd, J = 8.3, 2.0 Hz, 1H), 8.99 (d, J = 2.0 Hz, 1H), 12.78 (s, 1H) |
| 102 | 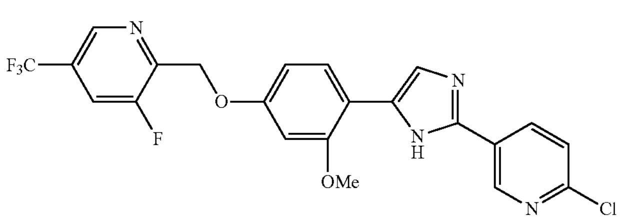 [SMILES: COc1cc(OCc2ncc(C(F)(F)F)cc2F)ccc1-c1cnc(-c2ccc(Cl)nc2)[nH]1] | 164-186 | 1H-NMR (DMSO) δ 3.80 (s, 3H), 5.67 (s, 2H), 6.41 (dd, J = 8.3, 2.4 Hz, 1H), 6.45 (d, J = 2.4 Hz, 1H), 7.57 (d, J = 8.3 Hz, 1H), 7.62 (s, 1H), 7.91 (d, J = 8.8 Hz, 1H), 8.10 (dd, J = 8.8, 2.4 Hz, 1H), 8.35 (dd, J = 9.8, 1.5 Hz, 1H), 8.67 (d, J = 2.4 Hz, 1H), 8.71-8.81 (m, 1H), 9.44 (s, 1H) |

TABLE 3-continued

| Example No. | Structure | Melting point (° C.) | 1H-NMR (δ:ppm) |
|---|---|---|---|
| 103 | 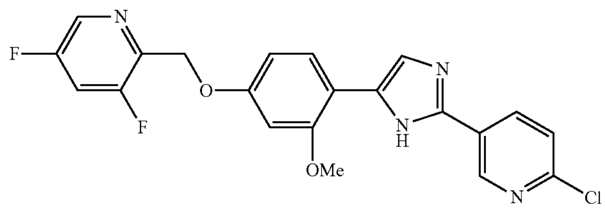 [SMILES: COc1cc(OCc2ncc(F)cc2F)ccc1-c1cnc(-c2ccc(Cl)nc2)[nH]1] | 190-192 | 1H-NMR (DMSO) δ 3.89 (s, 3H), 5.18-5.29 (m, 2H), 6.64-6.81 (m, 2H), 7.45-7.67 (m, 2H), 7.92-8.12 (m, 2H), 8.36 (dd, J = 8.3, 2.4 Hz, 1H), 8.56 (d, J = 2.2 Hz, 1H), 9.00 (d, J = 2.4 Hz, 1H), 12.72 (s, 1H) |
| 104 | 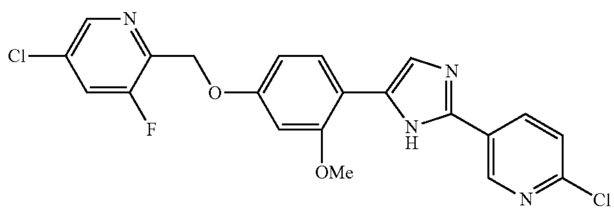 | 211-218 | 1H-NMR (DMSO) δ 3.89 (s, 3H), 5.26 (d, J = 1.5 Hz, 2H), 6.64-6.82 (m, 2H), 7.49-7.59 (m, 1H), 7.62 (d, J = 8.3 Hz, 1H), 8.00 (s, 1H), 8.18 (dd, J = 9.8, 2.0 Hz, 1H), 8.37 (dd, J = 8.3, 2.4 Hz, 1H), 8.57 (d, J = 2.0 Hz, 1H), 8.99 (d, J = 2.4 Hz, 1H) |
| 105 | 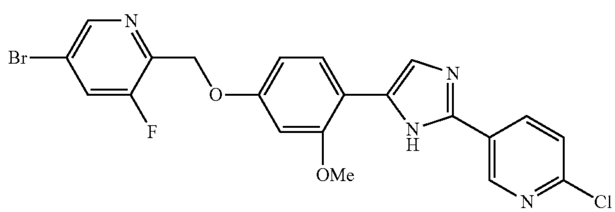 [SMILES: COc1cc(OCc2ncc(Cl)cc2F)ccc1-c1cnc(-c2ccc(Cl)nc2)[nH]1] | 219-225 | 1H-NMR (DMSO) δ 3.89 (s, 3H), 5.25 (d, J = 2.0 Hz, 2H), 6.67-6.79 (m, 2H), 7.56 (s, 1H), 7.62 (dd, J = 8.3, 0.7 Hz, 1H), 7.99 (s, 1H), 8.28 (dd, J = 9.4, 1.8 Hz, 1H), 8.37 (dd, J = 8.3, 2.4 Hz, 1H), 8.64 (dd, J = 1.8, 1.1 Hz, 1H), 8.99 (d, J = 2.4 Hz, 1H), 12.73 (s, 1H) |
| 106 | 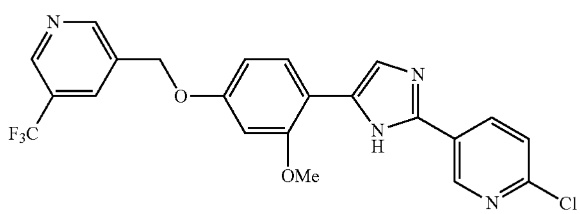 [SMILES: COc1cc(OCc2cncc(C(F)(F)F)c2)ccc1-c1cnc(-c2ccc(Cl)nc2)[nH]1] | 191-203 | 1H-NMR (DMSO) δ 3.91 (s, 3H), 5.30 (s, 2H), 6.71-6.80 (m, 2H), 7.58-7.65 (m, 2H), 8.10 (d, J = 8.8 Hz, 1H), 8.31-8.40 (m, 2H), 8.94-9.05 (m, 3H), 12.79 (s, 1H) |
| 107 | 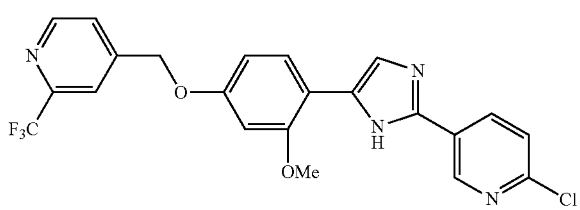 [SMILES: COc1cc(OCc2ccnc(C(F)(F)F)c2)ccc1-c1cnc(-c2ccc(Cl)nc2)[nH]1] | 174-223 | 1H-NMR (DMSO) δ 3.91 (s, 3H), 5.35 (s, 2H), 6.68-6.83 (m, 2H), 7.54-7.71 (m, 2H), 7.80 (d, J = 4.9 Hz, 1H), 7.98 (s, 1H), 8.09 (d, J = 8.3 Hz, 1H), 8.36 (d, J = 8.3 Hz, 1H), 8.79 (d, J = 4.9 Hz, 1H), 8.99 (s, 1H) |
| 108 | 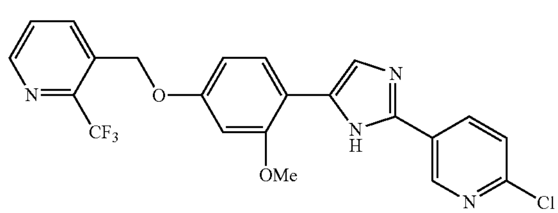 [SMILES: COc1cc(OCc2cccnc2C(F)(F)F)ccc1-c1cnc(-c2ccc(Cl)nc2)[nH]1] | 231-233 | 1H-NMR (DMSO) δ 3.89 (s, 3H), 5.33 (s, 2H), 6.68-6.78 (m, 2H), 7.49-7.71 (m, 2H), 7.78 (dd, J = 7.9, 4.6 Hz, 1H), 8.07 (s, 1H), 8.26 (d, J = 7.9 Hz, 1H), 8.37 (dd, J = 8.3, 2.5 Hz, 1H), 8.73 (d, J = 4.6 Hz, 1H), 8.99 (d, J = 2.5 Hz, 1H) |
| 109 | 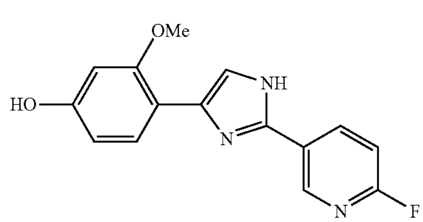 [SMILES: COc1cc(O)ccc1-c1c[nH]c(-c2ccc(F)nc2)n1] | 249-251 Decomposition | 1H-NMR (DMSO) δ 3.84 (s, 3H), 6.35-6.56 (m, 2H), 7.29 (dd, J = 8.5, 2.7 Hz, 1H), 7.50 (s, 1H), 7.94 (s, OH), 8.40-8.58 (m, 1H), 8.81 (s, 1H), 9.41 (s, 1H), 12.61 (s, 1H) |

TABLE 3-continued

| Example No. | Structure | Melting point (° C.) | 1H-NMR (δ:ppm) |
|---|---|---|---|
| 110 | 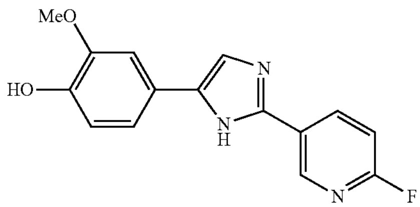 [SMILES: COc1cc(-c2cnc(-c3ccc(F)nc3)[nH]2)ccc1O] | | 1H-NMR (DMSO) δ 3.83 (s, 3H), 6.79 (d, J = 8.3 Hz, 1H), 7.24 (dd, J = 8.3, 2.0 Hz, 1H), 7.30 (dd, J = 8.5, 2.7 Hz, 1H), 7.37 (d, J = 2.0 Hz, 1H), 7.60 (s, 1H), 8.48 (ddd, J = 8.5, 8.5, 2.4 Hz, 1H), 8.80 (d, J = 2.4 Hz, 1H), 8.96 (s, 1H), 11.95 (s, 1H) |
| 111 | 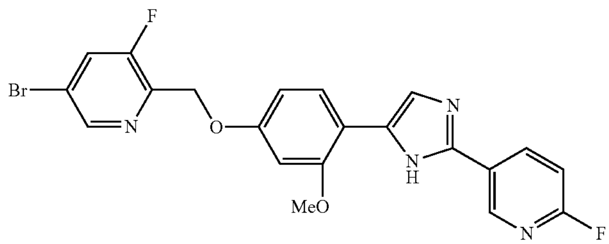 [SMILES: COc1cc(OCc2ncc(Br)cc2F)ccc1-c1cnc(-c2ccc(F)nc2)[nH]1] | Oil | 1H-NMR (CDCL3) δ 3.97 (s, 3H), 5.26 (d, J = 2.0 Hz, 2H), 6.67-6.77 (m, 2H), 7.02 (dd, J = 8.3, 2.9 Hz, 1H), 7.40-7.79 (m, 3H), 8.29-8.40 (m, 1H), 8.56 (d, J = 1.0 Hz, 1H), 8.62 (d, J = 2.0 Hz, 1H), 10.55 (s, 1H) |
| 112 | 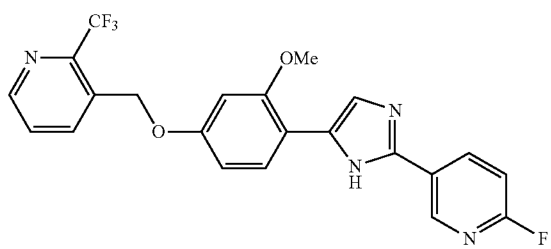 [SMILES: COc1cc(OCc2cccnc2C(F)(F)F)ccc1-c1cnc(-c2ccc(F)nc2)[nH]1] | 187-190 | 1H-NMR (DMSO) δ 3.90 (s, 3H), 5.33 (s, 2H), 6.68-6.77 (m, 2H), 7.30 (dd, J = 8.5, 2.7 Hz, 1H), 7.49-7.63 (m, 1H), 7.79 (dd, J = 7.8, 4.9 Hz, 1H), 7.96-8.15 (m, 1H), 8.27 (dd, J = 7.8, 1.2 Hz, 1H), 8.50 (ddd, J = 8.5, 8.5, 2.0 Hz, 1H), 8.73 (dd, J = 4.9, 1.2 Hz, 1H), 8.81 (d, J = 2.0 Hz, 1H) |
| 113 | 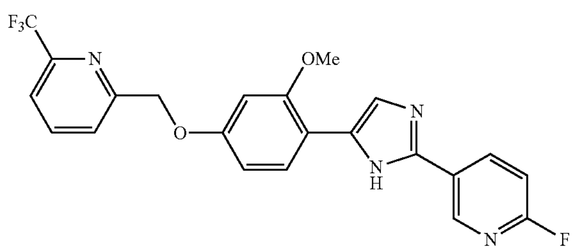 [SMILES: COc1cc(OCc2cccc(C(F)(F)F)n2)ccc1-c1cnc(-c2ccc(F)nc2)[nH]1] | | 1H-NMR (DMSO) δ 3.91 (s, 3H), 5.32 (s, 2H), 6.73 (d, J = 8.3 Hz, 1H), 6.81 (s, 1H), 7.30 (dd, J = 8.5, 2.7 Hz, 1H), 7.57 (s, 1H), 7.82-7.98 (m, 2H), 7.99-8.27 (m, 2H), 8.50 (ddd, J = 8.5, 8.5, 2.1 Hz, 1H), 8.82 (d, J = 2.1 Hz, 1H), 12.70 (s, 1H) |
| 114 | 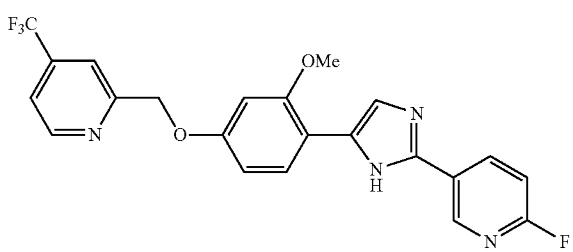 [SMILES: COc1cc(OCc2cc(C(F)(F)F)ccn2)ccc1-c1cnc(-c2ccc(F)nc2)[nH]1] | 183-186 | 1H-NMR (DMSO) δ 3.87-3.95 (3H), 5.34 (s, 2H), 6.75 (dd, J = 8.7, 2.1 Hz, 1H), 6.82 (d, J = 2.1 Hz, 1H), 7.29 (dd, J = 8.3, 2.5 Hz, 1H), 7.53 (s, 1H), 7.76 (d, J = 5.4 Hz, 1H), 7.90 (s, 1H), 8.02 (s, 1H), 8.51 (ddd, J = 8.3, 8.3, 2.5 Hz, 1H), 8.82 (d, J = 2.5 Hz, 1H), 8.89 (d, J = 5.4 Hz, 1H), 12.69 (s, 1H) |
| 115 | 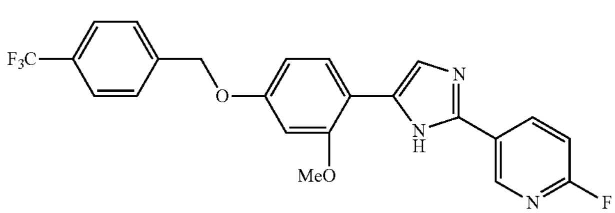 [SMILES: COc1cc(OCc2ccc(C(F)(F)F)cc2)ccc1-c1cnc(-c2ccc(F)nc2)[nH]1] | 125-135 | 1H-NMR (CDCL3) δ 3.97 (s, 3H), 5.16 (s, 2H), 6.58-6.69 (m, 2H), 7.00 (dd, J = 8.3, 2.9 Hz, 1H), 7.40-7.81 (m, 6H), 8.28-8.40 (m, 1H), 8.58-8.67 (m, 1H), 10.62 (s, 1H) |

TABLE 3-continued

| Example No. | Structure | Melting point (° C.) | 1H-NMR (δ:ppm) |
|---|---|---|---|
| 116 | 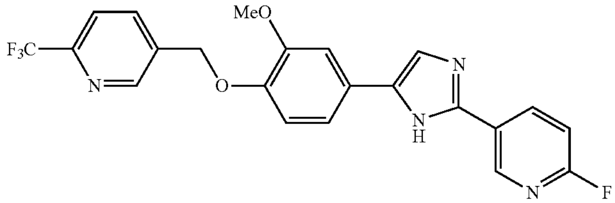 [SMILES: COc1cc(-c2cnc(-c3ccc(F)nc3)[nH]2)ccc1OCc1ccc(C(F)(F)F)nc1] | 144-146 | 1H-NMR (CDCL3) δ 3.96 (s, 3H), 5.25 (s, 2H), 6.92 (d, J = 8.3 Hz, 1H), 7.03 (dd, J = 8.5, 2.7 Hz, 1H), 7.31-7.58 (m, 2H), 7.70 (d, J = 8.3 Hz, 1H), 8.00 (d, J = 8.5 Hz, 1H), 8.39 (ddd, J = 8.5, 8.5, 2.4 Hz, 1H), 8.65 (d, J = 2.4 Hz, 1H), 8.80 (d, J = 2.4 Hz, 1H), 9.87 (s, 1H) |
| 117 | 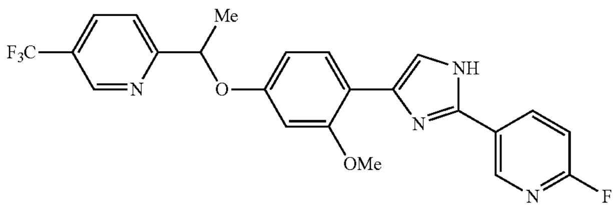 | Oil | 1H-NMR (CDCL3) δ 1.72 (d, J = 6.5 Hz, 3H), 3.94 (s, 3H), 5.52 (q, J = 6.5 Hz, 1H), 6.48 (dd, J = 8.5, 2.2 Hz, 1H), 6.52-6.73 (m, 1H), 7.00 (dd, J = 8.5, 2.7 Hz, 1H), 7.30-7.66 (m, 3H), 7.91 (d, J = 7.8 Hz, 1H), 8.22-8.43 (m, 1H), 8.51-8.69 (m, 1H), 8.78-8.93 (m, 1H), 10.51 (s, 1H) |
| 118 | 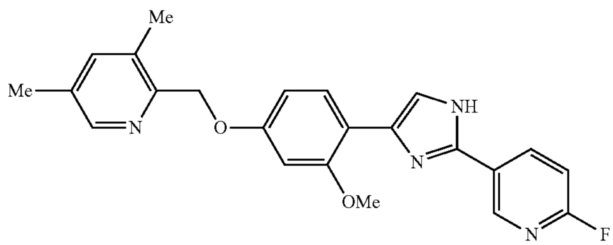 [SMILES: COc1cc(OCc2ncc(C)cc2C)ccc1-c1c[nH]c(-c2ccc(F)nc2)n1] | 219-223 Decomposition | 1H-NMR (CDCL3) δ 2.30 (s, 3H), 2.39 (s, 3H), 3.83 (s, 3H), 5.19 (s, 2H), 6.54-6.69 (m, 2H), 6.85-6.96 (m, 1H), 7.34 (s, 1H), 7.44 (s, 1H), 7.71 (s, 1H), 8.18-8.36 (m, 2H), 8.62 (d, J = 1.5 Hz, 1H) |
| 119 | 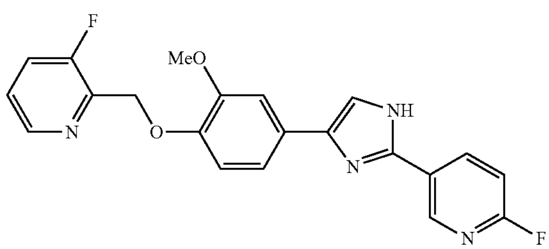 [SMILES: COc1cc(-c2c[nH]c(-c3ccc(F)nc3)n2)ccc1OCc1ncccc1F] | 68-79 | 1H-NMR (DMSO) δ 3.81 (s, 3H), 5.20 (s, 2H), 7.11 (d, J = 8.3 Hz, 1H), 7.31 (dd, J = 8.5, 2.7 Hz, 1H), 7.35 (d, J = 8.3 Hz, 1H), 7.43 (s, 1H), 7.49-7.58 (m, 1H), 7.71 (s, 1H), 7.79 (dd, J = 9.8, 8.8 Hz, 1H), 8.37-8.59 (m, 2H), 8.81 (d, J = 2.0 Hz, 1H), 12.73 (s, 1H) |
| 120 | 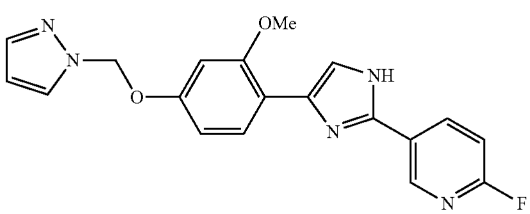 [SMILES: COc1cc(OCn2cccn2)ccc1-c1c[nH]c(-c2ccc(F)nc2)n1] | 172-175 | 1H-NMR (DMSO) δ 3.89 (s, 3H), 6.10 (s, 2H), 6.34 (dd, J = 2.0, 2.0 Hz, 1H), 6.75-6.89 (m, 2H), 7.30 (dd, J = 8.3, 2.4 Hz, 1H), 7.56-7.68 (m, 2H), 7.99 (d, J = 2.0 Hz, 1H), 8.07 (d, J = 8.3 Hz, 1H), 8.50 (ddd, J = 8.3, 8.3, 2.0 Hz, 1H), 8.81 (d, J = 2.0 Hz, 1H), 12.71 (s, 1H) |
| 121 | 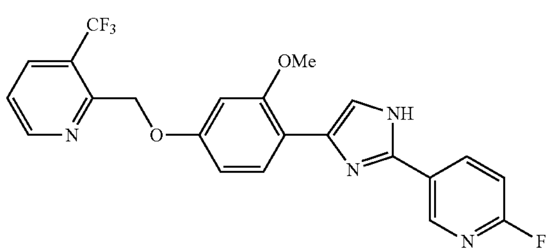 [SMILES: COc1cc(OCc2ncccc2C(F)(F)F)ccc1-c1c[nH]c(-c2ccc(F)nc2)n1] | 201-202 | 1H-NMR (DMSO) δ 3.88 (s, 3H), 5.32 (s, 2H), 6.64-6.79 (m, 2H), 7.30 (dd, J = 8.5, 2.7 Hz, 1H), 7.57 (s, 1H), 7.67 (dd, J = 8.0, 4.4 Hz, 1H), 8.07 (d, J = 5.9 Hz, 1H), 8.28 (d, J = 8.0 Hz, 1H), 8.50 (ddd, J = 8.5, 8.5, 1.6 Hz, 1H), 8.81 (s, 1H), 8.89 (d, J = 4.4 Hz, 1H), 12.70 (s, 1H) |

TABLE 3-continued

| Example No. | Structure | Melting point (° C.) | 1H-NMR (δ:ppm) |
|---|---|---|---|
| 122 | 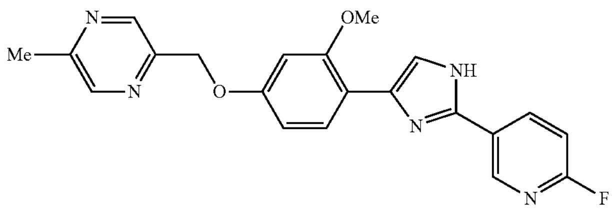 [SMILES: COc1cc(OCc2cnc(C)cn2)ccc1-c1c[nH]c(-c2ccc(F)nc2)n1] | 167-170 | 1H-NMR (CDCL3) δ 2.59 (s, 3H), 3.96 (s, 3H), 5.23 (s, 2H), 6.61-6.73 (m, 2H), 6.98 (dd, J = 8.8, 2.4 Hz, 1H), 7.39-7.74 (m, 2H), 8.23-8.39 (m, 1H), 8.46 (d, J = 1.0 Hz, 1H), 8.53-8.65 (m, 1H), 8.69 (d, J = 1.0 Hz, 1H), 10.70 (s, 1H) |
| 123 | 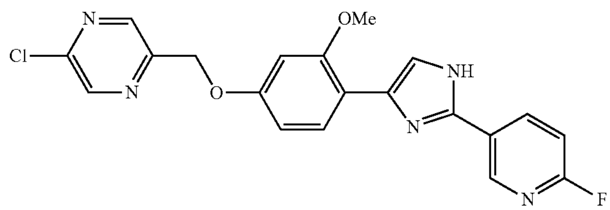 [SMILES: COc1cc(OCc2cnc(Cl)cn2)ccc1-c1c[nH]c(-c2ccc(F)nc2)n1] | 197-199 | 1H-NMR (DMSO) δ 3.91 (s, 3H), 5.31 (s, 2H), 6.64-6.91 (m, 2H), 7.30 (d, J = 8.8 Hz, 1H), 7.59 (s, 1H), 8.09 (d, J = 8.3 Hz, 1H), 8.40-8.60 (m, 1H), 8.69 (s, 1H), 8.76-8.88 (m, 2H), 12.70 (s, 1H) |
| 124 | 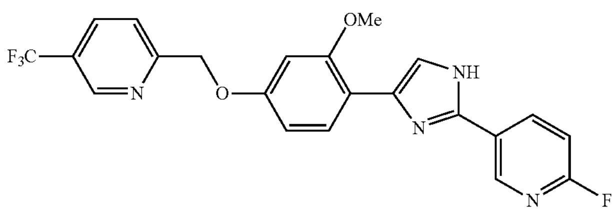 [SMILES: COc1cc(OCc2ccc(C(F)(F)F)cn2)ccc1-c1c[nH]c(-c2ccc(F)nc2)n1] | 141-144 | 1H-NMR (CDCL3) δ 3.98 (s, 3H), 5.31 (s, 2H), 6.65 (dd, J = 8.8, 2.4 Hz, 1H), 6.69 (d, J = 2.0 Hz, 1H), 7.01 (dd, J = 8.3, 2.9 Hz, 1H), 7.48 (s, 1H), 7.56-7.89 (m, 2H), 7.98 (dd, J = 8.3, 2.0 Hz, 1H), 8.34 (ddd, J = 8.3, 8.3, 2.0 Hz, 1H), 8.62 (d, J = 2.0 Hz, 1H), 8.88 (s, 1H), 10.57 (s, 1H) |
| 125 | 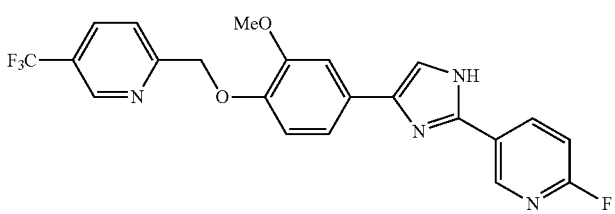 [SMILES: COc1cc(-c2c[nH]c(-c3ccc(F)nc3)n2)ccc1OCc1ccc(C(F)(F)F)cn1] | Oil | 1H-NMR (CDCL3) δ 4.00 (s, 3H), 5.36 (s, 2H), 6.89 (d, J = 8.3 Hz, 1H), 7.03 (dd, J = 8.3, 2.9 Hz, 1H), 7.22 (d, J = 8.3 Hz, 1H), 7.34 (s, 1H), 7.43 (s, 1H), 7.74 (d, J = 8.3 Hz, 1H), 7.95 (dd, J = 8.3, 2.0 Hz, 1H), 8.40 (ddd, J = 8.3, 8.3, 2.0 Hz, 1H), 8.65 (d, J = 2.0 Hz, 1H), 8.86 (d, J = 2.0 Hz, 1H) |
| 126 | 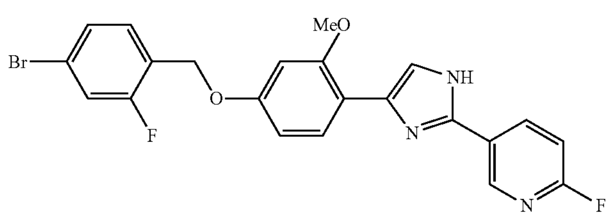 [SMILES: COc1cc(OCc2ccc(Br)cc2F)ccc1-c1c[nH]c(-c2ccc(F)nc2)n1] | 172-176 | 1H-NMR (DMSO) δ 3.94 (s, 3H), 5.15 (s, 2H), 6.67-6.83 (m, 2H), 7.30 (dd, J = 8.3, 2.7 Hz, 1H), 7.46 (d, J = 8.3 Hz, 1H), 7.52-7.72 (m, 3H), 8.08 (d, J = 8.3 Hz, 1H), 8.50 (ddd, J = 8.3, 8.3, 2.4 Hz, 1H), 8.81 (d, J = 2.4 Hz, 1H), 12.70 (s, 1H) |
| 127 | 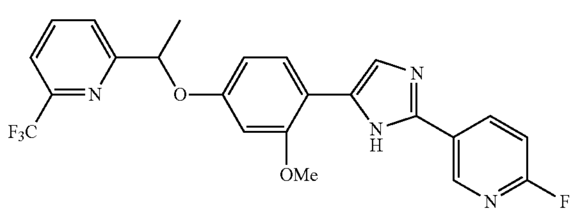 [SMILES: COc1cc(OC(C)c2cccc(C(F)(F)F)n2)ccc1-c1cnc(-c2ccc(F)nc2)[nH]1] | | 1H-NMR (CDCL3) δ 1.73 (d, J = 6.6 Hz, 3H), 3.92 (s, 3H), 5.54 (q, J = 6.6 Hz, 1H), 6.53 (dd, J = 8.5, 2.3 Hz, 1H), 6.62 (d, J = 2.3 Hz, 1H), 7.01 (dd, J = 8.7, 2.9 Hz, 1H), 7.43 (s, 1H), 7.54-7.71 (m, 3H), 7.85 (dd, J = 7.9, 7.9 Hz, 1H), 8.32 (ddd, J = 8.7, 8.7, 2.5 Hz, 1H), 8.59 (d, J = 2.5 Hz, 1H) |

TABLE 3-continued

| Example No. | Structure | Melting point (° C.) | 1H-NMR (δ:ppm) |
|---|---|---|---|
| 128 | 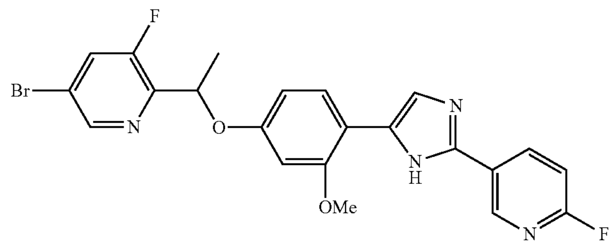 [SMILES: COc1cc(OC(C)c2ncc(Br)cc2F)ccc1-c1cnc(-c2ccc(F)nc2)[nH]1] | | 1H-NMR (CDCL3) δ 1.76 (d, J = 6.3 Hz, 3H), 3.95 (s, 3H), 5.71 (q, J = 6.3 Hz, 1H), 6.55 (dd, J = 8.3, 1.5 Hz, 1H), 6.67 (s, 1H), 7.01 (dd, J = 8.3, 2.4 Hz, 1H), 7.39 (s, 1H), 7.49 (d, J = 8.3 Hz, 1H), 7.60 (d, J = 8.3 Hz, 1H), 8.21-8.42 (m, 1H), 8.51 (s, 1H), 8.59 (s, 1H), 10.51 (s, 1H) |
| 129 | 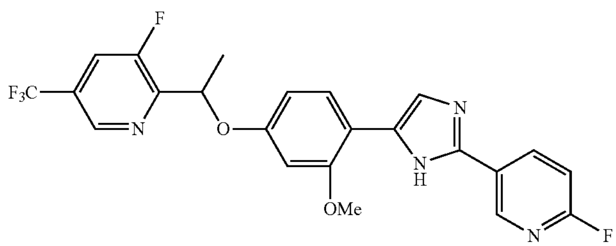 [SMILES: COc1cc(OC(C)c2ncc(C(F)(F)F)cc2F)ccc1-c1cnc(-c2ccc(F)nc2)[nH]1] | | 1H-NMR (CDCL3) δ 1.79 (d, J = 6.3 Hz, 3H), 3.95 (s, 3H), 5.80 (q, J = 6.3 Hz, 1H), 6.54 (dd, J = 8.5, 2.2 Hz, 1H), 6.68 (s, 1H), 7.01 (dd, J = 8.3, 2.4 Hz, 1H), 7.40 (s, 1H), 7.45-7.56 (m, 1H), 7.66 (d, J = 9.3 Hz, 1H), 8.22-8.42 (m, 1H), 8.59 (s, 1H), 8.71 (s, 1H), 10.51 (s, 1H) |
| 130 | 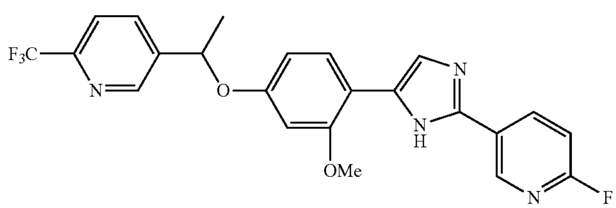 [SMILES: COc1cc(OC(C)c2ccc(C(F)(F)F)nc2)ccc1-c1cnc(-c2ccc(F)nc2)[nH]1] | 72-105 | 1H-NMR (CDCL3) δ 1.71 (d, J = 6.8 Hz, 3H), 3.95 (s, 3H), 5.51 (q, J = 6.8 Hz, 1H), 6.47 (dd, J = 8.3, 2.0 Hz, 1H), 6.60 (s, 1H), 7.01 (dd, J = 8.8, 2.4 Hz, 1H), 7.32-7.62 (m, 2H), 7.68 (d, J = 8.3 Hz, 1H), 7.91 (d, J = 8.3 Hz, 1H), 8.22-8.43 (m, 1H), 8.60 (s, 1H), 8.69-8.85 (m, 1H), 10.52 (s, 1H) |
| 131 | 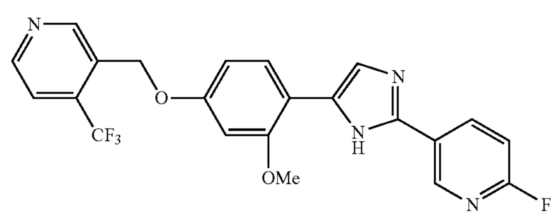 [SMILES: COc1cc(OCc2cnccc2C(F)(F)F)ccc1-c1cnc(-c2ccc(F)nc2)[nH]1] | 178-180 | 1H-NMR (DMSO) δ 3.90 (s, 3H), 5.32 (s, 2H), 6.69-6.82 (m, 2H), 7.30 (dd, J = 8.5, 2.7 Hz, 1H), 7.55 (s, 1H), 7.82 (d, J = 5.4 Hz, 1H), 8.05 (s, 0H), 8.51 (ddd, J = 8.5, 8.5, 2.4 Hz, 1H), 8.82 (d, J = 2.4 Hz, 1H), 8.87 (d, J = 5.4 Hz, 1H), 9.04 (s, 1H), 12.66 (s, 1H) |
| 132 | 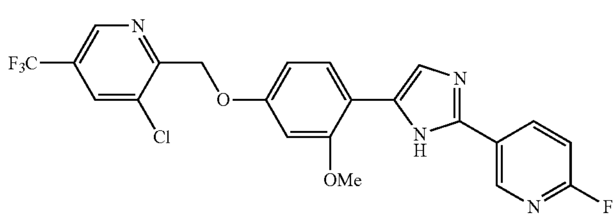 [SMILES: COc1cc(OCc2ncc(C(F)(F)F)cc2Cl)ccc1-c1cnc(-c2ccc(F)nc2)[nH]1] | 185-187 | 1H-NMR (DMSO) δ 3.89 (s, 3H), 5.39 (s, 2H), 6.71 (dd, J = 8.5, 2.2 Hz, 1H), 6.75 (d, J = 2.2 Hz, 1H), 7.30 (dd, J = 8.8, 2.4 Hz, 1H), 7.53 (s, 1H), 8.01 (s, 1H), 8.50 (ddd, J = 8.8, 8.8, 2.3 Hz, 1H), 8.55 (s, 1H), 8.81 (s, 1H), 8.98 (s, 1H) |
| 133 | 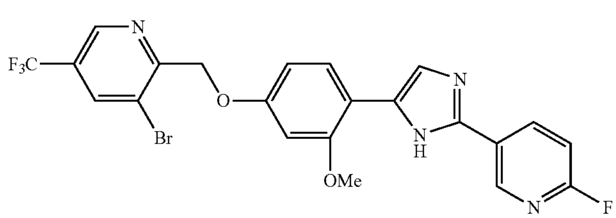 [SMILES: COc1cc(OCc2ncc(C(F)(F)F)cc2Br)ccc1-c1cnc(-c2ccc(F)nc2)[nH]1] | 153-170 | 1H-NMR (DMSO) δ 3.90 (s, 3H), 5.37 (s, 2H), 6.66-6.81 (m, 2H), 7.30 (dd, J = 8.5, 2.7 Hz, 1H), 7.55 (s, 1H), 8.06 (s, 1H), 8.50 (ddd, J = 8.5, 8.5, 2.3 Hz, 1H), 8.66 (d, J = 1.7 Hz, 1H), 8.82 (d, J = 2.3 Hz, 1H), 9.01 (d, J = 1.7 Hz, 1H), 12.68 (s, 1H) |

TABLE 3-continued

| Example No. | Structure | Melting point (° C.) | 1H-NMR (δ:ppm) |
|---|---|---|---|
| 134 | 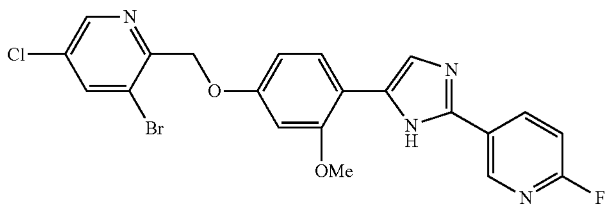 [SMILES: COc1cc(OCc2ncc(Cl)cc2Br)ccc1-c1cnc(-c2ccc(F)nc2)[nH]1] | 176-180 | 1H-NMR (DMSO) δ 3.90 (s, 3H), 5.26 (s, 2H), 6.65-6.83 (m, 2H), 7.30 (dd, J = 8.5, 2.7 Hz, 1H), 7.58 (s, 1H), 8.07 (d, J = 8.3 Hz, 1H), 8.43 (d, J = 2.4 Hz, 1H), 8.50 (ddd, J = 8.5, 8.5, 2.0 Hz, 1H), 8.68 (d, J = 2.4 Hz, 1H), 8.82 (d, J = 2.0 Hz, 1H), 12.69 (s, 1H) |
| 135 | 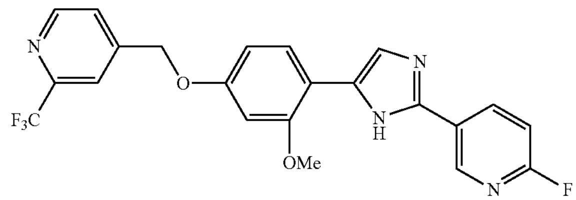 [SMILES: COc1cc(OCc2ccnc(C(F)(F)F)c2)ccc1-c1cnc(-c2ccc(F)nc2)[nH]1] | 212-244 | 1H-NMR (CDCL3) δ 3.95 (s, 3H), 5.16 (s, 2H), 6.55-6.71 (m, 2H), 6.86-7.04 (m, 1H), 7.43-7.62 (m, 2H), 7.70-7.85 (m, 1H), 7.96-8.01 (m, 1H), 8.37 (s, 1H), 8.60-8.80 (m, 2H), 11.77 (s, 1H) |
| 136 | 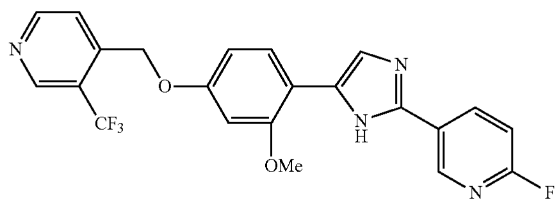 [SMILES: COc1cc(OCc2ccncc2C(F)(F)F)ccc1-c1cnc(-c2ccc(F)nc2)[nH]1] | 181-192 | 1H-NMR (DMSO) δ 3.90 (s, 3H), 5.36 (s, 2H), 6.69 (dd, J = 8.5, 2.2 Hz, 1H), 6.76 (d, J = 2.2 Hz, 1H), 7.30 (dd, J = 8.8, 2.4 Hz, 1H), 7.56 (s, 1H), 7.83 (d, J = 4.9 Hz, 1H), 8.11 (s, 1H), 8.50 (ddd, J = 8.8, 8.8, 2.0 Hz, 1H), 8.81 (d, J = 2.0 Hz, 1H), 8.91 (d, J = 4.9 Hz, 1H), 8.97 (s, 1H) |
| 137 | 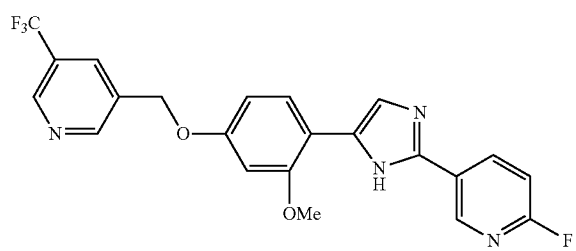 [SMILES: COc1cc(OCc2cncc(C(F)(F)F)c2)ccc1-c1cnc(-c2ccc(F)nc2)[nH]1] | 210-212 Decomposition | 1H-NMR (DMSO) δ 3.91 (s, 3H), 5.31 (s, 2H), 6.69-6.85 (m, 2H), 7.30 (dd, J = 8.5, 2.7 Hz, 1H), 7.57 (s, 1H), 8.08 (s, 1H), 8.26-8.40 (m, 1H), 8.51 (ddd, J = 8.5, 8.5, 2.4 Hz, 1H), 8.82 (d, J = 2.4 Hz, 1H), 8.97 (d, J = 1.5 Hz, 1H), 9.01 (d, J = 1.5 Hz, 1H), 12.70 (s, 1H) |
| 138 | 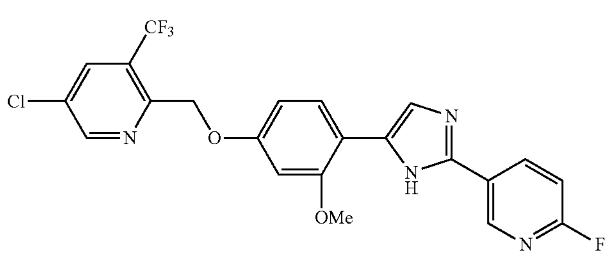 | Amorphous | 1H-NMR (CDCL3) δ 3.95 (s, 3H), 5.35 (s, 2H), 6.58-6.73 (m, 2H), 6.99 (dd, J = 8.5, 2.7 Hz, 1H), 7.35-7.74 (m, 2H), 8.03 (d, J = 2.1 Hz, 1H), 8.22-8.40 (m, 1H), 8.52-8.70 (m, 1H), 8.77 (d, J = 2.7 Hz, 1H), 10.66 (s, 1H) |
| 139 | 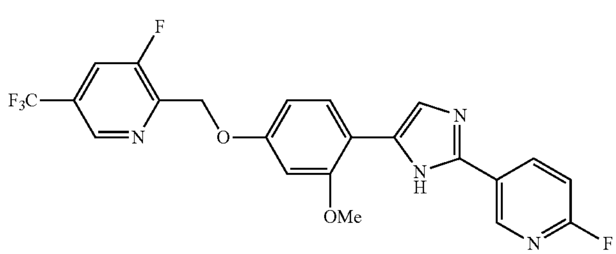 | >230 | 1H-NMR (CDCL3) δ 3.97 (s, 3H), 5.36 (d, J = 1.0 Hz, 2H), 6.66-6.77 (m, 2H), 7.02 (dd, J = 8.8, 2.9 Hz, 1H), 7.48 (s, 1H), 7.57-7.89 (m, 2H), 8.30-8.42 (m, 1H), 8.58-8.68 (m, 1H), 8.71-8.80 (m, 1H), 10.58 (s, 1H) |

TABLE 3-continued

| Example No. | Structure | Melting point (° C.) | 1H-NMR (δ:ppm) |
|---|---|---|---|
| 140 | 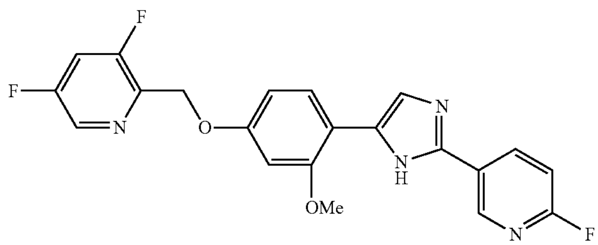 [SMILES: COc1cc(OCc2ncc(F)cc2F)ccc1-c1cnc(-c2ccc(F)nc2)[nH]1] | 188-191 | 1H-NMR (DMSO) δ 3.89 (s, 3H), 5.24 (s, 2H), 6.68-6.78 (m, 2H), 7.30 (dd, J = 8.7, 2.5 Hz, 1H), 7.54 (s, 1H), 8.03 (ddd, J = 9.5, 9.5, 2.5 Hz, 2H), 8.50 (ddd, J = 8.7, 8.7, 2.1 Hz, 1H), 8.56 (d, J = 2.5 Hz, 1H), 8.82 (d, J = 2.1 Hz, 1H), 12.66 (s, 1H) |
| 141 | 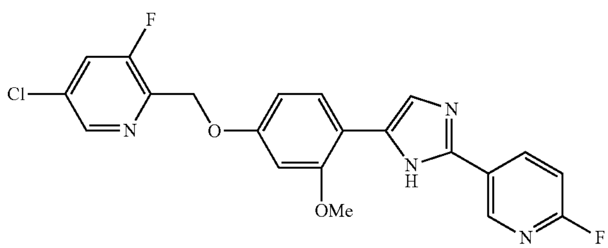 [SMILES: COc1cc(OCc2ncc(Cl)cc2F)ccc1-c1cnc(-c2ccc(F)nc2)[nH]1] | 174-176 | 1H-NMR (CDCL3) δ 3.98 (s, 3H), 5.27 (d, J = 2.1 Hz, 2H), 6.66-6.77 (m, 2H), 7.02 (dd, J = 8.3, 2.5 Hz, 1H), 7.41-7.49 (m, 1H), 7.52 (dd, J = 8.9, 2.1 Hz, 1H), 7.56-7.67 (m, 1H), 8.27-8.41 (m, 1H), 8.46 (dd, J = 2.1, 0.8 Hz, 1H), 8.54-8.70 (m, 1H), 10.54 (s, 1H) |
| 142 | 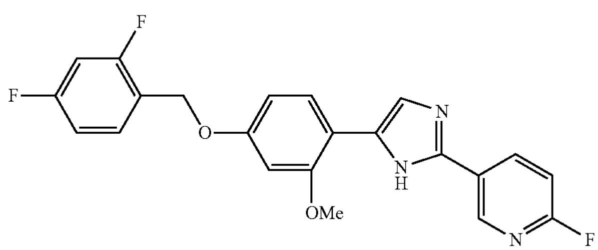 [SMILES: COc1cc(OCc2ccc(F)cc2F)ccc1-c1cnc(-c2ccc(F)nc2)[nH]1] | 168-173 | 1H-NMR (DMSO) δ 3.90 (s, 3H), 5.14 (s, 2H), 6.66-6.81 (m, 2H), 7.14 (ddd, J = 8.3, 8.3, 2.4 Hz, 1H), 7.22-7.40 (m, 2H), 7.49-7.75 (m, 2H), 8.08 (s, 1H), 8.51 (ddd, J = 8.2, 8.2, 2.4 Hz, 1H), 8.82 (d, J = 2.4 Hz, 1H), 12.66 (s, 1H) |
| 143 | 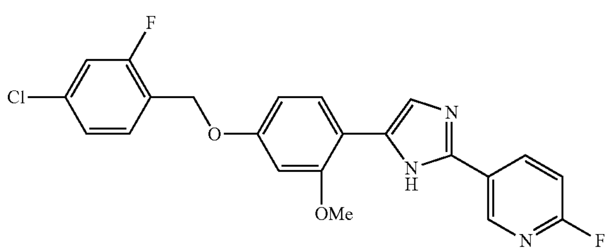 | 178-180 | 1H-NMR (DMSO) δ 3.91 (s, 3H), 5.16 (s, 2H), 6.65-6.86 (m, 2H), 7.30 (dd, J = 8.5, 2.7 Hz, 1H), 7.34 (dd, J = 8.3, 2.0 Hz, 1H), 7.50 (dd, J = 10.2, 2.0 Hz, 1H), 7.55-7.75 (m, 2H), 8.08 (d, J = 8.3 Hz, 1H), 8.41-8.60 (m, 1H), 8.82 (s, 1H), 12.70 (s, 1H) |
| 144 | 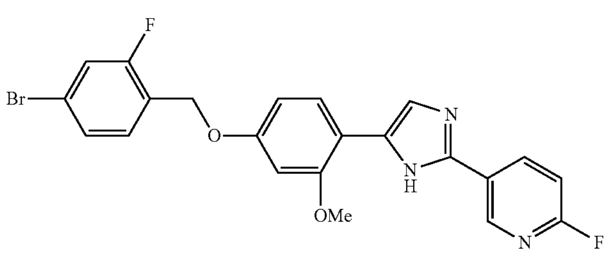 [SMILES: COc1cc(OCc2ccc(Cl)cc2F)ccc1-c1cnc(-c2ccc(F)nc2)[nH]1] | 177-180 | 1H-NMR (DMSO) δ 3.90 (s, 3H), 5.15 (s, 2H), 6.65-6.82 (m, 2H), 7.30 (dd, J = 8.3, 2.4 Hz, 1H), 7.47 (dd, J = 8.3, 1.5 Hz, 1H), 7.51-7.70 (m, 3H), 8.08 (d, J = 8.3 Hz, 1H), 8.41-8.60 (m, 1H), 8.82 (s, 1H), 12.70 (s, 1H) |
| 145 | 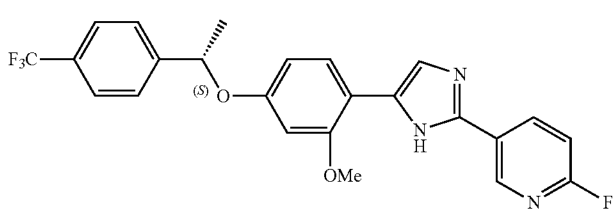 | | 1H-NMR (CDCL3) δ 1.67 (d, J = 6.3 Hz, 4H), 3.93 (s, 3H), 5.40 (q, J = 6.3 Hz, 1H), 6.46 (dd, J = 8.8, 2.0 Hz, 1H), 6.58 (s, 1H), 7.00 (dd, J = 8.5, 2.7 Hz, 1H), 7.32-7.72 (m, 6H), 8.22-8.41 (m, 1H), 8.59 (s, 1H), 10.51 (s, 1H) |

TABLE 3-continued

| Example No. | Structure | Melting point (° C.) | 1H-NMR (δ:ppm) |
|---|---|---|---|
| 146 | 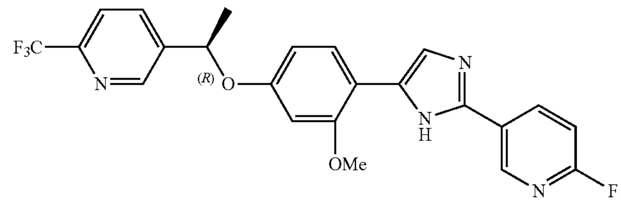 | Amorphous | 1H-NMR (CDCL3) δ 1.72 (d, J = 6.5 Hz, 3H), 3.93 (s, 3H), 5.52 (q, J = 6.5 Hz, 1H), 6.50 (dd, J = 8.8, 2.4 Hz, 1H), 6.62 (d, J = 2.4 Hz, 1H), 7.01 (dd, J = 8.5, 2.7 Hz, 1H), 7.69 (d, J = 8.3 Hz, 1H), 7.87-7.99 (m, 2H), 8.30 (ddd, J = 9.2, 8.5, 1.5 Hz, 1H), 8.57 (s, 1H), 8.77 (d, J = 1.5 Hz, 1H), 10.51 (s, 1H |
| 147 | 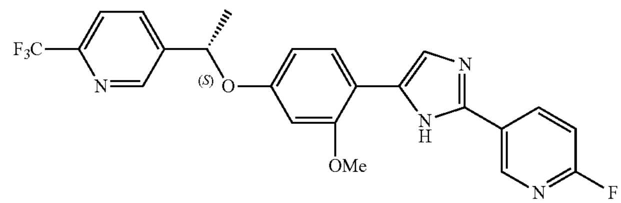 | | 1H-NMR (CDCL3) δ 1.72 (d, J = 6.8 Hz, 3H), 3.96 (s, 3H), 5.51 (q, J = 6.8 Hz, 1H), 6.47 (dd, J = 8.8, 2.0 Hz, 1H), 6.60 (s, 1H), 7.01 (dd, J = 8.5, 2.7 Hz, 1H), 7.32-7.63 (m, 2H), 7.68 (d, J = 7.8 Hz, 1H), 7.91 (dd, J = 8.3, 2.0 Hz, 1H), 8.22-8.43 (m, 1H), 8.60 (s, 1H), 8.77 (d, J = 1.5 Hz, 1H), 10.50 (s, 1H) |
| 148 | 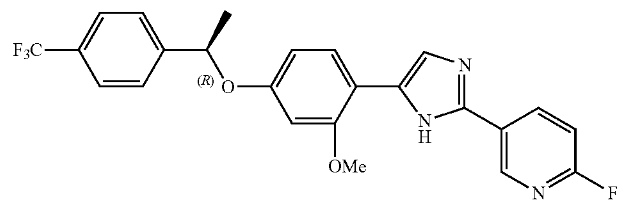 | | 1H-NMR (CDCL3) δ 1.67 (d, J = 6.3 Hz, 3H), 3.94 (s, 3H), 5.40 (q, J = 6.3 Hz, 1H), 6.46 (dd, J = 8.8, 1.5 Hz, 1H), 6.58 (s, 1H), 7.01 (dd, J = 8.5, 2.2 Hz, 1H), 7.33-7.68 (m, 6H), 8.21-8.42 (m, 1H), 8.59 (s, 1H), 10.50 (s, 1H) |
| 149 | 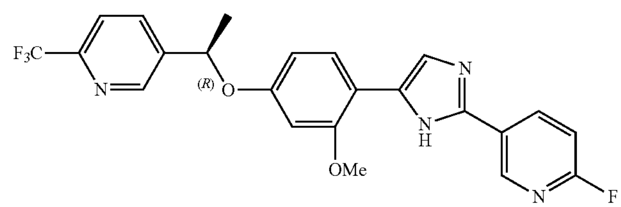 | Amorphous | 1H-NMR (CDCL3) δ 1.71 (d, J = 6.8 Hz, 3H), 3.91 (s, 3H), 5.50 (q, J = 6.8 Hz, 1H), 6.45 (dd, J = 8.5, 2.2 Hz, 1H), 6.58 (d, J = 2.0 Hz, 1H), 6.96 (dd, J = 8.5, 2.7 Hz, 1H), 7.44 (s, 1H), 7.52-7.84 (m, 2H), 7.91 (dd, J = 8.0, 1.7 Hz, 1H), 8.30 (ddd, J = 8.5, 8.5, 1.5 Hz, 1H), 8.60 (s, 1H), 8.76 (d, J = 1.5 Hz, 1H) |
| 150 | 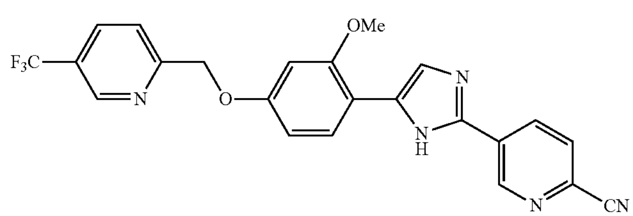 [SMILES: COc1cc(OCc2ccc(C(F)(F)F)cn2)ccc1-c1cnc(-c2ccc(C#N)nc2)[nH]1] | 241-244 Decomposition | 1H-NMR (DMSO) δ 3.92 (s, 3H), 5.35 (s, 2H), 6.72 (dd, J = 8.5, 2.2 Hz, 1H), 6.79 (d, J = 2.2 Hz, 1H), 7.70 (s, 1H), 7.79 (d, J = 8.3 Hz, 1H), 8.07-8.14 (m, 2H), 8.27 (dd, J = 8.3, 2.0 Hz, 1H), 8.49 (dd, J = 8.3, 2.2 Hz, 1H), 8.99 (s, 1H), 9.32 (d, J = 2.2 Hz, 1H), 13.04 (s, 1H) |
| 151 | 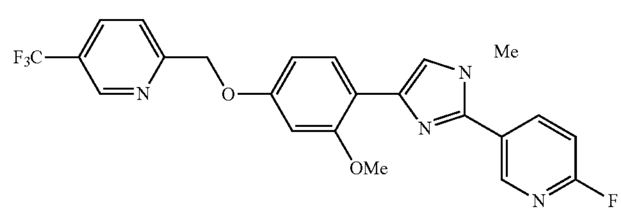 [SMILES: COc1cc(OCc2ccc(C(F)(F)F)cn2)ccc1-c1c[nH]c(-c2ccc(F)nc2)n1 ; "Me"] | 168-171 | 1H-NMR (CDCL3) δ 3.78 (s, 3H), 3.95 (s, 3H), 5.31 (s, 2H), 6.56-6.77 (m, 2H), 7.05 (dd, J = 8.0, 2.7 Hz, 1H), 7.50 (s, 1H), 7.71 (d, J = 8.3 Hz, 1H), 7.96 (dd, J = 8.3, 2.0 Hz, 1H), 8.08-8.26 (m, 2H), 8.52 (d, J = 2.4 Hz, 1H), 8.87 (s, 1H) |

TABLE 3-continued

| Example No. | Structure | Melting point (° C.) | 1H-NMR (δ:ppm) |
|---|---|---|---|
| 152 | 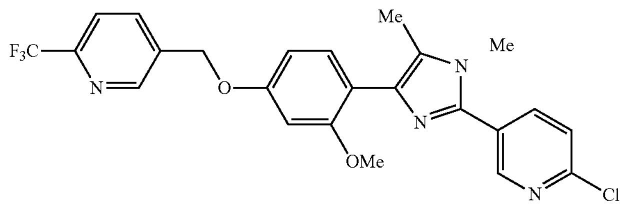 [SMILES: COc1cc(OCc2ccc(C(F)(F)F)nc2)ccc1-c1nc(-c2ccc(Cl)nc2)[nH]c1C ; "Me"] | 185-188 | 1H-NMR (DMSO) δ 2.11 (s, 3H), 3.64 (s, 3H), 3.76 (s, 3H), 5.33 (s, 2H), 6.68 (dd, J = 8.3, 2.4 Hz, 1H), 6.75 (d, J = 2.4 Hz, 1H), 7.28 (d, J = 8.3 Hz, 1H), 7.62 (d, J = 8.3 Hz, 1H), 7.96 (d, J = 8.3 Hz, 1H), 8.12 (dd, J = 8.3, 2.4 Hz, 1H), 8.19 (d, J = 8.3, 2.0 Hz, 1H), 8.69 (d, J = 2.4 Hz, 1H), 8.89 (d, J = 2.0 Hz, 1H) |
| 153 | 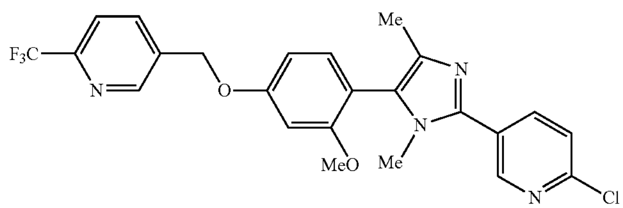 [SMILES: COc1cc(OCc2ccc(C(F)(F)F)nc2)ccc1-c1c(C)nc(-c2ccc(Cl)nc2)n1C] | 148-150 | 1H-NMR (DMSO) δ 2.01 (s, 3H), 3.42 (s, 3H), 3.79 (s, 3H), 5.36 (s, 2H), 6.77 (dd, J = 8.5, 2.4 Hz, 1H), 6.85 (d, J = 2.4 Hz, 1H), 7.19 (d, J = 8.3 Hz, 1H), 7.61 (d, J = 8.3 Hz, 1H), 7.98 (d, J = 8.5 Hz, 1H), 8.17 (dd, J = 8.3, 2.4 Hz, 1H), 8.21 (dd, J = 8.3, 1.6 Hz, 1H), 8.74 (d, J = 2.4 Hz, 1H), 8.91 (d, J = 1.6 Hz, 1H) |
| 154 | 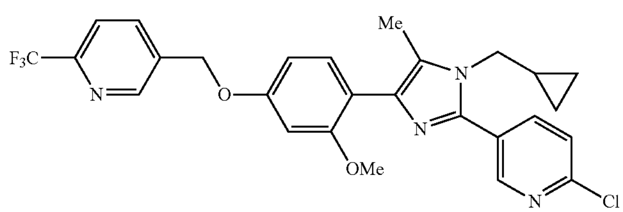 | 110-112 | 1H-NMR (CDCL3) δ 0.07-0.22 (m, 2H), 0.47-0.63 (m, 2H), 0.98-1.10 (m, 1H), 2.26 (s, 3H), 3.82 (s, 3H), 3.88 (d, J = 6.3 Hz, 2H), 5.19 (s, 2H), 6.52-6.70 (m, 2H), 7.33-7.52 (m, 2H), 7.73 (d, J = 7.8 Hz, 1H), 7.89-8.08 (m, 2H), 8.67 (d, J = 2.4 Hz, 1H), 8.74-8.89 (m, 1H) |
| 155 | 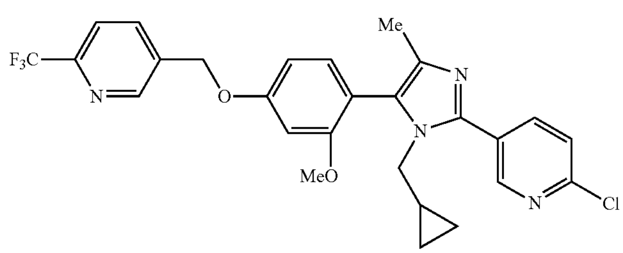 [SMILES: COc1cc(OCc2ccc(C(F)(F)F)nc2)ccc1-c1c(C)nc(-c2ccc(Cl)nc2)n1CC1CC1] | 164-166 | 1H-NMR (CDCL3) δ -0.42--0.14 (m, 2H), 0.13-0.39 (m, 2H), 0.58-0.82 (m, 1H), 2.16 (s, 3H), 3.52-3.68 (m, 1H), 3.76-3.88 (m, 4H), 5.23 (s, 2H), 6.58-6.78 (m, 2H), 7.15-7.24 (m, 1H), 7.43 (d, J = 8.3 Hz, 1H), 7.76 (d, J = 7.8 Hz, 1H), 7.91-8.17 (m, 2H), 8.69 (d, J = 2.4 Hz, 1H), 8.78-8.98 (m, 1H) |
| 156 | 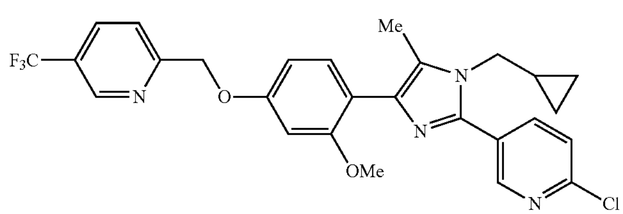 | Oil | 1H-NMR (CDCL3) δ 0.10-0.22 (m, 2H), 0.53-0.64 (m, 2H), 0.99-1.13 (m, 1H), 2.25 (s, 3H), 3.83 (s, 3H), 3.88 (d, J = 6.3 Hz, 2H), 5.31 (s, 2H), 6.61 (dd, J = 8.5, 2.4 Hz, 1H), 6.66 (d, J = 2.4 Hz, 1H), 7.35-7.45 (m, 2H), 7.71 (d, J = 8.5 Hz, 1H), 7.88-8.08 (m, 2H), 8.67 (d, J = 2.4 Hz, 1H), 8.84-8.91 (m, 1H) |

TABLE 3-continued

| Example No. | Structure | Melting point (° C.) | 1H-NMR (δ:ppm) |
|---|---|---|---|
| 157 | 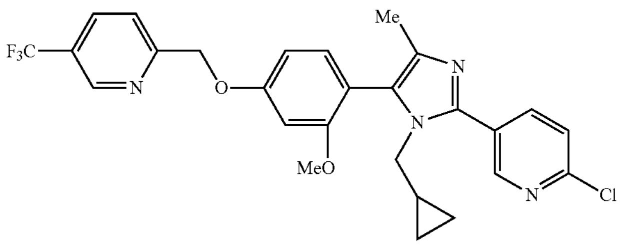 [SMILES: COc1cc(OCc2ccc(C(F)(F)F)cn2)ccc1-c1c(C)nc(-c2ccc(Cl)nc2)n1CC1CC1] | 145-148 | 1H-NMR (DMSO) δ -0.45--0.25 (m, 2H), 0.06-0.24 (m, 2H), 0.52-0.71 (m, 1H), 1.98 (s, 3H), 3.52-3.62 (m, 1H), 3.76-3.90 (m, 4H), 5.38 (s, 2H), 6.76 (dd, J = 8.3, 2.0 Hz, 1H), 6.87 (d, J = 2.0 Hz, 1H), 7.18 (d, J = 8.5 Hz, 1H), 7.62 (d, J = 8.3 Hz, 1H), 7.82 (d, J = 7.8 Hz, 1H), 8.14 (dd, J = 8.5, 2.4 Hz, 1H), 8.30 (dd, J = 7.8, 2.2 Hz, 1H), 8.70 (d, J = 2.4 Hz, 1H), 8.96-9.08 (m, 1H) |
| 158 | 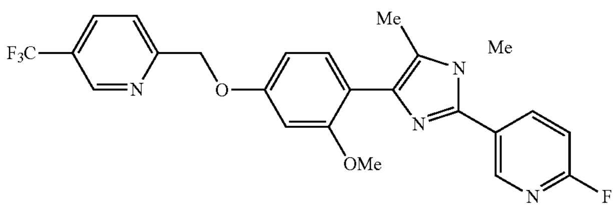 [SMILES: COc1cc(OCc2ccc(C(F)(F)F)cn2)ccc1-c1nc(-c2ccc(F)nc2)[nH]c1C ; "Me"] | 166-169 | 1H-NMR (CDCL3) δ 2.23 (s, 3H), 3.64 (s, 3H), 3.83 (s, 3H), 5.31 (s, 2H), 6.60 (dd, J = 8.8, 2.4 Hz, 1H), 6.65 (d, J = 2.0 Hz, 1H), 7.02 (dd, J = 8.5, 2.7 Hz, 1H), 7.38 (d, J = 8.8 Hz, 1H), 7.71 (d, J = 8.3 Hz, 1H), 7.97 (dd, J = 8.3, 2.0 Hz, 1H), 8.12 (ddd, J = 8.5, 8.5, 2.4 Hz, 1H), 8.47 (d, J = 2.4 Hz, 1H), 8.87 (s, 1H), 10.15 (s, 0H) |
| 159 | 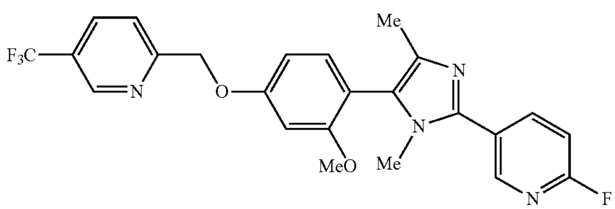 | 136-138 | 1H-NMR (CDCL3) δ 2.18 (s, 3H), 3.45 (s, 3H), 3.84 (s, 3H), 5.33 (s, 2H), 6.65 (dd, J = 8.5, 2.4 Hz, 1H), 6.72 (d, J = 2.4 Hz, 1H), 7.04 (dd, J = 8.8, 2.9 Hz, 1H), 7.16 (d, J = 8.5 Hz, 1H), 7.74 (d, J = 8.3 Hz, 1H), 8.01 (dd, J = 8.3, 2.0 Hz, 1H), 8.17 (ddd, J = 8.8, 8.8, 2.4 Hz, 1H), 8.52 (d, J = 2.4 Hz, 1H), 8.82-8.97 (m, 1H) |
| 160 | 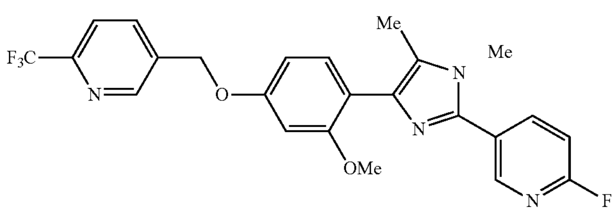 | 176-178 | 1H-NMR (DMSO) δ 2.13 (s, 3H), 3.63 (s, 3H), 3.78 (s, 3H), 5.34 (s, 2H), 6.69 (dd, J = 8.3, 2.0 Hz, 1H), 6.77 (d, J = 2.0 Hz, 1H), 7.26-7.35 (m, 2H), 7.97 (d, J = 8.3 Hz, 1H), 8.20 (d, J = 8.3 Hz, 1H), 8.26 (ddd, J = 8.3, 8.3, 2.0 Hz, 1H), 8.52 (d, J = 2.0 Hz, 1H), 8.87-8.95 (m, 1H) |
| 161 | 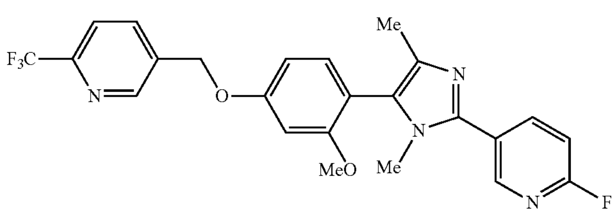 | 123-126 | 1H-NMR (DMSO) δ 2.01 (s, 3H), 3.40 (s, 3H), 3.81 (s, 3H), 5.36 (s, 2H), 6.77 (dd, J = 8.3, 2.4 Hz, 1H), 6.85 (d, J = 2.4 Hz, 1H), 7.19 (d, J = 8.3 Hz, 1H), 7.30 (dd, J = 8.3, 2.4 Hz, 1H), 7.98 (d, J = 8.3 Hz, 1H), 8.21 (d, J = 8.3 Hz, 1H), 8.30 (ddd, J = 8.3, 8.3, 2.4 Hz, 1H), 8.56 (s, 1H), 8.91 (s, 1H) |

TABLE 3-continued

| Example No. | Structure | Melting point (° C.) | 1H-NMR (δ:ppm) |
|---|---|---|---|
| 162 | 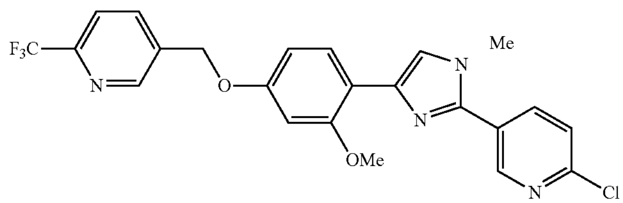 [SMILES: COc1cc(OCc2ccc(C(F)(F)F)nc2)ccc1-c1c[nH]c(-c2ccc(Cl)nc2)n1 ; "Me"] | 170-176 Decomposition | 1H-NMR (CDCL3) δ 3.80 (s, 3H), 3.95 (s, 3H), 5.20 (s, 2H), 6.62 (d, J = 2.3 Hz, 1H), 6.66 (dd, J = 8.5, 2.3 Hz, 1H), 7.44 (d, J = 8.3 Hz, 1H), 7.73 (d, J = 8.5 Hz, 1H), 7.96-8.03 (m, 1H), 8.05 (dd, J = 8.3, 2.3 Hz, 1H), 8.16 (d, J = 8.5 Hz, 1H), 8.71 (d, J = 2.3 Hz, 1H), 8.78-8.86 (m, 1H) |
| 163 | 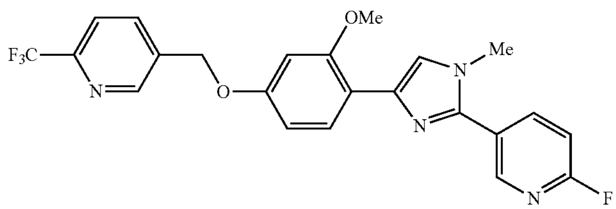 [SMILES: COc1cc(OCc2ccc(C(F)(F)F)nc2)ccc1-c1cn(C)c(-c2ccc(F)nc2)n1] | 163-165 | 1H-NMR (CDCL3) δ 3.79 (s, 3H), 3.95 (s, 3H), 5.20 (s, 2H), 6.62 (d, J = 2.4 Hz, 1H), 6.66 (dd, J = 8.3, 2.4 Hz, 1H), 7.05 (dd, J = 8.5, 3.2 Hz, 1H), 7.51 (s, 1H), 7.72 (d, J = 8.3 Hz, 1H), 7.99 (dd, J = 7.8, 1.5 Hz, 1H), 8.13-8.23 (m, 2H), 8.53 (d, J = 2.4 Hz, 1H), 8.82 (d, J = 1.5 Hz, 1H) |
| 164 | 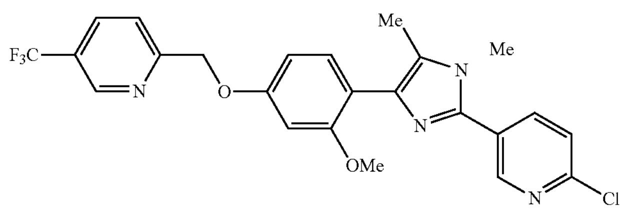 [SMILES: COc1cc(OCc2ccc(C(F)(F)F)cn2)ccc1-c1nc(-c2ccc(Cl)nc2)[nH]c1C ; "Me"] | 133-141 | 1H-NMR (CDCL3) δ 2.23 (s, 3H), 3.65 (s, 3H), 3.83 (s, 3H), 5.31 (s, 2H), 6.60 (dd, J = 8.3, 2.4 Hz, 1H), 6.65 (d, J = 2.4 Hz, 1H), 7.35-7.44 (m, 2H), 7.70 (d, J = 8.3 Hz, 1H), 7.93-8.04 (m, 2H), 8.65 (d, J = 2.4 Hz, 1H), 8.87 (s, 1H) |
| 165 | 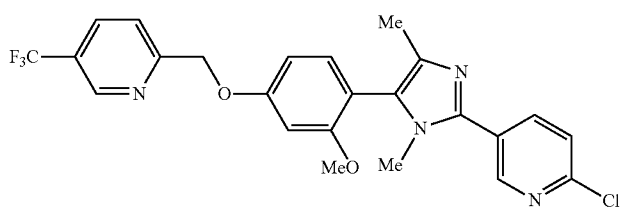 [SMILES: COc1cc(OCc2ccc(C(F)(F)F)cn2)ccc1-c1c(C)nc(-c2ccc(Cl)nc2)n1C] | 152-154 | 1H-NMR (CDCL3) δ 2.16 (s, 3H), 3.45 (s, 3H), 3.81 (s, 3H), 5.31 (s, 2H), 6.63 (dd, J = 8.3, 2.4 Hz, 1H), 6.70 (d, J = 2.4 Hz, 1H), 7.14 (d, J = 8.3 Hz, 1H), 7.39 (d, J = 8.3 Hz, 1H), 7.72 (d, J = 8.3 Hz, 1H), 7.95-8.06 (m, 2H), 8.68 (d, J = 2.4 Hz, 1H), 8.87 (d, J = 1.0 Hz, 1H |
| 166 | 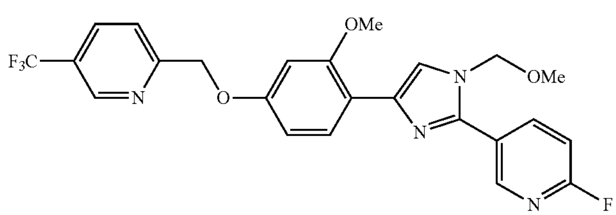 [SMILES: COCn1cc(-c2ccc(OCc3ccc(C(F)(F)F)cn3)cc2OC)nc1-c1ccc(F)nc1] | 172-174 | 1H-NMR (DMSO) δ 3.34 (s, 3H), 3.94 (s, 3H), 5.36 (s, 2H), 5.40 (s, 2H), 6.72 (dd, J = 8.3, 2.4 Hz, 1H), 6.82 (d, J = 2.4 Hz, 1H), 7.36 (dd, J = 8.3, 2.9 Hz, 1H), 7.80 (d, J = 8.3 Hz, 1H), 7.84 (s, 1H), 8.06 (d, J = 8.3 Hz, 1H), 8.28 (dd, J = 8.3, 2.4 Hz, 1H), 8.38 (ddd, J = 8.3, 8.3, 2.4 Hz, 1H), 8.65 (d, J = 2.4 Hz, 1H), 9.01 (d, J = 2.4 Hz, 1H) |
| 167 | 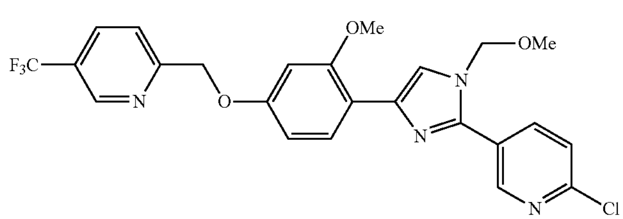 [SMILES: COCn1cc(-c2ccc(OCc3ccc(C(F)(F)F)cn3)cc2OC)nc1-c1ccc(Cl)nc1] | 138-140 | 1H-NMR (CDCL3) δ 3.45 (s, 3H), 3.95 (s, 3H), 5.24 (s, 2H), 5.31 (s, 2H), 6.63-6.71 (m, 2H), 7.4 (d, J = 8.2 Hz, 1H), 7.65 (s, 1H), 7.70 (d, J = 8.2 Hz, 1H), 7.97 (dd, J = 8.2, 2.0 Hz, 1H), 8.14-8.25 (m, 2H), 8.84-8.95 (m, 2H) |

TABLE 3-continued

| Example No. | Structure | Melting point (° C.) | 1H-NMR (δ:ppm) |
|---|---|---|---|
| 168 | 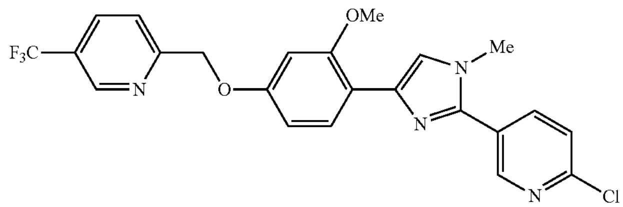 [SMILES: COc1cc(OCc2ccc(C(F)(F)F)cn2)ccc1-c1cn(C)c(-c2ccc(Cl)nc2)n1] | 186-190 | 1H-NMR (DMSO) δ 3.82 (s, 3H), 3.91 (s, 3H), 5.33 (s, 2H), 6.69 (dd, J = 8.7, 2.3 Hz, 1H), 6.78 (d, J = 2.3 Hz, 1H), 7.59-7.68 (m, 2H), 7.78 (d, J = 8.3 Hz, 1H), 8.01 (d, J = 8.7 Hz, 1H), 8.22 (dd, J = 8.3, 2.4 Hz, 1H), 8.27 (dd, J = 8.2, 2.1 Hz, 1H), 8.79 (d, J = 2.4 Hz, 1H), 8.92-9.06 (m, 1H) |
| 169 | 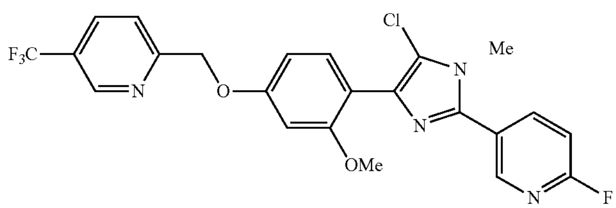 | 158-160 Decomposition | 1H-NMR (CDCL3) δ 3.72 (s, 3H), 3.86 (s, 3H), 5.31 (s, 2H), 6.61 (dd, J = 8.3, 2.4 Hz, 1H), 6.67 (d, J = 2.4 Hz, 1H), 7.05 (dd, J = 8.8, 3.4 Hz, 1H), 7.41 (d, J = 8.3 Hz, 1H), 7.70 (d, J = 8.3 Hz, 1H), 7.97 (dd, J = 8.3, 2.0 Hz, 1H), 8.13 (ddd, J = 8.8, 6.7, 1.8 Hz, 1H), 8.43-8.58 (m, 1H), 8.87 (s, 1H) |
| 170 | 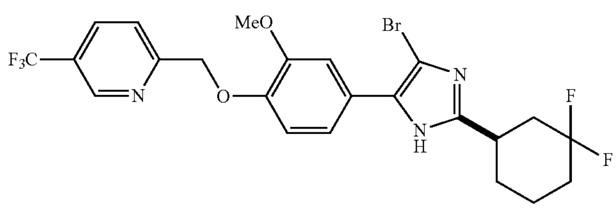 | 158-160 | 1H-NMR (DMSO) δ 1.41-1.64 (m, 2H), 1.69-2.18 (m, 5H), 2.24-2.40 (m, 1H), 2.82-3.04 (m, 1H), 3.85 (s, 3H), 5.31 (s, 2H), 7.11 (d, J = 8.8 Hz, 1H), 7.22 (d, J = 8.8 Hz, 1H), 7.31 (s, 1H), 7.75 (d, J = 8.3 Hz, 1H), 8.28 (dd, J = 8.3, 2.0 Hz, 1H), 8.98 (d, J = 2.0 Hz, 1H), 12.36 (s 1H) |
| 171 | 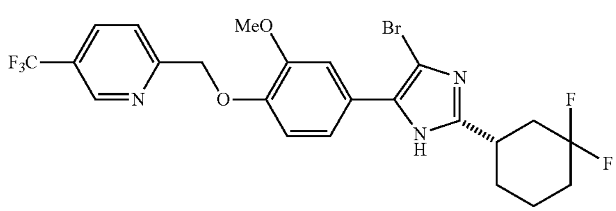 | 158-160 | 1H-NMR (DMSO) δ 1.41-1.64 (m, 2H), 1.65-2.20 (m, 5H), 2.21-2.43 (m, 1H), 2.82-3.03 (m, 1H), 3.85 (s, 3H), 5.31 (s, 2H), 7.12 (d, J = 8.3 Hz, 1H), 7.22 (d, J = 8.3 Hz, 1H), 7.31 (s, 1H), 7.75 (d, J = 8.3 Hz, 1H), 8.28 (dd, J = 8.3, 2.0 Hz, 1H), 8.98 (d, J = 2.0 Hz, 1H), 12.37 (s, 1H) |
| 172 | 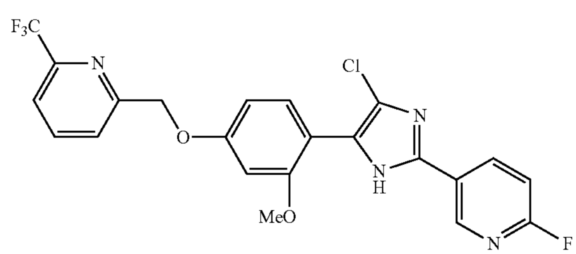 [SMILES: COc1cc(OCc2cccc(C(F)(F)F)n2)ccc1-c1[nH]c(-c2ccc(F)nc2)nc1Cl] | 189-191 | 1H-NMR (CDCL3) δ 3.97 (s, 3H), 5.33 (s, 2H), 6.65-6.77 (m, 2H), 7.03 (dd, J = 8.3, 2.9 Hz, 1H), 7.66 (d, J = 7.8 Hz, 1H), 7.78 (d, J = 7.8 Hz, 1H), 7.95 (dd, J = 7.8, 7.8 Hz, 1H), 8.03 (d, J = 8.8 Hz, 1H), 8.31 (ddd, J = 8.3, 8.3, 2.0 Hz, 1H), 8.58 (d, J = 2.0 Hz, 1H), 10.51 (s, 1H) |

TABLE 3-continued

| Example No. | Structure | Melting point (° C.) | 1H-NMR (δ:ppm) |
|---|---|---|---|
| 173 | 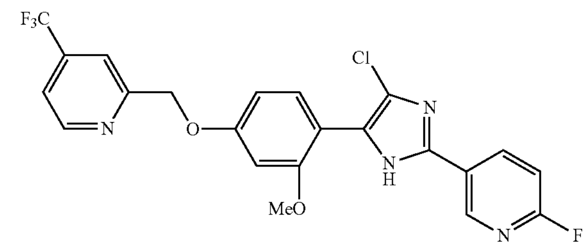 [SMILES: COc1cc(OCc2cc(C(F)(F)F)ccn2)ccc1-c1[nH]c(-c2ccc(F)nc2)nc1Cl] | 185-187 | 1H-NMR (CDCL3) δ 4.00 (s, 3H), 5.31 (s, 2H), 6.73 (dd, J = 8.7, 2.5 Hz, 1H), 6.75 (d, J = 2.5 Hz, 1H), 7.04 (dd, J = 8.3, 2.9 Hz, 1H), 7.50 (d, J = 5.0 Hz, 1H), 7.81 (s, 1H), 8.06 (d, J = 8.7 Hz, 1H), 8.32 (ddd, J = 8.3, 8.3, 2.5 Hz, 1H), 8.59 (d, J = 2.5 Hz, 1H), 8.81 (d, J = 5.0 Hz, 1H), 10.51 (s, 1H) |
| 174 | 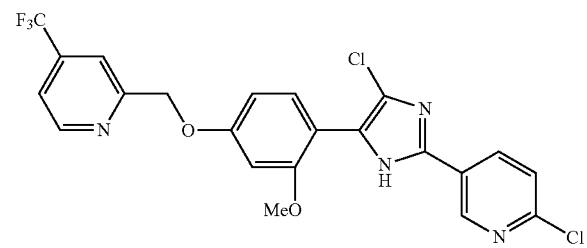 [SMILES: COc1cc(OCc2cc(C(F)(F)F)ccn2)ccc1-c1[nH]c(-c2ccc(Cl)nc2)nc1Cl] | 176-178 | 1H-NMR (DMSO) δ 3.81 (s, 3H), 5.38 (s, 2H), 6.79 (dd, J = 8.3, 2.0 Hz, 1H), 6.90 (d, J = 2.0 Hz, 1H), 7.36 (d, J = 8.3 Hz, 1H), 7.62 (d, J = 8.3 Hz, 1H), 7.77 (d, J = 5.4 Hz, 1H), 7.92 (s, 1H), 8.30 (dd, J = 8.3, 2.4 Hz, 1H), 8.90 (d, J = 5.4 Hz, 1H), 8.93 (d, J = 2.4 Hz, 1H), 13.02 (s, 1H) |
| 175 | 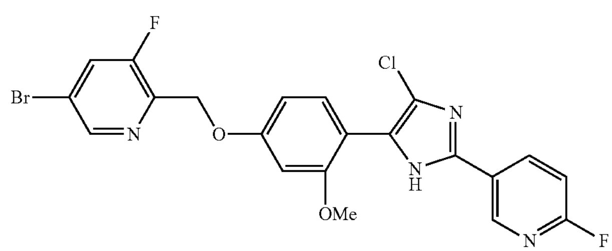 | 122-124 | 1H-NMR (CDCL3) δ 3.80-4.05 (3H), 5.27 (d, J = 2.0 Hz, 2H), 6.69-6.81 (m, 2H), 7.03 (dd, J = 8.8, 2.9 Hz, 1H), 7.68 (dd, J = 8.5, 1.8 Hz, 1H), 8.03 (d, J = 8.3 Hz, 1H), 8.31 (ddd, J = 8.5, 8.5, 1.7 Hz, 1H), 8.52-8.64 (m, 2H), 10.52 (s, 1H) |
| 176 | 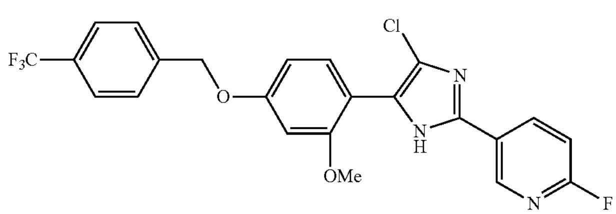 [SMILES: COc1cc(OCc2ccc(C(F)(F)F)cc2)ccc1-c1[nH]c(-c2ccc(F)nc2)nc1Cl] | 163-166 | 1H-NMR (CDCL3) δ 3.97 (s, 3H), 5.18 (s, 2H), 6.66-6.73 (m, 2H), 7.04 (dd, J = 8.3, 2.9 Hz, 1H), 7.54-7.73 (m, 4H), 8.05 (d, J = 8.8 Hz, 1H), 8.33 (ddd, J = 8.3, 8.3, 2.4 Hz, 1H), 8.59 (d, J = 2.4 Hz, 1H), 10.50 (s, 1H) |
| 177 | 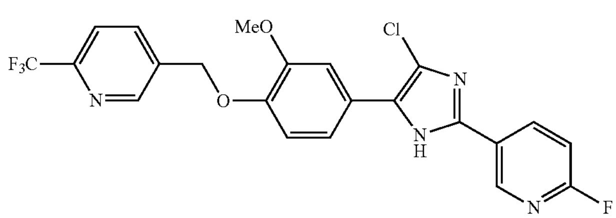 [SMILES: COc1cc(-c2[nH]c(-c3ccc(F)nc3)nc2Cl)ccc1OCc1ccc(C(F)(F)F)nc1] | 202-204 | 1H-NMR (CDCL3) δ 3.91 (s, 3H), 5.24 (s, 2H), 6.91 (d, J = 8.3 Hz, 1H), 7.01 (dd, J = 8.0, 2.9 Hz, 1H), 7.12 (d, J = 8.3 Hz, 1H), 7.29-7.40 (m, 1H), 7.71 (d, J = 7.8 Hz, 1H), 7.98 (dd, J = 7.8, 1.5 Hz, 1H), 8.31 (ddd, J = 8.0, 8.0, 2.4 Hz, 1H), 8.59 (d, J = 2.4 Hz, 1H), 8.68-8.83 (m, 1H), 10.27 (s, 1H) |
| 178 | 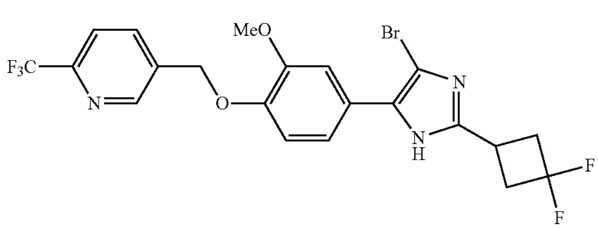 [SMILES: COc1cc(-c2[nH]c(C3CC(F)(F)C3)nc2Br)ccc1OCc1ccc(C(F)(F)F)nc1] | 168-170 | 1H-NMR (CDCL3) δ 2.87-3.05 (m, 4H), 3.28-3.43 (m, 1H), 3.91 (s, 3H), 5.25 (s, 2H), 6.93 (d, J = 8.8 Hz, 1H), 7.06 (d, J = 7.8 Hz, 1H), 7.18-7.37 (m, 1H), 7.72 (d, J = 7.8 Hz, 1H), 8.00 (dd, J = 8.8, 1.5 Hz, 1H), 8.78 (d, J = 1.5 Hz, 1H), 9.47 (s, 1H) |

TABLE 3-continued

| Example No. | Structure | Melting point (° C.) | 1H-NMR (δ:ppm) |
|---|---|---|---|
| 179 | 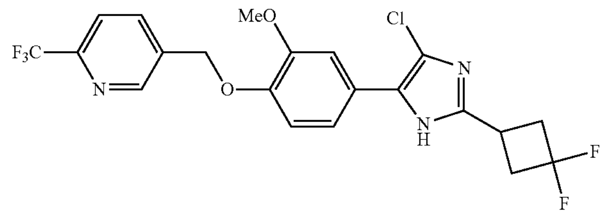 [SMILES: COc1cc(-c2[nH]c(C3CC(F)(F)C3)nc2Cl)ccc1OCc1ccc(C(F)(F)F)nc1] | 170-174 | 1H-NMR (CDCL3) δ 2.88-3.05 (m, 4H), 3.28-3.41 (m, 1H), 3.93 (s, 3H), 5.25 (s, 2H), 6.93 (d, J = 8.5 Hz, 1H), 7.04 (dd, J = 8.2, 2.0 Hz, 1H), 7.22-7.28 (m, 1H), 7.73 (d, J = 8.2 Hz, 1H), 8.00 (dd, J = 8.5, 1.8 Hz, 1H), 8.78 (d, J = 1.8 Hz, 1H), 9.35 (s, 1H) |
| 180 | 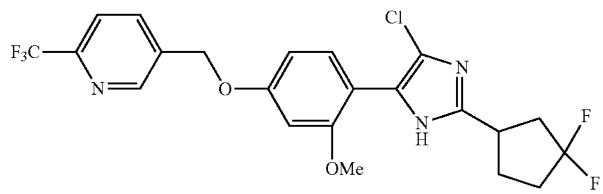 [SMILES: COc1cc(OCc2ccc(C(F)(F)F)nc2)ccc1-c1[nH]c(C2CCC(F)(F)C2)nc1Cl] | 172-174 | 1H-NMR (CDCL3) δ 2.05-2.63 (m, 6H), 3.39-3.50 (m, 1H), 3.93 (s, 3H), 5.20 (s, 2H), 6.57-6.75 (m, 2H), 7.74 (d, J = 8.3 Hz, 1H), 7.99 (dd, J = 8.0, 3.2 Hz, 2H), 8.74-8.89 (m, 1H), 9.94 (s, 1H) |
| 181 | 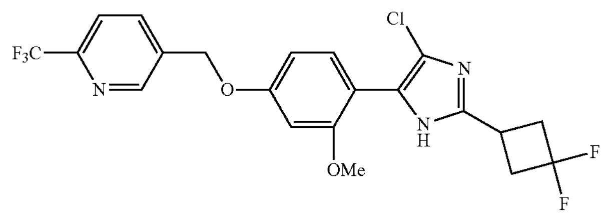 [SMILES: COc1cc(OCc2ccc(C(F)(F)F)nc2)ccc1-c1[nH]c(C2CC(F)(F)C2)nc1Cl] | 199-201 | 1H-NMR (CDCL3) δ 2.86-3.08 (m, 4H), 3.33-3.46 (m, 1H), 3.92 (s, 3H), 5.21 (s, 2H), 6.64 (d, J = 2.5 Hz, 1H), 6.67 (dd, J = 8.6, 2.5 Hz, 1H), 7.74 (d, J = 8.6 Hz, 1H), 7.94-8.04 (m, 2H), 8.81 (d, J = 1.5 Hz, 1H), 10.01 (s, 1H) |
| 182 | 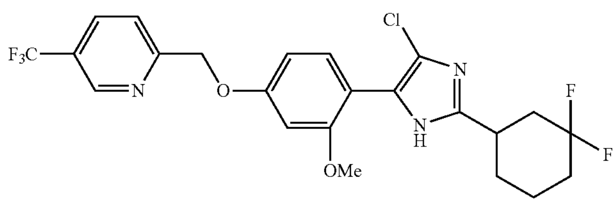 [SMILES: COc1cc(OCc2ccc(C(F)(F)F)cn2)ccc1-c1[nH]c(C2CCCC(F)(F)C2)nc1Cl] | 162-164 | 1H-NMR (DMSO) δ 1.42-1.61 (m, 2H), 1.68-2.17 (m, 5H), 2.25-2.40 (m, 1H), 2.85-3.02 (m, 1H), 3.86 (s, 3H), 5.31 (s, 2H), 7.12 (d, J = 8.3 Hz, 1H), 7.22 (dd, J = 8.3, 1.7 Hz, 1H), 7.30 (d, J = 1.7 Hz, 1H), 7.75 (d, J = 8.3 Hz, 1H), 8.28 (dd, J = 8.3, 2.4 Hz, 1H), 8.98 (d, J = 2.4 Hz, 1H), 12.33 (s, 1H) |
| 183 | 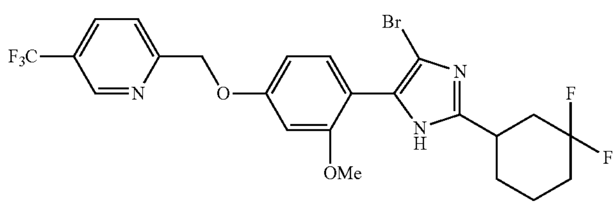 [SMILES: COc1cc(OCc2ccc(C(F)(F)F)cn2)ccc1-c1[nH]c(C2CCCC(F)(F)C2)nc1Br] | 170-171 | 1H-NMR (CDCL3) δ 1.53-2.22 (m, 7H), 2.30-2.48 (m, 1H), 2.91-3.10 (m, 1H), 3.95 (s, 3H), 5.35 (s, 2H), 6.90 (d, J = 8.3 Hz, 1H), 7.02 (d, J = 8.3 Hz, 1H), 7.28 (s, 1H), 7.73 (d, J = 8.5 Hz, 1H), 7.96 (dd, J = 8.5, 1.9 Hz, 1H), 8.86 (d, J = 1.9 Hz, 1H), 9.21 (s, 1H) |
| 184 | 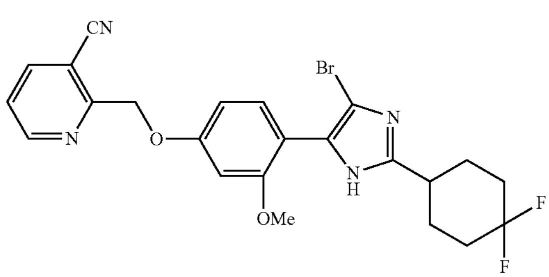 [SMILES: COc1cc(OCc2ncccc2C#N)ccc1-c1[nH]c(C2CCC(F)(F)CC2)nc1Br] | 160-161 | 1H-NMR (DMSO) δ 1.68-2.16 (m, 8H), 2.77-2.91 (m, 1H), 3.76 (s, 3H), 5.38 (s, 2H), 6.71 (dd, J = 8.5, 2.2 Hz, 1H), 6.77 (d, J = 2.2 Hz, 1H), 7.28 (d, J = 8.3 Hz, 1H), 7.64 (dd, J = 7.8, 4.9 Hz, 1H), 8.41 (dd, J = 7.8, 1.5 Hz, 1H), 8.87 (dd, J = 4.9, 1.5 Hz, 1H), 12.06 (s, 1H) |

TABLE 3-continued

| Example No. | Structure | Melting point (° C.) | 1H-NMR (δ:ppm) |
|---|---|---|---|
| 185 | 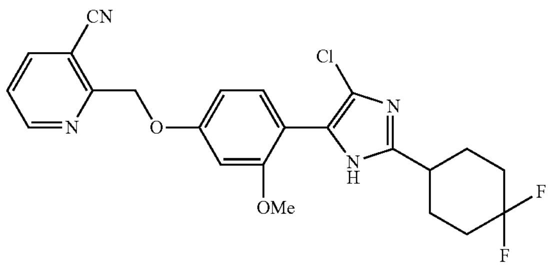 [SMILES: COc1cc(OCc2ncccc2C#N)ccc1-c1[nH]c(C2CCC(F)(F)CC2)nc1Cl] | 161-162 | 1H-NMR (DMSO) δ 1.64-2.19 (m, 8H), 2.74-2.96 (m, 1H), 3.77 (s, 3H), 5.38 (s, 2H), 6.72 (dd, J = 8.3, 2.0 Hz, 1H), 6.78 (d, J = 2.0 Hz, 1H), 7.30 (d, J = 8.3 Hz, 1H), 7.64 (dd, J = 7.8, 4.9 Hz, 1H), 8.41 (dd, J = 7.8, 1.5 Hz, 1H), 8.86 (dd, J = 4.9, 1.5 Hz, 1H), 11.99 (s, 1H) |
| 186 | 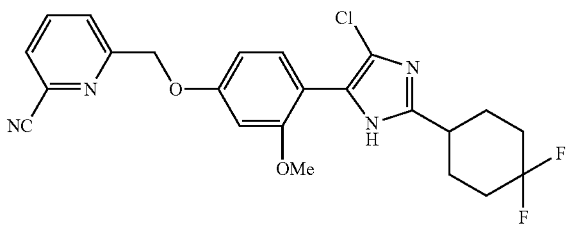 [SMILES: COc1cc(OCc2cccc(C#N)n2)ccc1-c1[nH]c(C2CCC(F)(F)CC2)nc1Cl] | | 1H-NMR (DMSO) δ 1.68-2.15 (m, 8H), 2.75-2.92 (m, 1H), 3.78 (s, 3H), 5.30 (s, 2H), 6.68 (dd, J = 8.5, 2.2 Hz, 1H), 6.80 (d, J = 2.2 Hz, 1H), 7.30 (d, J = 8.5 Hz, 1H), 7.89 (d, J = 7.8 Hz, 1H), 8.02 (d, J = 7.8 Hz, 1H), 8.13 (dd, J = 7.8, 7.8 Hz, 1H), 11.99 (s, 1H) |
| 187 | 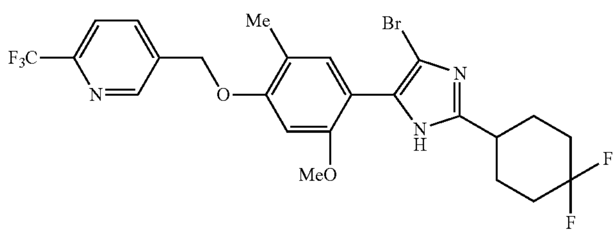 [SMILES: COc1cc(OCc2ccc(C(F)(F)F)nc2)c(C)cc1-c1[nH]c(C2CCC(F)(F)CC2)nc1Br] | 195-196 | 1H-NMR (DMSO) δ 1.68-2.13 (m, 8H), 2.15 (s, 3H), 2.72-2.93 (m, 1H), 3.77 (s, 3H), 5.40 (s, 2H), 6.83 (s, 1H), 7.15 (s, 1H), 7.97 (d, J = 8.3 Hz, 1H), 8.20 (dd, J = 8.3, 1.2 Hz, 1H), 8.90 (d, J = 1.2 Hz, 1H), 12.03 (s, 1H) |
| 188 | 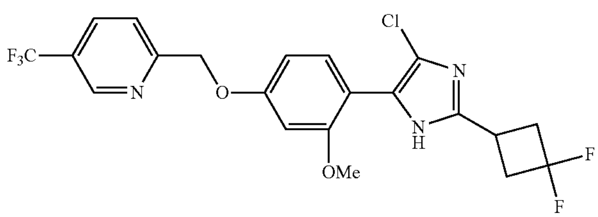 [SMILES: COc1cc(OCc2ccc(C(F)(F)F)cn2)ccc1-c1[nH]c(C2CC(F)(F)C2)nc1Cl] | 191-193 | 1H-NMR (CDCL3) δ 2.86-3.07 (m, 4H), 3.31-3.48 (m, 1H), 3.93 (s, 3H), 5.32 (s, 2H), 6.57-6.76 (m, 2H), 7.69 (d, J = 8.3 Hz, 1H), 7.89-8.09 (m, 2H), 8.80-8.96 (m, 1H), 9.99 (s, 1H) |
| 189 | 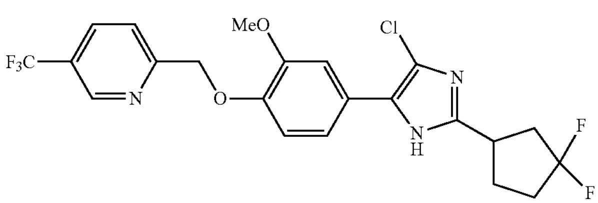 [SMILES: COc1cc(-c2[nH]c(C3CCC(F)(F)C3)nc2Cl)ccc1OCc1ccc(C(F)(F)F)cn1] | 159-161 | 1H-NMR (DMSO) δ 1.91-2.59 (m, 6H), 3.34-3.47 (m, 1H), 3.86 (s, 3H), 5.31 (s, 2H), 7.12 (d, J = 8.3 Hz, 1H), 7.21 (dd, J = 8.3, 2.0 Hz, 1H), 7.30 (d, J = 2.0 Hz, 1H), 7.75 (d, J = 8.3 Hz, 1H), 8.28 (dd, J = 8.3, 2.4 Hz, 1H), 8.97 (s, 1H), 12.39 (s, 1H) |
| 190 | 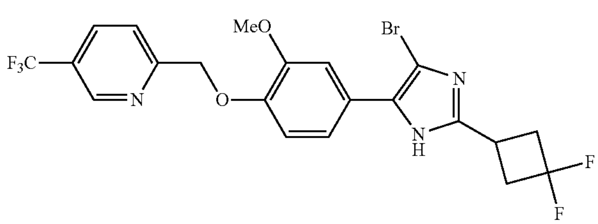 [SMILES: COc1cc(-c2[nH]c(C3CC(F)(F)C3)nc2Br)ccc1OCc1ccc(C(F)(F)F)cn1] | 151-157 | 1H-NMR (CDCL3) δ 2.88-3.05 (m, 4H), 3.31-3.43 (m, 1H), 3.95 (s, 3H), 5.35 (s, 2H), 6.89 (d, J = 8.3 Hz, 1H), 6.95-7.11 (m, 1H), 7.22-7.39 (m, 1H), 7.73 (d, J = 8.3 Hz, 1H), 7.96 (dd, J = 8.3, 2.0 Hz, 1H), 8.77-8.95 (m, 1H), 9.41 (s, 1H) |

TABLE 3-continued

| Example No. | Structure | Melting point (° C.) | 1H-NMR (δ:ppm) |
|---|---|---|---|
| 191 | 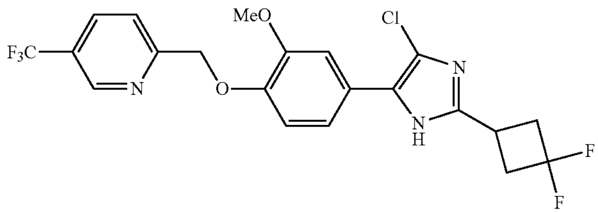 [SMILES: COc1cc(-c2[nH]c(C3CC(F)(F)C3)nc2Cl)ccc1OCc1ccc(C(F)(F)F)cn1] | 201-203 Decomposition | 1H-NMR (CDCL3) δ 2.84-3.07 (m, 4H), 3.29-3.43 (m, 1H), 3.95 (s, 3H), 5.35 (s, 2H), 6.90 (d, J = 8.3 Hz, 1H), 7.01 (d, J = 8.3 Hz, 1H), 7.22-7.32 (m, 1H), 7.72 (d, J = 8.3 Hz, 1H), 7.96 (dd, J = 8.3, 2.0 Hz, 1H), 8.81-8.90 (m, 1H), 9.32 (s, 1H) |
| 192 | 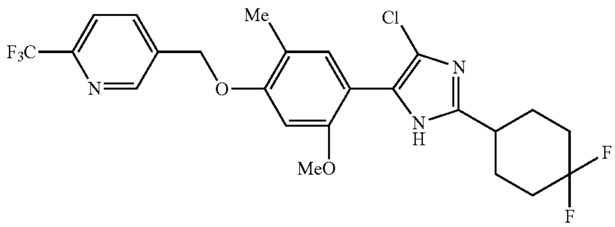 [SMILES: COc1cc(OCc2ccc(C(F)(F)F)nc2)c(C)cc1-c1[nH]c(C2CCC(F)(F)CC2)nc1Cl] | 175-178 | 1H-NMR (DMSO) δ 1.68-2.13 (m, 8H), 2.15 (s, 3H), 2.72-2.93 (m, 1H), 3.78 (s, 3H), 5.40 (s, 2H), 6.83 (s, 1H), 7.16 (s, 1H), 7.97 (d, J = 8.3 Hz, 1H), 8.20 (d, J = 8.3 Hz, 1H), 8.90 (s, 1H), 11.96 (s, 1H) |
| 193 | 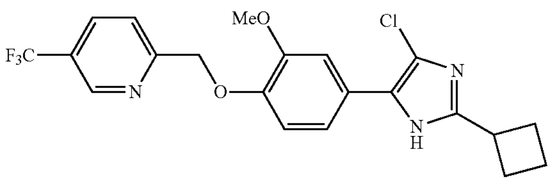 [SMILES: COc1cc(-c2[nH]c(C3CCC3)nc2Cl)ccc1OCc1ccc(C(F)(F)F)cn1] | 158-170 | 1H-NMR (CDCL3) δ 0.78-0.95 (m, 1H), 1.82-2.61 (m, 5H), 3.45-3.60 (m, 1H), 3.94 (s, 3H), 5.33 (s, 2H), 6.88 (d, J = 8.3 Hz, 1H), 7.03 (d, J = 8.3 Hz, 1H), 7.29 (s, 1H), 7.72 (d, J = 8.3 Hz, 1H), 7.96 (d, J = 8.3 Hz, 1H), 8.85 (s, 1H), 9.35 (s, 1H) |
| 194 | 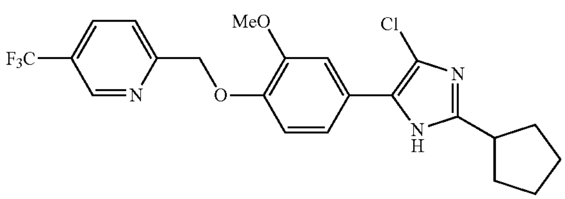 [SMILES: COc1cc(-c2[nH]c(C3CCCC3)nc2Cl)ccc1OCc1ccc(C(F)(F)F)cn1] | 182-184 Decomposition | 1H-NMR (DMSO) δ 1.52-2.04 (m, 8H), 3.00-3.13 (m, 1H), 3.85 (s, 3H), 5.31 (s, 2H), 7.11 (d, J = 8.3 Hz, 1H), 7.21 (dd, J = 8.3, 1.0 Hz, 1H), 7.30 (d, J = 1.0 Hz, 1H), 7.75 (d, J = 8.3 Hz, 1H), 8.28 (dd, J = 8.3, 1.5 Hz, 1H), 8.97 (d, J = 1.5 Hz, 1H), 12.19 (s, 1H) |
| 195 | 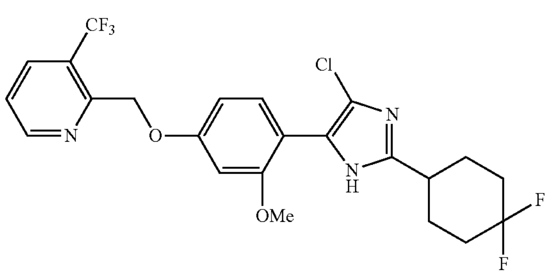 | 162-164 | 1H-NMR (DMSO) δ 1.69-2.17 (m, 8H), 2.72-2.93 (m, 1H), 3.75 (s, 3H), 5.33 (s, 2H), 6.68 (dd, J = 8.3, 2.4 Hz, 1H), 6.76 (d, J = 2.4 Hz, 1H), 7.28 (d, J = 8.3 Hz, 1H), 7.67 (dd, J = 8.3, 4.9 Hz, 1H), 8.28 (d, J = 8.3 Hz, 1H), 8.89 (d, J = 4.9 Hz, 1H), 11.98 (s, 1H) |
| 196 | 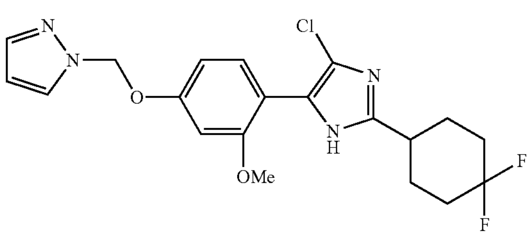 [SMILES: COc1cc(OCn2cccn2)ccc1-c1[nH]c(C2CCC(F)(F)CC2)nc1Cl] | 182-184 | 1H-NMR (DMSO) δ 1.67-2.16 (m, 8H), 2.77-2.90 (m, 1H), 3.76 (s, 3H), 6.13 (s, 2H), 6.35 (dd, J = 2.4, 2.4 Hz, 1H), 6.79 (dd, J = 8.3, 2.4 Hz, 1H), 6.83 (d, J = 2.4 Hz, 1H), 7.29 (d, J = 8.3 Hz, 1H), 7.58 (d, J = 2.4 Hz, 1H), 8.01 (d, J = 2.4 Hz, 1H), 12.00 (s, 1H) |

TABLE 3-continued

| Example No. | Structure | Melting point (° C.) | 1H-NMR (δ:ppm) |
|---|---|---|---|
| 197 | 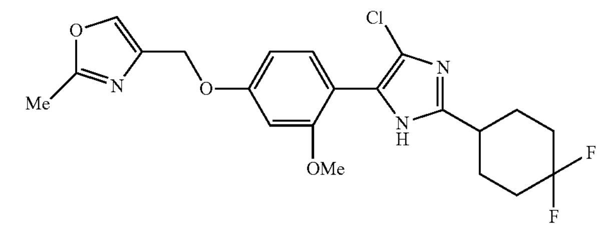 [SMILES: COc1cc(OCc2coc(C)n2)ccc1-c1[nH]c(C2CCC(F)(F)CC2)nc1Cl] | 130-131 | 1H-NMR (DMSO) δ 1.69-2.15 (m, 8H), 2.40 (s, 3H), 2.76-2.89 (m, 1H), 3.77 (s, 3H), 4.97 (s, 2H), 6.68 (dd, J = 8.3, 2.4 Hz, 1H), 6.73 (d, J = 2.4 Hz, 1H), 7.28 (d, J = 8.3 Hz, 1H), 8.06 (s, 1H), 11.98 (s, 1H) |
| 198 | 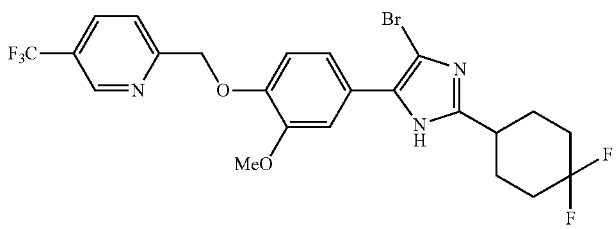 | 158-165 | 1H-NMR (CDCL3) δ 1.72-2.32 (m, 8H), 2.75-2.93 (m, 1H), 3.95 (s, 3H), 5.35 (s, 2H), 6.90 (d, J = 8.3 Hz, 1H), 7.01 (dd, J = 8.3, 2.0 Hz, 1H), 7.29 (d, J = 2.0 Hz, 1H), 7.73 (d, J = 8.3 Hz, 1H), 7.97 (d, J = 8.3 Hz, 1H), 8.78-8.95 (m, 1H), 9.12 (s, 1H) |
| 199 | 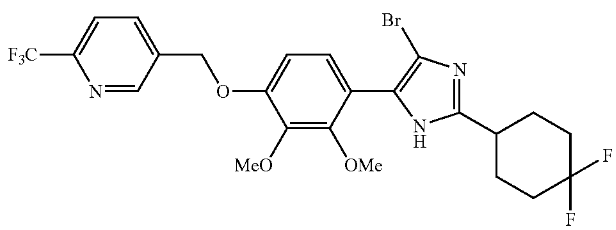 [SMILES: COc1c(OCc2ccc(C(F)(F)F)nc2)ccc(-c2[nH]c(C3CCC(F)(F)CC3)nc2Cl)c1OC] | 162-165 | 1H-NMR (CDCL3) δ 1.75-2.01 (m, 4H), 2.08-2.31 (m, 4H), 2.81-2.94 (m, 1H), 3.83 (s, 3H), 3.98 (s, 3H), 5.34 (s, 2H), 6.80 (d, J = 9.1 Hz, 1H), 7.64-7.82 (m, 2H), 7.99 (dd, J = 8.2, 2.0 Hz, 1H), 8.81-8.95 (m, 1H), 9.91 (s, 1H) |
| 200 | 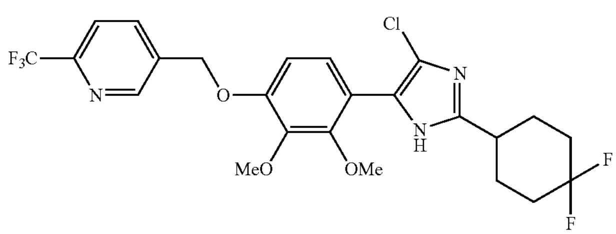 | 148-150 | 1H-NMR (DMSO) δ 1.69-2.15 (m, 8H), 2.75-2.95 (m, 1H), 3.63 (s, 3H), 3.82 (s, 3H), 5.35 (s, 2H), 6.99 (d, J = 8.8 Hz, 1H), 7.11 (d, J = 8.8 Hz, 1H), 7.98 (d, J = 8.3 Hz, 1H), 8.19 (d, J = 8.3 Hz, 1H), 8.89 (s, 1H), 12.11 (s, 1H) |
| 201 | 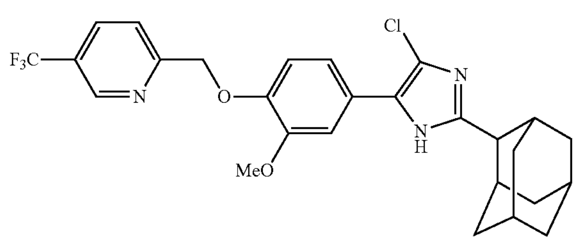 [SMILES: COc1cc(-c2[nH]c(C3C4CC5CC(C4)CC3C5)nc2Cl)ccc1OCc1ccc(C(F)(F)F)cn1] | 238-240 Decomposition | 1H-NMR (DMSO) δ 1.66-1.80 (m, 6H), 1.89-1.99 (m, 6H), 1.99-2.07 (m, 3H), 3.86 (s, 3H), 5.32 (s, 2H), 7.11 (d, J = 8.3 Hz, 1H), 7.19 (dd, J = 8.3, 2.0 Hz, 1H), 7.29 (d, J = 2.0 Hz, 1H), 7.75 (d, J = 8.3 Hz, 1H), 8.28 (dd, J = 8.3, 2.0 Hz, 1H), 8.98 (d, J = 2.0 Hz, 1H), 11.86 (s, 1H) |
| 202 | 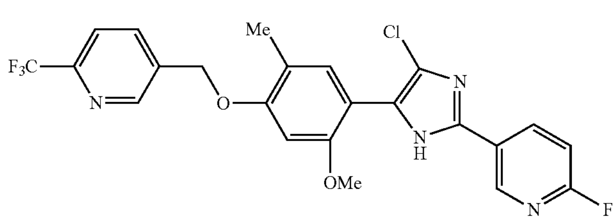 [SMILES: COc1cc(OCc2ccc(C(F)(F)F)nc2)c(C)cc1-c1[nH]c(-c2ccc(F)nc2)nc1Cl] | 213-215 Decomposition | 1H-NMR (DMSO) δ 2.19 (s, 3H), 3.82 (s, 3H), 5.43 (s, 2H), 6.90 (s, 1H), 7.22 (s, 1H), 7.29 (dd, J = 8.3, 2.7 Hz, 1H), 7.98 (d, J = 8.3 Hz, 1H), 8.21 (dd, J = 8.3, 1.5 Hz, 1H), 8.44 (ddd, J = 8.3, 8.3, 2.0 Hz, 1H), 8.76 (d, J = 2.0 Hz, 1H), 8.91 (d, J = 1.5 Hz, 1H), 12.91 (s, 1H) |

TABLE 3-continued

| Example No. | Structure | Melting point (° C.) | 1H-NMR (δ:ppm) |
|---|---|---|---|
| 203 | 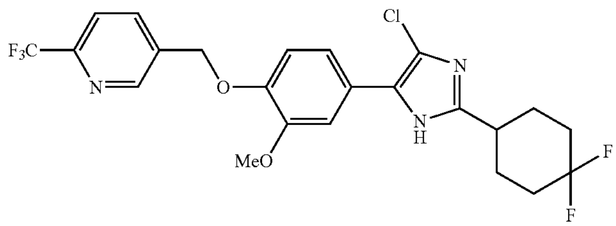 [SMILES: COc1cc(-c2[nH]c(C3CCC(F)(F)CC3)nc2Cl)ccc1OCc1ccc(C(F)(F)F)nc1] | 164-167 | 1H-NMR (CDCL3) δ 1.72-2.32 (m, 8H), 2.74-2.88 (m, 1H), 3.91 (s, 3H), 5.25 (s, 2H), 6.92 (d, J = 8.3 Hz, 1H), 7.03 (d, J = 8.3 Hz, 1H), 7.21-7.33 (m, 1H), 7.72 (d, J = 8.3 Hz, 1H), 8.00 (dd, J = 8.3, 1.5 Hz, 1H), 8.79 (d, J = 1.5 Hz, 1H), 9.27 (s, 1H) |
| 204 | 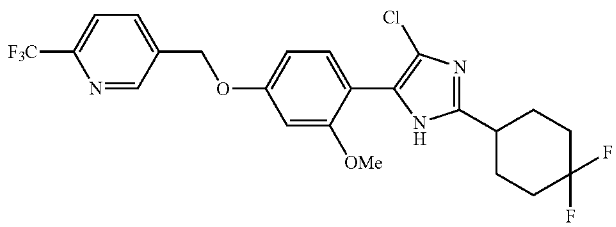 [SMILES: COc1cc(OCc2ccc(C(F)(F)F)nc2)ccc1-c1[nH]c(C2CCC(F)(F)CC2)nc1Cl] | 122-125 | 1H-NMR (CDCL3) δ 1.74-2.03 (m, 4H), 2.07-2.35 (m, 4H), 2.70-2.94 (m, 1H), 3.92 (s, 3H), 5.19 (s, 2H), 6.52-6.77 (m, 2H), 7.74 (d, J = 8.3 Hz, 1H), 7.87-8.10 (m, 2H), 8.72-8.91 (m, 1H), 9.87 (s, 1H) |
| 205 | 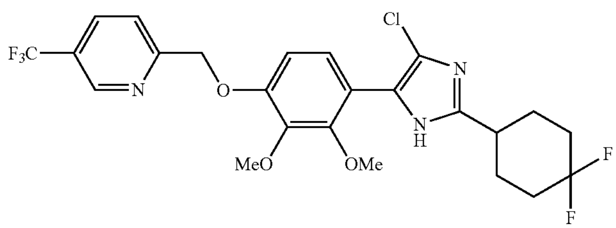 [SMILES: COc1c(OCc2ccc(C(F)(F)F)cn2)ccc(-c2[nH]c(C3CCC(F)(F)CC3)nc2Cl)c1OC] | 175-177 | 1H-NMR (CDCL3) δ 1.74-2.05 (m, 4H), 2.09-2.32 (m, 4H), 2.78-2.96 (m, 1H), 3.86 (s, 3H), 3.98 (s, 3H), 5.34 (s, 2H), 6.80 (d, J = 8.8 Hz, 1H), 7.69 (d, J = 8.8 Hz, 1H), 7.73 (d, J = 8.8 Hz, 1H), 7.99 (dd, J = 8.8, 2.0 Hz, 1H), 8.80-8.96 (m, 1H), 9.97 (s, 1H) |
| 206 | 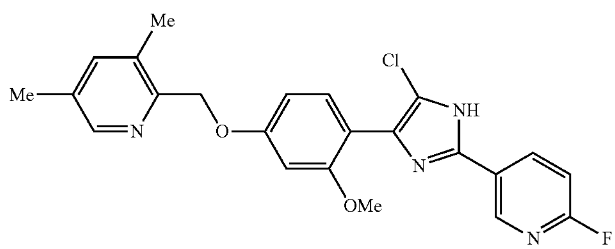 [SMILES: COc1cc(OCc2ncc(C)cc2C)ccc1-c1nc(-c2ccc(F)nc2)[nH]c1Cl] | 109-124 | 1H-NMR (DMSO) δ 2.20 (s, 3H), 2.29 (s, 3H), 3.72 (s, 3H), 5.16 (s, 2H), 6.69 (dd, J = 8.3, 2.4 Hz, 1H), 6.76 (d, J = 2.4 Hz, 1H), 7.20-7.29 (m, 2H), 7.41 (s, 1H), 8.17 (s, 1H), 8.37 (ddd, J = 8.0, 8.0, 2.4 Hz, 1H), 8.68 (d, J = 2.4 Hz, 1H), 12.84 (s, 1H) |
| 207 | 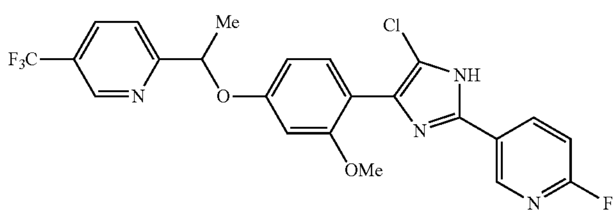 [SMILES: COc1cc(OC(C)c2ccc(C(F)(F)F)cn2)ccc1-c1nc(-c2ccc(F)nc2)[nH]c1Cl] | 166-169 | 1H-NMR (CDCL3) δ 1.73 (d, J = 6.8 Hz, 3H), 3.92 (s, 3H), 5.53 (q, J = 6.8 Hz, 1H), 6.52 (dd, J = 8.8, 2.4 Hz, 1H), 6.64 (d, J = 2.4 Hz, 1H), 7.01 (dd, J = 8.5, 2.4 Hz, 1H), 7.57 (d, J = 8.3 Hz, 1H), 7.87-7.98 (m, 2H), 8.29 (ddd, J = 8.5, 8.5, 2.4 Hz, 1H), 8.56 (d, J = 2.4 Hz, 1H), 8.79-8.94 (m, 1H), 10.49 (s, 1H) |
| 208 | 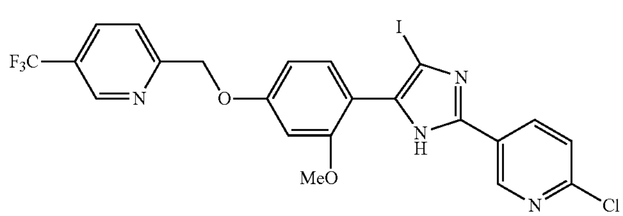 [SMILES: COc1cc(OCc2ccc(C(F)(F)F)cn2)ccc1-c1[nH]c(-c2ccc(Cl)nc2)nc1I] | 204-208 Decomposition | 1H-NMR (CDCL3) δ 3.87 (s, 3H), 5.30 (s, 2H), 6.59-6.71 (m, 2H), 7.37 (d, J = 8.2 Hz, 1H), 7.70 (d, J = 8.2 Hz, 1H), 7.86 (d, J = 8.5 Hz, 1H), 7.99 (dd, J = 8.2, 1.8 Hz, 1H), 8.16 (dd, J = 8.5, 2.3 Hz, 1H), 8.73 (d, J = 2.3 Hz, 1H), 8.88 (s, 1H), 10.57 (s, 1H) |

TABLE 3-continued

| Example No. | Structure | Melting point (° C.) | 1H-NMR (δ:ppm) |
|---|---|---|---|
| 209 | 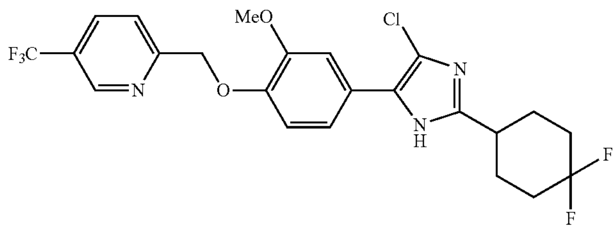 [SMILES: COc1cc(-c2[nH]c(C3CCC(F)(F)CC3)nc2Cl)ccc1OCc1ccc(C(F)(F)F)cn1] | 175-177 | 1H-NMR (DMSO) δ 1.71-2.20 (m, 8H), 2.80-2.92 (m, 1H), 3.88 (s, 3H), 5.31 (s, 2H), 7.12 (d, J = 8.3 Hz, 1H), 7.21 (dd, J = 8.3, 2.0 Hz, 1H), 7.30 (d, J = 2.0 Hz, 1H), 7.75 (d, J = 8.3 Hz, 1H), 8.28 (dd, J = 8.3, 2.0 Hz, 1H), 8.98 (d, J = 2.0 Hz, 1H), 12.28 (s, 1H) |
| 210 | 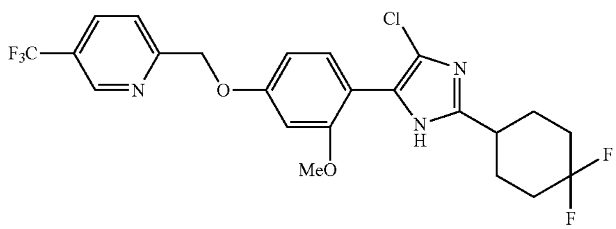 [SMILES: COc1cc(OCc2ccc(C(F)(F)F)cn2)ccc1-c1[nH]c(C2CCC(F)(F)CC2)nc1Cl] | 147-149 | 1H-NMR (CDCL3) δ 1.76-2.27 (m, 8H), 2.77-2.89 (m, 1H), 3.92 (s, 3H), 5.30 (s, 2H), 6.62-6.71 (m, 2H), 7.69 (d, J = 8.3 Hz, 1H), 7.94 (d, J = 8.5 Hz, 1H), 7.98 (dd, J = 8.3, 2.0 Hz, 1H), 8.88 (d, J = 2.0 Hz, 1H), 9.87 (s, 1H) |
| 211 | 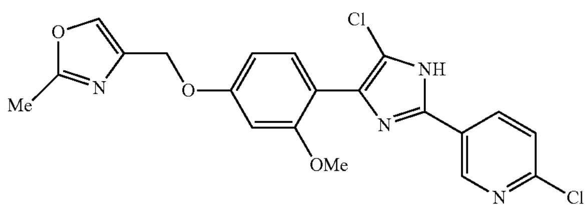 [SMILES: COc1cc(OCc2coc(C)n2)ccc1-c1nc(-c2ccc(Cl)nc2)[nH]c1Cl] | 136-155 | 1H-NMR (CDCL3) δ 2.48 (s, 3H), 3.88 (s, 3H), 4.97 (s, 2H), 6.58-6.69 (m, 2H), 7.37 (d, J = 8.3 Hz, 1H), 7.62 (s, 1H), 7.91 (d, J = 8.7 Hz, 1H), 8.13 (dd, J = 8.3, 2.5 Hz, 1H), 8.76 (d, J = 2.5 Hz, 1H), 10.89 (s, 1H) |
| 212 | 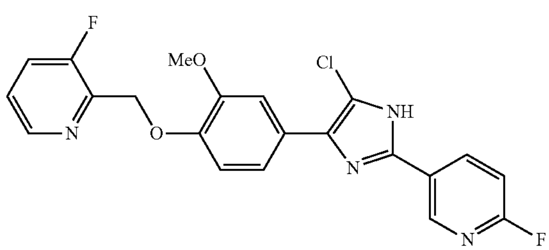 [SMILES: COc1cc(-c2nc(-c3ccc(F)nc3)[nH]c2Cl)ccc1OCc1ncccc1F] | 161-163 | 1H-NMR (CDCL3) δ 3.44 (s, 3H), 5.19 (s, 2H), 6.83-6.95 (m, 2H), 7.07-7.15 (m, 2H), 7.22-7.31 (m, 1H), 7.40 (dd, J = 8.7, 8.7 Hz, 1H), 8.22-8.34 (m, 2H), 8.64 (d, J = 1.7 Hz, 1H), 12.10 (s, 1H) |
| 213 | 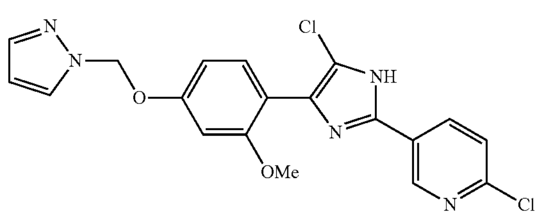 [SMILES: COc1cc(OCn2cccn2)ccc1-c1nc(-c2ccc(Cl)nc2)[nH]c1Cl] | 166-169 | 1H-NMR (DMSO) δ 3.80 (s, 3H), 6.17 (s, 2H), 6.35 (dd, J = 2.4, 2.4 Hz, 1H), 6.85 (dd, J = 8.5, 2.4 Hz, 1H), 6.89 (d, J = 2.4 Hz, 1H), 7.30 (dd, J = 8.5, 2.7 Hz, 1H), 7.35 (d, J = 8.5 Hz, 1H), 7.59 (d, J = 2.4 Hz, 1H), 8.02 (d, J = 2.4 Hz, 1H), 8.44 (ddd, J = 8.5, 8.5, 2.4 Hz, 1H), 8.75 (d, J = 2.4 Hz, 1H), 12.94 (s, 1H) |
| 214 | 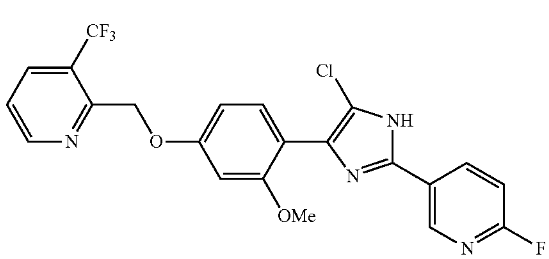 [SMILES: COc1cc(OCc2ncccc2C(F)(F)F)ccc1-c1nc(-c2ccc(F)nc2)[nH]c1Cl] | 143-146 | 1H-NMR (DMSO) δ 3.79 (s, 3H), 5.37 (s, 2H), 6.73 (dd, J = 8.3, 2.2 Hz, 1H), 6.81 (d, J = 2.2 Hz, 1H), 7.30 (dd, J = 8.0, 2.4 Hz, 1H), 7.34 (d, J = 8.3 Hz, 1H), 7.68 (dd, J = 8.3, 5.1 Hz, 1H), 8.29 (d, J = 8.3 Hz, 1H), 8.43 (ddd, J = 8.0, 8.0, 2.4 Hz, 1H), 8.75 (d, J = 2.4 Hz, 1H), 8.90 (d, J = 5.1 Hz, 1H), 12.93 (s, 1H) |

TABLE 3-continued

| Example No. | Structure | Melting point (° C.) | 1H-NMR (δ:ppm) |
|---|---|---|---|
| 215 | 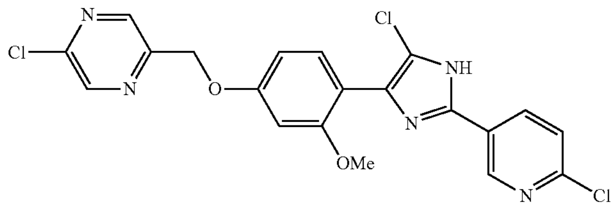 [SMILES: COc1cc(OCc2cnc(Cl)cn2)ccc1-c1nc(-c2ccc(Cl)nc2)[nH]c1Cl] | 232-234 | 1H-NMR (DMSO) δ 3.81 (s, 3H), 5.36 (s, 2H), 6.78 (dd, J = 8.3, 2.4 Hz, 1H), 6.87 (d, J = 2.4 Hz, 1H), 7.36 (d, J = 8.3 Hz, 1H), 7.61 (d, J = 8.3 Hz, 1H), 8.31 (dd, J = 8.3, 2.4 Hz, 1H), 8.73 (s, 1H), 8.85 (d, J = 1.0 Hz, 1H), 8.93 (d, J = 2.4 Hz, 1H), 13.04 (s, 1H) |
| 216 | 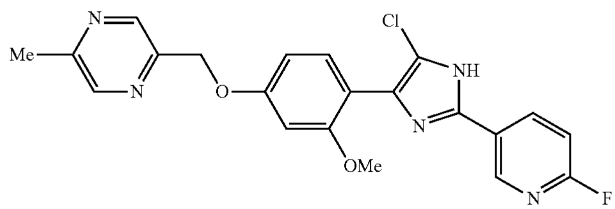 [SMILES: COc1cc(OCc2cnc(C)cn2)ccc1-c1nc(-c2ccc(F)nc2)[nH]c1Cl] | 208-210 Decomposition | 1H-NMR (CDCL3) δ 2.60 (s, 3H), 3.95 (s, 3H), 5.24 (s, 2H), 6.62-6.81 (m, 2H), 7.02 (dd, J = 8.8, 2.9 Hz, 1H), 8.00 (d, J = 9.3 Hz, 1H), 8.31 (ddd, J = 8.8, 8.8, 2.4 Hz, 1H), 8.47 (s, 1H), 8.58 (d, J = 2.4 Hz, 1H), 8.69 (s, 1H), 10.61 (s, 1H) |
| 217 | 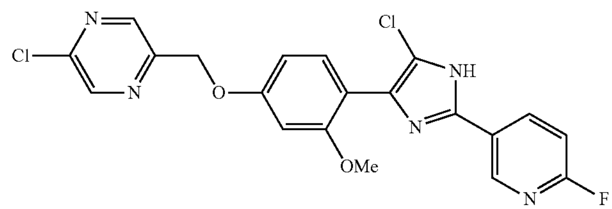 [SMILES: COc1cc(OCc2cnc(Cl)cn2)ccc1-c1nc(-c2ccc(F)nc2)[nH]c1Cl] | 231-233 Decomposition | 1H-NMR (DMSO) δ 3.81 (s, 3H), 5.36 (s, 2H), 6.78 (dd, J = 8.5, 2.4 Hz, 1H), 6.87 (d, J = 2.4 Hz, 1H), 7.30 (dd, J = 8.3, 2.7 Hz, 1H), 7.35 (d, J = 8.5 Hz, 1H), 8.44 (ddd, J = 8.3, 8.3, 2.4 Hz, 1H), 8.72 (s, 1H), 8.75 (d, J = 2.4 Hz, 1H), 8.85 (s, 1H), 12.91 (s, 1H) |
| 218 | 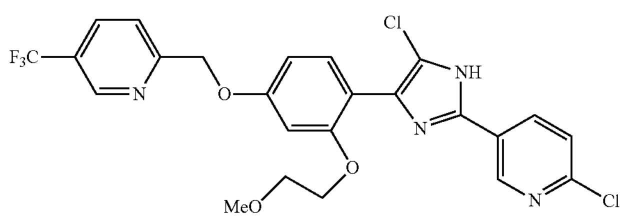 [SMILES: COCCOc1cc(OCc2ccc(C(F)(F)F)cn2)ccc1-c1nc(-c2ccc(Cl)nc2)[nH]c1Cl] | 170-172 | 1H-NMR (DMSO) δ 3.21 (s, 3H), 3.68 (t, J = 4.6 Hz, 2H), 4.19 (t, J = 4.6 Hz, 2H), 5.40 (s, 2H), 6.78 (dd, J = 8.5, 2.4 Hz, 1H), 6.92 (d, J = 2.4 Hz, 1H), 7.42 (d, J = 8.3 Hz, 1H), 7.64 (d, J = 8.5 Hz, 1H), 7.79 (d, J = 7.8 Hz, 1H), 8.28-8.36 (m, 2H), 8.93 (d, J = 2.4 Hz, 1H), 9.01 (d, J = 1.6 Hz, 1H), 12.90 (s, 1H) |
| 219 | 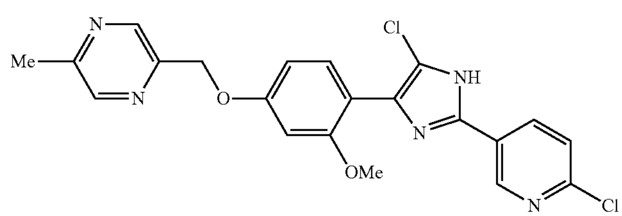 [SMILES: COc1cc(OCc2cnc(C)cn2)ccc1-c1nc(-c2ccc(Cl)nc2)[nH]c1Cl] | 196-189 | 1H-NMR (DMSO) δ 2.49 (s, 3H), 3.78 (s, 3H), 5.27 (s, 2H), 6.74 (dd, J = 8.8, 2.4 Hz, 1H), 6.83 (d, J = 2.4 Hz, 1H), 7.32 (d, J = 8.3 Hz, 1H), 7.59 (d, J = 8.8 Hz, 1H), 8.28 (dd, J = 8.3, 2.4 Hz, 1H), 8.55 (d, J = 1.0 Hz, 1H), 8.67 (d, J = 1.0 Hz, 1H), 8.90 (d, J = 2.4 Hz, 1H), 12.99 (s, 1H) |
| 220 | 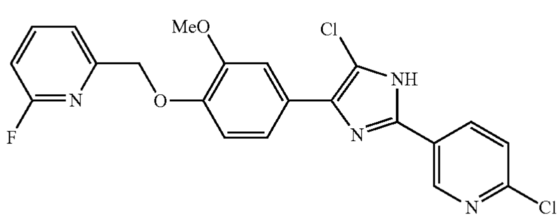 [SMILES: COc1cc(-c2nc(-c3ccc(Cl)nc3)[nH]c2Cl)ccc1OCc1cccc(F)n1] | 198-201 | 1H-NMR (DMSO) δ 3.88 (s, 3H), 5.18 (s, 2H), 7.14 (dd, J = 8.3, 2.4 Hz, 1H), 7.17 (d, J = 8.8 Hz, 1H), 7.31 (dd, J = 8.3, 2.0 Hz, 1H), 7.40 (d, J = 2.0 Hz, 1H), 7.49 (dd, J = 7.3, 2.4 Hz, 1H), 7.64 (d, J = 8.3 Hz, 1H), 8.05 (dd, J = 8.3, 7.3 Hz, 1H), 8.35 (dd, J = 8.8, 2.4 Hz, 1H), 8.97 (d, J = 2.4 Hz, 1H), 13.06 (s, 1H) |

TABLE 3-continued

| Example No. | Structure | Melting point (° C.) | 1H-NMR (δ:ppm) |
|---|---|---|---|
| 221 | 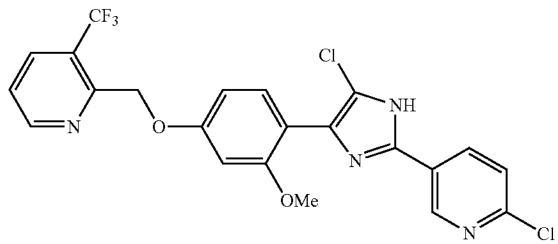 [SMILES: COc1cc(OCc2ncccc2C(F)(F)F)ccc1-c1nc(-c2ccc(Cl)nc2)[nH]c1Cl] | 182-184 | 1H-NMR (DMSO) δ 3.79 (s, 3H), 5.37 (s, 2H), 6.74 (dd, J = 8.3, 2.2 Hz, 1H), 6.79 (d, J = 2.2 Hz, 1H), 7.34 (d, J = 8.3 Hz, 1H), 7.61 (d, J = 8.3 Hz, 1H), 7.68 (dd, J = 8.3, 4.9 Hz, 1H), 8.24-8.38 (m, 2H), 8.90 (d, J = 4.9 Hz, 1H), 8.92 (d, J = 2.4 Hz, 1H), 13.01 (s, 1H) |
| 222 | 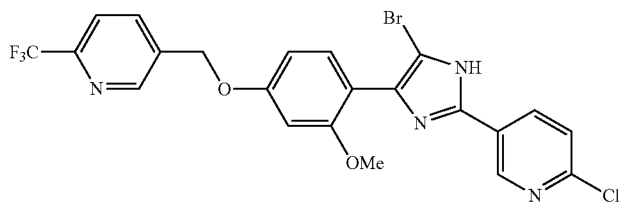 | 222-223 Decomposition | 1H-NMR (DMSO) δ 3.80 (s, 3H), 5.38 (s, 2H), 6.77 (dd, J = 8.5, 2.2 Hz, 1H), 6.85 (d, J = 2.4 Hz, 1H), 7.35 (d, J = 8.5 Hz, 1H), 7.61 (d, J = 8.3 Hz, 1H), 7.97 (d, J = 8.3 Hz, 1H), 8.19 (dd, J = 8.3, 1.5 Hz, 1H), 8.30 (dd, J = 8.3, 2.4 Hz, 1H), 8.82-8.91 (m, 1H), 8.92 (d, J = 2.4 Hz, 1H), 13.07 (s, 1H) |
| 223 | 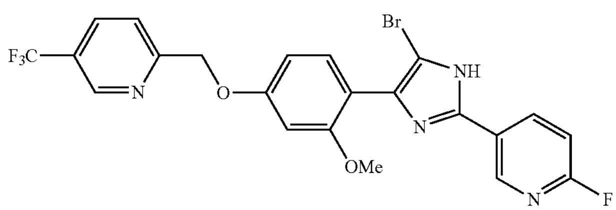 [SMILES: COc1cc(OCc2ccc(C(F)(F)F)cn2)ccc1-c1nc(-c2ccc(F)nc2)[nH]c1Br] | 176-178 | 1H-NMR (CDCL3) δ 3.95 (s, 3H), 5.32 (s, 2H), 6.61-6.79 (m, 2H), 7.03 (dd, J = 8.8, 2.9 Hz, 1H), 7.70 (d, J = 8.3 Hz, 1H), 7.99 (dd, J = 8.3, 2.0 Hz, 1H), 8.04 (d, J = 8.3 Hz, 1H), 8.24-8.42 (m, 1H), 8.58 (d, J = 2.4 Hz, 1H), 8.89 (s, 1H), 10.43 (s, 1H) |
| 224 | 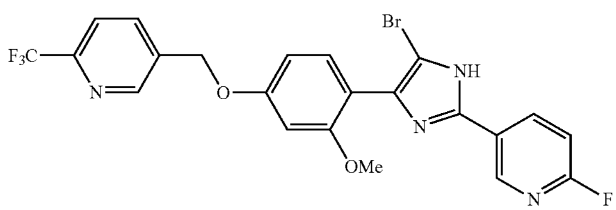 [SMILES: COc1cc(OCc2ccc(C(F)(F)F)nc2)ccc1-c1nc(-c2ccc(F)nc2)[nH]c1Br] | 195-197 Decomposition | 1H-NMR (DMSO) δ 3.80 (s, 3H), 5.38 (s, 2H), 6.75 (dd, J = 8.3, 2.0 Hz, 1H), 6.85 (d, J = 2.0 Hz, 1H), 7.30 (dd, J = 8.5, 2.4 Hz, 1H), 7.35 (d, J = 8.3 Hz, 1H), 7.97 (d, J = 8.3 Hz, 1H), 8.19 (dd, J = 8.3, 1.2 Hz, 1H), 8.44 (ddd, J = 8.5, 8.5, 2.4 Hz, 1H), 8.75 (d, J = 2.0 Hz, 1H), 8.82-8.97 (m, 1H), 12.99 (s, 1H) |
| 225 | 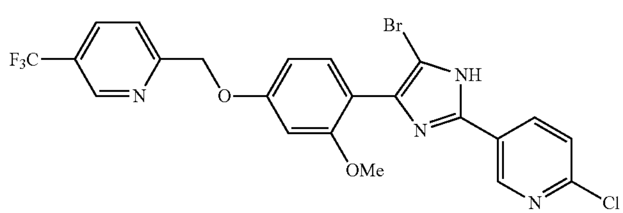 [SMILES: COc1cc(OCc2ccc(C(F)(F)F)cn2)ccc1-c1nc(-c2ccc(Cl)nc2)[nH]c1Br] | 186-188 | 1H-NMR (DMSO) δ 3.80 (s, 3H), 5.39 (s, 2H), 6.74 (dd, J = 8.3, 1.9 Hz, 1H), 6.86 (d, J = 1.9 Hz, 1H), 7.34 (d, J = 8.3 Hz, 1H), 7.61 (d, J = 8.3 Hz, 1H), 7.79 (d, J = 8.3 Hz, 1H), 8.25-8.36 (m, 2H), 8.92 (d, J = 2.5 Hz, 1H), 9.00 (s, 1H) |
| 226 | 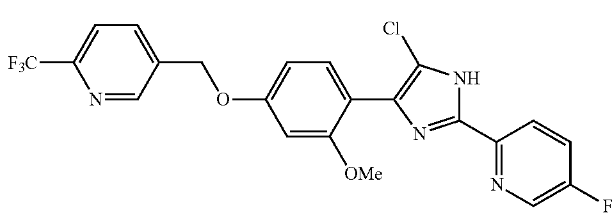 [SMILES: COc1cc(OCc2ccc(C(F)(F)F)nc2)ccc1-c1nc(-c2ccc(F)cn2)[nH]c1Cl] | 186-193 Decomposition | 1H-NMR (DMSO) δ 3.80 (s, 3H), 5.37 (s, 2H), 6.75 (dd, J = 8.3, 2.4 Hz, 1H), 6.82 (d, J = 2.4 Hz, 1H), 7.35 (d, J = 8.3 Hz, 1H), 7.85 (ddd, J = 8.8, 8.8, 2.9 Hz, 1H), 7.99 (d, J = 8.3 Hz, 1H), 8.05 (dd, J = 8.8, 8.8 Hz, 1H), 8.21 (dd, J = 8.3, 1.5 Hz, 1H), 8.61 (d, J = 2.9 Hz, 1H), 8.91 (d, J = 1.5 Hz, 1H), 13.01 (s, 1H) |

TABLE 3-continued

| Example No. | Structure | Melting point (°C.) | 1H-NMR (δ:ppm) |
|---|---|---|---|
| 227 | 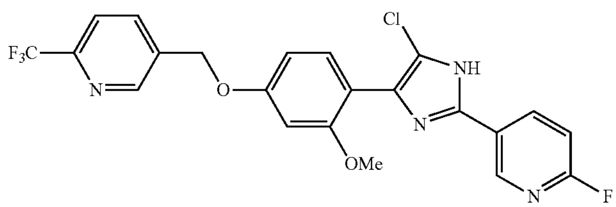 [SMILES: COc1cc(OCc2ccc(C(F)(F)F)nc2)ccc1-c1nc(-c2ccc(F)nc2)[nH]c1Cl] | 176-177 | 1H-NMR (CDCL3) δ 3.98 (s, 3H), 5.22 (s, 2H), 6.65-6.74 (m, 2H), 7.03 (dd, J = 8.8, 2.9 Hz, 1H), 7.75 (d, J = 8.3 Hz, 1H), 8.00 (dd, J = 8.3, 1.0 Hz, 1H), 8.06 (d, J = 8.3 Hz, 1H), 8.32 (ddd, J = 8.8, 8.8, 2.4 Hz, 1H), 8.59 (d, J = 2.4 Hz, 1H), 8.82 (s, 1H), 10.50 (s, 1H) |
| 228 | 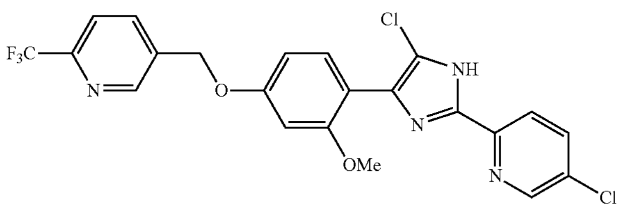 [SMILES: COc1cc(OCc2ccc(C(F)(F)F)nc2)ccc1-c1nc(-c2ccc(Cl)cn2)[nH]c1Cl] | 193-196 | 1H-NMR (CDCL3) δ 3.97 (s, 3H), 5.22 (s, 2H), 6.49-6.76 (m, 2H), 7.64-7.88 (m, 2H), 7.91-8.25 (m, 3H), 8.48 (d, J = 2.4 Hz, 1H), 8.74-8.90 (m, 1H), 11.05 (s, 1H) |
| 229 | 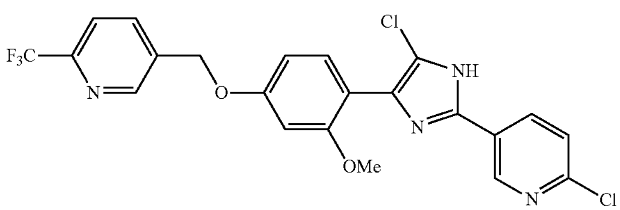 [SMILES: COc1cc(OCc2ccc(C(F)(F)F)nc2)ccc1-c1nc(-c2ccc(Cl)nc2)[nH]c1Cl] | 205-208 | 1H-NMR (CDCL3) δ 3.98 (s, 3H), 5.22 (s, 2H), 6.61-6.79 (m, 2H), 7.41 (d, J = 8.3 Hz, 1H), 7.75 (d, J = 7.8 Hz, 1H), 8.00 (dd, J = 7.8, 1.5 Hz, 1H), 8.07 (d, J = 8.8 Hz, 1H), 8.16 (dd, J = 8.8, 2.9 Hz, 1H), 8.76 (d, J = 2.9 Hz, 1H), 8.82 (d, J = 1.5 Hz, 1H), 10.54 (s, 1H) |
| 230 | 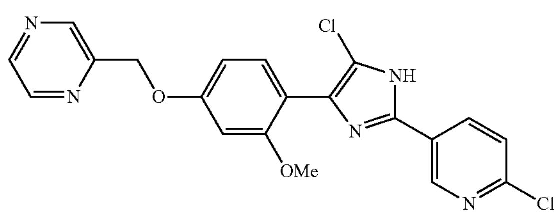 [SMILES: COc1cc(OCc2cnccn2)ccc1-c1nc(-c2ccc(Cl)nc2)[nH]c1Cl] | 172-174 | 1H-NMR (DMSO) δ 3.83 (s, 3H), 5.37 (s, 2H), 6.80 (dd, J = 8.3, 2.1 Hz, 1H), 6.89 (d, J = 2.1 Hz, 1H), 7.37 (d, J = 8.3 Hz, 1H), 7.63 (d, J = 8.7 Hz, 1H), 8.32 (dd, J = 8.7, 2.5 Hz, 1H), 8.64-8.75 (m, 2H), 8.87 (s, 1H), 8.94 (d, J = 2.5 Hz, 1H), 13.06 (s, 1H) |
| 231 | 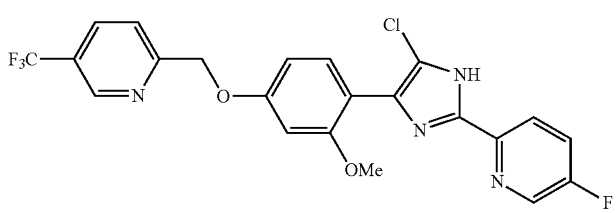 [SMILES: COc1cc(OCc2ccc(C(F)(F)F)cn2)ccc1-c1nc(-c2ccc(F)cn2)[nH]c1Cl] | 222-224 Decomposition | 1H-NMR (DMSO) δ 3.79 (s, 3H), 5.38 (s, 2H), 6.71 (dd, J = 8.8, 2.4 Hz, 1H), 6.83 (d, J = 2.4 Hz, 1H), 7.32 (d, J = 8.8 Hz, 1H), 7.71-7.92 (m, 2H), 8.04 (dd, J = 8.8, 4.6 Hz, 1H), 8.29 (dd, J = 8.3, 2.4 Hz, 1H), 8.59 (d, J = 2.4 Hz, 1H), 8.92-9.08 (m, 1H), 12.98 (s, 1H) |
| 232 | 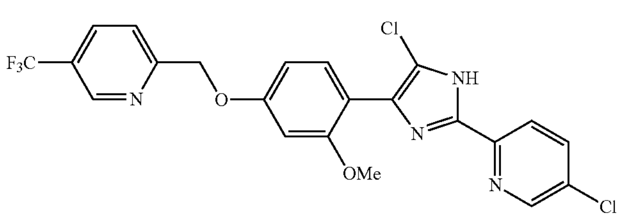 [SMILES: COc1cc(OCc2ccc(C(F)(F)F)cn2)ccc1-c1nc(-c2ccc(Cl)cn2)[nH]c1Cl] | 197-199 Decomposition | 1H-NMR (DMSO) δ 3.79 (s, 3H), 5.38 (s, 2H), 6.71 (dd, J = 8.5, 2.4 Hz, 1H), 6.83 (d, J = 2.4 Hz, 1H), 27.23-7.41 (1H), 7.80 (d, J = 8.3 Hz, 1H), 7.90-8.12 (m, 2H), 8.29 (dd, J = 8.3, 2.0 Hz, 1H), 8.64 (d, J = 2.4 Hz, 1H), 8.92-9.09 (1H), 13.13 (s, 1H) |

TABLE 3-continued

| Example No. | Structure | Melting point (° C.) | 1H-NMR (δ:ppm) |
|---|---|---|---|
| 233 | 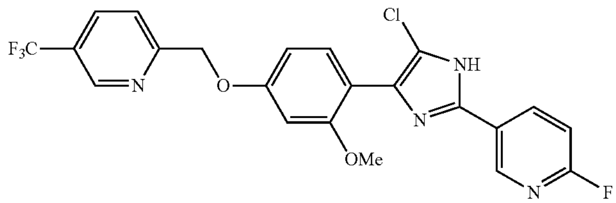 [SMILES: COc1cc(OCc2ccc(C(F)(F)F)cn2)ccc1-c1nc(-c2ccc(F)nc2)[nH]c1Cl] | 190-193 | 1H-NMR (DMSO) δ 3.81 (s, 3H), 5.39 (s, 2H), 6.75 (dd, J = 8.3, 2.4 Hz, 1H), 6.87 (d, J = 2.0 Hz, 1H), 7.30 (dd, J = 8.8, 2.9 Hz, 1H), 7.35 (d, J = 8.3 Hz, 1H), 7.79 (d, J = 8.3 Hz, 1H), 8.29 (dd, J = 8.3, 2.4 Hz, 1H), 8.44 (ddd, J = 8.3, 8.3, 2.4 Hz, 1H), 8.76 (d, J = 2.0 Hz, 1H), 9.00 (s, 1H), 12.94 (s, 1H) |
| 234 | 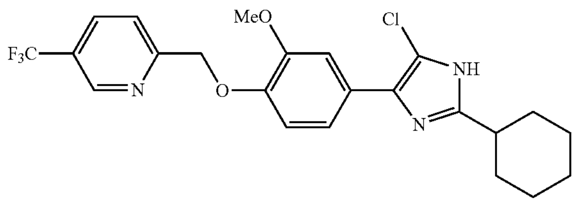 [SMILES: COc1cc(-c2nc(C3CCCCC3)[nH]c2Cl)ccc1OCc1ccc(C(F)(F)F)cn1] | 171-175 | 1H-NMR (CDCL3) δ 1.10-2.07 (m, 10H), 2.64 (tt, J = 11.8, 3.5 Hz, 1H), 3.90 (s, 3H), 5.32 (s, 2H), 6.87 (d, J = 8.2 Hz, 1H), 7.06 (dd, J = 8.2, 2.0 Hz, 1H), 7.29 (d, J = 2.0 Hz, 1H), 7.72 (d, J = 8.2 Hz, 1H), 7.95 (dd, J = 8.2, 2.0 Hz, 1H), 8.84 (s, 1H), 9.97 (s, 1H) |
| 235 | 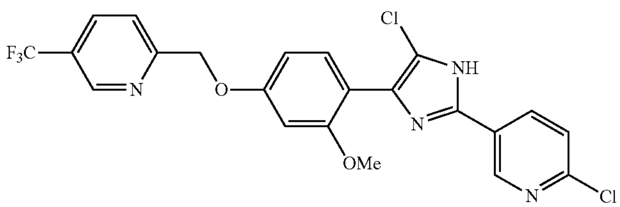 [SMILES: COc1cc(OCc2ccc(C(F)(F)F)cn2)ccc1-c1nc(-c2ccc(Cl)nc2)[nH]c1Cl] | 180-182 | 1H-NMR (CDCL3) δ 3.94 (s, 3H), 5.30 (s, 2H), 6.62-6.72 (m, 2H), 7.38 (d, J = 8.5 Hz, 1H), 7.69 (d, J = 8.2 Hz, 1H), 7.95-8.03 (m, 2H), 8.13 (dd, J = 8.5, 2.6 Hz, 1H), 8.74 (d, J = 2.6 Hz, 1H), 8.88 (s, 1H), 10.69 (s, 1H) |
| 236 | 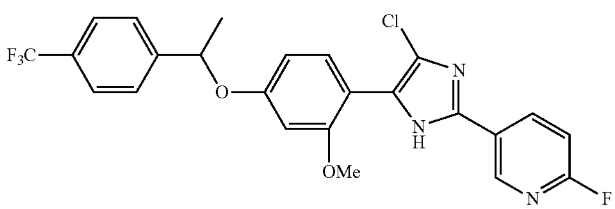 [SMILES: COc1cc(OC(C)c2ccc(C(F)(F)F)cc2)ccc1-c1[nH]c(-c2ccc(F)nc2)nc1Cl] | 137-146 | 1H-NMR (CDCL3) δ 1.68 (d, J = 6.3 Hz, 3H), 3.91 (s, 3H), 5.41 (q, J = 6.3 Hz, 1H), 6.49 (dd, J = 8.8, 2.4 Hz, 1H), 6.59 (d, J = 2.4 Hz, 1H), 7.00 (dd, J = 8.5, 2.7 Hz, 1H), 7.50 (d, J = 8.3 Hz, 2H), 7.62 (d, J = 8.3 Hz, 2H), 7.91 (d, J = 8.8 Hz, 1H), 8.28 (ddd, J = 9.1, 8.5, 2.4 Hz, 1H), 10.50 (s, 1H) |
| 237 | 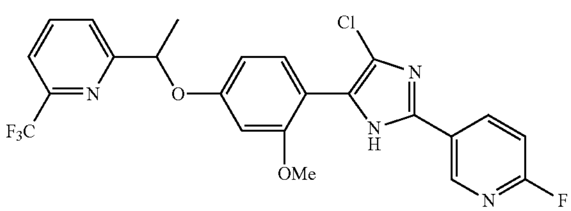 [SMILES: COc1cc(OC(C)c2cccc(C(F)(F)F)n2)ccc1-c1[nH]c(-c2ccc(F)nc2)nc1Cl] | 170-175 | 1H-NMR (DMSO) δ 1.65 (d, J = 6.6 Hz, 3H), 3.75 (s, 3H), 5.71 (q, J = 6.6 Hz, 1H), 6.60 (dd, J = 8.5, 1.9 Hz, 1H), 6.78 (d, J = 1.9 Hz, 1H), 7.20-7.35 (m, 2H), 7.77-7.91 (m, 2H), 8.12 (dd, J = 7.9, 7.9 Hz, 1H), 8.41 (ddd, J = 8.0, 8.0, 1.7 Hz, 1H), 8.73 (d, J = 1.7 Hz, 1H), 12.87 (s, 1H) |
| 238 | 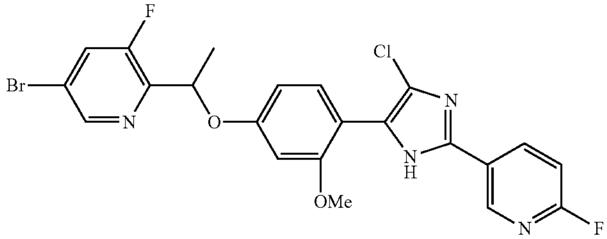 [SMILES: COc1cc(OC(C)c2ncc(Br)cc2F)ccc1-c1[nH]c(-c2ccc(F)nc2)nc1Cl] | 173-175 | 1H-NMR (CDCL3) δ 1.76 (d, J = 6.8 Hz, 3H), 3.92 (s, 3H), 5.72 (q, J = 6.8 Hz, 1H), 6.58 (dd, J = 8.8, 2.4 Hz, 1H), 6.69 (d, J = 2.4 Hz, 1H), 7.01 (dd, J = 8.3, 2.4 Hz, 1H), 7.62 (dd, J = 9.0, 1.7 Hz, 1H), 7.94 (d, J = 8.8 Hz, 1H), 8.29 (ddd, J = 8.3, 8.3, 2.4 Hz, 1H), 8.51 (d, J = 1.7 Hz, 1H), 8.56 (s, 1H), 10.50 (s, 1H) |

TABLE 3-continued

| Example No. | Structure | Melting point (° C.) | 1H-NMR (δ:ppm) |
|---|---|---|---|
| 239 | 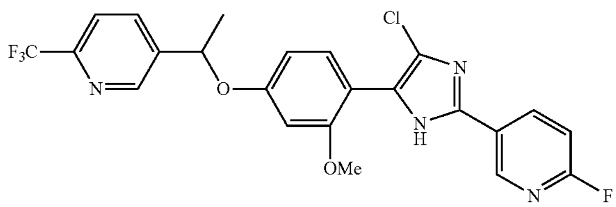 | 148-150 | 1H-NMR (CDCL3) δ 1.72 (d, J = 6.5 Hz, 3H), 3.92 (s, 3H), 5.51 (q, J = 6.5 Hz, 1H), 6.49 (dd, J = 8.7, 2.1 Hz, 1H), 6.60 (d, J = 2.1 Hz, 1H), 7.00 (dd, J = 8.5, 2.7 Hz, 1H), 7.70 (d, J = 7.9 Hz, 1H), 7.85-7.98 (m, 2H), 8.17-8.37 (m, 1H), 8.55 (d, J = 1.7 Hz, 1H), 8.76 (s, 1H), 10.57 (s, 1H) |
| 240 | 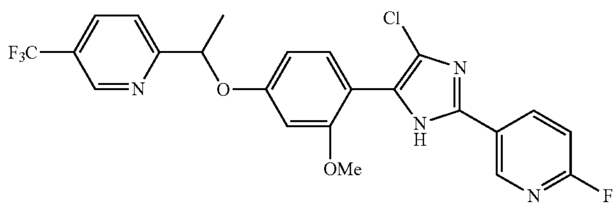 [SMILES: COc1cc(OC(C)c2ccc(C(F)(F)F)cn2)ccc1-c1[nH]c(-c2ccc(F)nc2)nc1Cl] | 165-168 | 1H-NMR (CDCL3) δ 1.73 (d, J = 6.5 Hz, 3H), 3.93 (s, 3H), 5.54 (q, J = 6.5 Hz, 1H), 6.53 (dd, J = 8.8, 2.4 Hz, 1H), 6.64 (d, J = 2.4 Hz, 1H), 7.02 (dd, J = 8.8, 2.9 Hz, 1H), 7.58 (d, J = 8.8 Hz, 1H), 7.87-8.02 (m, 2H), 8.30 (ddd, J = 8.8, 8.8, 2.4 Hz, 1H), 8.56 (d, J = 2.0 Hz, 1H), 8.79-8.94 (m, 1H), 10.45 (s, 1H) |
| 241 | 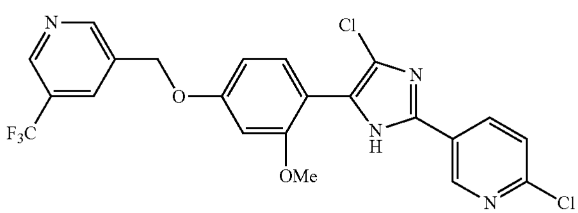 [SMILES: COc1cc(OCc2cncc(C(F)(F)F)c2)ccc1-c1[nH]c(-c2ccc(Cl)nc2)nc1Cl] | 198-201 | 1H-NMR (DMSO) δ 3.81 (s, 3H), 5.35 (s, 2H), 6.79 (dd, J = 8.3, 2.4 Hz, 1H), 6.86 (d, J = 2.4 Hz, 1H), 7.37 (d, J = 8.3 Hz, 1H), 7.62 (d, J = 8.3 Hz, 1H), 8.31 (dd, J = 8.3, 2.4 Hz, 1H), 8.33-8.39 (m, 1H), 8.93 (d, J = 2.4 Hz, 1H), 8.98 (s, 1H), 9.02 (d, J = 1.0 Hz, 1H), 13.02 (s, 1H) |
| 242 | 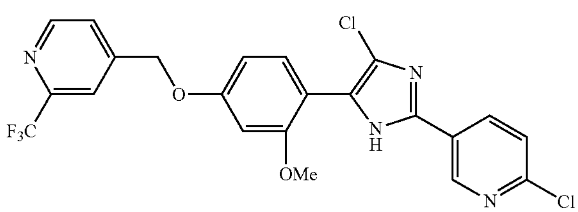 [SMILES: COc1cc(OCc2ccnc(C(F)(F)F)c2)ccc1-c1[nH]c(-c2ccc(Cl)nc2)nc1Cl] | 236-239 | 1H-NMR (DMSO) δ 3.81 (s, 3H), 5.40 (s, 2H), 6.75 (dd, J = 8.3, 2.4 Hz, 1H), 6.87 (d, J = 2.4 Hz, 1H), 7.36 (d, J = 8.3 Hz, 1H), 7.61 (d, J = 8.3 Hz, 1H), 7.80 (d, J = 4.9 Hz, 1H), 7.92-8.05 (m, 1H), 8.30 (dd, J = 8.3, 2.4 Hz, 1H), 8.80 (d, J = 4.9 Hz, 1H), 8.92 (d, J = 2.4 Hz, 1H) |
| 243 | 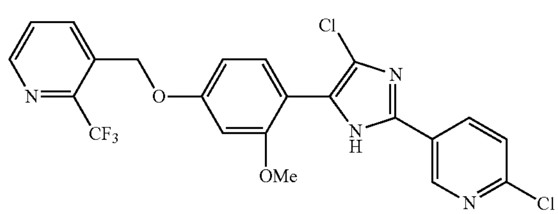 [SMILES: COc1cc(OCc2cccnc2C(F)(F)F)ccc1-c1[nH]c(-c2ccc(Cl)nc2)nc1Cl] | 195-199 | 1H-NMR (DMSO) δ 3.81 (s, 3H), 5.37 (s, 2H), 6.74 (dd, J = 8.8, 2.4 Hz, 1H), 6.81 (d, J = 2.4 Hz, 1H), 7.36 (d, J = 8.3 Hz, 1H), 7.61 (d, J = 8.8 Hz, 1H), 7.80 (dd, J = 8.0, 4.6 Hz, 1H), 8.23-8.36 (m, 2H), 8.74 (d, J = 4.6 Hz, 1H), 8.92 (d, J = 2.4 Hz, 1H) |
| 244 | 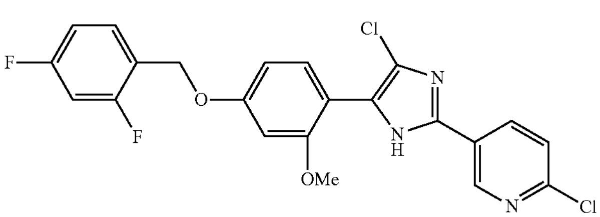 [SMILES: COc1cc(OCc2ccc(F)cc2F)ccc1-c1[nH]c(-c2ccc(Cl)nc2)nc1Cl] | 173-177 | 1H-NMR (DMSO) δ 3.80 (s, 3H), 5.18 (s, 2H), 6.76 (dd, J = 8.5, 2.4 Hz, 1H), 6.80 (d, J = 2.4 Hz, 1H), 7.15 (ddd, J = 8.5, 8.5, 2.4 Hz, 1H), 7.27-7.41 (m, 2H), 7.57-7.71 (m, 2H), 8.30 (dd, J = 8.3, 2.4 Hz, 1H), 8.92 (d, J = 2.4 Hz, 1H) |

TABLE 3-continued

| Example No. | Structure | Melting point (° C.) | 1H-NMR (δ:ppm) |
|---|---|---|---|
| 245 | 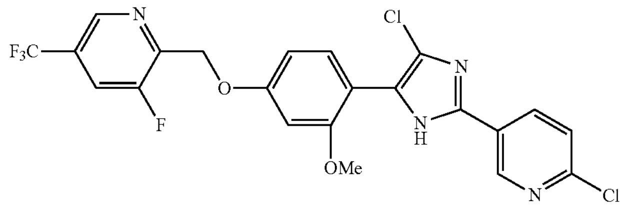 [SMILES: COc1cc(OCc2ncc(C(F)(F)F)cc2F)ccc1-c1[nH]c(-c2ccc(Cl)nc2)nc1Cl] | 116-131 | 1H-NMR (DMSO) δ 3.69 (s, 3H), 5.60 (s, 2H), 6.41 (dd, J = 8.3, 2.4 Hz, 1H), 6.46 (d, J = 2.4 Hz, 1H), 7.18 (d, J = 8.3 Hz, 1H), 7.60 (d, J = 8.8 Hz, 1H), 8.11 (dd, J = 8.8, 2.4 Hz, 1H), 8.41 (d, J = 9.8 Hz, 1H), 8.68 (d, J = 2.4 Hz, 1H), 8.85 (s, 1H), 9.63 (s, 1H) |
| 246 | 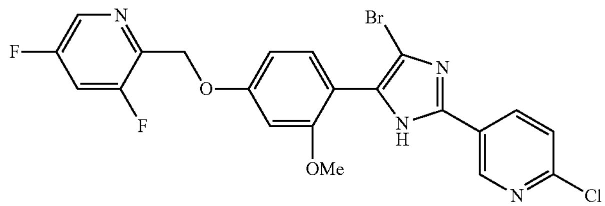 [SMILES: COc1cc(OCc2ncc(F)cc2F)ccc1-c1[nH]c(-c2ccc(Cl)nc2)nc1Br] | 190-193 | 1H-NMR (DMSO) δ 3.79 (s, 3H), 5.30 (d, J = 1.5 Hz, 2H), 6.77 (dd, J = 8.3, 2.4 Hz, 1H), 6.82 (d, J = 2.4 Hz, 1H), 7.34 (d, J = 8.3 Hz, 1H), 7.61 (d, J = 8.3 Hz, 1H), 8.00 (ddd, J = 9.4, 9.4, 2.4 Hz, 1H), 8.30 (dd, J = 8.3, 2.4 Hz, 1H), 8.57 (d, J = 2.4 Hz, 1H), 8.92 (d, J = 2.4 Hz, 1H), 13.06 (s, 1H) |
| 247 | 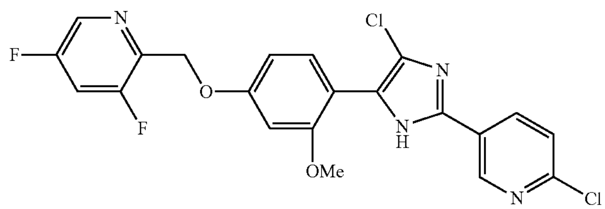 [SMILES: COc1cc(OCc2ncc(F)cc2F)ccc1-c1[nH]c(-c2ccc(Cl)nc2)nc1Cl] | 187-190 | 1H-NMR (DMSO) δ 3.80 (s, 3H), 5.30 (d, J = 2.0 Hz, 2H), 6.77 (dd, J = 8.3, 2.4 Hz, 1H), 6.83 (d, J = 2.4 Hz, 1H), 7.35 (d, J = 8.5 Hz, 1H), 7.62 (d, J = 8.3 Hz, 1H), 8.04 (ddd, J = 9.6, 8.4, 2.7 Hz, 1H), 8.31 (dd, J = 8.5, 2.7 Hz, 1H), 8.57 (d, J = 2.7 Hz, 1H), 8.93 (dd, J = 2.7, 1.0 Hz, 1H), 13.01 (s, 1H) |
| 248 | 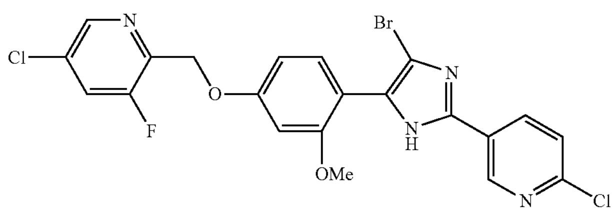 | 172-176 | 1H-NMR (DMSO) δ 3.79 (s, 3H), 5.31 (d, J = 2.0 Hz, 2H), 6.75 (dd, J = 8.5, 2.4 Hz, 1H), 6.81 (d, J = 2.4 Hz, 1H), 7.33 (d, J = 8.5 Hz, 1H), 7.61 (d, J = 8.3 Hz, 1H), 8.20 (dd, J = 9.8, 2.0 Hz, 1H), 8.30 (dd, J = 8.3, 2.4 Hz, 1H), 8.58 (dd, J = 2.0, 1.0 Hz, 1H), 8.92 (d, J = 2.4 Hz, 1H), 13.07 (s, 1H) |
| 249 | 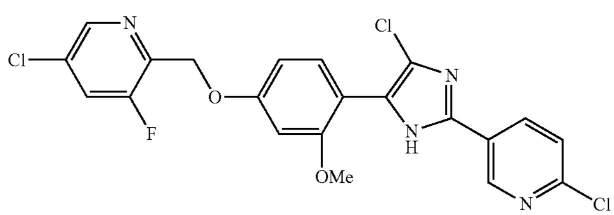 | 174-181 | 1H-NMR (DMSO) δ 3.79 (s, 3H), 5.31 (d, J = 1.5 Hz, 2H), 6.76 (dd, J = 8.3, 2.4 Hz, 1H), 6.82 (d, J = 2.4 Hz, 1H), 7.34 (d, J = 8.5 Hz, 1H), 7.62 (d, J = 8.3 Hz, 1H), 8.19 (dd, J = 9.8, 2.0 Hz, 1H), 8.30 (dd, J = 8.5, 2.4 Hz, 1H), 8.58 (d, J = 2.0 Hz, 1H), 8.92 (d, J = 2.4 Hz, 1H), 13.01 (s, 1H) |
| 250 | 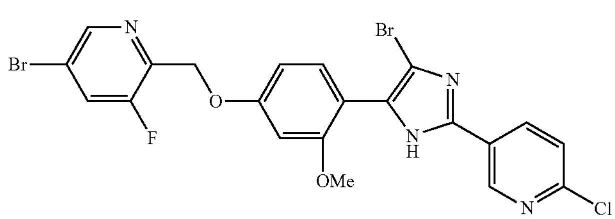 [SMILES: COc1cc(OCc2ncc(Cl)cc2F)ccc1-c1[nH]c(-c2ccc(Cl)nc2)nc1Br] | 174-179 | 1H-NMR (DMSO) δ 3.79 (s, 3H), 5.30 (d, J = 2.0 Hz, 2H), 6.75 (dd, J = 8.3, 2.4 Hz, 1H), 6.82 (d, J = 2.4 Hz, 1H), 7.33 (d, J = 8.3 Hz, 1H), 7.61 (d, J = 8.3 Hz, 1H), 8.21-8.39 (m, 2H), 8.65 (d, J = 1.5 Hz, 1H), 8.92 (d, J = 2.4 Hz, 1H), 13.06 (s, 1H) |

TABLE 3-continued

| Example No. | Structure | Melting point (° C.) | 1H-NMR (δ:ppm) |
|---|---|---|---|
| 251 | 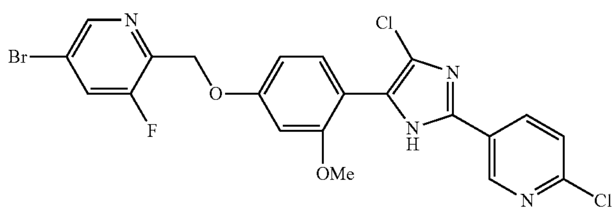 [SMILES: COc1cc(OCc2ncc(Br)cc2F)ccc1-c1[nH]c(-c2ccc(Cl)nc2)nc1Cl] | 189-191 | 1H-NMR (DMSO) δ 3.79 (s, 3H), 5.30 (d, J = 2.0 Hz, 2H), 6.75 (dd, J = 8.3, 2.4 Hz, 1H), 6.82 (d, J = 2.4 Hz, 1H), 7.34 (d, J = 8.3 Hz, 1H), 7.62 (d, J = 8.3 Hz, 1H), 8.26-8.34 (m, 2H), 8.62-8.68 (m, 1H), 8.92 (d, J = 2.4 Hz, 1H), 13.01 (s, 1H) |
| 252 | 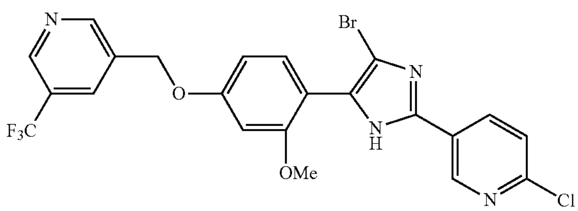 [SMILES: COc1cc(OCc2cncc(C(F)(F)F)c2)ccc1-c1[nH]c(-c2ccc(Cl)nc2)nc1Br] | 186-199 | 1H-NMR (DMSO) δ 3.81 (s, 3H), 5.35 (s, 2H), 6.78 (dd, J = 8.3, 2.4 Hz, 1H), 6.86 (d, J = 2.4 Hz, 1H), 7.37 (d, J = 8.3 Hz, 1H), 7.61 (d, J = 8.3 Hz, 1H), 8.30 (dd, J = 8.3, 2.4 Hz, 1H), 8.33-8.38 (m, 1H), 8.92 (d, J = 2.4 Hz, 1H), 8.98 (d, J = 1.5 Hz, 1H), 9.02 (d, J = 1.5 Hz, 1H), 13.07 (s, 1H) |
| 253 | 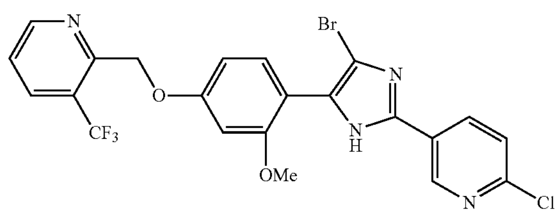 [SMILES: COc1cc(OCc2ncccc2C(F)(F)F)ccc1-c1[nH]c(-c2ccc(Cl)nc2)nc1Br] | 176-186 | 1H-NMR (DMSO) δ 3.77 (s, 3H), 5.37 (s, 2H), 6.64-6.84 (m, 2H), 7.31 (d, J = 8.8 Hz, 1H), 7.52-7.65 (m, 1H), 7.68 (dd, J = 7.3, 4.9 Hz, 1H), 8.20-8.37 (m, 2H), 8.83-8.98 (m, 2H) |
| 254 | 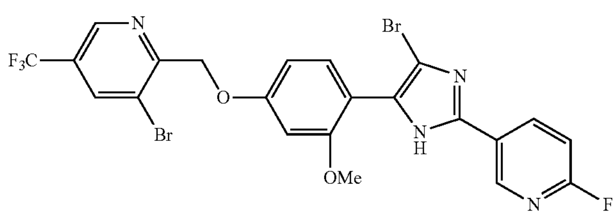 [SMILES: COc1cc(OCc2ncc(C(F)(F)F)cc2Br)ccc1-c1[nH]c(-c2ccc(F)nc2)nc1Br] | 148-170 | 1H-NMR (DMSO) δ 3.79 (s, 3H), 5.42 (s, 2H), 6.73 (dd, J = 8.5, 2.2 Hz, 1H), 6.82 (d, J = 2.2 Hz, 1H), 7.30 (dd, J = 8.8, 2.7 Hz, 1H), 7.33 (d, J = 8.5 Hz, 1H), 8.43 (ddd, J = 8.8, 8.8, 2.2 Hz, 1H), 8.67 (d, J = 1.5 Hz, 1H), 8.75 (d, J = 2.2 Hz, 1H), 9.02 (d, J = 1.5 Hz, 1H), 12.99 (s, 1H) |
| 255 | 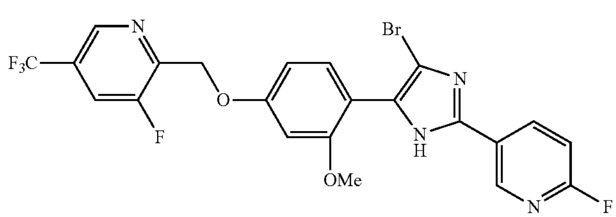 [SMILES: COc1cc(OCc2ncc(C(F)(F)F)cc2F)ccc1-c1[nH]c(-c2ccc(F)nc2)nc1Br] | 156-158 | 1H-NMR (CDCL3) δ 3.93 (s, 3H), 5.38 (s, 2H), 6.65-6.85 (m, 2H), 7.02 (dd, J = 8.5, 2.7 Hz, 1H), 7.73 (dd, J = 9.3, 1.5 Hz, 1H), 8.03 (d, J = 8.3 Hz, 1H), 8.32 (ddd, J = 9.1, 8.5, 2.4 Hz, 1H), 8.58 (d, J = 2.4 Hz, 1H), 8.77 (s, 1H), 10.47 (s, 1H) |
| 256 | 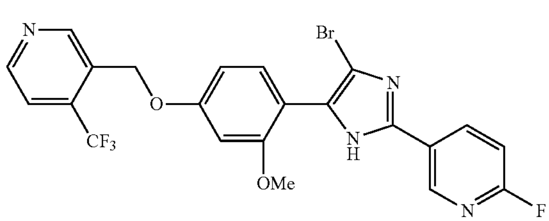 [SMILES: COc1cc(OCc2cnccc2C(F)(F)F)ccc1-c1[nH]c(-c2ccc(F)nc2)nc1Br] | 132-162 | 1H-NMR (DMSO) δ 3.73 (s, 3H), 5.30 (s, 2H), 6.70 (dd, J = 8.5, 2.3 Hz, 1H), 6.75 (d, J = 2.3 Hz, 1H), 7.23 (dd, J = 8.7, 2.9 Hz, 1H), 7.29 (d, J = 8.5 Hz, 1H), 7.77 (d, J = 5.0 Hz, 1H), 8.37 (ddd, J = 8.7, 8.7, 2.1 Hz, 1H), 8.69 (d, J = 2.1 Hz, 1H), 8.82 (d, J = 5.0 Hz, 1H), 8.98 (s, 1H), 12.93 (s, 1H) |

TABLE 3-continued

| Example No. | Structure | Melting point (° C.) | 1H-NMR (δ:ppm) |
|---|---|---|---|
| 257 | 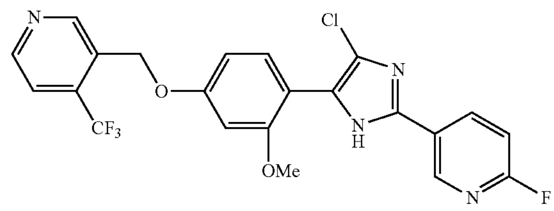 [SMILES: COc1cc(OCc2cnccc2C(F)(F)F)ccc1-c1[nH]c(-c2ccc(F)nc2)nc1Cl] | 133-153 | 1H-NMR (DMSO) δ 3.74 (s, 3H), 5.30 (s, 2H), 6.71 (dd, J = 8.3, 2.1 Hz, 1H), 6.77 (d, J = 2.1 Hz, 1H), 7.23 (dd, J = 8.5, 2.7 Hz, 1H), 7.30 (d, J = 8.3 Hz, 1H), 7.77 (d, J = 5.4 Hz, 1H), 8.37 (ddd, J = 8.5, 8.5, 2.4 Hz, 1H), 8.69 (d, J = 2.4 Hz, 1H), 8.82 (d, J = 5.4 Hz, 1H), 8.98 (s, 1H) |
| 258 | 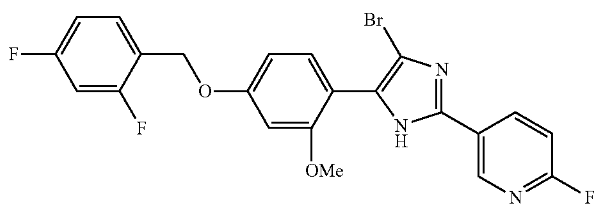 [SMILES: COc1cc(OCc2ccc(F)cc2F)ccc1-c1[nH]c(-c2ccc(F)nc2)nc1Br] | 164-166 | 1H-NMR (DMSO) δ 3.81 (s, 3H), 5.20 (s, 2H), 6.77 (dd, J = 8.5, 2.1 Hz, 1H), 6.82 (d, J = 2.1 Hz, 1H), 7.16 (ddd, J = 8.5, 8.5, 2.5 Hz, 1H), 7.25-7.41 (m, 3H), 7.68 (dd, J = 8.3, 7.7 Hz, 1H), 8.45 (ddd, J = 8.0, 8.0, 2.4 Hz, 1H), 8.77 (d, J = 2.4 Hz, 1H), 13.00 (s, 1H) |
| 259 | 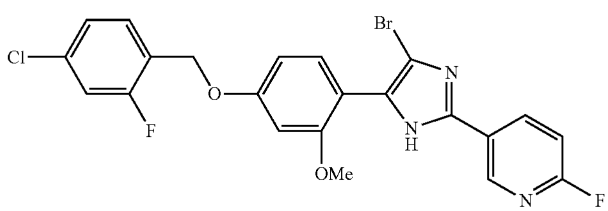 [SMILES: COc1cc(OCc2ccc(Cl)cc2F)ccc1-c1[nH]c(-c2ccc(F)nc2)nc1Br] | 165-167 | 1H-NMR (DMSO) δ 3.81 (s, 3H), 5.23 (s, 2H), 6.77 (dd, J = 8.3, 1.7 Hz, 1H), 6.82 (d, J = 1.7 Hz, 1H), 7.31 (dd, J = 8.5, 2.3 Hz, 1H), 7.33-7.41 01, 2H), 7.52 (d, J = 9.5 Hz, 1H), 7.65 (dd, J = 8.1, 8.1 Hz, 1H), 8.45 (ddd, J = 8.5, 8.5, 2.1 Hz, 1H), 8.77 (d, J = 2.1 Hz, 1H), 13.01 (s, 1H) |
| 260 | 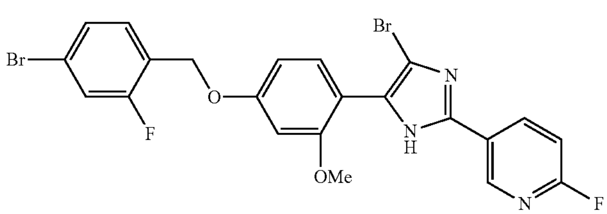 [SMILES: COc1cc(OCc2ccc(Br)cc2F)ccc1-c1[nH]c(-c2ccc(F)nc2)nc1Br] | 158-161 | 1H-NMR (DMSO) δ 3.81 (s, 3H), 5.21 (s, 2H), 6.76 (dd, J = 8.7, 1.7 Hz, 1H), 6.82 (d, J = 1.7 Hz, 1H), 7.31 (dd, J = 8.5, 2.3 Hz, 1H), 7.35 (d, J = 8.7 Hz, 1H), 7.50 (d, J = 8.3 Hz, 1H), 7.58 (dd, J = 8.3, 8.3 Hz, 1H), 7.64 (d, J = 10.0 Hz, 1H), 8.45 (ddd, J = 8.5, 8.5, 1.9 Hz, 1H), 8.77 (d, J = 1.9 Hz, 1H), 13.00 (s, 1H) |
| 261 | 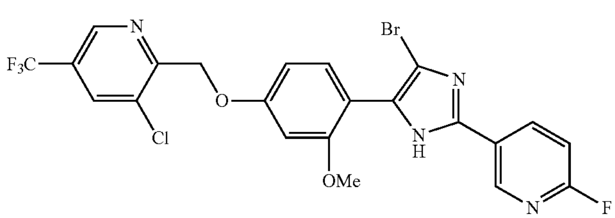 | 179-180 | 1H-NMR (DMSO) δ 3.81 (s, 3H), 5.46 (s, 2H), 6.75 (dd, J = 8.5, 2.5 Hz, 1H), 6.84 (d, J = 2.5 Hz, 1H), 7.31 (dd, J = 8.5, 2.7 Hz, 1H), 7.35 (d, J = 8.5 Hz, 1H), 8.43 (ddd, J = 8.5, 8.5, 2.5 Hz, 1H), 8.58 (d, J = 1.7 Hz, 1H), 8.76 (d, J = 2.5 Hz, 1H), 9.01 (d, J = 1.7 Hz, 1H), 13.01 (s, 1H) |

TABLE 3-continued

| Example No. | Structure | Melting point (° C.) | 1H-NMR (δ:ppm) |
|---|---|---|---|
| 262 | 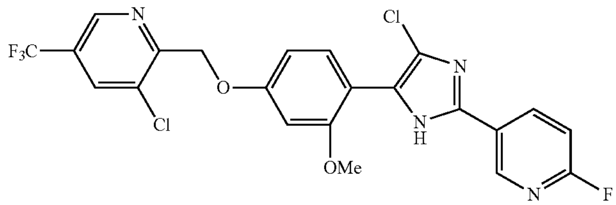 | 160-162 | 1H-NMR (CDCL3) δ 3.97 (s, 3H), 5.42 (s, 2H), 6.73 (dd, J = 8.8, 2.4 Hz, 1H), 6.76 (d, J = 2.4 Hz, 1H), 7.03 (dd, J = 8.8, 2.9 Hz, 1H), 8.01 (d, J = 2.0 Hz, 1H), 8.04 (d, J = 8.8 Hz, 1H), 8.31 (ddd, J = 9.3, 8.8, 2.4 Hz, 1H), 8.58 (d, J = 2.4 Hz, 1H), 8.82 (d, J = 2.0 Hz, 1H), 10.53 (s, 1H) |
| 263 | 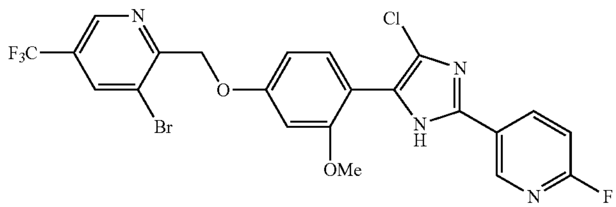 | 166-170 | 1H-NMR (DMSO) δ 3.80 (s, 3H), 5.43 (s, 2H), 6.73 (dd, J = 8.8, 2.4 Hz, 1H), 6.82 (d, J = 2.4 Hz, 1H), 7.30 (dd, J = 8.5, 2.7 Hz, 1H), 7.34 (d, J = 8.8 Hz, 1H), 8.44 (ddd, J = 8.5, 8.5, 2.4 Hz, 1H), 8.67 (d, J = 1.5 Hz, 1H), 8.75 (d, J = 2.4 Hz, 1H), 9.02 (d, J = 1.5 Hz, 1H), 12.93 (s, 1H) |
| 264 | 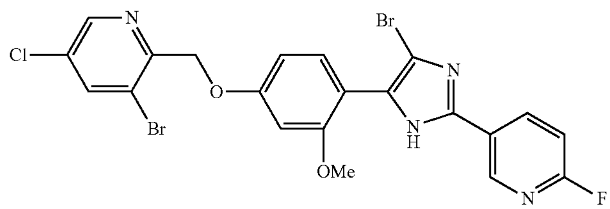 | 196-203 | 1H-NMR (DMSO) δ 3.79 (s, 3H), 5.32 (s, 2H), 6.73 (dd, J = 8.3, 2.2 Hz, 1H), 6.81 (d, J = 2.2 Hz, 1H), 7.30 (dd, J = 8.5, 2.7 Hz, 1H), 7.33 (d, J = 8.3 Hz, 1H), 8.39-8.50 (m, 2H), 8.69 (d, J = 2.2 Hz, 1H), 8.75 (d, J = 2.4 Hz, 1H), 12.98 (s, 1H |
| 265 | 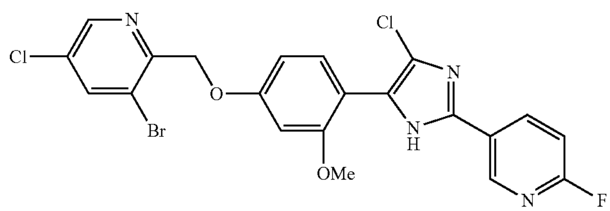 | 195-199 | 1H-NMR (DMSO) δ 3.81 (s, 3H), 5.33 (s, 2H), 6.75 (dd, J = 8.5, 2.4 Hz, 1H), 6.83 (d, J = 2.4 Hz, 1H), 7.29 (dd, J = 8.7, 2.6 Hz, 1H), 7.35 (d, J = 8.5 Hz, 1H), 7.96 (s, 1H), 8.40-8.52 (m, 2H), 8.70 (d, J = 2.2 Hz, 1H), 8.76 (d, J = 2.4 Hz, 1H), 12.94 (s, 1H) |
| 266 | 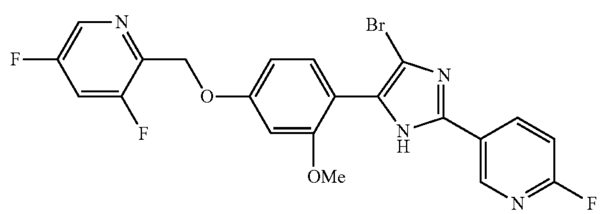 [SMILES: COc1cc(OCc2ncc(F)cc2F)ccc1-c1[nH]c(-c2ccc(F)nc2)nc1Br] | 161-164 | 1H-NMR (DMSO) δ 3.79 (s, 3H), 5.30 (d, J = 2.0 Hz, 2H), 6.76 (dd, J = 8.3, 2.2 Hz, 1H), 6.82 (d, J = 2.2 Hz, 1H), 7.30 (dd, J = 8.5, 2.7 Hz, 1H), 7.33 (d, J = 8.3 Hz, 1H), 8.04 (ddd, J = 8.5, 8.0, 2.0 Hz, 1H), 8.44 (ddd, J = 8.5, 8.5, 2.4 Hz, 1H), 8.57 (d, J = 2.0 Hz, 1H), 8.75 (d, J = 2.4 Hz, 1H), 12.99 (s, 1H) |
| 267 | 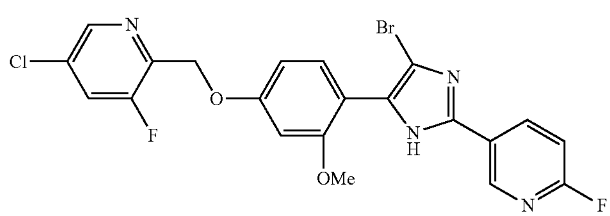 | 175-178 | 1H-NMR (DMSO) δ 3.79 (s, 3H), 5.31 (d, J = 1.5 Hz, 2H), 6.75 (dd, J = 8.3, 2.4 Hz, 1H), 6.82 (d, J = 2.4 Hz, 1H), 7.30 (dd, J = 8.5, 2.7 Hz, 1H), 7.33 (d, J = 8.3 Hz, 1H), 8.19 (dd, J = 9.3, 2.0 Hz, 1H), 8.43 (ddd, J = 8.5, 8.5, 2.4 Hz, 1H), 8.58 (dd, J = 2.0, 1.0 Hz, 1H), 8.75 (d, J = 2.4 Hz, 1H), 12.99 (s, 1H) |

TABLE 3-continued

| Example No. | Structure | Melting point (° C.) | 1H-NMR (δ:ppm) |
|---|---|---|---|
| 268 | 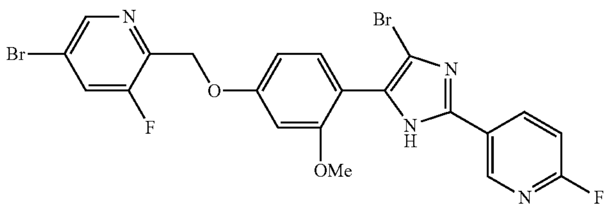 [SMILES: COc1cc(OCc2ncc(Br)cc2F)ccc1-c1[nH]c(-c2ccc(F)nc2)nc1Br] | 179-181 | 1H-NMR (DMSO) δ 3.79 (s, 3H), 5.30 (d, J = 2.0 Hz, 2H), 6.75 (dd, J = 8.3, 2.4 Hz, 1H), 6.81 (d, J = 2.4 Hz, 1H), 7.30 (dd, J = 8.5, 2.7 Hz, 1H), 7.36 (d, J = 8.3 Hz, 1H), 8.29 (dd, J = 9.3, 2.0 Hz, 1H), 8.43 (ddd, J = 8.5, 8.5, 2.4 Hz, 1H), 8.65 (dd, J = 2.0, 1.0 Hz, 1H), 8.75 (d, J = 2.4 Hz, 1H), 12.98 (s, 1H) |
| 269 | 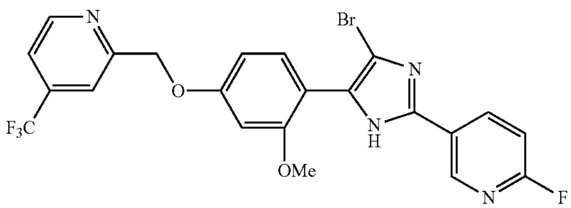 [SMILES: COc1cc(OCc2cc(C(F)(F)F)ccn2)ccc1-c1[nH]c(-c2ccc(F)nc2)nc1Br] | 179-181 | 1H-NMR (DMSO) δ 3.81 (s, 3H), 5.38 (s, 2H), 6.78 (dd, J = 8.3, 2.4 Hz, 1H), 6.89 (d, J = 2.4 Hz, 1H), 7.30 (dd, J = 8.8, 2.4 Hz, 1H), 7.35 (d, J = 8.3 Hz, 1H), 7.77 (d, J = 4.9 Hz, 1H), 7.92 (s, 1H), 8.44 (ddd, J = 8.8, 8.8, 2.4 Hz, 1H), 8.75 (d, J = 2.4 Hz, 1H), 8.90 (d, J = 4.9 Hz, 1H), 12.99 (s, 1H) |
| 270 | 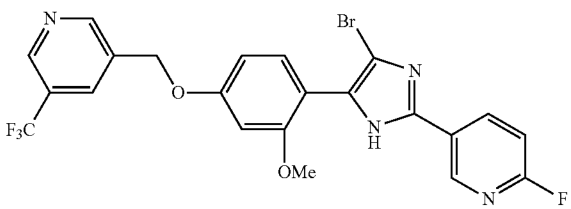 [SMILES: COc1cc(OCc2cncc(C(F)(F)F)c2)ccc1-c1[nH]c(-c2ccc(F)nc2)nc1Br] | 176-179 | 1H-NMR (CDCL3) δ 3.96 (s, 3H), 5.21 (s, 2H), 6.62-6.80 (m, 2H), 7.03 (dd, J = 8.5, 2.7 Hz, 1H), 7.99-8.15 (m, 2H), 8.25-8.43 (m, 1H), 8.59 (d, J = 1.5 Hz, 1H), 8.83-8.98 (m, 2H), 10.41 (s, 1H) |
| 271 | 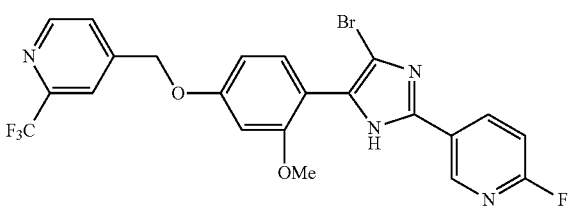 [SMILES: COc1cc(OCc2ccnc(C(F)(F)F)c2)ccc1-c1[nH]c(-c2ccc(F)nc2)nc1Br] | 223-225 Decomposition | 1H-NMR (DMSO) δ 3.81 (s, 3H), 5.40 (s, 2H), 6.75 (dd, J = 8.3, 2.4 Hz, 1H), 6.87 (d, J = 2.4 Hz, 1H), 7.29 (dd, J = 8.5, 2.7 Hz, 1H), 7.35 (d, J = 8.3 Hz, 1H), 7.80 (d, J = 4.9 Hz, 1H), 7.97-8.00 (m, 1H), 8.44 (ddd, J = 8.5, 8.5, 2.4 Hz, 1H), 8.75 (d, J = 2.4 Hz, 1H), 8.80 (d, J = 4.9 Hz, 1H), 12.99 (s, 1H) |
| 272 | 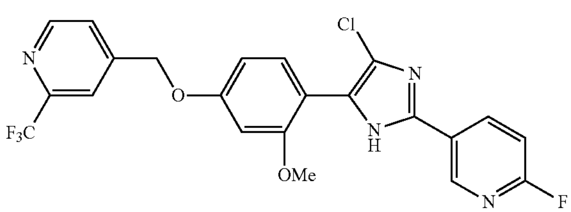 [SMILES: COc1cc(OCc2ccnc(C(F)(F)F)c2)ccc1-c1[nH]c(-c2ccc(F)nc2)nc1Cl] | 236-238 | 1H-NMR (DMSO) δ 3.81 (s, 3H), 5.40 (s, 2H), 6.75 (dd, J = 8.3, 2.4 Hz, 1H), 6.87 (d, J = 2.4 Hz, 1H), 7.29 (dd, J = 8.5, 2.7 Hz, 1H), 7.35 (d, J = 8.3 Hz, 1H), 7.80 (d, J = 5.4 Hz, 1H), 7.98 (s, 1H), 8.44 (ddd, J = 8.5, 8.5, 2.4 Hz, 1H), 8.75 (d, J = 2.4 Hz, 1H), 8.80 (d, J = 5.4 Hz, 1H), 12.99 (s, 1H) |
| 273 | 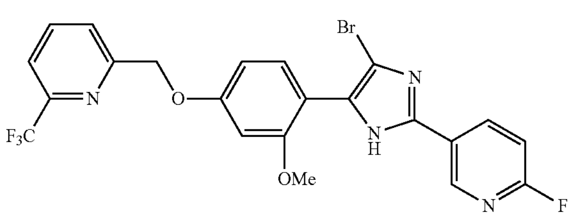 [SMILES: COc1cc(OCc2cccc(C(F)(F)F)n2)ccc1-c1[nH]c(-c2ccc(F)nc2)nc1Br] | 200-202 Decomposition | 1H-NMR (CDCL3) δ 3.95 (s, 3H), 5.33 (s, 2H), 6.67-6.75 (m, 2H), 7.03 (dd, J = 8.5, 2.7 Hz, 1H), 7.66 (d, J = 7.8 Hz, 1H), 7.78 (d, J = 7.8 Hz, 1H), 7.95 (dd, J = 7.8, 7.8 Hz, 1H), 8.03 (d, J = 8.3 Hz, 1H), 8.32 (ddd, J = 9.1, 8.5, 2.4 Hz, 1H), 8.58 (d, J = 2.4 Hz, 1H), 10.43 (s, 1H) |

TABLE 3-continued

| Example No. | Structure | Melting point (° C.) | 1H-NMR (δ:ppm) |
|---|---|---|---|
| 274 | 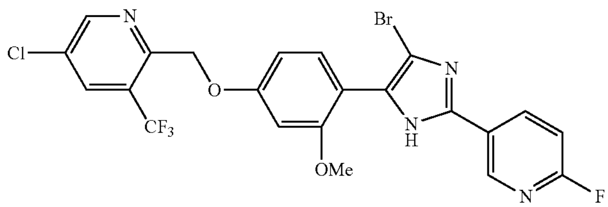 | 167-168 | 1H-NMR (DMSO) δ 3.78 (s, 3H), 5.37 (s, 2H), 6.71 (dd, J = 8.3, 2.4 Hz, 1H), 6.78 (d, J = 2.4 Hz, 1H), 7.28 (dd, J = 8.5, 2.7 Hz, 1H), 7.33 (d, J = 8.3 Hz, 1H), 8.43 (ddd, J = 8.5, 8.5, 2.4 Hz, 1H), 8.49 (d, J = 2.0 Hz, 1H), 8.74 (d, J = 2.4 Hz, 1H), 8.99 (d, J = 2.0 Hz, 1H), 12.99 (s, 1H) |
| 275 | 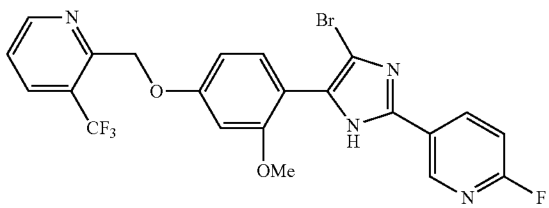 [SMILES: COc1cc(OCc2ncccc2C(F)(F)F)ccc1-c1[nH]c(-c2ccc(F)nc2)nc1Br] | 144-154 | 1H-NMR (DMSO) δ 3.78 (s, 3H), 5.37 (s, 2H), 6.73 (dd, J = 8.3, 2.0 Hz, 1H), 6.81 (d, J = 2.0 Hz, 1H), 7.24-7.41 (m, 2H), 7.68 (dd, J = 7.8, 4.4 Hz, 1H), 8.29 (d, J = 7.8 Hz, 1H), 8.43 (ddd, J = 8.3, 8.3, 2.4 Hz, 1H), 8.74 (d, J = 2.4 Hz, 1H), 8.90 (d, J = 4.4 Hz, 1H), 12.98 (s, 1H) |
| 276 | 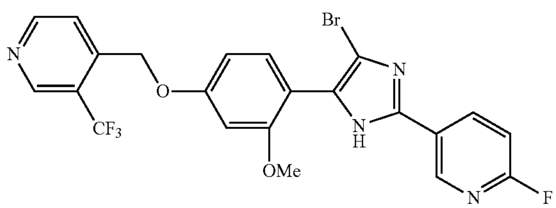 | 199-203 Decomposition | 1H-NMR (CDCL3) δ 3.97 (s, 3H), 5.35 (s, 2H), 6.66 (dd, J = 8.8, 2.4 Hz, 1H), 6.69 (d, J = 2.4 Hz, 1H), 7.04 (dd, J = 8.3, 2.9 Hz, 1H), 7.75 (d, J = 5.4 Hz, 1H), 8.06 (d, J = 8.8 Hz, 1H), 8.34 (ddd, J = 8.3, 7.6, 2.4 Hz, 1H), 8.59 (d, J = 2.4 Hz, 1H), 8.84 (d, J = 5.4 Hz, 1H), 8.93 (s, 1H), 10.38 (s, 1H) |
| 277 | 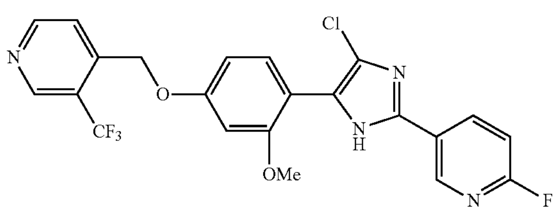 [SMILES: COc1cc(OCc2ccncc2C(F)(F)F)ccc1-c1[nH]c(-c2ccc(F)nc2)nc1Cl] | 203-208 | 1H-NMR (DMSO) δ 3.80 (s, 3H), 5.41 (s, 2H), 6.72 (dd, J = 8.3, 2.4 Hz, 1H), 6.84 (d, J = 2.4 Hz, 1H), 7.30 (dd, J = 8.8, 2.4 Hz, 1H), 7.36 (d, J = 8.3 Hz, 1H), 7.83 (d, J = 5.4 Hz, 1H), 8.43 (ddd, J = 8.8, 8.8, 2.4 Hz, 1H), 8.75 (d, J = 2.4 Hz, 1H), 8.92 (d, J = 5.4 Hz, 1H), 8.99 (s, 1H), 12.94 (s, 1H) |
| 278 | 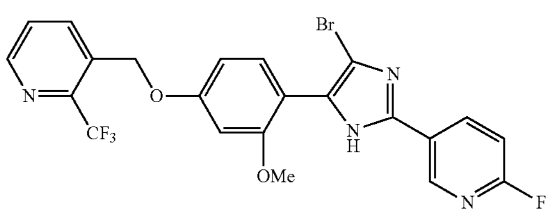 [SMILES: COc1cc(OCc2cccnc2C(F)(F)F)ccc1-c1[nH]c(-c2ccc(F)nc2)nc1Br] | 176-179 | 1H-NMR (DMSO) δ 3.79 (s, 3H), 5.37 (s, 2H), 6.74 (dd, J = 8.3, 2.2 Hz, 1H), 6.81 (d, J = 2.2 Hz, 1H), 7.30 (dd, J = 8.8, 2.9 Hz, 1H), 7.35 (d, J = 8.3 Hz, 1H), 7.80 (dd, J = 7.8, 4.4 Hz, 1H), 8.27 (d, J = 7.8 Hz, 1H), 8.43 (ddd, J = 8.8, 8.8, 2.4 Hz, 1H), 8.70-8.80 (m, 2H), 13.00 (s, 1H) |

TABLE 3-continued

| Example No. | Structure | Melting point (° C.) | 1H-NMR (δ:ppm) |
|---|---|---|---|
| 279 | 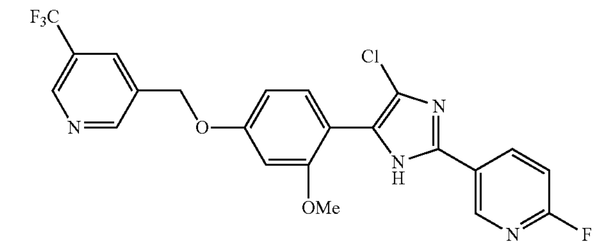 [SMILES: COc1cc(OCc2cncc(C(F)(F)F)c2)ccc1-c1[nH]c(-c2ccc(F)nc2)nc1Cl] | 188-190 | 1H-NMR (CDCL3) δ 3.99 (s, 3H), 5.20 (s, 2H), 6.66-6.77 (m, 2H), 7.04 (dd, J = 8.3, 2.9 Hz, 1H), 7.99-8.15 (m, 2H), 8.32 (ddd, J = 9.1, 8.3, 2.4 Hz, 1H), 8.59 (d, J = 2.4 Hz, 1H), 8.82-8.98 (m, 2H), 10.53 (s, 1H) |
| 280 | 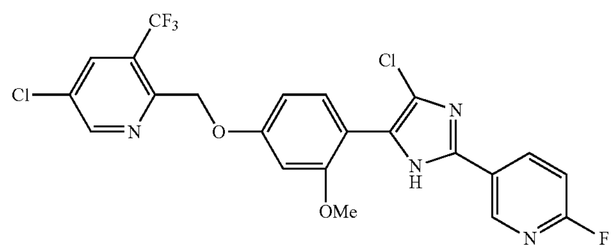 [SMILES: COc1cc(OCc2ncc(Cl)cc2C(F)(F)F)ccc1-c1[nH]c(-c2ccc(F)nc2)nc1Cl] | 156-158 | 1H-NMR (CDCL3) δ 3.93 (s, 3H), 5.36 (s, 2H), 6.59-6.79 (m, 2H), 7.01 (dd, J = 8.8, 2.4 Hz, 1H), 7.91-8.13 (m, 2H), 8.20-8.39 (m, 1H), 8.58 (s, 1H), 8.78 (s, 1H), 10.58 (s, 1H) |
| 281 | 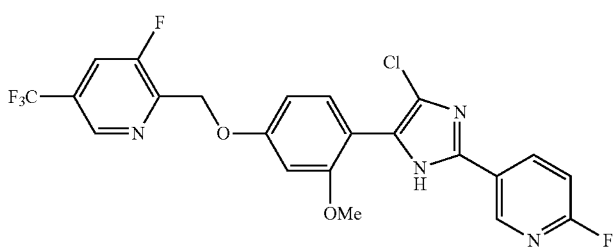 | 150-152 | 1H-NMR (CDCL3) δ 3.96 (s, 3H), 5.37 (s, 2H), 6.70-6.81 (m, 2H), 7.03 (dd, J = 8.5, 2.7 Hz, 1H), 7.73 (dd, J = 9.0, 2.0 Hz, 1H), 8.04 (d, J = 8.3 Hz, 1H), 8.31 (ddd, J = 8.5, 8.5, 2.7 Hz, 1H), 8.58 (d, J = 2.0 Hz, 1H), 8.77 (s, 1H), 10.53 (s, 1H) |
| 282 | 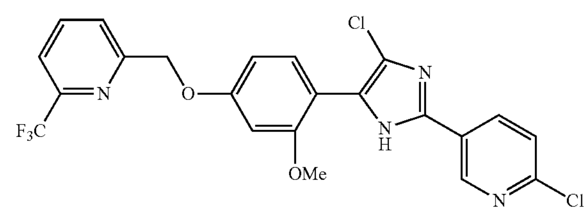 [SMILES: COc1cc(OCc2cccc(C(F)(F)F)n2)ccc1-c1[nH]c(-c2ccc(Cl)nc2)nc1Cl] | 190-193 | 1H-NMR (CDCL3) δ 3.97 (s, 3H), 5.33 (s, 2H), 6.67-6.75 (2H), 7.41 (dd, J = 8.3, 0.8 Hz, 1H), 7.66 (d, J = 7.7 Hz, 1H), 7.78 (d, J = 7.7 Hz, 1H), 7.94 (dd, J = 7.7, 7.7 Hz, 1H), 8.04 (d, J = 8.7 Hz, 1H), 8.15 (dd, J = 8.3, 2.5 Hz, 1H), 8.76 (d, J = 2.5 Hz, 1H), 10.54 (s, 1H) |
| 283 | 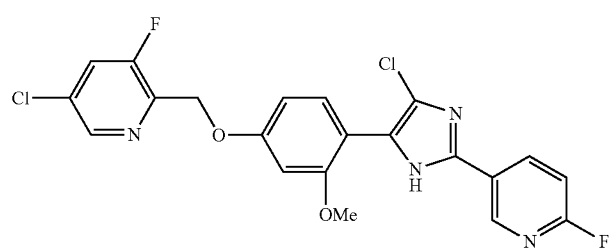 [SMILES: COc1cc(OCc2ncc(Cl)cc2F)ccc1-c1[nH]c(-c2ccc(F)nc2)nc1Cl] | 172-175 | 1H-NMR (DMSO) δ 3.80 (s, 3H), 5.31 (d, J = 2.1 Hz, 2H), 6.76 (dd, J = 8.3, 2.5 Hz, 1H), 6.84 (d, J = 2.5 Hz, 1H), 7.30 (dd, J = 8.5, 2.3 Hz, 1H), 7.34 (d, J = 8.3 Hz, 1H), 8.19 (dd, J = 9.5, 2.1 Hz, 1H), 8.44 (ddd, J = 8.5, 8.5, 2.5 Hz, 1H), 8.58 (dd, J = 2.1, 0.8 Hz, 1H), 8.75 (d, J = 2.5 Hz, 1H), 12.93 (s, 1H) |
| 284 | 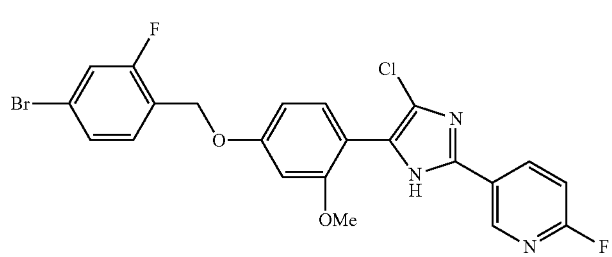 [SMILES: COc1cc(OCc2ccc(Br)cc2F)ccc1-c1[nH]c(-c2ccc(F)nc2)nc1Cl] | 183-185 | 1H-NMR (CDCL3) δ 3.92 (s, 3H), 5.10 (s, 2H), 6.63 (d, J = 2.5 Hz, 1H), 6.67 (dd, J = 8.7, 2.5 Hz, 1H), 6.99 (dd, J = 8.7, 2.9 Hz, 1H), 7.27-7.44 (m, 3H), 7.97 (d, J = 8.7 Hz, 1H), 8.28 (ddd, J = 8.7, 8.7, 2.5 Hz, 1H), 8.57 (d, J = 2.5 Hz, 1H), 10.66 (s, 1H) |

TABLE 3-continued

| Example No. | Structure | Melting point (° C.) | 1H-NMR (δ:ppm) |
|---|---|---|---|
| 285 | 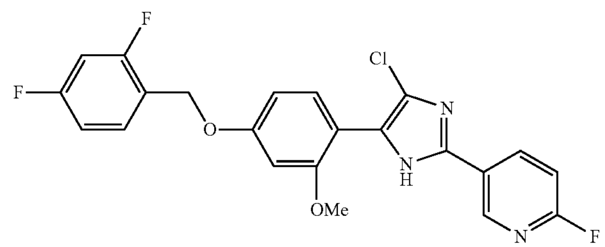 [SMILES: COc1cc(OCc2ccc(F)cc2F)ccc1-c1[nH]c(-c2ccc(F)nc2)nc1Cl] | 163-165 | 1H-NMR (DMSO) δ 3.81 (s, 3H), 5.19 (s, 2H), 6.76 (dd, J = 8.3, 2.4 Hz, 1H), 6.81 (d, J = 2.4 Hz, 1H), 7.15 (ddd, J = 11.1, 11.1, 2.0 Hz, 1H), 7.27-7.40 (m, 3H), 7.66 (dd, J = 8.5, 8.5, 6.8 Hz, 1H), 8.44 (ddd, J = 8.0, 8.0, 2.4 Hz, 1H), 8.76 (d, J = 2.4 Hz, 1H), 12.92 (s, 1H) |
| 286 | 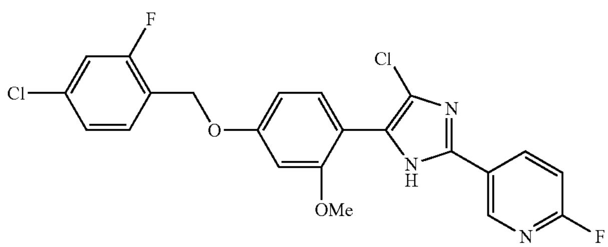 | 163-166 | 1H-NMR (DMSO) δ 3.80 (s, 3H), 5.21 (s, 2H), 6.75 (dd, J = 8.5, 2.4 Hz, 1H), 6.83 (d, J = 2.4 Hz, 1H), 7.30 (dd, J = 8.8, 2.4 Hz, 1H), 7.33-7.39 (m, 2H), 7.51 (dd, J = 9.8, 2.0 Hz, 1H), 7.63 (dd, J = 8.0, 8.0 Hz, 1H), 8.44 (ddd, J = 8.8, 8.8, 2.4 Hz, 1H), 8.76 (d, J = 2.4 Hz, 1H), 12.94 (s, 1H) |
| 287 | 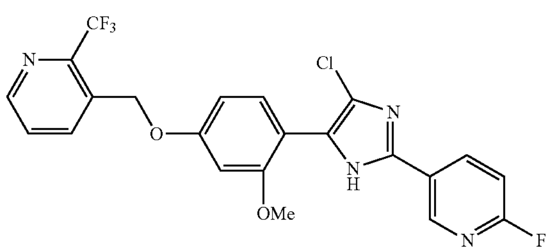 [SMILES: COc1cc(OCc2cccnc2C(F)(F)F)ccc1-c1[nH]c(-c2ccc(F)nc2)nc1Cl] | 165-171 | 1H-NMR (CDCL3) δ 3.98 (s, 3H), 5.35 (s, 2H), 6.64-6.72 (m, 2H), 7.03 (dd, J = 8.8, 2.9 Hz, 1H), 7.57 (dd, J = 7.8, 4.9 Hz, 1H), 8.04 (d, J = 8.3 Hz, 1H), 8.15 (d, J = 7.8 Hz, 1H), 8.31 (ddd, J = 8.8, 8.8, 2.4 Hz, 1H), 8.58 (d, J = 2.4 Hz, 1H), 8.68 (d, J = 4.9 Hz, 1H), 10.51 (s, 1H) |
| 288 | 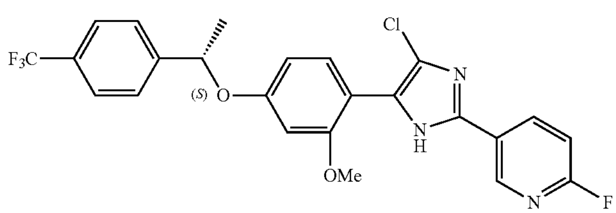 | 137-139 | 1H-NMR (CDCL3) δ 1.68 (d, J = 6.5 Hz, 3H), 3.91 (s, 3H), 5.42 (q, J = 6.5 Hz, 1H), 6.49 (dd, J = 8.8, 2.4 Hz, 1H), 6.60 (d, J = 2.4 Hz, 1H), 7.01 (dd, J = 8.5, 2.7 Hz, 1H), 7.51 (d, J = 8.3 Hz, 2H), 7.63 (d, J = 8.3 Hz, 2H), 7.92 (d, J = 8.8 Hz, 1H), 8.28 (ddd, J = 8.5, 8.5, 2.4 Hz, 1H), 8.55 (d, J = 2.4 Hz, 1H), 10.48 (s, 1H) |
| 289 | 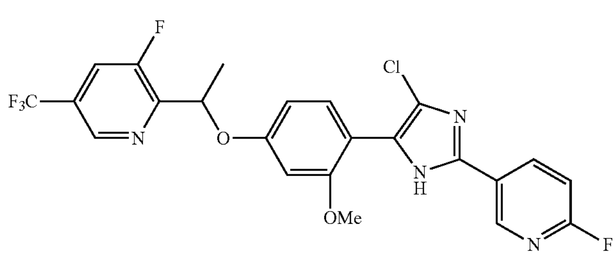 [SMILES: COc1cc(OC(C)c2ncc(C(F)(F)F)cc2F)ccc1-c1[nH]c(-c2ccc(F)nc2)nc1Cl] | 155-159 | 1H-NMR (CDCL3) δ 1.79 (d, J = 6.5 Hz, 3H), 3.93 (s, 3H), 5.82 (q, J = 6.5 Hz, 1H), 6.57 (dd, J = 8.8, 2.4 Hz, 1H), 6.70 (d, J = 2.4 Hz, 1H), 7.02 (dd, J = 8.5, 2.7 Hz, 1H), 7.67 (d, J = 8.8 Hz, 1H), 7.95 (d, J = 8.8 Hz, 1H), 8.29 (ddd, J = 8.5, 8.5, 2.4 Hz, 1H), 8.56 (d, J = 1.5 Hz, 1H), 8.72 (s, 1H), 10.49 (s, 1H) |

TABLE 3-continued

| Example No. | Structure | Melting point (° C.) | 1H-NMR (δ:ppm) |
|---|---|---|---|
| 290 | 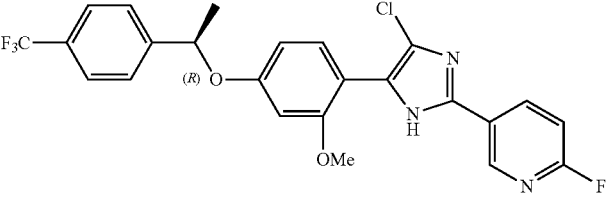 | 137-139 | 1H-NMR (CDCL3) δ 1.70 (d, J = 6.8 Hz, 3H), 3.92 (s, 3H), 5.42 (q, J = 6.8 Hz, 1H), 6.50 (dd, J = 8.8, 2.0 Hz, 1H), 6.60 (d, J = 2.0 Hz, 1H), 7.02 (dd, J = 8.3, 2.4 Hz, 1H), 7.51 (d, J = 8.3 Hz, 2H), 7.63 (d, J = 8.3 Hz, 2H), 7.93 (d, J = 8.8 Hz, 1H), 8.30 (ddd, J = 8.3, 8.3, 2.4 Hz, 1H), 8.56 (s, 1H), 10.46 (s, 1H) |
| 291 | 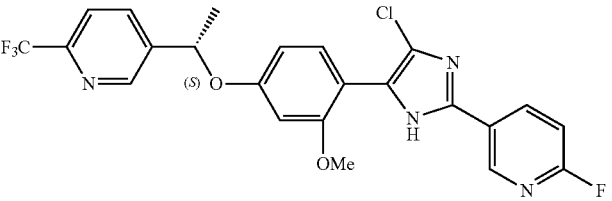 | 74-97 | 1H-NMR (CDCL3) δ 1.72 (d, J = 6.5 Hz, 3H), 3.93 (s, 3H), 5.52 (q, J = 6.5 Hz, 1H), 6.50 (dd, J = 8.5, 2.4 Hz, 1H), 6.61 (d, J = 2.4 Hz, 1H), 7.01 (dd, J = 8.5, 2.7 Hz, 1H), 7.69 (d, J = 7.8 Hz, 1H), 7.87-8.01 (m, 2H), 8.29 (ddd, J = 9.1, 8.5, 1.2 Hz, 1H), 8.56 (d, J = 2.4 Hz, 1H), 8.77 (d, J = 1.2 Hz, 1H), 10.51 (s, 1H) |
| 292 | 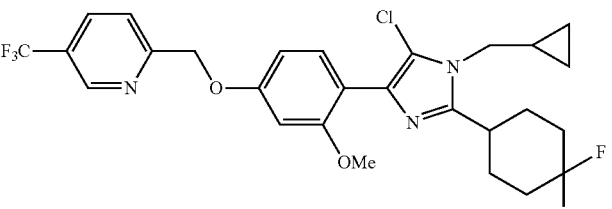 | 144-146 | 1H-NMR (CDCL3) δ 0.34-0.49 (m, 2H), 0.57-0.74 (m, 2H), 1.08-1.23 (m, 1H), 1.73-2.41 (m, 8H), 2.64-2.85 (m, 1H), 3.80-3.87 (m, 5H), 5.30 (s, 2H), 6.55 (dd, J = 8.3, 2.4 Hz, 1H), 6.62 (d, J = 2.4 Hz, 1H), 7.40 (d, J = 8.3 Hz, 1H), 7.69 (d, J = 8.3 Hz, 1H), 7.96 (d, J = 8.3 Hz, 1H), 8.79-8.95 (m, 1H) |
| 293 | 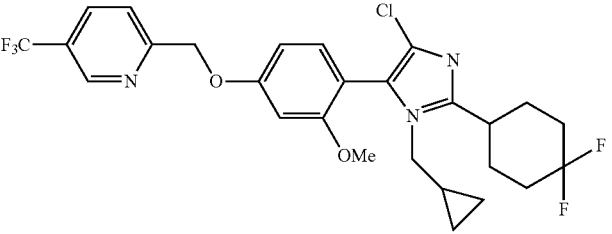 | 149-151 | 1H-NMR (DMSO) δ -0.16-0.17 (m, 2H), 0.25-0.49 (m, 2H), 0.72-0.92 (m, 1H), 1.73-2.24 (m, 8H), 3.00-3.14 (m, 1H), 3.46-3.55 (m, 1H), 3.79 (s, 3H), 3.81-3.93 (m, 1H), 5.42 (s, 2H), 6.78 (dd, J = 8.3, 2.4 Hz, 1H), 6.89 (d, J = 2.4 Hz, 1H), 7.20 (d, J = 8.3 Hz, 1H), 7.86 (d J = 8.3 Hz, 1H), 8.34 (dd, J = 8.3, 2.0 Hz, 1H), 9.05 (d, J = 2.0 Hz, 1H) |
| 294 | 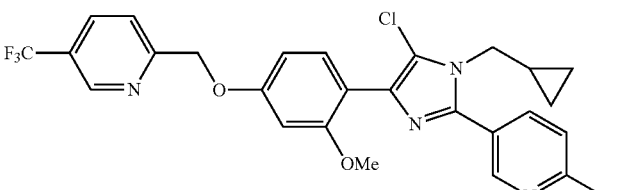 | 123-126 | 1H-NMR (CDCL3) δ 0.20-0.30 (m, 2H), 0.44-0.66 (m, 2H), 1.02-1.19 (m, 1H), 3.85 (s, 3H), 3.98 (d, J = 6.8 Hz, 2H), 5.32 (s, 2H), 6.61 (dd, J = 8.3, 2.4 Hz, 1H), 6.67 (d, J = 2.4 Hz, 1H), 7.34-7.53 (m, 2H), 7.71 (d, J = 8.3 Hz, 1H), 7.89-8.09 (m, 2H), 8.70 (d, J = 2.0 Hz, 1H), 8.79-8.96 (m, 1H) |

TABLE 3-continued

| Example No. | Structure | Melting point (° C.) | 1H-NMR (δ:ppm) |
|---|---|---|---|
| 295 | 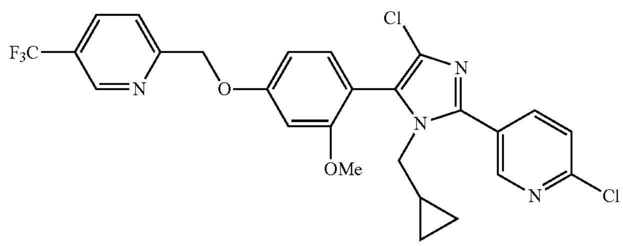 [SMILES: COc1cc(OCc2ccc(C(F)(F)F)cn2)ccc1-c1c(Cl)nc(-c2ccc(Cl)nc2)n1CC1CC1] | 130-132 | 1H-NMR (CDCL3) δ -0.38--0.15 (m, 2H), 0.20-0.36 (m, 2H), 0.63-0.79 (m, 1H), 3.52-3.70 (m, 1H), 3.75-3.97 (m, 4H), 5.33 (s, 2H), 6.60-6.77 (m, 2H), 7.19-7.35 (m, 2H), 7.45 (d, J = 8.3 Hz, 1H), 7.73 (d, J = 8.3 Hz, 1H), 7.93-8.09 (m, 2H), 8.70 (d, J = 2.0 Hz, 1H), 8.89 (s, 1H) |
| 296 | 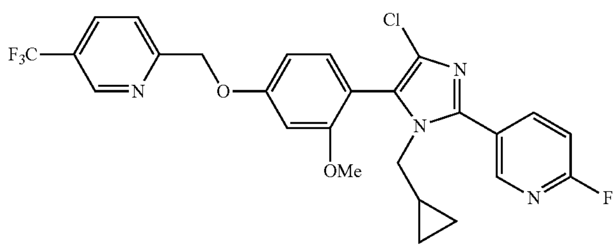 [SMILES: COc1cc(OCc2ccc(C(F)(F)F)cn2)ccc1-c1c(Cl)nc(-c2ccc(F)nc2)n1CC1CC1] | Oil | 1H-NMR (CDCL3) δ -0.39--0.16 (m, 2H), 0.18-0.37 (m, 2H), 0.62-0.79 (m, 1H), 3.51-3.70 (m, 1H), 3.74-3.95 (m, 4H), 4.03-4.21 (m, 1H), 5.33 (s, 2H), 6.60-6.78 (m, 2H), 7.06 (dd, J = 8.8, 2.9 Hz, 1H), 7.23-7.35 (m, 2H), 7.74 (d, J = 8.3 Hz, 1H), 7.98-8.04 (m, 1H), 8.10-8.17 (m, 1H), 8.52 (d, J = 2.0 Hz, 1H), 8.82-8.97 (m, 1H) |
| 297 | 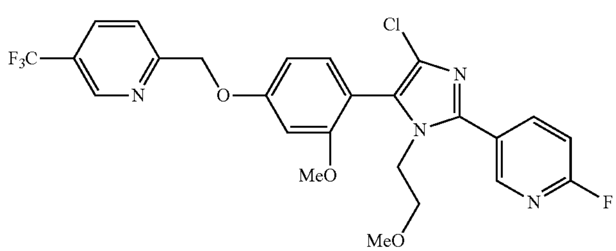 [SMILES: COCCn1c(-c2ccc(F)nc2)nc(Cl)c1-c1ccc(OCc2ccc(C(F)(F)F)cn2)cc1OC] | 131-136 | 1H-NMR (CDCL3) δ 3.11 (s, 3H), 3.16-3.34 (m, 2H), 3.82 (s, 3H), 3.93-4.18 (m, 2H), 5.33 (s, 2H), 6.61-6.78 (m, 2H), 7.03 (dd, J = 8.3, 2.9 Hz, 1H), 7.19-7.35 (m, 1H), 7.74 (d, J = 7.8 Hz, 1H), 8.01 (dd, J = 8.3, 2.0 Hz, 1H), 8.22 (ddd, J = 8.3, 8.3, 2.4 Hz, 1H), 8.63 (d, J = 2.4 Hz, 1H), 8.82-8.97 (m, 1H) |
| 298 | 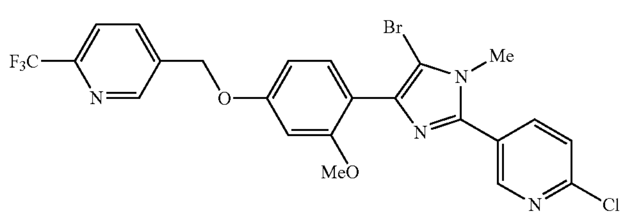 [SMILES: COc1cc(OCc2ccc(C(F)(F)F)nc2)ccc1-c1nc(-c2ccc(Cl)nc2)n(C)c1Br] | 177-182 | 1H-NMR (DMSO) δ 3.74 (s, 3H), 3.78 (s, 3H), 5.36 (s, 2H), 6.71 (dd, J = 8.3, 2.0 Hz, 1H), 6.79 (d, J = 2.0 Hz, 1H), 7.27 (d, J = 8.3 Hz, 1H), 7.68 (d, J = 8.8 Hz, 1H), 7.98 (d, J = 7.8 Hz, 1H), 8.17-8.23 (m, 2H), 8.75 (d, J = 2.4 Hz, 1H), 8.90 (s, 1H) |
| 299 | 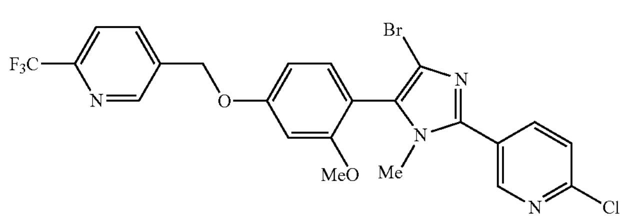 [SMILES: COc1cc(OCc2ccc(C(F)(F)F)nc2)ccc1-c1c(Br)nc(-c2ccc(Cl)nc2)n1C] | 140-142 | 1H-NMR (DMSO) δ 3.50 (s, 3H), 3.83 (s, 3H), 5.39 (s, 2H), 6.81 (dd, J = 8.3, 2.0 Hz, 1H), 6.89 (d, J = 2.0 Hz, 1H), 7.27 (d, J = 8.3 Hz, 1H), 7.67 (d, J = 8.3 Hz, 1H), 7.99 (d, J = 8.3 Hz, 1H), 8.17-8.31 (m, 2H), 8.78 (d, J = 2.4 Hz, 1H), 8.90-8.98 (m, 1H) |

TABLE 3-continued

| Example No. | Structure | Melting point (° C.) | 1H-NMR (δ:ppm) |
|---|---|---|---|
| 300 | 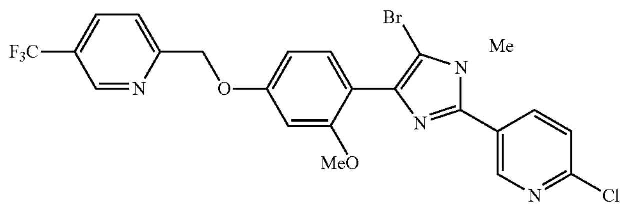 [SMILES: COc1cc(OCc2ccc(C(F)(F)F)cn2)ccc1-c1nc(-c2ccc(Cl)nc2)[nH]c1Br ; "Me"] | 141-143 | 1H-NMR (DMSO) δ 3.73 (s, 3H), 3.77 (s, 3H), 5.36 (s, 2H), 6.67 (dd, J = 8.3, 2.2 Hz, 1H), 6.80 (d, J = 2.2 Hz, 1H), 7.25 (d, J = 8.2 Hz, 1H), 7.66 (d, J = 8.3 Hz, 1H), 7.79 (d, J = 8.2 Hz, 1H), 8.17 (dd, J = 8.2, 2.3 Hz, 1H), 8.27 (dd, J = 8.2, 2.0 Hz, 1H), 8.73 (d, J = 2.3 Hz, 1H), 8.99 (s, 1H) |
| 301 | 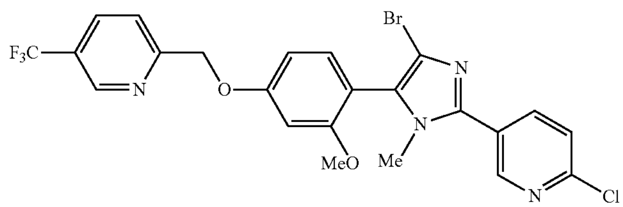 | 125-127 | 1H-NMR (DMSO) δ 3.48 (s, 3H), 3.82 (s, 3H), 5.39 (s, 2H), 6.78 (dd, J = 8.5, 2.0 Hz, 1H), 6.90 (d, J = 2.0 Hz, 1H), 7.23 (d, J = 8.5 Hz, 1H), 7.65 (d, J = 8.5 Hz, 1H), 7.82 (d, J = 8.5 Hz, 1H), 8.20 (dd, J = 8.5, 2.3 Hz, 1H), 8.30 (dd, J = 8.5, 2.0 Hz, 1H), 8.76 (d, J = 2.3 Hz, 1H), 9.00 (d, J = 2.0 Hz, 1H) |
| 302 | 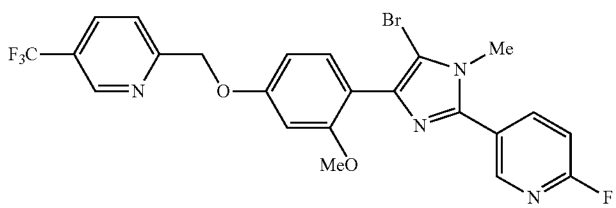 [SMILES: COc1cc(OCc2ccc(C(F)(F)F)cn2)ccc1-c1nc(-c2ccc(F)nc2)n(C)c1Br] | 179-181 | 1H-NMR (DMSO) δ 3.72 (s, 3H), 3.78 (s, 3H), 5.37 (s, 2H), 6.66 (dd, J = 8.8, 2.0 Hz, 1H), 6.81 (d, J = 2.0 Hz, 1H), 7.26 (dd, J = 8.3, 1.5 Hz, 1H), 7.36 (d, J = 8.3 Hz, 1H), 7.80 (d, J = 8.3 Hz, 1H), 8.21-8.39 (m, 2H), 8.57 (s, 1H), 9.01 (s, 1H) |
| 303 | 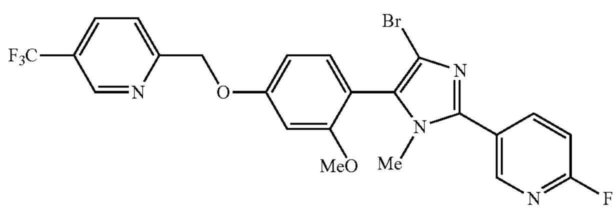 | 130-132 | 1H-NMR (DMSO) δ 3.47 (s, 3H), 3.83 (s, 3H), 5.41 (s, 2H), 6.79 (dd, J = 8.5, 2.4 Hz, 1H), 6.91 (d, J = 2.4 Hz, 1H), 7.25 (d, J = 8.3 Hz, 1H), 7.36 (dd, J = 8.5, 2.7 Hz, 1H), 7.84 (d, J = 8.5 Hz, 1H), 8.28-8.40 (m, 2H), 8.60 (d, J = 2.0 Hz, 1H), 9.02 (d, J = 1.0 Hz, 1H) |
| 304 | 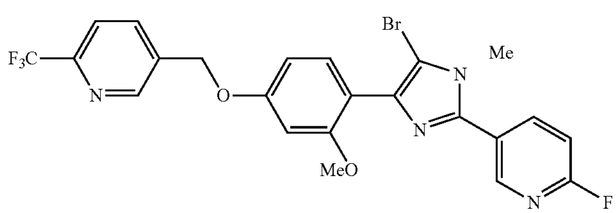 [SMILES: COc1cc(OCc2ccc(C(F)(F)F)nc2)ccc1-c1nc(-c2ccc(F)nc2)[nH]c1Br ; "Me"] | | 1H-NMR (CDCL3) δ 3.75 (s, 3H), 3.86 (s, 3H), 5.21 (s, 2H), 6.53-6.75 (m, 2H), 7.06 (dd, J = 8.3, 2.9 Hz, 1H), 7.41 (d, J = 7.8 Hz, 1H), 7.73 (d, J = 8.3 Hz, 1H), 8.00 (d, J = 7.8 Hz, 1H), 8.13 (ddd, J = 8.3, 8.3, 2.4 Hz, 1H), 8.51 (d, J = 2.4 Hz, 1H), 8.74-8.90 (m, 1H) |
| 305 | 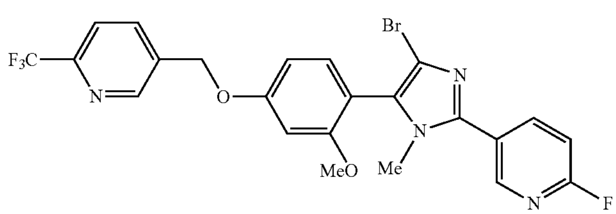 [SMILES: COc1cc(OCc2ccc(C(F)(F)F)nc2)ccc1-c1c(Br)nc(-c2ccc(F)nc2)n1C] | 134-136 | 1H-NMR (CDCL3) δ 3.52 (s, 3H), 3.85 (s, 3H), 5.23 (s, 2H), 6.60-6.77 (m, 2H), 7.06 (dd, J = 8.8, 3.4 Hz, 1H), 7.31 (d, J = 8.8 Hz, 1H), 7.76 (d, J = 8.8 Hz, 1H), 8.01 (dd, J = 8.8, 1.5 Hz, 1H), 8.18 (ddd, J = 8.8, 8.8, 2.4 Hz, 1H), 8.53 (d, J = 2.4 Hz, 1H), 8.76-8.91 (m, 1H) |

TABLE 3-continued

| Example No. | Structure | Melting point (° C.) | 1H-NMR (δ:ppm) |
|---|---|---|---|
| 306 | 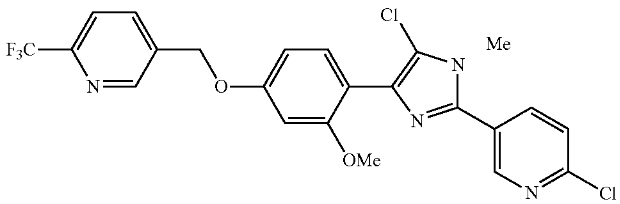 [SMILES: COc1cc(OCc2ccc(C(F)(F)F)nc2)ccc1-c1nc(-c2ccc(Cl)nc2)[nH]c1Cl ; "Me"] | 180-182 | 1H-NMR (DMSO) δ 3.73 (s, 3H), 3.79 (s, 3H), 5.36 (s, 2H), 6.72 (dd, J = 8.3, 2.4 Hz, 1H), 6.80 (d, J = 2.4 Hz, 1H), 7.31 (d, J = 8.3 Hz, 1H), 7.68 (d, J = 8.3 Hz, 1H), 7.98 (d, J = 8.3 Hz, 1H), 8.16-8.26 (m, 2H), 8.76 (d, J = 2.4 Hz, 1H), 8.90 (d, J = 1.6 Hz, 1H) |
| 307 | 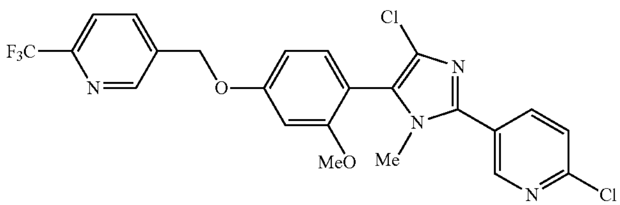 [SMILES: COc1cc(OCc2ccc(C(F)(F)F)nc2)ccc1-c1c(Cl)nc(-c2ccc(Cl)nc2)n1C] | 149-151 | 1H-NMR (DMSO) δ 3.49 (s, 3H), 3.84 (s, 3H), 5.39 (s, 2H), 6.82 (dd, J = 8.3, 2.0 Hz, 1H), 6.91 (d, J = 2.0 Hz, 1H), 7.27 (d, J = 8.3 Hz, 1H), 7.68 (d, J = 8.3 Hz, 1H), 7.99 (d, J = 8.3 Hz, 1H), 8.17-8.29 (m, 2H), 8.78 (d, J = 2.9 Hz, 1H), 8.92 (s, 1H) |
| 308 | 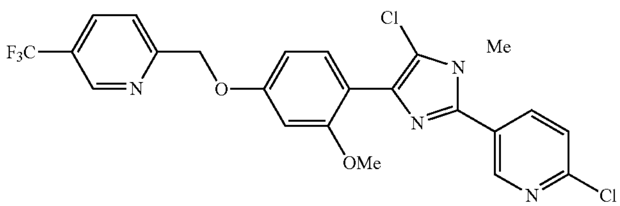 | 114-117 | 1H-NMR (CDCL3) δ 3.73 (s, 3H), 3.85 (s, 3H), 5.31 (s, 2H), 6.60 (dd, J = 8.8, 2.4 Hz, 1H), 6.68 (d, J = 2.4 Hz, 1H), 7.37-7.48 (m, 2H), 7.70 (d, J = 8.3 Hz, 1H), 7.88-8.08 (m, 2H), 8.68 (d, J = 2.0 Hz, 1H), 8.79-8.94 (m, 1H) |
| 309 | 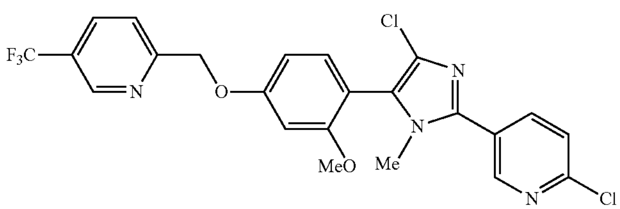 | 133-135 | 1H-NMR (CDCL3) δ 3.51 (s, 3H), 3.85 (s, 3H), 5.33 (s, 2H), 6.68 (dd, J = 8.5, 2.4 Hz, 1H), 6.72 (d, J = 2.4 Hz, 1H), 7.19-7.36 (m, 1H), 7.44 (d, J = 8.5 Hz, 1H), 7.73 (d, J = 8.3 Hz, 1H), 8.01 (dd, J = 8.3, 2.0 Hz, 1H), 8.05 (dd, J = 8.3, 2.4 Hz, 1H), 8.71 (d, J = 2.4 Hz, 1H), 8.87-8.92 (m, 1H) |
| 310 | 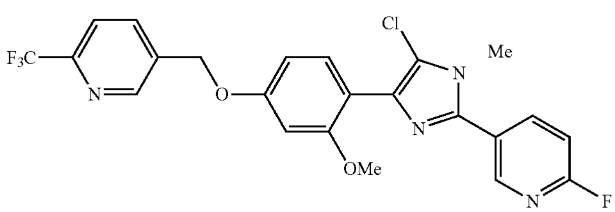 | 162-165 | 1H-NMR (CDCL3) δ 8.82 (s, 1H), 8.51 (d, J = 2.4 Hz, 1H), 8.13 (ddd, J = 8.3, 8.3, 2.4 Hz, 1H), 8.00 (d, J = 7.8 Hz, 1H), 7.73 (d, J = 8.3 Hz, 1H), 7.43 (d, J = 7.8 Hz, 1H), 7.06 (dd, J = 8.3, 2.9 Hz, 1H), 6.75-6.55 (m, 2H), 5.21 (s, 2H), 4.00-3.81 (3H), 3.82-3.66 (3H) |
| 311 | 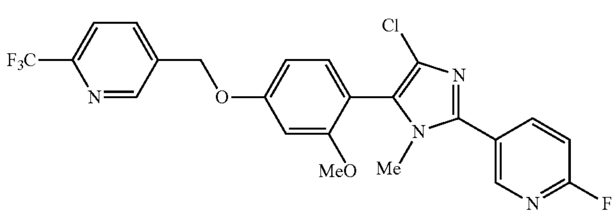 [SMILES: COc1cc(OCc2ccc(C(F)(F)F)nc2)ccc1-c1c(Cl)nc(-c2ccc(F)nc2)n1C] | 138-140 | 1H-NMR (DMSO) δ 3.47 (s, 3H), 3.84 (s, 3H), 5.39 (s, 2H), 6.81 (dd, J = 8.3, 2.4 Hz, 1H), 6.89 (d, J = 2.4 Hz, 1H), 7.27 (d, J = 8.3 Hz, 1H), 7.36 (dd, J = 8.5, 2.7 Hz, 1H), 7.99 (d, J = 8.3 Hz, 1H), 8.22 (d, J = 8.3 Hz, 1H), 8.35 (ddd, J = 8.5, 8.5, 2.4 Hz, 1H), 8.61 (d, J = 2.4 Hz, 1H), 8.92 (s, 1H) |

TABLE 3-continued

| Example No. | Structure | Melting point (° C.) | 1H-NMR (δ:ppm) |
|---|---|---|---|
| 312 | F₃C-pyridine-CH₂-O-phenyl(MeO)-imidazole(Cl, Me)-pyridine-F | 142-144 | 1H-NMR (DMSO) δ 3.47 (s, 3H), 3.83 (s, 3H), 5.41 (s, 2H), 6.79 (dd, J = 8.3, 2.4 Hz, 1H), 6.91 (d, J = 2.4 Hz, 1H), 7.26 (d, J = 8.3 Hz, 1H), 7.36 (dd, J = 8.5, 2.7 Hz, 1H), 7.83 (d, J = 8.3 Hz, 1H), 8.27-8.42 (m, 2H), 8.60 (d, J = 2.0 Hz, 1H), 9.02 (d, J = 1.0 Hz, 1H) |

Examples 313 to 405

The compounds of Examples 313 to 405, which have the structures and melting points shown in Table 4 below, were produced in the same manner as in any of the Examples mentioned above.

TABLE 4

| Example No. | Structure | Melting point (° C.) | 1H-NMR (δ:ppm) |
|---|---|---|---|
| 313 | HO-phenyl(OMe)-imidazole(Cl)-pyridine-F | 209-214 Decomposition | 1H-NMR (DMSO) δ 6.47 (dd, J = 8.3, 2.4 Hz, 1H), 6.53 (d, J = 2.4 Hz, 1H), 7.20 (d, J = 8.3 Hz, 1H), 7.29 (dd, J = 8.5, 2.7 Hz, 1H), 8.43 (ddd, J = 8.5, 8.5, 2.6 Hz, 1H), 8.75 (d, J = 2.6 Hz, 1H), 9.85 (s, 1H), 12.86 (s, 1H) |
| 314 | F₃C-pyridine(N-oxide)-CH₂-O-phenyl(OMe)-imidazole-pyridine-F | 234-239 | 1H-NMR (DMSO) δ 3.91 (s, 3H), 5.24 (s, 2H), 6.71 (dd, J = 8.5, 1.8 Hz, 1H), 6.78 (d, J = 1.8 Hz, 1H), 7.30 (dd, J = 8.5, 2.6 Hz, 1H), 7.44-7.69 (m, 2H), 7.98 (d, J = 8.5 Hz, 1H), 8.09 (s, 1H), 8.50 (ddd, J = 8.5, 8.5, 2.3 Hz, 1H), 8.57 (s, 1H), 8.82 (d, J = 2.3 Hz, 1H) |
| 315 | F₃C-pyridine(N-oxide)-CH₂-O-phenyl(OMe)-imidazole(Cl)-pyridine-F | >250 | 1H-NMR (DMSO) δ 3.82 (s, 3H), 5.30 (s, 2H), 6.75 (dd, J = 8.5, 2.3 Hz, 1H), 6.86 (d, J = 2.3 Hz, 1H), 7.30 (dd, J = 8.8, 2.6 Hz, 1H), 7.37 (d, J = 8.5 Hz, 1H), 7.59 (d, J = 8.5 Hz, 1H), 8.00 (d, J = 8.5 Hz, 1H), 8.44 (ddd, J = 8.8, 8.8, 2.3 Hz, 1H), 8.58 (s, 1H), 8.76 (d, J = 2.3 Hz, 1H) |

TABLE 4-continued

| Example No. | Structure | Melting point (° C.) | 1H-NMR (δ:ppm) |
|---|---|---|---|
| 316 | 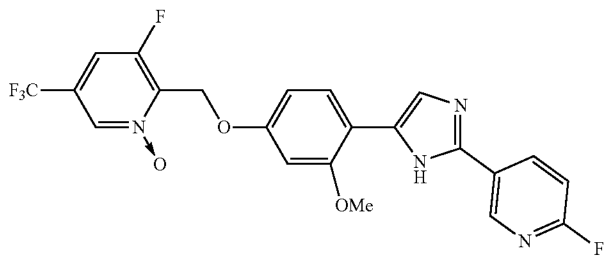 [SMILES: COc1cc(OCc2c(F)cc(C(F)(F)F)c[n+]2[O-])ccc1-c1cnc(-c2ccc(F)nc2)[nH]1] | 162-167 | 1H-NMR (DMSO) δ 3.90 (s, 3H), 5.36 (s, 2H), 6.63-6.87 (m, 2H), 7.30 (dd, J = 8.5, 2.7 Hz, 1H), 7.57 (s, 1H), 7.91-8.20 (m, 2H), 8.51 (ddd, J = 8.5, 8.5, 2.4 Hz, 1H), 8.82 (d, J = 2.4 Hz, 1H), 8.90 (s, 1H), 12.71 (s, 1H) |
| 317 | 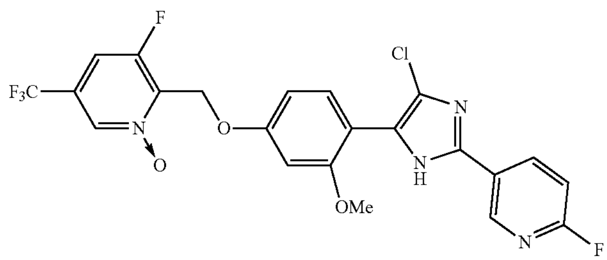 [SMILES: COc1cc(OCc2c(F)cc(C(F)(F)F)c[n+]2[O-])ccc1-c1[nH]c(-c2ccc(F)nc2)nc1Cl] | 105-110 | 1H-NMR (CDCL3) δ 3.83 (s, 3H), 5.38 (s, 2H), 6.54-6.74 (m, 2H), 6.94 (dd, J = 8.6, 2.8 Hz, 1H), 7.32 (d, J = 8.8 Hz, 1H), 7.76 (d, J = 8.8 Hz, 1H), 8.16-8.32 (m, 1H), 8.38 (s, 1H), 8.59 (d, J = 2.6 Hz, 1H), 11.03 (s, 1H) |
| 318 | 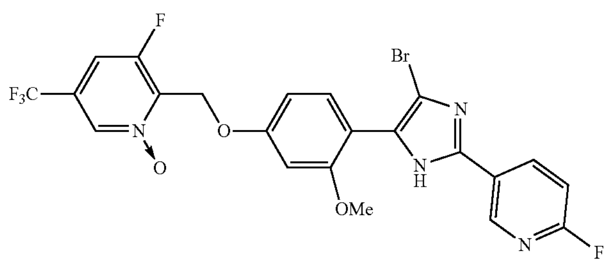 [SMILES: COc1cc(OCc2c(F)cc(C(F)(F)F)c[n+]2[O-])ccc1-c1[nH]c(-c2ccc(F)nc2)nc1Br] | 105-120 | 1H-NMR (CDCL3) δ 3.87 (s, 3H), 5.42 (s, 2H), 6.60-6.79 (m, 2H), 6.98 (dd, J = 8.5, 2.6 Hz, 1H), 7.32 (d, J = 8.5 Hz, 1H), 7.87 (d, J = 8.5 Hz, 1H), 8.21-8.36 (m, 1H), 8.41 (s, 1H), 8.60 (d, J = 2.6 Hz, 1H), 10.77 (s, 1H) |
| 319 | 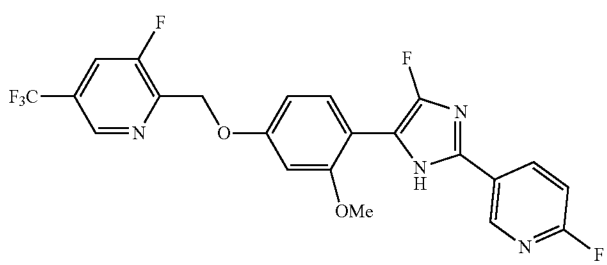 [SMILES: COc1cc(OCc2ncc(C(F)(F)F)cc2F)ccc1-c1[nH]c(-c2ccc(F)nc2)nc1F] | 156-158 | 1H-NMR (CDCL3) δ 4.00 (s, 3H), 5.36 (s, 2H), 6.68-6.82 (m, 2H), 7.02 (dd, J = 8.8, 2.9 Hz, 1H), 7.64-7.84 (m, 2H), 8.23 (ddd, J = 8.8, 8.8, 2.0 Hz, 1H), 8.56 (d, J = 2.0 Hz, 1H), 8.76 (s, 1H), 10.39 (s, 1H) |
| 320 | 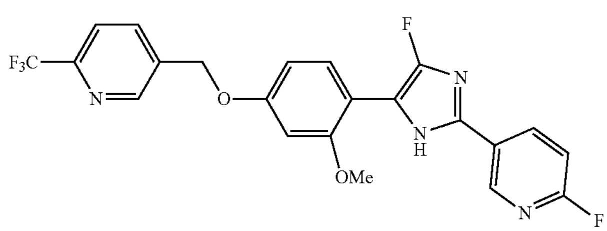 [SMILES: COc1cc(OCc2ccc(C(F)(F)F)nc2)ccc1-c1[nH]c(-c2ccc(F)nc2)nc1F] | 194-196 | 1H-NMR (DMSO) δ 3.84 (s, 3H), 5.36 (s, 2H), 6.77 (dd, J = 8.5, 2.4 Hz, 1H), 6.84 (d, J = 2.4 Hz, 1H), 7.29 (dd, J = 8.3, 2.4 Hz, 1H), 7.36 (d, J = 8.3 Hz, 1H), 7.97 (d, J = 8.3 Hz, 1H), 8.19 (d, J = 8.5 Hz, 1H), 8.42 (ddd, J = 8.3, 8.3, 2.4 Hz, 1H), 8.74 (d, J = 2.4 Hz, 1H), 8.90 (s, 1H), 12.56 (s, 1H) |
| 321 | 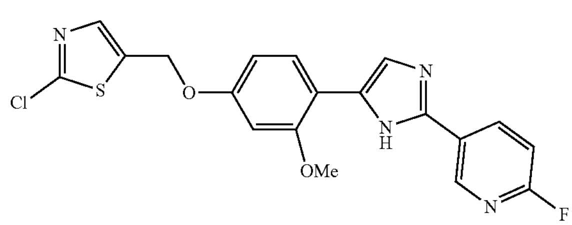 [SMILES: COc1cc(OCc2cnc(Cl)s2)ccc1-c1cnc(-c2ccc(F)nc2)[nH]1] | 109-116 | 1H-NMR (DMSO) δ 3.90 (s, 3H), 5.37 (s, 2H), 6.63-6.88 (m, 2H), 7.30 (dd, J = 8.3, 2.4 Hz, 1H), 7.58 (s, 1H), 7.81 (s, 1H), 8.00-8.17 (m, 1H), 8.41-8.60 (m, 1H), 8.82 (s, 1H), 12.72 (s, 1H) |

TABLE 4-continued

| Example No. | Structure | Melting point (° C.) | 1H-NMR (δ:ppm) |
|---|---|---|---|
| 322 | 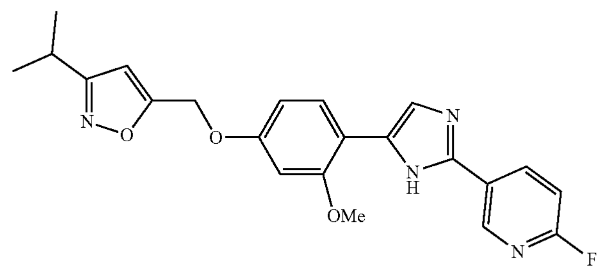 [SMILES: COc1cc(OCc2cc(C(C)C)no2)ccc1-c1cnc(-c2ccc(F)nc2)[nH]1] | 227-232 | 1H-NMR (CDCL3) δ 1.30 (d, J = 7.3 Hz, 6H), 3.00-3.16 (m, 1H), 3.99 (s, 3H), 5.16 (s, 2H), 6.24 (s, 1H), 6.58-6.74 (m, 2H), 7.03 (dd, J = 8.8, 2.9 Hz, 1H), 7.36-7.79 (m, 2H), 8.26-8.44 (m, 1H), 8.62 (s, 1H) |
| 323 | 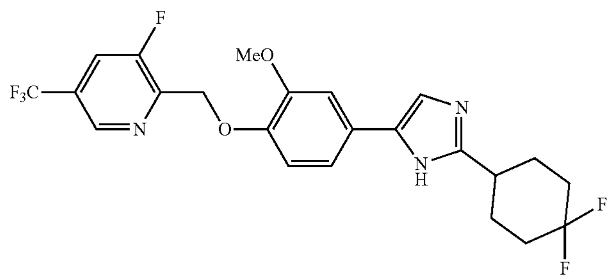 [SMILES: COc1cc(-c2cnc(C3CCC(F)(F)CC3)[nH]2)ccc1OCc1ncc(C(F)(F)F)cc1F] | 157-159 | 1H-NMR (CDCL3) δ 1.75-2.34 (m, 8H), 2.80-3.02 (m, 1H), 3.90 (s, 3H), 5.36 (s, 2H), 6.91-7.46 (m, 4H), 7.66 (d, J = 8.8 Hz, 1H), 8.72 (s, 1H), 9.04 (s, 1H) |
| 324 | 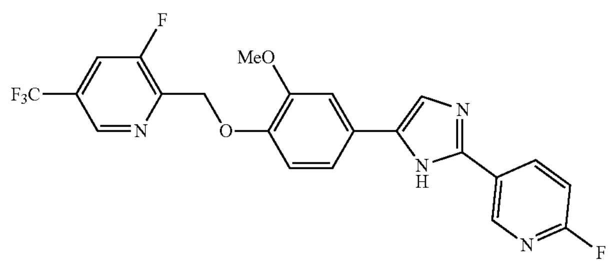 [SMILES: COc1cc(-c2cnc(-c3ccc(F)nc3)[nH]2)ccc1OCc1ncc(C(F)(F)F)cc1F] | | 1H-NMR (CDCL3) δ 3.90 (s, 3H), 5.37 (s, 2H), 6.91-7.12 (m, 2H), 7.18-7.58 (m, 3H), 7.66 (dd, J = 9.0, 1.2 Hz, 1H), 8.28-8.48 (m, 1H), 8.65 (d, J = 2.4 Hz, 1H), 8.70 (d, J = 1.2 Hz, 1H), 10.13 (s, 1H) |
| 325 | 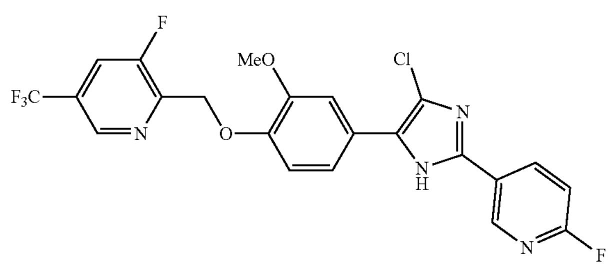 [SMILES: COc1cc(-c2[nH]c(-c3ccc(F)nc3)nc2Cl)ccc1OCc1ncc(C(F)(F)F)cc1F] | 165-170 | 1H-NMR (DMSO) δ 3.82 (s, 3H), 5.37 (s, 2H), 7.23 (d, J = 8.3 Hz, 1H), 7.28-7.46 (m, 3H), 8.41 (d, J = 9.3 Hz, 1H), 8.49 (ddd, J = 8.3, 8.3, 2.3 Hz, 1H), 8.81 (d, J = 2.3 Hz, 1H), 8.89 (s, 1H), 13.00 (s, 1H) |
| 326 | 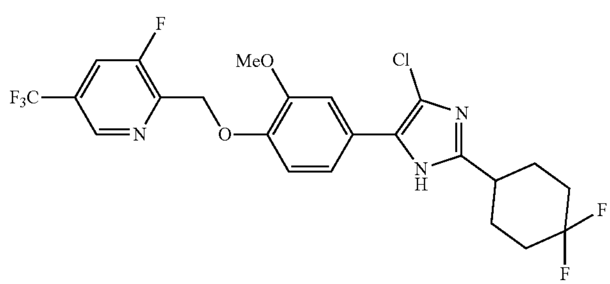 [SMILES: COc1cc(-c2[nH]c(C3CCC(F)(F)CC3)nc2Cl)ccc1OCc1ncc(C(F)(F)F)cc1F] | 173-176 | 1H-NMR (CDCL3) δ 1.73-2.32 (m, 8H), 2.69-2.91 (m, 1H), 3.86 (s, 3H), 5.37 (s, 2H), 6.97-7.17 (m, 2H), 7.14-7.26 (m, 1H), 7.68 (d, J = 8.8 Hz, 1H), 8.72 (s, 1H), 9.46 (s, 1H) |

TABLE 4-continued

| Example No. | Structure | Melting point (° C.) | 1H-NMR (δ:ppm) |
|---|---|---|---|
| 327 | 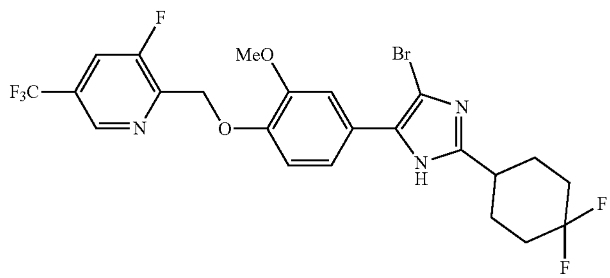 [SMILES: COc1cc(-c2[nH]c(C3CCC(F)(F)CC3)nc2Br)ccc1OCc1ncc(C(F)(F)F)cc1F] | 203-204 | 1H-NMR (CDCL3) δ 1.72-2.34 (m, 8H), 2.71-2.92 (m, 1H), 3.88 (s, 3H), 5.38 (s, 2H), 6.96-7.16 (m, 2H), 7.16-7.26 (m, 1H), 7.69 (dd, J = 9.3, 2.0 Hz, 1H), 8.72 (d, J = 2.0 Hz, 1H), 9.28 (s, 1H) |
| 328 | 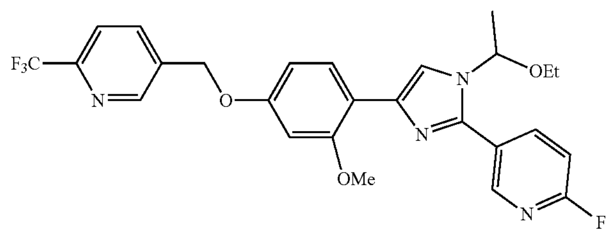 [SMILES: CCOC(C)n1cc(-c2ccc(OCc3ccc(C(F)(F)F)nc3)cc2OC)nc1-c1ccc(F)nc1] | 102-104 | 1H-NMR (CDCL3) δ 1.12 (t, J = 7.0 Hz, 3H), 1.72 (d, J = 5.9 Hz, 3H), 3.12-3.40 (m, 2H), 3.96 (s, 3H), 5.20 (s, 2H), 5.40 (q, J = 5.9 Hz, 1H), 6.54-6.73 (m, 2H), 7.07 (dd, J = 8.3, 3.1 Hz, 1H), 7.63-7.81 (m, 2H), 7.92-8.04 (m, 1H), 8.04-8.14 (m, 1H), 8.20 (d, J = 8.4 Hz, 1H), 8.46 (d, J = 2.3 Hz, 1H), 8.81 (s, 1H) |
| 329 | 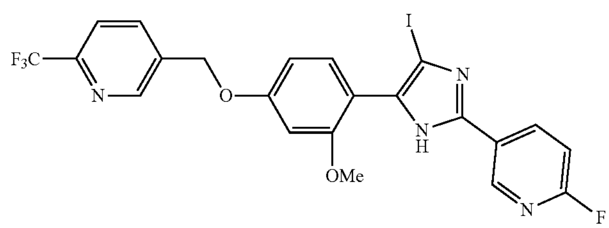 [SMILES: COc1cc(OCc2ccc(C(F)(F)F)nc2)ccc1-c1[nH]c(-c2ccc(F)nc2)nc1I] | 195-208 | 1H-NMR (CDCL3) δ 3.79 (s, 3H), 5.17 (s, 2H), 6.48-6.68 (m, 2H), 6.97 (dd, J = 8.6, 2.5 Hz, 1H), 7.49 (d, J = 8.2 Hz, 1H), 7.71 (d, J = 8.2 Hz, 1H), 7.98 (dd, J = 8.2, 1.6 Hz, 1H), 8.24-8.43 (m, 1H), 8.53 (d, J = 2.0 Hz, 1H), 8.74 (d, J = 1.6 Hz, 1H) |
| 330 | 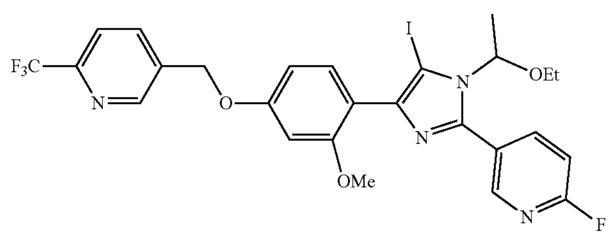 [SMILES: CCOC(C)n1c(-c2ccc(F)nc2)nc(-c2ccc(OCc3ccc(C(F)(F)F)nc3)cc2OC)c1I] | 129-131 | 1H-NMR (DMSO) δ 0.94 (t, J = 7.0 Hz, 3H), 1.30 (d, J = 6.2 Hz, 3H), 3.32-3.46 (m, 2H), 3.76 (s, 3H), 5.07 (q, J = 6.2 Hz, 1H), 5.37 (s, 2H), 6.81 (dd, J = 8.5, 2.3 Hz, 1H), 6.85 (d, J = 2.3 Hz, 1H), 7.20 (d, J = 8.4 Hz, 1H), 7.32 (dd, J = 8.6, 2.8 Hz, 1H), 7.98 (d, J = 8.4 Hz, 1H), 8.22 (d, J = 8.5 Hz, 1H), 8.32 (ddd, J = 8.6, 8.6, 2.5 Hz, 1H), 8.52 (d, J = 2.5 Hz, 1H), 8.91 (s, 1H) |
| 331 | 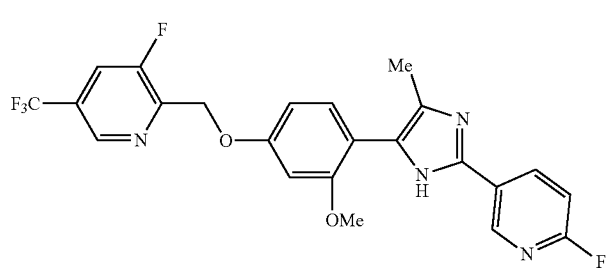 [SMILES: COc1cc(OCc2ncc(C(F)(F)F)cc2F)ccc1-c1[nH]c(-c2ccc(F)nc2)nc1C] | 100-105 | 1H-NMR (CDCL3) δ 2.44 (s, 3H), 3.90 (s, 3H), 5.36 (s, 2H), 6.62-6.82 (m, 2H), 6.99 (dd, J = 8.3, 2.4 Hz, 1H), 7.41 (d, J = 8.8 Hz, 1H), 7.73 (dd, J = 9.2, 1.6 Hz, 1H), 8.30 (ddd, J = 8.3, 8.3, 2.4 Hz, 1H), 8.57 (d, J = 2.4 Hz, 1H), 8.76 (d, J = 1.6 Hz, 1H), 10.12 (s, 1H) |

TABLE 4-continued

| Example No. | Structure | Melting point (° C.) | 1H-NMR (δ:ppm) |
|---|---|---|---|
| 332 | 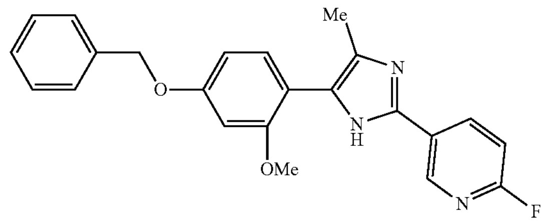 [SMILES: COc1cc(OCc2ccccc2)ccc1-c1[nH]c(-c2ccc(F)nc2)nc1C] | 169-171 | 1H-NMR (CDCL3) δ 2.43 (s, 3H), 3.87 (s, 3H), 5.10 (s, 2H), 6.54-6.76 (m, 2H), 6.97 (dd, J = 8.4, 2.0 Hz, 1H), 7.29-7.54 (m, 6H), 8.29 (ddd, J = 8.4, 8.4, 2.4 Hz, 1H), 8.57 (d, J = 2.4 Hz, 1H), 10.24 (s, 1H) |
| 333 | 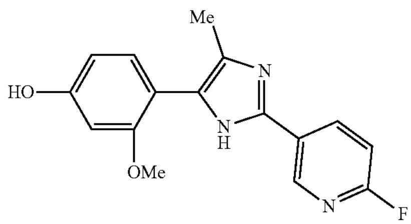 [SMILES: COc1cc(O)ccc1-c1[nH]c(-c2ccc(F)nc2)nc1C] | 154-159 | 1H-NMR (DMSO) δ 2.09 (s, 3H), 3.72 (s, 3H), 6.32-6.60 (m, 2H), 7.00-7.20 (m, 1H), 7.24 (dd, J = 8.8, 2.4 Hz, 1H), 8.30-8.52 (m, 1H), 8.72 (s, 1H), 12.24 (s, 1H) |
| 334 | 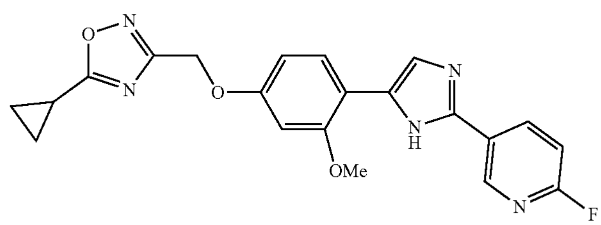 [SMILES: COc1cc(OCc2noc(C3CC3)n2)ccc1-c1cnc(-c2ccc(F)nc2)[nH]1] | 153-158 | 1H-NMR (CDCL3) δ 1.18-1.35 (m, 4H), 2.15-2.33 (m, 1H), 3.99 (s, 3H), 5.16 (s, 2H), 6.61-6.81 (m, 2H), 7.03 (dd, J = 8.8, 2.9 Hz, 1H), 7.45 (s, 1H), 7.52-7.69 (m, 1H), 8.25-8.42 (m, 1H), 8.62 (s, 1H), 10.53 (s, 1H) |
| 335 | 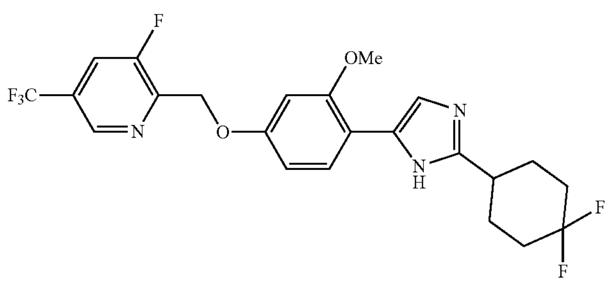 [SMILES: COc1cc(OCc2ncc(C(F)(F)F)cc2F)ccc1-c1cnc(C2CCC(F)(F)CC2)[nH]1] | 105-110 | 1H-NMR (CDCL3) δ 1.79-2.35 (m, 8H), 2.81-3.01 (m, 1H), 3.92 (s, 3H), 5.34 (s, 2H), 6.59-6.78 (m, 2H), 7.27-7.37 (m, 1H), 7.53-7.84 (m, 2H), 8.75 (s, 1H) |
| 336 | 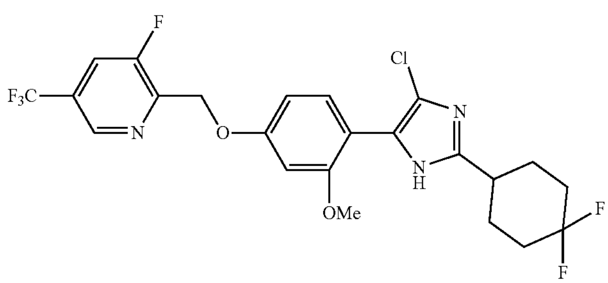 [SMILES: COc1cc(OCc2ncc(C(F)(F)F)cc2F)ccc1-c1[nH]c(C2CCC(F)(F)CC2)nc1Cl] | 172-174 | 1H-NMR (CDCL3) δ 1.72-2.32 (m, 8H), 2.73-2.93 (m, 1H), 3.91 (s, 3H), 5.35 (s, 2H), 6.63-6.81 (m, 2H), 7.72 (dd, J = 8.8, 1.5 Hz, 1H), 7.96 (d, J = 8.3 Hz, 1H), 8.76 (d, J = 1.5 Hz, 1H), 9.82 (s, 1H) |
| 337 | 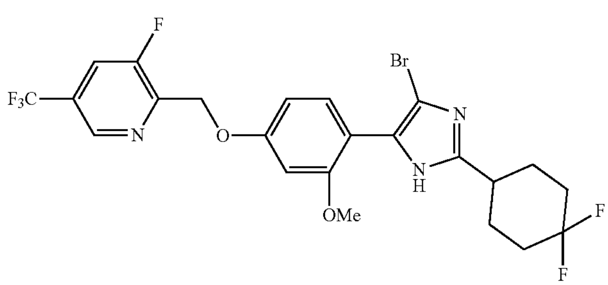 [SMILES: COc1cc(OCc2ncc(C(F)(F)F)cc2F)ccc1-c1[nH]c(C2CCC(F)(F)CC2)nc1Br] | 190-191 | 1H-NMR (CDCL3) δ 1.71-2.32 (m, 8H), 2.74-2.94 (m, 1H), 3.88 (s, 3H), 5.35 (s, 2H), 6.62-6.81 (m, 2H), 7.72 (dd, J = 8.8, 1.5 Hz, 1H), 7.95 (d, J = 8.8 Hz, 1H), 8.76 (d, J = 1.5 Hz, 1H), 9.75 (s, 1H) |

TABLE 4-continued

| Example No. | Structure | Melting point (° C.) | 1H-NMR (δ:ppm) |
|---|---|---|---|
| 338 | 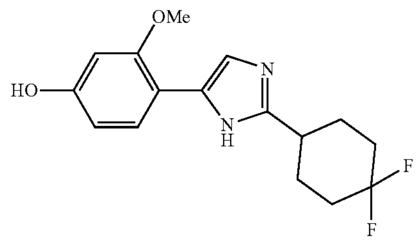 [SMILES: COc1cc(O)ccc1-c1cnc(C2CCC(F)(F)CC2)[nH]1] | Oil | 1H-NMR (DMSO) δ 1.67-2.22 (m, 8H), 2.75-2.97 (m, 1H), 3.79 (s, 3H), 6.28-6.54 (m, 2H), 7.28 (s, 1H), 7.80 (dd, J = 8.4, 1.2 Hz, 1H), 9.30 (s, 1H), 11.62 (s, 1H) |
| 339 | 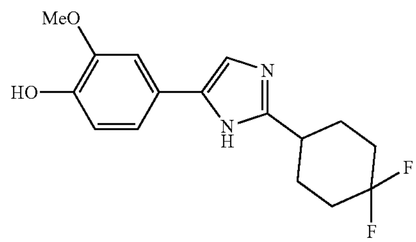 [SMILES: COc1cc(-c2cnc(C3CCC(F)(F)CC3)[nH]2)ccc1O] | 131-136 | 1H-NMR (DMSO) d 1.66-2.21 (m, 8H), 2.75-2.96 (m, 1H), 3.78 (s, 3H), 6.70 (d, J = 8.3 Hz, 1H), 7.12 (dd, J = 8.3, 1.7 Hz, 1H), 7.26 (d, J = 1.7 Hz, 1H), 7.31 (s, 1H), 8.75 (s, 1H), 11.71 (s, 1H) |
| 340 | 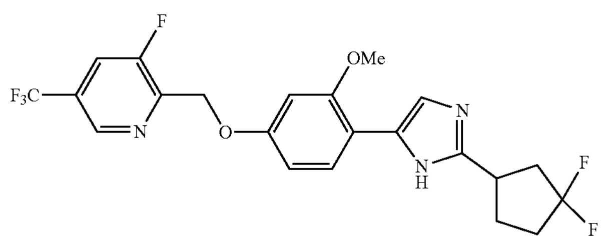 [SMILES: COc1cc(OCc2ncc(C(F)(F)F)cc2F)ccc1-c1cnc(C2CCC(F)(F)C2)[nH]1] | Oil | 1H-NMR (CDCL3) d 2.02-2.70 (m, 6H), 3.40-3.61 (m, 1H), 3.92 (s, 3H), 5.36 (s, 2H), 6.59-6.78 (m, 2H), 7.26-7.38 (m, 1H), 7.50-7.82 (m, 2H), 8.75 (s, 1H) |
| 341 | 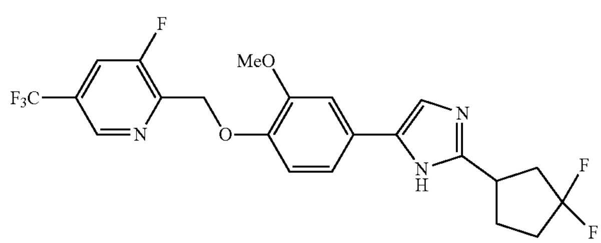 [SMILES: COc1cc(-c2cnc(C3CCC(F)(F)C3)[nH]2)ccc1OCc1ncc(C(F)(F)F)cc1F] | Oil | 1H-NMR (CDCL3) δ 2.00-2.69 (m, 6H), 3.38-3.60 (m, 1H), 3.91 (s, 3H), 5.36 (s, 2H), 7.00 (d, J = 8.3 Hz, 1H), 7.10-7.19 (m, 2H), 7.28 (s, 1H), 7.66 (dd, J = 8.8, 1.5 Hz, 1H), 8.72 (d, J = 1.5 Hz, 1H) |
| 342 | 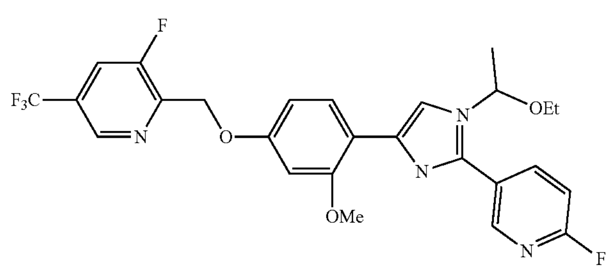 | 117-119 | 1H-NMR (CDCL3) δ 1.11 (t, J = 7.1 Hz, 3H), 1.71 (d, J = 6.0 Hz, 3H), 3.11-3.38 (m, 2H), 3.93 (s, 3H), 5.34 (s, 2H), 5.39 (q, J = 6.0 Hz, 1H), 6.60-6.80 (m, 2H), 7.06 (dd, J = 8.3, 2.9 Hz, 1H), 7.69 (dd, J = 9.3, 1.5 Hz, 1H), 7.72 (s, 1H), 8.09 (ddd, J = 8.3, 8.3, 2.4 Hz, 1H), 8.16 (d, J = 8.8 Hz, 1H), 8.45 (d, J = 2.4 Hz, 1H), 8.74 (d, J = 1.5 Hz, 1H) |
| 343 | 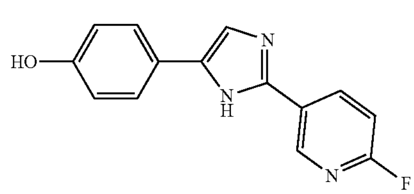 [SMILES: Oc1ccc(-c2cnc(-c3ccc(F)nc3)[nH]2)cc1] | >270 | 1H-NMR (DMSO) δ 6.76 (d, J = 8.8 Hz, 2H), 7.29 (dd, J = 8.8, 2.9 Hz, 1H), 7.49-7.77 (m, 3H), 8.37-8.60 (m, 1H), 8.78 (d, J = 2.0 Hz, 1H), 9.34 (s, 1H), 12.70 (s, 1H) |

TABLE 4-continued

| Example No. | Structure | Melting point (° C.) | 1H-NMR (δ:ppm) |
|---|---|---|---|
| 344 | 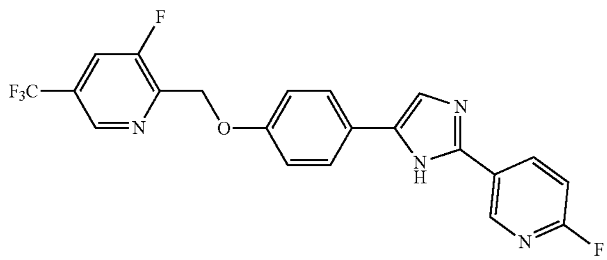 [SMILES: Fc1ccc(-c2ncc(-c3ccc(OCc4ncc(C(F)(F)F)cc4F)cc3)[nH]2)cn1] | 174-177 | 1H-NMR (CDCL3) δ 5.34 (s, 2H), 6.93-7.17 (m, 3H), 7.33 (s, 1H), 7.59-7.82 (m, 3H), 8.28-8.47 (m, 1H), 8.63 (d, J = 2.4 Hz, 1H), 8.74 (s, 1H) |
| 345 | 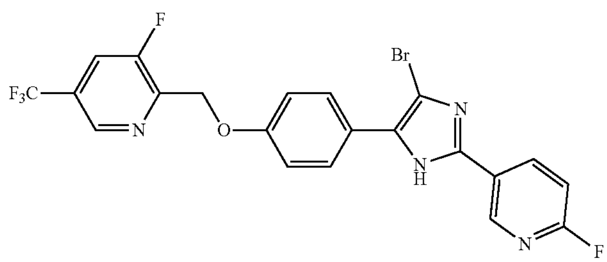 | 155-158 | 1H-NMR (DMSO) δ 5.42 (s, 2H), 7.19 (d, J = 8.8 Hz, 2H), 7.32 (dd, J = 8.8, 2.0 Hz, 1H), 7.72 (d, J =8.8 Hz, 2H), 8.41 (d, J = 9.8 Hz, 1H), 8.48 (ddd, J = 8.8, 8.8, 2.4 Hz, 1H), 8.80 (d, J = 2.4 Hz, 1H), 8.89 (s, 1H), 13.06 (s, 1H) |
| 346 | 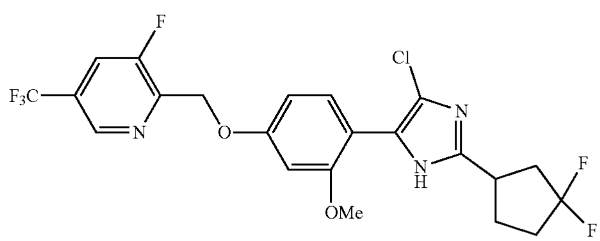 [SMILES: COc1cc(OCc2ncc(C(F)(F)F)cc2F)ccc1-c1[nH]c(C2CCC(F)(F)C2)nc1Cl] | 147-149 | 1H-NMR (CDCL3) δ 1.98-2.67 (m, 6H), 3.33-3.54 (m, 1H), 3.91 (s, 3H), 5.35 (s, 2H), 6.63-6.81 (m, 2H), 7.72 (dd, J = 8.8, 1.5 Hz, 1H), 7.98 (d, J = 8.8 Hz, 1H), 8.76 (d, J = 1.5 Hz, 1H), 9.95 (s, 1H) |
| 347 | 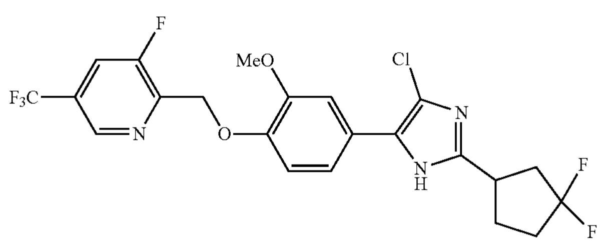 [SMILES: COc1cc(-c2[nH]c(C3CCC(F)(F)C3)nc2Cl)ccc1OCc1ncc(C(F)(F)F)cc1F] | 142-147 | 1H-NMR (CDCL3) δ 2.01-2.62 (m, 6H), 3.28-3.49 (m, 1H), 3.87 (s, 3H), 5.38 (s, 2H), 6.97-7.15 (m, 2H), 7.22 (s, 1H), 7.68 (dd, J = 8.8, 1.6 Hz, 1H), 8.72 (d, J = 1.6 Hz, 1H), 9.33 (s, 1H) |
| 348 | 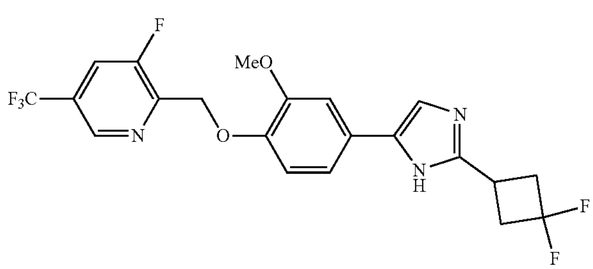 [SMILES: COc1cc(-c2cnc(C3CC(F)(F)C3)[nH]2)ccc1OCc1ncc(C(F)(F)F)cc1F] | 105-110 | 1H-NMR (CDCL3) δ 2.85-3.17 (m, 4H), 3.42-3.67 (m, 1H), 3.90 (s, 3H), 5.36 (s, 2H), 7.00 (d, J = 8.3 Hz, 1H), 7.12-7.23 (m, 2H), 7.33 (d, J = 2.0 Hz, 1H), 7.66 (dd, J = 9.0, 1.7 Hz, 1H), 8.71 (s, 1H) |
| 349 | 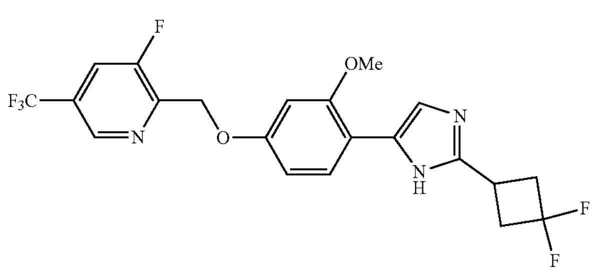 [SMILES: COc1cc(OCc2ncc(C(F)(F)F)cc2F)ccc1-c1cnc(C2CC(F)(F)C2)[nH]1] | 70-75 | 1H-NMR (CDCL3) δ 2.86-3.12 (m, 4H), 3.38-3.47 (m, 1H), 3.93 (s, 3H), 5.34 (s, 2H), 6.63-6.75 (m, 2H), 7.27-7.38 (m, 1H), 7.49-7.80 (m, 2H), 8.75 (s, 1H) |

TABLE 4-continued

| Example No. | Structure | Melting point (° C.) | 1H-NMR (δ:ppm) |
|---|---|---|---|
| 350 | 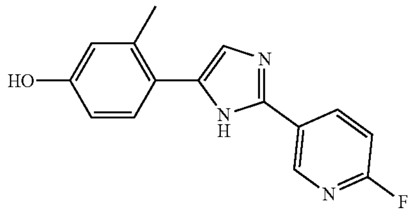 [SMILES: Cc1cc(O)ccc1-c1cnc(-c2ccc(F)nc2)[nH]1] | 218-220 | 1H-NMR (DMSO) δ 2.38 (s, 3H), 6.53-6.83 (m, 2H), 7.19-7.40 (m, 2H), 7.61 (s, 1H), 8.41-8.56 (m, 1H), 8.80 (s, 1H), 12.73 (s, 1H) |
| 351 | 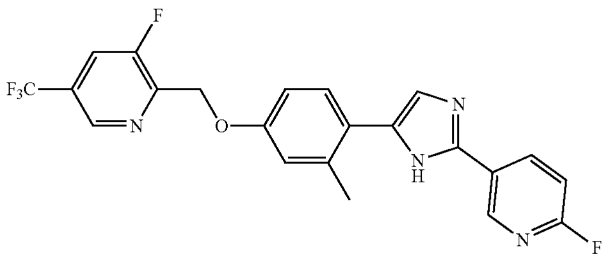 [SMILES: Cc1cc(OCc2ncc(C(F)(F)F)cc2F)ccc1-c1cnc(-c2ccc(F)nc2)[nH]1] | 216-222 | 1H-NMR (CDCL3) δ 2.44 (s, 3H), 5.33 (s, 2H), 6.90 (dd, J = 8.3, 2.9 Hz, 1H), 6.93 (d, J = 2.9 Hz, 1H), 7.00 (dd, J = 8.3, 2.9 Hz, 1H), 7.16 (s, 1H), 7.42-7.63 (m, 1H), 7.70 (dd, J = 8.8, 1.5 Hz, 1H), 8.35 (ddd, J = 8.3, 8.3, 2.4 Hz, 1H), 8.62 (d, J = 2.4 Hz, 1H), 8.74 (d, J = 1.5 Hz, 1H) |
| 352 | 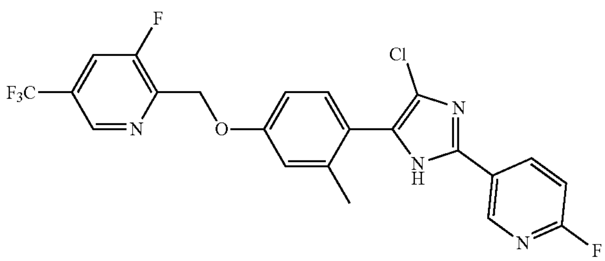 [SMILES: Cc1cc(OCc2ncc(C(F)(F)F)cc2F)ccc1-c1[nH]c(-c2ccc(F)nc2)nc1Cl] | 204-206 | 1H-NMR (CDCL3) δ 2.25 (s, 3H), 5.27 (s, 2H), 6.80 (d, J = 8.3 Hz, 1H), 6.87 (s, 1H), 6.95 (d, J = 8.3 Hz, 1H), 7.19 (d, J = 8.3 Hz, 1H), 7.71 (d, J = 8.8 Hz, 1H), 8.17-8.37 (m, 1H), 8.56 (s, 1H), 8.69 (s, 1H), 11.26 (s, 1H) |
| 353 | 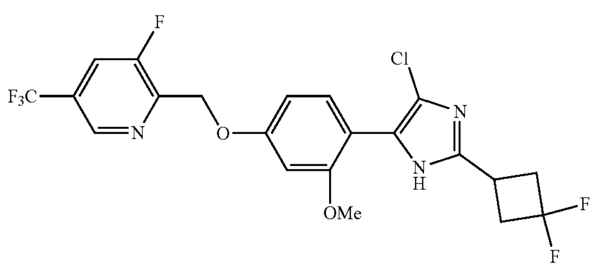 [SMILES: COc1cc(OCc2ncc(C(F)(F)F)cc2F)ccc1-c1[nH]c(C2CC(F)(F)C2)nc1Cl] | 167-169 | 1H-NMR (CDCL3) δ 2.82-3.09 (m, 4H), 3.25-3.54 (m, 1H), 3.91 (s, 3H), 5.34 (s, 2H), 6.60-6.80 (m, 2H), 7.71 (d, J = 8.8 Hz, 1H), 7.98 (d, J = 8.3 Hz, 1H), 8.74 (s, 1H), 10.00 (s, 1H) |
| 354 | 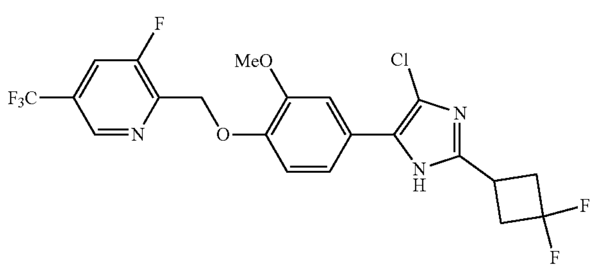 [SMILES: COc1cc(-c2[nH]c(C3CC(F)(F)C3)nc2Cl)ccc1OCc1ncc(C(F)(F)F)cc1F] | 159-161 | 1H-NMR (CDCL3) δ 2.85-3.06 (m, 4H), 3.26-3.43 (m, 1H), 3.85 (s, 3H), 5.37 (s, 2H), 6.95-7.16 (m, 2H), 7.13-7.26 (m, 1H), 7.68 (dd, J = 8.2, 1.6 Hz, 1H), 8.71 (d, J = 1.6 Hz, 1H), 9.56 (s, 1H) |
| 355 | 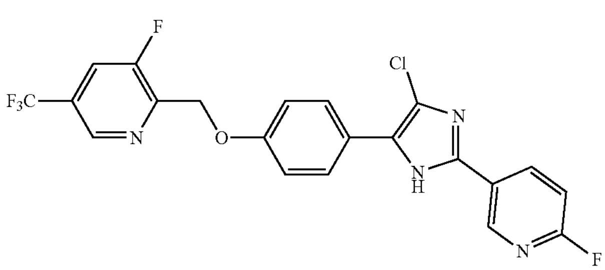 [SMILES: Fc1ccc(-c2nc(Cl)c(-c3ccc(OCc4ncc(C(F)(F)F)cc4F)cc3)[nH]2)cn1] | 180-183 | 1H-NMR (CDCL3) δ 5.33 (s, 2H), 6.99 (dd, J = 8.8, 2.9 Hz, 1H), 7.06 (d, J = 8.8 Hz, 2H), 7.60 (d, J = 8.8 Hz, 2H), 7.72 (d, J = 8.8 Hz, 1H), 8.29 (ddd, J = 8.8, 8.8, 2.0 Hz, 1H), 8.59 (d, J = 2.0 Hz, 1H), 8.73 (s, 1H) |

TABLE 4-continued

| Example No. | Structure | Melting point (° C.) | 1H-NMR (δ:ppm) |
|---|---|---|---|
| 356 | 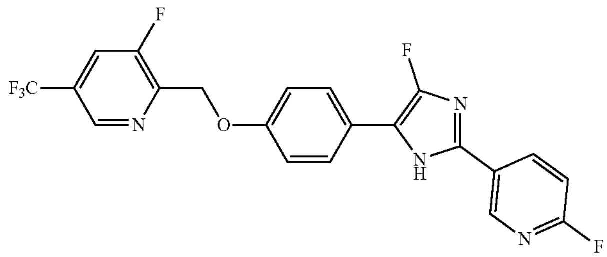 [SMILES: Fc1ccc(-c2nc(F)c(-c3ccc(OCc4ncc(C(F)(F)F)cc4F)cc3)[nH]2)cn1] | 222-227 | 1H-NMR (DMSO) δ 5.39 (s, 2H), 7.18 (d, J = 9.1 Hz, 2H), 7.33 (dd, J = 8.7, 2.9 Hz, 1H), 7.62 (d, J = 9.1 Hz, 2H), 8.41 (dd, J = 10.0, 1.2 Hz, 1H), 8.46 (ddd, J = 8.7, 8.7, 2.5 Hz, 1H), 8.78 (d, J = 2.5 Hz, 1H), 8.89 (d, J = 1.2 Hz, 1H), 12.77 (s, 1H) |
| 357 | 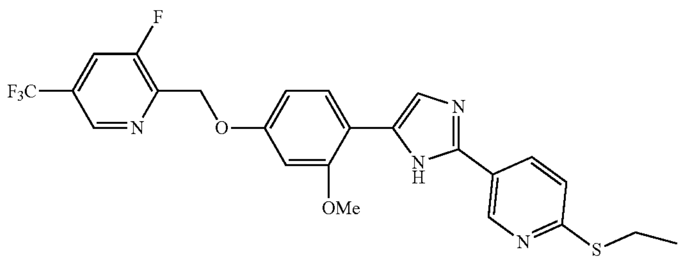 [SMILES: CCSc1ccc(-c2ncc(-c3ccc(OCc4ncc(C(F)(F)F)cc4F)cc3OC)[nH]2)cn1] | 145-149 | 1H-NMR (CDCL3) δ 1.39 (t, J = 7.3 Hz, 3H), 3.04 (q, J = 7.3 Hz, 2H), 3.95 (s, 3H), 5.34 (s, 2H), 6.69 (dd, J = 8.5, 2.2 Hz, 1H), 6.72 (s, 1H), 6.90-7.09 (m, 1H), 7.46 (s, 1H), 7.59-7.78 (m, 1H), 7.78-7.90 (m, 1H), 8.23-8.43 (m, 1H), 8.61 (d, J = 2.4 Hz, 1H), 8.65 (d, J = 1.2 Hz, 1H) |
| 358 | 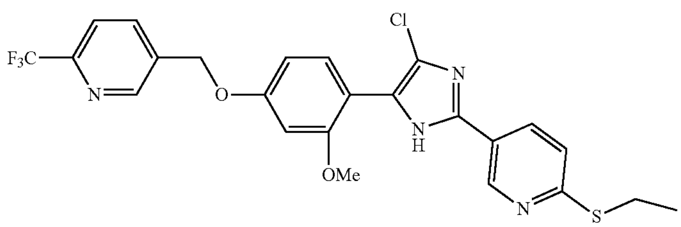 [SMILES: CCSc1ccc(-c2nc(Cl)c(-c3ccc(OCc4ccc(C(F)(F)F)nc4)cc3OC)[nH]2)cn1] | 160-163 | 1H-NMR (DMSO) δ 1.30 (t, J = 7.3 Hz, 3H), 3.15 (q, J = 7.3 Hz, 2H), 3.81 (s, 3H), 5.37 (s, 2H), 6.76 (dd, J = 8.8, 2.4 Hz, 1H), 6.84 (d, J = 2.4 Hz, 1H), 7.27-7.45 (m, 2H), 7.97 (d, J = 8.3 Hz, 1H), 8.09 (dd, J = 8.3, 2.4 Hz, 1H), 8.19 (dd, J = 8.0, 1.2 Hz, 1H), 8.89 (d, J = 1.2 Hz, 1H), 8.94 (d, J = 2.4 Hz, 1H), 12.82 (s, 1H) |
| 359 | 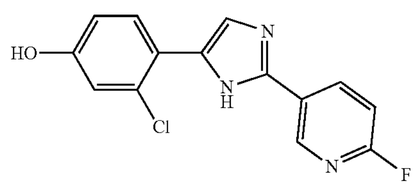 [SMILES: Oc1ccc(-c2cnc(-c3ccc(F)nc3)[nH]2)c(Cl)c1] | 223-225 | 1H-NMR (DMSO) δ 6.74-6.97 (m, 2H), 7.31 (dd, J = 8.5, 2.7 Hz, 1H), 7.72 (s, 1H), 7.96 (d, J = 8.8 Hz, 1H), 8.49 (ddd, J = 8.5, 8.5, 2.4 Hz, 1H), 8.81 (d, J = 2.4 Hz, 1H), 9.88 (s, 1H), 12.86 (s, 1H) |
| 360 | 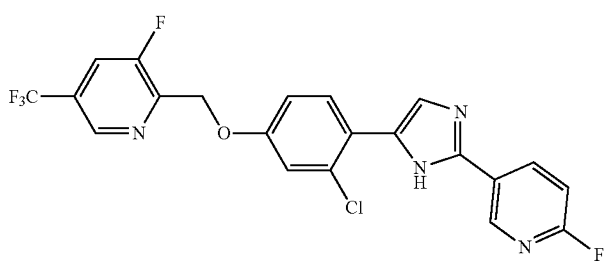 [SMILES: Fc1ccc(-c2ncc(-c3ccc(OCc4ncc(C(F)(F)F)cc4F)cc3Cl)[nH]2)cn1] | 169-171 | 1H-NMR (DMSO) δ 5.42 (s, 2H), 7.11 (dd, J = 8.8, 2.4 Hz, 1H), 7.23 (d, J = 2.4 Hz, 1H), 7.31 (dd, J = 8.5, 2.7 Hz, 1H), 7.74 (s, 1H), 8.03 (d, J = 8.8 Hz, 1H), 8.41 (dd, J = 9.8, 1.5 Hz, 1H), 8.51 (ddd, J = 8.5, 8.5, 2.4 Hz, 1H), 8.82 (d, J = 2.4 Hz, 1H), 8.89 (d, J = 1.5 Hz, 1H) |
| 361 | 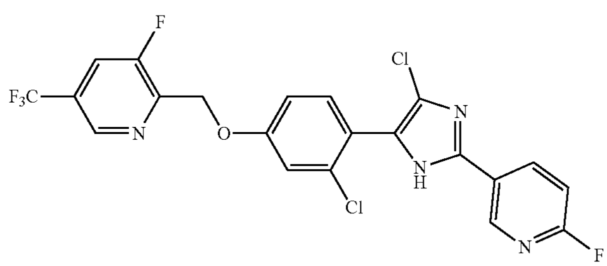 [SMILES: Fc1ccc(-c2nc(Cl)c(-c3ccc(OCc4ncc(C(F)(F)F)cc4F)cc3Cl)[nH]2)cn1] | 158-160 | 1H-NMR (DMSO) δ 5.48 (s, 2H), 7.16 (dd, J = 8.8, 2.4 Hz, 1H), 7.32 (dd, J = 8.8, 2.4 Hz, 1H), 7.37 (d, J = 2.4 Hz, 1H), 7.49 (d, J = 8.8 Hz, 1H), 8.33-8.54 (m, 2H), 8.75 (d, J = 2.4 Hz, 1H), 8.90 (s, 1H), 13.23 (s, 1H) |

TABLE 4-continued

| Example No. | Structure | Melting point (° C.) | 1H-NMR (δ:ppm) |
|---|---|---|---|
| 362 | 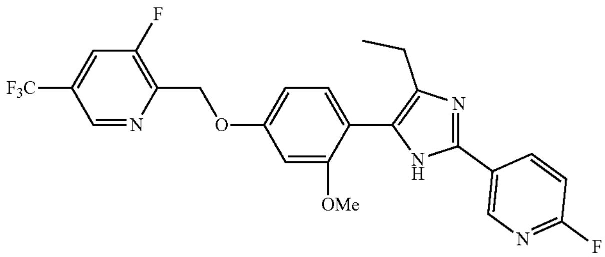 [SMILES: CCc1nc(-c2ccc(F)nc2)[nH]c1-c1ccc(OCc2ncc(C(F)(F)F)cc2F)cc1OC] | Oil | 1H-NMR (CDCL3) δ 1.31 (t, J = 7.6 Hz, 3H), 2.75 (q, J = 7.6 Hz, 2H), 3.87 (s, 3H), 5.35 (s, 2H), 6.64-6.80 (m, 2H), 6.98 (dd, J = 8.5, 2.7 Hz, 1H), 7.37 (d, J = 8.8 Hz, 1H), 7.72 (dd, J = 7.3, 1.6 Hz, 1H), 8.32 (ddd, J = 8.5, 8.5, 2.0 Hz, 1H), 8.57 (d, J = 2.0 Hz, 1H), 8.76 (d, J = 1.6 Hz, 1H) |
| 363 | 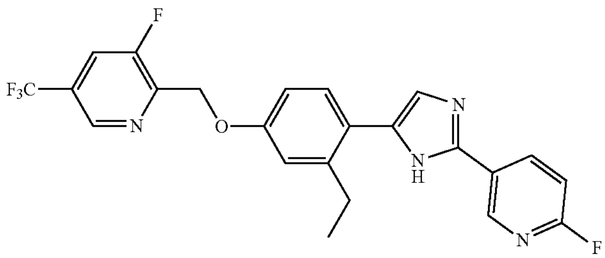 [SMILES: CCc1cc(OCc2ncc(C(F)(F)F)cc2F)ccc1-c1cnc(-c2ccc(F)nc2)[nH]1] | 115-117 | 1H-NMR (DMSO) δ 1.14 (t, J = 7.6 Hz, 3H), 2.70-2.94 (m, 2H), 5.36 (s, 2H), 6.81-7.12 (m, 2H), 7.17-7.44 (m, 2H), 7.44-7.69 (m, 1H), 8.40 (d, J = 9.3 Hz, 1H), 8.48 (ddd, J = 8.2, 8.2, 1.5 Hz, 1H), 8.79 (d, J = 1.5 Hz, 1H), 8.89 (s, 1H), 12.74 (s, 1H) |
| 364 | 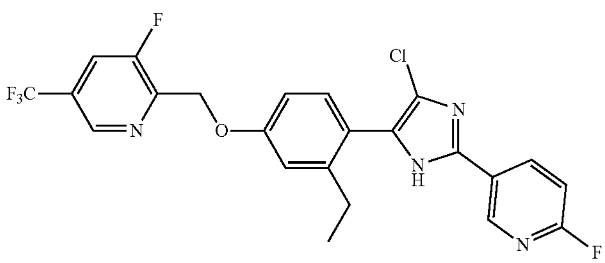 [SMILES: CCc1cc(OCc2ncc(C(F)(F)F)cc2F)ccc1-c1[nH]c(-c2ccc(F)nc2)nc1Cl] | 187-188 | 1H-NMR (DMSO) δ 1.03 (t, J = 7.6 Hz, 3H), 2.55 (q, J = 7.6 Hz, 2H), 5.41 (s, 2H), 6.92-7.18 (m, 2H), 7.15-7.42 (m, 2H), 8.30-8.55 (m, 2H), 8.74 (s, 1H), 8.90 (s, 1H), 13.13 (s, 1H) |
| 365 | 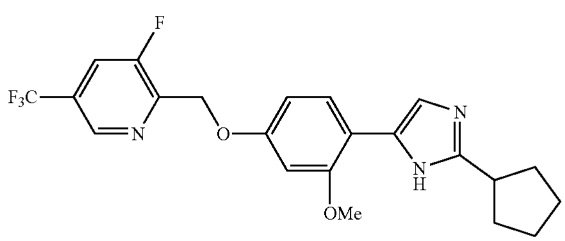 [SMILES: COc1cc(OCc2ncc(C(F)(F)F)cc2F)ccc1-c1cnc(C2CCCC2)[nH]1] | 97-102 | 1H-NMR (CDCL3) δ 1.62-1.95 (m, 6H), 1.98-2.22 (m, 2H), 3.08-3.29 (m, 1H), 3.92 (s, 3H), 5.34 (s, 2H), 6.59-6.75 (m, 2H), 7.16-7.26 (m, 1H), 7.45-7.81 (m, 2H), 8.75 (d, J = 1.6 Hz, 1H) |
| 366 | 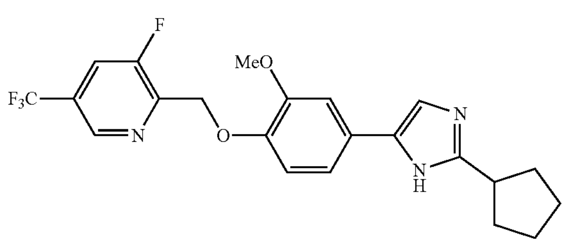 [SMILES: COc1cc(-c2cnc(C3CCCC3)[nH]2)ccc1OCc1ncc(C(F)(F)F)cc1F] | Amorphous | 1H-NMR (CDCL3) δ 1.56-1.93 (m, 6H), 2.00-2.22 (m, 2H), 3.09-3.29 (m, 1H), 3.89 (s, 3H), 5.36 (s, 2H), 6.99 (d, J = 8.7 Hz, 1H), 7.06-7.21 (m, 2H), 7.28 (s, 1H), 7.65 (dd, J = 9.1, 1.7 Hz, 1H), 8.72 (d, J = 1.7 Hz, 1H) |
| 367 | 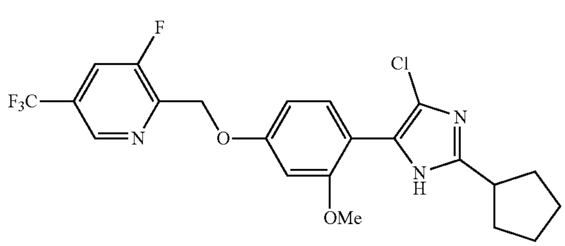 [SMILES: COc1cc(OCc2ncc(C(F)(F)F)cc2F)ccc1-c1[nH]c(C2CCCC2)nc1Cl] | 139-142 | 1H-NMR (CDCL3) δ 1.64-1.94 (m, 6H), 1.97-2.20 (m, 2H), 3.01-3.22 (m, 1H), 3.90 (s, 3H), 5.35 (s, 2H), 6.62-6.80 (m, 2H), 7.71 (dd, J = 9.0, 1.2 Hz, 1H), 7.95 (d, J = 8.3 Hz, 1H), 8.76 (d, J = 1.2 Hz, 1H), 9.74 (s, 1H) |

TABLE 4-continued

| Example No. | Structure | Melting point (° C.) | 1H-NMR (δ:ppm) |
|---|---|---|---|
| 368 | 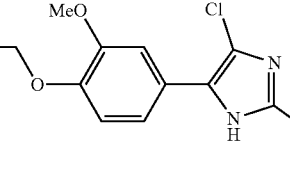 | 158-163 | 1H-NMR (CDCL3) δ 1.64-2.17 (m, 8H), 2.98-3.20 (m, 1H), 3.89 (s, 3H), 5.38 (s, 2H), 6.95-7.15 (m, 2H), 7.18-7.26 (m, 1H), 7.68 (dd, J = 8.8, 1.5 Hz, 1H), 8.73 (d, J = 1.5 Hz, 1H), 9.05 (s, 1H) |
| 369 | 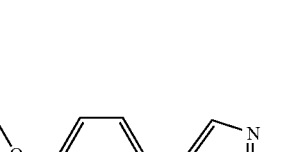 | 167-172 | 1H-NMR (DMSO) δ 5.40 (s, 2H), 6.97 (dd, J = 8.8, 2.4 Hz, 1H), 7.05 (dd, J = 12.9, 2.4 Hz, 1H), 7.32 (dd, J = 8.8, 2.9 Hz, 1H), 7.53 (s, 1H), 7.92-8.11 (m, 1H), 8.41 (dd, J = 8.8, 1.6 Hz, 1H), 8.51 (ddd, J = 8.8, 8.8, 2.4 Hz, 1H), 8.83 (d, J = 2.4 Hz, 1H), 8.89 (s, 1H), 12.89 (s, 1H) |
| 370 | 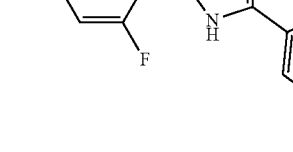 | 144-146 | 1H-NMR (DMSO) δ 5.46 (s, 2H), 7.05 (dd, J = 8.8, 2.4 Hz, 1H), 7.18 (dd, J = 12.2, 2.4 Hz, 1H), 7.33 (dd, J = 8.5, 2.4 Hz, 1H), 7.53 (dd, J = 8.8, 8.8 Hz, 1H), 8.33-8.54 (m, 2H), 8.77 (d, J = 2.4 Hz, 1H), 8.90 (s, 1H), 13.24 (s, 1H) |
| 371 | 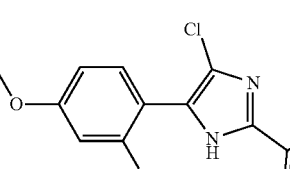 | Amorphous | 1H-NMR (CDCL3) δ 1.84-2.17 (m, 2H), 2.25-2.49 (m, 4H), 3.52-3.73 (m, 1H), 3.92 (s, 3H), 5.33 (s, 2H), 6.57-6.75 (m, 2H), 7.28 (s, 1H), 7.53-7.78 (m, 2H), 8.75 (d, J = 1.6 Hz, 1H) |
| 372 | 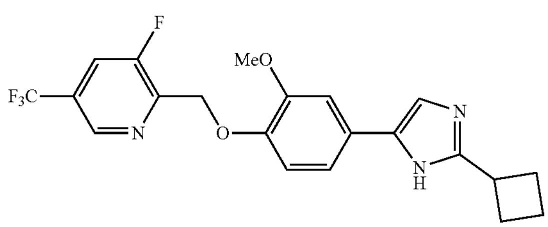 [SMILES: COc1cc(-c2cnc(C3CCC3)[nH]2)ccc1OCc1ncc(C(F)(F)F)cc1F] | Amorphous | 1H-NMR (CDCL3) δ 1.82-2.17 (m, 2H), 2.24-2.47 (m, 4H), 3.53-3.75 (m, 1H), 3.89 (s, 3H), 5.36 (s, 2H), 6.99 (d, J = 8.8 Hz, 1H), 7.07-7.21 (m, 2H), 7.28 (s, 1H), 7.66 (dd, J = 9.0, 1.7 Hz, 1H), 8.72 (d, J = 1.7 Hz, 1H) |
| 373 | 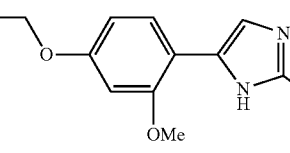 | 155-157 | 1H-NMR (CDCL3) δ 1.85-2.16 (m, 2H), 2.27-2.48 (m, 4H), 3.43-3.65 (m, 1H), 3.90 (s, 3H), 5.35 (s, 2H), 6.62-6.80 (m, 2H), 7.71 (dd, J = 8.8, 1.5 Hz, 1H), 7.95 (d, J = 8.3 Hz, 1H), 8.76 (d, J = 1.5 Hz, 1H), 9.74 (s, 1H) |

TABLE 4-continued

| Example No. | Structure | Melting point (° C.) | 1H-NMR (δ:ppm) |
|---|---|---|---|
| 374 | 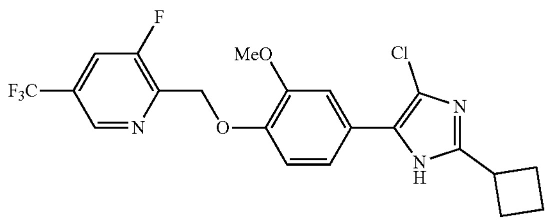 [SMILES: COc1cc(-c2[nH]c(C3CCC3)nc2Cl)ccc1OCc1ncc(C(F)(F)F)cc1F] | 159-162 | 1H-NMR (CDCL3) δ 1.81-2.14 (m, 2H), 2.20-2.48 (m, 4H), 3.41-3.62 (m, 1H), 3.86 (s, 3H), 5.37 (s, 2H), 6.96-7.17 (m, 2H), 7.16-7.25 (m, 1H), 7.68 (dd, J = 9.3, 2.0 Hz, 1H), 8.72 (d, J = 2.0 Hz, 1H), 9.46 (s, 1H) |
| 375 | 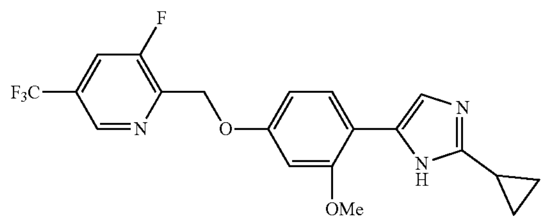 [SMILES: COc1cc(OCc2ncc(C(F)(F)F)cc2F)ccc1-c1cnc(C2CC2)[nH]1] | Amorphous | 1H-NMR (CDCL3) δ 0.82-1.08 (m, 4H), 1.89-2.05 (m, 1H), 3.92 (s, 3H), 5.33 (s, 2H), 6.58-6.75 (m, 2H), 7.21 (s, 1H), 7.57-7.68 (m 1H), 7.70 (dd, J = 9.0, 1.7 Hz, 1H), 8.75 (d, J = 1.7 Hz, 1H) |
| 376 | 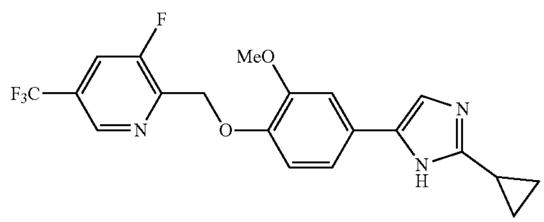 [SMILES: COc1cc(-c2cnc(C3CC3)[nH]2)ccc1OCc1ncc(C(F)(F)F)cc1F] | Amorphous | 1H-NMR (CDCL3) δ 0.91-1.05 (m, 4H), 1.87-2.11 (m, 1H), 3.89 (s, 3H), 5.36 (s, 2H), 6.97 (d, J = 8.3 Hz, 1H), 7.07 (s, 1H), 7.13 (dd, J = 8.3, 1.5 Hz, 1H), 7.26-7.31 (m, 1H), 7.66 (dd, J = 9.3, 1.5 Hz, 1H), 8.72 (d, J = 1.5 Hz, 1H) |
| 377 | 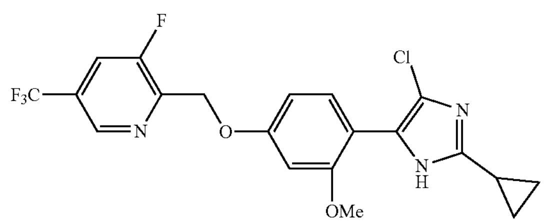 [SMILES: COc1cc(OCc2ncc(C(F)(F)F)cc2F)ccc1-c1[nH]c(C2CC2)nc1Cl] | 151-154 | 1H-NMR (CDCL3) δ 0.88-1.11 (m, 4H), 1.78-1.98 (m, 1H), 3.91 (s, 3H), 5.35 (s, 2H), 6.62-6.79 (m, 2H), 7.71 (dd, J = 8.8, 1.5 Hz, 1H), 7.93 (d, J = 8.8 Hz, 1H), 8.76 (d, J = 1.5 Hz, 1H), 9.80 (s, 1H) |
| 378 | 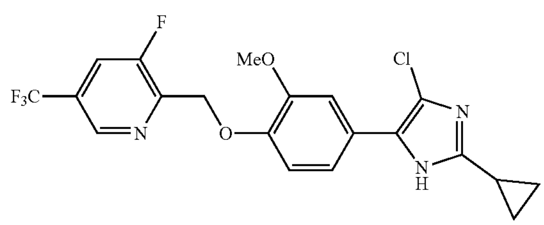 [SMILES: COc1cc(-c2[nH]c(C3CC3)nc2Cl)ccc1OCc1ncc(C(F)(F)F)cc1F] | 161-165 Decomposition | 1H-NMR (CDCL3) δ 0.81-1.11 (m, 4H), 1.79-1.98 (m, 1H), 3.88 (s, 3H), 5.38 (s, 2H), 6.96-7.13 (m, 2H), 7.17-7.26 (m, 1H), 7.68 (dd, J = 9.0, 1.7 Hz, 1H), 8.73 (d, J = 1.7 Hz, 1H) |
| 379 | 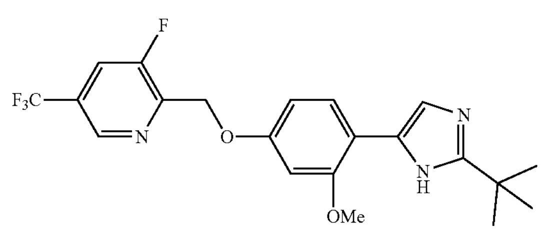 [SMILES: COc1cc(OCc2ncc(C(F)(F)F)cc2F)ccc1-c1cnc(C(C)(C)C)[nH]1] | 141-144 | 1H-NMR (CDCL3) δ 1.41 (s, 9H), 3.92 (s, 3H), 5.34 (s, 2H), 6.57-6.80 (m, 2H), 7.13-7.25 (m, 1H), 7.54 (s, 1H), 7.71 (d, J = 8.8 Hz, 1H), 8.75 (s, 1H), 9.89 (s, 1H) |

TABLE 4-continued

| Example No. | Structure | Melting point (° C.) | 1H-NMR (δ:ppm) |
|---|---|---|---|
| 380 | 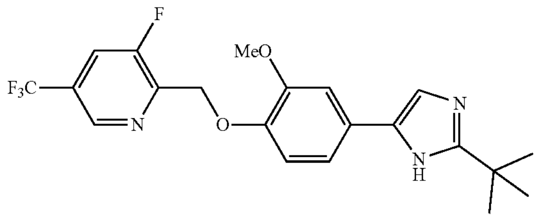 [SMILES: COc1cc(-c2cnc(C(C)(C)C)[nH]2)ccc1OCc1ncc(C(F)(F)F)cc1F] | 178-182 | 1H-NMR (CDCL3) δ 1.42 (s, 9H), 3.91 (s, 3H), 5.36 (s, 2H), 6.99 (d, J = 8.3 Hz, 1H), 7.10 (s, 1H), 7.12-7.42 (m, 2H), 7.66 (dd, J = 8.8, 1.6 Hz, 1H), 8.72 (d, J = 1.6 Hz, 1H) |
| 381 | 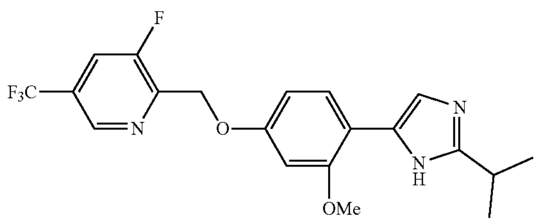 [SMILES: COc1cc(OCc2ncc(C(F)(F)F)cc2F)ccc1-c1cnc(C(C)C)[nH]1] | 84-89 | 1H-NMR (CDCL3) δ 1.37 (d, J = 6.8 Hz, 6H), 3.01-3.21 (m, 1H), 3.92 (s, 3H), 5.33 (s, 2H), 6.56-6.75 (m, 2H), 7.26-7.36 (m, 1H), 7.54-7.78 (m, 2H), 8.75 (d, J = 1.6 Hz, 1H) |
| 382 | 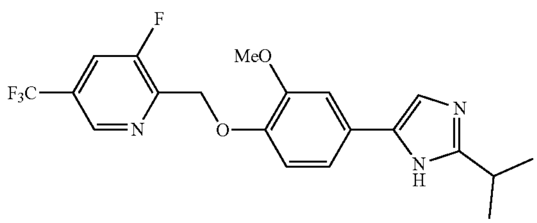 [SMILES: COc1cc(-c2cnc(C(C)C)[nH]2)ccc1OCc1ncc(C(F)(F)F)cc1F] | Oil | 1H-NMR (CDCL3) δ 1.36 (d, J = 7.3 Hz, 6H), 3.03-3.23 (m, 1H), 3.90 (s, 3H), 5.36 (s, 2H), 6.99 (d, J = 8.3 Hz, 1H), 7.04-7.20 (m, 2H), 7.28 (s, 1H), 7.66 (dd, J = 9.3, 1.5 Hz, 1H), 8.72 (d, J = 1.5 Hz, 1H) |
| 383 | 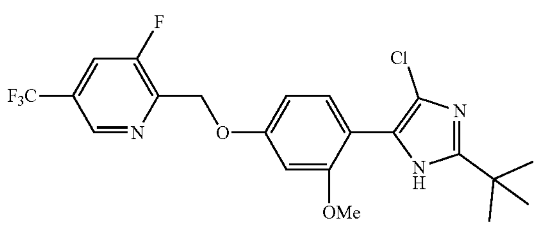 [SMILES: COc1cc(OCc2ncc(C(F)(F)F)cc2F)ccc1-c1[nH]c(C(C)(C)C)nc1Cl] | 170-172 | 1H-NMR (CDCL3) δ 1.39 (s, 9H), 3.90 (s, 3H), 5.35 (s, 2H), 6.63-6.80 (m, 2H), 7.72 (dd, J = 9.3, 2.0 Hz, 1H), 7.97 (d, J = 8.3 Hz, 1H), 8.76 (d, J = 2.0 Hz, 1H), 9.83 (s, 1H) |
| 384 | 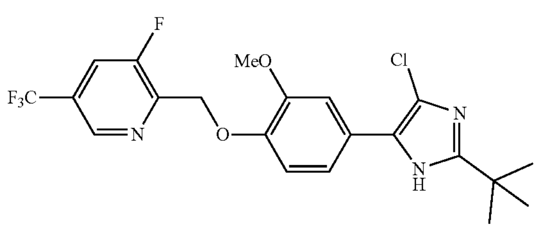 [SMILES: COc1cc(-c2[nH]c(C(C)(C)C)nc2Cl)ccc1OCc1ncc(C(F)(F)F)cc1F] | 179-184 | 1H-NMR (CDCL3) δ 1.40 (s, 9H), 3.91 (s, 3H), 5.38 (s, 2H), 7.07-7.00 (m, 2H), 7.25 (s, 1H), 7.68 (dd, J = 9.0, 1.7 Hz, 1H), 8.73 (d, J = 1.7 Hz, 1H), 8.82 (s, 1H) |
| 385 | 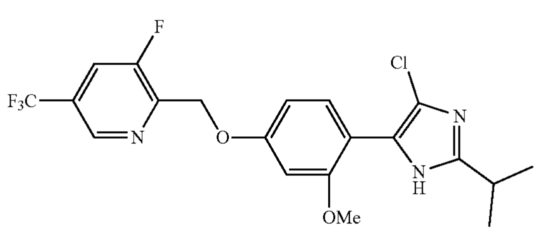 [SMILES: COc1cc(OCc2ncc(C(F)(F)F)cc2F)ccc1-c1[nH]c(C(C)C)nc1Cl] | 131-135 | 1H-NMR (CDCL3) δ 1.36 (d, J = 6.8 Hz, 6H), 2.90-3.16 (m, 1H), 3.90 (s, 3H), 5.35 (s, 2H), 6.63-6.80 (m, 2H), 7.71 (dd, J = 8.8, 1.5 Hz, 1H), 7.96 (d, J = 8.3 Hz, 1H), 8.76 (d, J = 1.5 Hz, 1H), 9.77 (s, 1H) |

TABLE 4-continued

| Example No. | Structure | Melting point (° C.) | 1H-NMR (δ:ppm) |
|---|---|---|---|
| 386 | 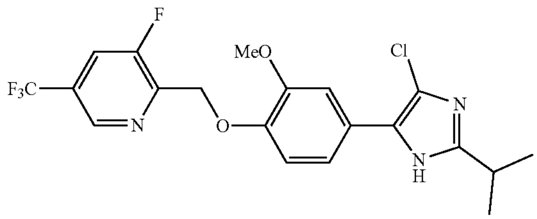 [SMILES: COc1cc(-c2[nH]c(C(C)C)nc2Cl)ccc1OCc1ncc(C(F)(F)F)cc1F] | 188-191 Decomposition | 1H-NMR (CDCL3) δ 1.36 (d, J = 7.3 Hz, 6H), 2.93-3.13 (m, 1H) 3.90 (s, 3H), 5.39 (s, 2H), 6.95-7.15 (m, 2H), 7.16-7.26 (m, 1H), 7.68 (dd, J = 9.3, 1.5 Hz, 1H), 8.73 (d, J = 1.5 Hz, 1H), 8.96 (s, 1H) |
| 387 | 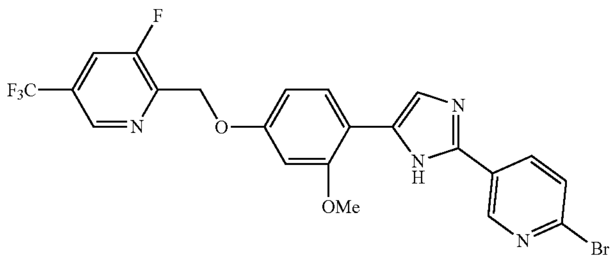 [SMILES: COc1cc(OCc2ncc(C(F)(F)F)cc2F)ccc1-c1cnc(-c2ccc(Br)nc2)[nH]1] | 191-193 | 1H-NMR (DMSO) δ 3.89 (s, 3H), 5.38 (s, 2H), 6.65-6.83 (m, 2H), 7.57 (s, 1H), 7.57 (d, J = 8.3 Hz, 1H), 7.85-8.15 (m, 1H), 8.26 (dd, J = 8.3, 2.4 Hz, 1H), 8.41 (d, J = 10.2 Hz, 1H), 8.90 (s, 1H), 8.97 (d, J = 2.4 Hz, 1H) |
| 388 | 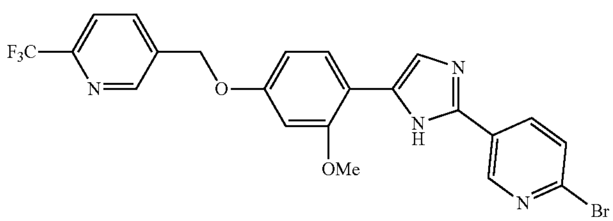 [SMILES: COc1cc(OCc2ccc(C(F)(F)F)nc2)ccc1-c1cnc(-c2ccc(Br)nc2)[nH]1] | 222-224 | 1H-NMR (CDCL3) δ 4.00 (s, 3H), 5.19 (s, 2H), 6.54-6.74 (m, 2H), 7.39-7.84 (m, 4H), 7.87-8.33 (m, 2H), 8.71-8.90 (m, 2H), 10.67 (s, 1H) |
| 389 | 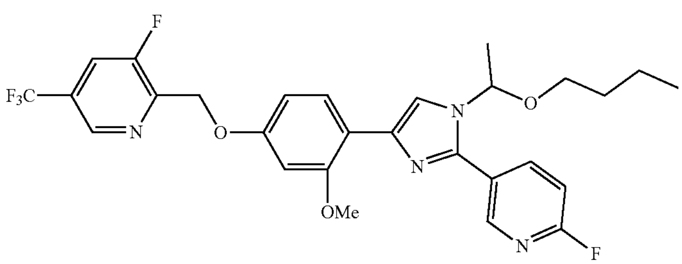 [SMILES: CCCCOC(C)n1cc(-c2ccc(OCc3ncc(C(F)(F)F)cc3F)cc2OC)nc1-c1ccc(F)nc1] | Oil | 1H-NMR (CDCL3) δ 0.84 (t, J = 7.3 Hz, 3H), 1.28-1.53 (m, 4H), 1.71 (d, J = 5.9 Hz, 3H), 3.06-3.31 (m, 2H), 3.94 (s, 3H), 5.27-5.46 (m, 3H), 6.59-6.79 (m, 2H), 7.06 (dd, J = 8.8, 2.9 Hz, 1H), 7.61-7.81 (m, 2H), 8.10 (ddd, J = 8.8, 8.8, 2.4 Hz, 1H), 8.16 (d, J = 8.8 Hz, 1H), 8.45 (d, J = 2.4 Hz, 1H), 8.75 (s, 1H) |
| 390 | 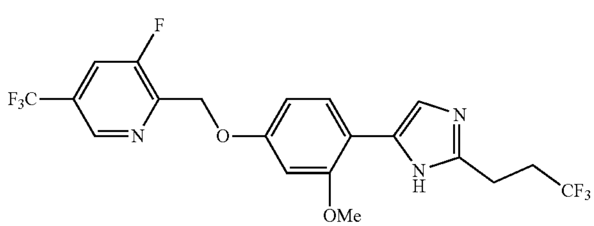 [SMILES: COc1cc(OCc2ncc(C(F)(F)F)cc2F)ccc1-c1cnc(CCC(F)(F)F)[nH]1] | 76-91 | 1H-NMR (CDCL3) δ 2.58-2.74 (m, 2H), 2.96-3.07 (m, 2H), 3.93 (s, 3H), 5.34 (s, 2H), 6.60-6.76 (m, 2H), 7.27-7.36 (m, 1H), 7.66 (s, 1H), 7.71 (dd, J = 9.0, 1.7 Hz, 1H), 8.75 (s, 1H) |
| 391 | 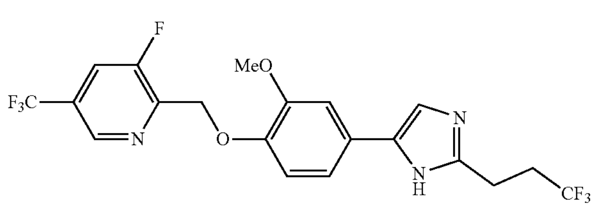 [SMILES: COc1cc(-c2cnc(CCC(F)(F)F)[nH]2)ccc1OCc1ncc(C(F)(F)F)cc1F] | Oil | 1H-NMR (CDCL3) δ 2.56-2.74 (m, 2H), 2.93-3.05 (m, 2H), 3.91 (s, 3H), 5.36 (s, 2H), 7.00 (d, J = 8.3 Hz, 1H), 7.04-7.19 (m, 2H), 7.28 (s, 1H), 7.66 (dd, J = 9.0, 1.7 Hz, 1H), 8.72 (s, 1H) |

TABLE 4-continued

| Example No. | Structure | Melting point (° C.) | 1H-NMR (δ:ppm) |
|---|---|---|---|
| 392 | 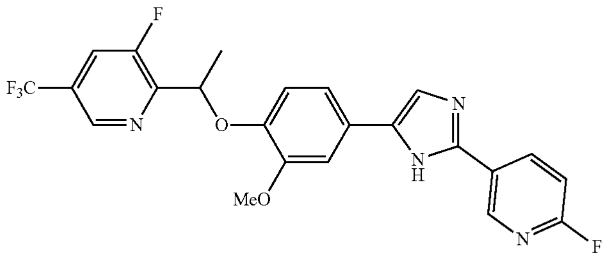 [SMILES: COc1cc(-c2cnc(-c3ccc(F)nc3)[nH]2)ccc1OC(C)c1ncc(C(F)(F)F)cc1F] | Oil | 1H-NMR (CDCL3) δ 1.78 (d, J = 6.8 Hz, 3H), 3.90 (s, 3H), 5.76 (q, J = 6.8 Hz, 1H), 6.84 (d, J = 8.3 Hz, 1H), 7.01 (dd, J = 8.5, 2.7 Hz, 1H), 7.13 (dd, J = 8.3, 1.5 Hz, 1H), 7.30 (s, 1H), 7.33 (d, J = 1.5 Hz, 1H), 7.61 (dd, J = 12.0, 2.7 Hz, 1H), 8.38 (ddd, J = 8.5, 8.5, 2.7 Hz, 1H), 8.64 (d, J = 2.7 Hz, 1H), 8.69 (d, J = 2.7 Hz, 1H) |
| 393 | 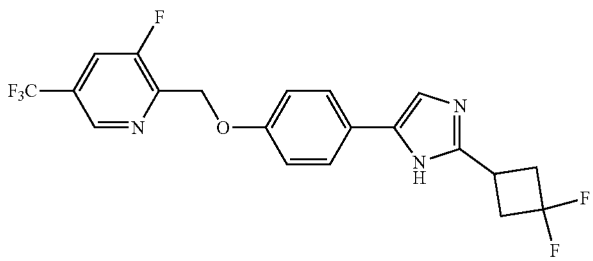 [SMILES: Fc1cc(C(F)(F)F)cnc1COc1ccc(-c2cnc(C3CC(F)(F)C3)[nH]2)cc1] | 191-196 | 1H-NMR (CDCL3) δ 2.87-3.10 (m, 4H), 3.36-3.53 (m, 1H), 5.33 (s, 2H), 7.03 (dd, J = 6.8, 2.0 Hz, 2H), 7.14 (s, 1H), 7.61 (dd, J = 6.8, 2.0 Hz, 2H), 7.70 (dd, J = 9.0, 1.7 Hz, 1H), 8.74 (d, J = 1.7 Hz, 1H) |
| 394 | 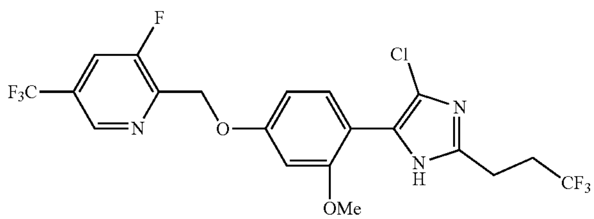 [SMILES: COc1cc(OCc2ncc(C(F)(F)F)cc2F)ccc1-c1[nH]c(CCC(F)(F)F)nc1Cl] | 154-159 | 1H-NMR (CDCL3) δ 2.52-2.76 (m, 2H), 2.88-3.06 (m, 2H), 3.90 (s, 3H), 5.36 (s, 2H), 6.63-6.81 (m, 2H), 7.72 (dd, J = 9.0, 1.7 Hz, 1H), 7.96 (d, J = 8.3 Hz, 1H), 8.76 (d, J = 1.7 Hz, 1H), 9.92 (s, 1H) |
| 395 | 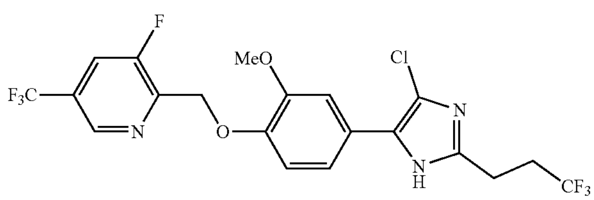 [SMILES: COc1cc(-c2[nH]c(CCC(F)(F)F)nc2Cl)ccc1OCc1ncc(C(F)(F)F)cc1F] | 116-119 | 1H-NMR (CDCL3) δ 2.49-2.74 (m, 2H), 2.84-3.04 (m, 2H), 3.87 (s, 3H), 5.38 (s, 2H), 6.99-7.11 (m, 2H), 7.19-7.26 (m, 1H), 7.69 (dd, J = 9.3, 1.5 Hz, 1H), 8.72 (d, J = 1.5 Hz, 1H), 9.54 (s, 1H) |
| 396 | 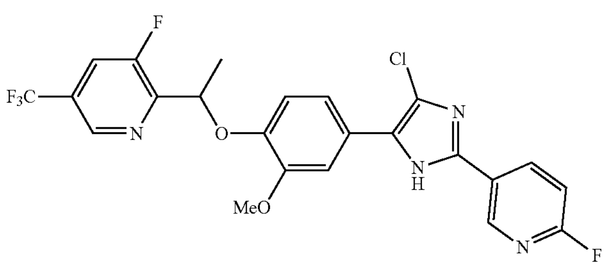 [SMILES: COc1cc(-c2[nH]c(-c3ccc(F)nc3)nc2Cl)ccc1OC(C)c1ncc(C(F)(F)F)cc1F] | 113-118 | 1H-NMR (CDCL3) δ 1.76 (d, J = 6.8 Hz, 3H), 3.82 (s, 3H), 5.76 (q, J = 6.8 Hz, 1H), 6.81 (d, J = 8.3 Hz, 1H), 6.96 (dd, J = 8.5, 2.7 Hz, 1H), 7.04 (d, J = 8.3, 1.5 Hz, 1H), 7.15-7.26 (m, 1H), 7.63 (dd, J = 9.3, 1.5 Hz, 1H), 8.32 (ddd, J = 8.5, 8.5, 2.7 Hz, 1H), 8.61 (s, J = 2.7 Hz, 1H), 8.66 (s, J = 1.5 Hz, 1H), 10.43 (s, 1H) |
| 397 | 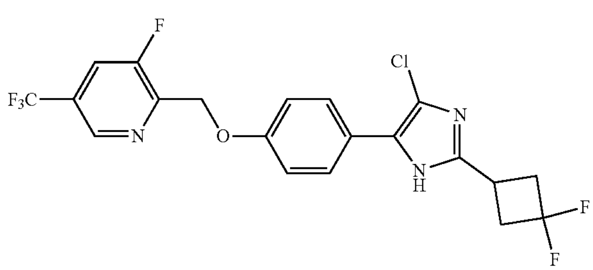 [SMILES: Fc1cc(C(F)(F)F)cnc1COc1ccc(-c2[nH]c(C3CC(F)(F)C3)nc2Cl)cc1] | 162-167 | 1H-NMR (CDCL3) δ 2.83-3.08 (m, 4H), 3.24-3.44 (m, 1H), 5.34 (s, 2H), 7.07 (d, J = 9.4 Hz, 2H), 7.55 (d, J = 8.8 Hz, 2H), 7.71 (dd, J = 8.8, 1.5 Hz, 1H), 8.74 (d, J = 1.5 Hz, 1H), 9.39 (s, 1H) |

TABLE 4-continued

| Example No. | Structure | Melting point (° C.) | 1H-NMR (δ:ppm) |
|---|---|---|---|
| 398 | 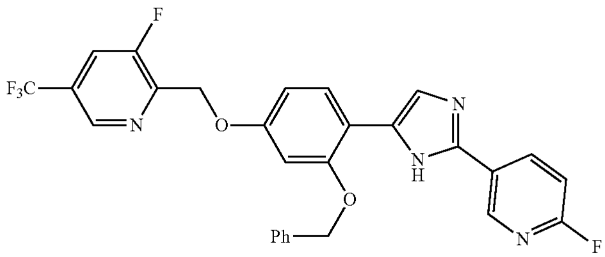 [SMILES: Fc1ccc(-c2ncc(-c3ccc(OCc4ncc(C(F)(F)F)cc4F)cc3OCc3ccccc3)[nH]2)cn1] | Oil | 1H-NMR (CDCL3) δ 5.14 (s, 2H), 5.37 (s, 2H), 6.75 (dd, J = 8.8, 2.4 Hz, 1H), 6.78-6.95 (m, 2H), 7.28-7.99 (m, 9H), 8.02-8.20 (m, 1H), 8.76 (s, 1H), 10.60 (s, 1H) |
| 399 | 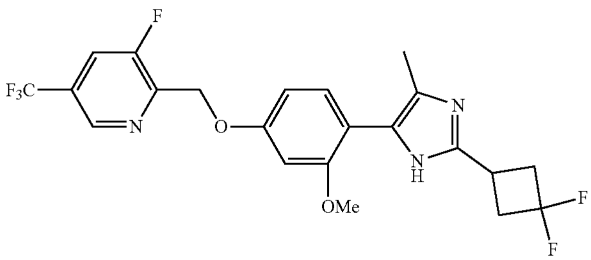 [SMILES: COc1cc(OCc2ncc(C(F)(F)F)cc2F)ccc1-c1[nH]c(C2CC(F)(F)C2)nc1C] | 172-174 | 1H-NMR (CDCL3) δ 2.37 (s, 3H), 2.83-3.09 (m, 4H), 3.32-3.50 (m, 1H), 3.87 (s, 3H), 5.35 (s, 2H), 6.61-6.78 (m, 2H), 7.35 (d, J = 9.3 Hz, 1H), 7.72 (d, J = 8.8, 1.2 Hz, 1H), 8.76 (d, J = 1.2 Hz, 1H), 9.51 (s, 1H) |
| 400 | 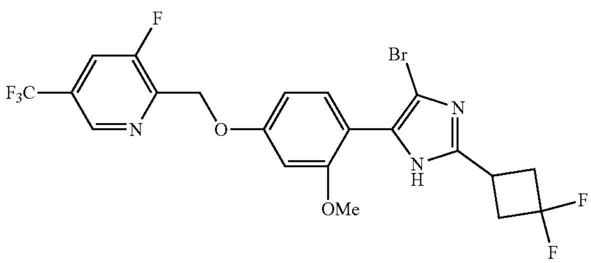 [SMILES: COc1cc(OCc2ncc(C(F)(F)F)cc2F)ccc1-c1[nH]c(C2CC(F)(F)C2)nc1Br] | 192-195 | 1H-NMR (CDCL3) δ 2.87-3.08 (m, 4H), 3.32-3.49 (m, 1H), 3.89 (s, 3H), 5.36 (s, 2H), 6.63-6.80 (m, 2H), 7.72 (dd, J = 8.8, 1.5 Hz, 1H), 7.98 (d, J = 8.8 Hz, 1H), 8.76 (d, J = 1.5 Hz, 1H), 9.92 (s, 1H) |
| 401 | 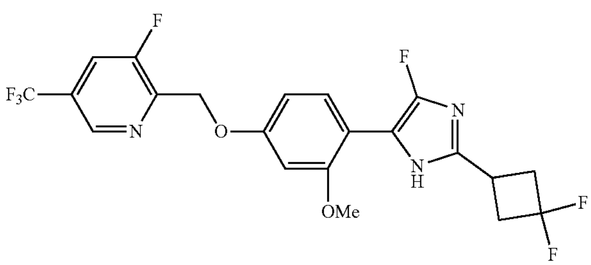 [SMILES: COc1cc(OCc2ncc(C(F)(F)F)cc2F)ccc1-c1[nH]c(C2CC(F)(F)C2)nc1F] | | 1H-NMR (CDCL3) δ 2.83-3.08 (m, 4H), 3.22-3.44 (m, 1H), 3.94 (s, 3H), 5.34 (s, 2H), 6.63-6.76 (m, 2H), 7.67 (d, J = 8.8 Hz, 1H), 7.71 (dd, J = 9.0, 1.7 Hz, 1H), 8.75 (d, J = 1.7 Hz, 1H), 9.89 (s, 1H) |
| 402 | 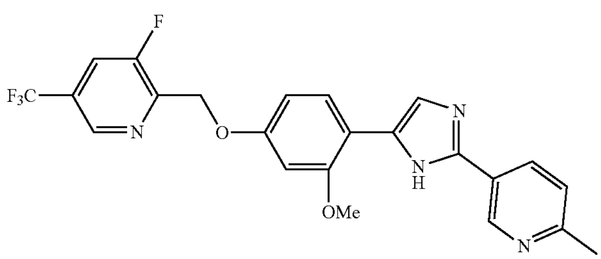 [SMILES: COc1cc(OCc2ncc(C(F)(F)F)cc2F)ccc1-c1cnc(-c2ccc(C)nc2)[nH]1] | | 1H-NMR (CDCL3) δ 2.60 (s, 3H), 3.97 (s, 3H), 5.36 (s, 2H), 6.63-6.82 (m, 2H), 7.24 (d, J = 8.8 Hz, 1H), 7.37-7.68 (m, 2H), 7.17 (d, J = 8.8 Hz, 1H), 8.11 (d, J = 7.3, 2.0 Hz, 1H), 8.76 (s, 1H), 8.92 (d, J = 2.0 Hz, 1H), 10.54 (s, 1H) |
| 403 | 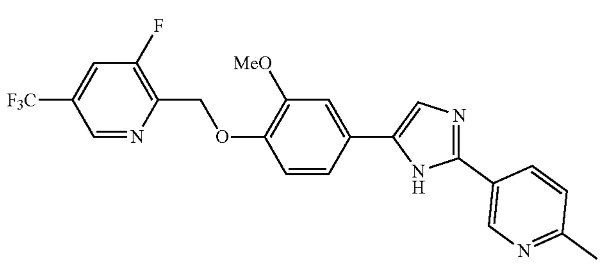 [SMILES: COc1cc(-c2cnc(-c3ccc(C)nc3)[nH]2)ccc1OCc1ncc(C(F)(F)F)cc1F] | | 1H-NMR (CDCL3) δ 2.55 (s, 3H), 3.87 (s, 3H), 5.36 (s, 2H), 7.01 (d, J = 8.3 Hz, 1H), 7.15-7.28 (m, 3H), 7.32 (s, 1H), 7.66 (dd, J = 9.0, 1.7 Hz, 1H), 8.17 (dd, J = 8.0, 2.2 Hz, 1H), 8.71 (s, 1H), 8.94 (d, J = 2.2 Hz, 1H) |

TABLE 4-continued

| Example No. | Structure | Melting point (° C.) | 1H-NMR (δ:ppm) |
|---|---|---|---|
| 404 | 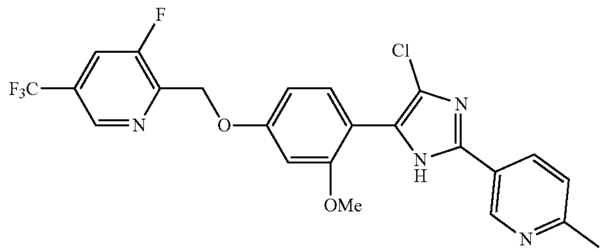 [SMILES: COc1cc(OCc2ncc(C(F)(F)F)cc2F)ccc1-c1[nH]c(-c2ccc(C)nc2)nc1Cl] | | 1H-NMR (CDCL3) δ 2.60 (s, 3H), 3.95 (s, 3H), 5.37 (s, 2H), 6.67-6.83 (m, 2H), 7.24 (d, J = 8.3 Hz, 1H), 7.73 (d, J = 8.8 Hz, 1H), 8.05 (d, J = 8.3 Hz, 1H), 8.08 (dd, J = 8.0, 2.2 Hz, 1H), 8.76 (s, 1H), 8.88 (d, J = 2.2 Hz, 1H), 10.51 (s, 1H) |
| 405 | 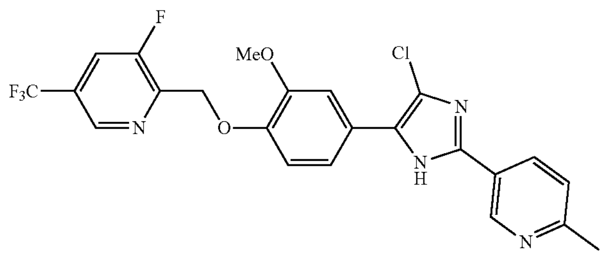 [SMILES: COc1cc(-c2[nH]c(-c3ccc(C)nc3)nc2Cl)ccc1OCc1ncc(C(F)(F)F)cc1F] | | 1H-NMR (DMSO) δ 2.51 (s, 3H), 3.83 (s, 3H), 5.36 (s, 2H), 7.21 (d, J = 8.3, 1H), 7.32 (dd, J = 8.3, 1.5 Hz, 1H), 7.35-7.46 (m, 2H), 8.19 (dd, J = 8.0, 2.4 Hz, 1H), 8.41 (d, J = 8.8 Hz, 1H), 8.89 (s, 1H), 9.03 (d, J = 2.4 Hz, 1H), 12.89 (s, 1H) |

Example 406

Production of 5-[[3-fluoro-5-(trifluoromethyl)pyridin-2-yl]methoxy]-2-[2-(6-fluoropyridin-3-yl)-1H-imidazol-5-yl]phenol The compound of Example 398 (150 mg, 0.28 mmol), which is 2-[(3-(benzyloxy)-4-(2-(6-fluoropyridin-3-yl)-1H-imidazol-5-yl)phenoxy)methyl]-3-fluoro-5-(trifluoromethyl)pyridine, was dissolved in ethanol (5 ml), and 10% palladium carbon (15 mg) was added thereto. After the atmosphere was replaced with hydrogen, the mixture was stirred at room temperature overnight. The palladium carbon was filtered through Celite, and the filtrate was distilled off under reduced pressure. The obtained crystals were washed with isopropanol and vacuum-dried at 60° C. for 1 hour to yield the desired product (90 mg, yield: 72%).

Examples 407 and 408

The compounds of Examples 407 and 408, which have the structures and melting points shown in Table 5 below, were produced in the same manner as in Example 406. Benzyloxy-substituted compounds that are precursors of the compounds of Examples 407 and 408 can be synthesized in the same manner as in any of Examples 1 to 405 described above.

Example 409

Production of 2-(6-fluoropyridin-3-yl)-5-[2-methoxy-4-((6-trifluoromethyl)pyridin-3-yl)methoxy)phenyl]-1H-imidazole-4-carbonitrile The compound of Example 224 (540 mg, 1.0 mmol), which is 5-[(4-(4-bromo-2-(6-fluoropyridin-3-yl)-1H-imidazol-5-yl)-3-methoxyphenoxy)methyl]-2-(trifluoromethyl)pyridine, and zinc cyanide (150 mg, 1.3 mmol) were added to N-methylpyrrolidone (11 ml), and the atmosphere was replaced with argon. Tetrakis triphenylphosphine palladium (180 mg, 0.16 mmol) was added to this solution, and the mixture was stirred at 130° C. for 11 hours. The reaction mixture was added to water (200 ml), and the precipitated solid was filtered, followed by purification using a silica gel column (eluent: chloroform/methanol). The crude crystals obtained by combining the desired fractions were recrystallized from methanol. The crystals were filtered and vacuum-dried at 40° C. to yield the desired product (140 mg, yield: 30%).

Example 410

The compound of Example 410, which has the structure and melting point shown in Table 5 below, was produced in the same manner as in Example 409.

Example 411

Production of 3-fluoro-2-[[4-(2-(6-fluoropyridin-3-yl)-4-(trifluoromethyl)-1H-imidazol-5-yl)-3-methoxyphenoxy]methyl]-5-(trifluoromethyl)pyridine The compound of Example 139 (300 mg, 0.65 mmol), which is 3-fluoro-2-[[4-(2-(6-fluoropyridin-3-yl)-1H-imidazol-5-yl)-3-methoxyphenoxy]methyl]-5-(trifluoromethyl)pyridine, S-(trifluoromethyl)dibenzothiophenium tetrafluoroborate (357 mg, 1.1 mmol), which is a trifluoromethylating reagent, and diazabicycloundecene (0.20 ml, 1.3 mmol) were added to DMF (5 ml). After the atmosphere was replaced with nitrogen, the mixture was stirred at room temperature for 3 hours. DMF was distilled off under reduced pressure, followed by purification using a silica gel column (eluent: hexane/ethyl acetate). The desired fractions were combined, and the solvent was distilled off under reduced pressure. Thereafter, the crystals were washed with hexane and vacuum-dried at 65° C. for 1 hour to yield the desired product (240 mg, yield: 70%).

Example 412

The compound of Example 412, which has the structure and melting point shown in Table 5 below, was produced in the same manner as in Example 411.

Example 413

Production of [5-(4-((3-fluoro-5-(trifluoromethyl)pyridin-2-yl)methoxy)-2-methoxyphenyl)-2-(6-fluoropyridin-3-yl)-1H-imidazol-4-yl]methanol The compound of Example 139 (220 mg, 0.48 mmol), which is 3-fluoro-2-[[4-(2-(6-fluoropyridin-3-yl)-1H-imidazol-5-yl)-3-methoxyphenoxy]methyl]-5-(trifluoromethyl)pyridine, was dissolved in THF (2 ml) and methanol (2 ml). A 3.8% formaldehyde aqueous solution (1.1 ml, 1.4 mmol) and a 4N sodium hydroxide aqueous solution (0.18 ml, 0.71 mmol) were added to this solution, and the mixture was stirred at 65° C. overnight, followed by extraction with 70 ml of ethyl acetate/hexane (=2/1). The organic layer was washed with water and brine, and dried over magnesium sulfate. The solvents were distilled off under reduced pressure, and the residue was purified with a silica gel column (eluent: hexane/ethyl acetate). The desired fractions were combined, and the solvent was distilled off under reduced pressure to yield the desired product (65 mg, yield: 27%).

TABLE 5

| Example No. | Structure | Melting point (° C.) | 1H-NMR (δ:ppm) |
|---|---|---|---|
| 406 | [structure] | 202-207 | 1H-NMR (DMSO) δ 5.32 (s, 2H), 6.44-6.72 (m, 2H), 7.36 (dd, J = 8.5, 1.5 Hz, 1H), 7.56-7.74 (m, 1H), 7.80 (s, 1H), 8.40 (d, J = 9.8 Hz, 1H), 8.45-8.62 (m, 1H), 8.81 (d, J = 1.0 Hz, 1H), 8.89 (d, J = 1.5 Hz, 1H), 11.78 (s, 1H), 13.21 (s, 1H) |
| 407 | [structure] | 229-233 Decomposition | 1H-NMR (DMSO) δ 5.34 (s, 2H), 6.53-6.72 (m 2H), 7.20-7.39 (m, 2H), 8.24-8.54 (m, 2H), 8.76 (d, J = 2.3 Hz, 1H), 8.89 (s, 1H), 10.05 (s, 1H) |
| 408 | [structure] | 202-204 | 1H-NMR (DMSO) δ 5.35 (s, 2H), 6.51-6.71 (m, 2H), 7.17-7.41 (m, 2H), 8.31-8.54 (m, 2H), 8.76 (d, J = 1.7 Hz, 1H), 8.90 (s, 1H), 10.04 (s, 1H), 12.96 (s, 1H) |
| 409 | [structure] | 212-219 | 1H-NMR (DMSO) δ 3.88 (s, 3H), 5.42 (s, 2H), 6.86 (dd, J = 8.4, 1.6 Hz, 1H), 6.93 (d, J = 1.6 Hz, 1H), 7.38 (dd, J = 8.8, 2.0 Hz, 1H), 7.54 (d, J = 8.4 Hz, 1H), 7.99 (d, J = 8.4 Hz, 1H), 8.22 (d, J = 8.4 Hz, 1H), 8.52-8.56 (m, 1H), 8.85 (s, 1H), 8.92 (s, 1H), 13.42 (s, 1H) |

TABLE 5-continued

| Example No. | Structure | Melting point (° C.) | 1H-NMR (δ:ppm) |
|---|---|---|---|
| 410 | (structure) | 165-167 | 1H-NMR (DMSO) δ 3.84 (s, 3H), 3.89 (s, 3H), 5.38 (s, 2H), 6.78 (dd, J = 8.6, 2.4 Hz, 1H), 6.86 (d, J = 2.4 Hz, 1H), 7.42 (dd, J = 8.6, 2.6 Hz, 1H), 7.74 (d, J = 8.8 Hz, 1H), 7.98 (d, J = 8.6 Hz, 1H), 8.21 (dd, J = 8.8, 1.6 Hz, 1H), 8.38-8.43 (m, 1H), 8.67 (d, J = 2.4 Hz, 1H), 8.91 (s, J = 1.6 Hz, 1H) |
| 411 | (structure) | 181-182 | 1H-NMR (CDCL3) δ 3.86 (s, 3H), 5.35 (s, 2H), 6.61-6.78 (m, 2H), 7.04 (dd, J = 9.1, 2.7 Hz, 1H), 7.35-7.51 (m, 1H), 7.73 (dd, J = 8.8, 1.5 Hz, 1H), 8.37 (ddd, J = 9.1, 6.7, 2.9 Hz, 1H), 8.59 (d, J = 2.9 Hz, 1H), 8.75 (s, 1H), 10.27 (s, 1H) |
| 412 | (structure) | 222-224 | 1H-NMR (DMSO) δ 3.77 (s, 3H), 5.38 (s, 2H), 6.76 (dd, J = 8.5, 2.4 Hz, 1H), 6.85 (d, J = 2.4 Hz, 1H), 7.23-7.40 (m, 2H), 7.97 (d, J = 8.5 Hz, 1H), 8.20 (dd, J = 8.3, 1.5 Hz, 1H), 8.49 (ddd, J = 8.3, 8.3, 2.4 Hz, 1H), 8.80 (d, J = 2.4 Hz, 1H), 8.89 (d, J = 1.5 Hz, 1H) |
| 413 | (structure) | Oil | 1H-NMR (CDCL3) δ 3.65-3.84 (m, 6H), 5.15 (s, 2H), 6.41-6.66 (m, 3H), 7.38-7.78 (m, 2H), 7.91 (dd, J = 8.8, 2.0 Hz, 1H), 8.40 (d, J = 2.0 Hz, 1H), 8.57 (s, 1H) |

Preparation Example 1

Preparation of Tablet

Using the compound obtained in Example 227 as an active ingredient, tablets (10000 tablets) each containing 300 mg of the compound were prepared according to the following formulation.

| | |
|---|---|
| Compound obtained in Example 227 | 3000 g |
| Lactose (product of Japanese Pharmacopoeia) | 335 g |
| Cornstarch (product of Japanese Pharmacopoeia) | 165 g |
| Carboxymethylcellulose calcium (product of Japanese Pharmacopoeia) | 125 g |
| Methylcellulose (product of Japanese Pharmacopoeia) | 60 g |
| Magnesium stearate (product of Japanese Pharmacopoeia) | 15 g |

According to the above formulation, the compound obtained in Example 227, lactose, cornstarch, and carboxymethylcellulose calcium were sufficiently mixed. The mixture was granulated using an aqueous methylcellulose solution, screened with a 24-mesh screen, mixed with magnesium stearate, and pressed into tablets, thereby yielding the desired tablets.

Preparation Example 2

Preparation of Capsule

Using the compound obtained in Example 255 as an active ingredient, hard gelatin capsules (10000 capsules) each containing 200 mg of the compound were prepared according to the following formulation.

| | |
|---|---|
| Compound obtained in Example 255 | 2000 g |
| Crystalline cellulose (product of Japanese Pharmacopoeia) | 300 g |
| Cornstarch (product of Japanese Pharmacopoeia) | 170 g |
| Talc (product of Japanese Pharmacopoeia) | 20 g |
| Magnesium stearate (product of Japanese Pharmacopoeia) | 10 g |

According to the above formulation, each of the components was ground into a fine powder, and the powders were mixed to form a uniform mixture and loaded into gelatin capsules of a desired size for oral administration, thereby yielding the desired capsules.

Test Example 1

LPL mRNA Elevating Action

C2Cl2 cells (cell strain derived from striated muscle of mouse) were seeded in 96-well plates using a DMEM medium (Gibco) (containing 2 mM L-glutamine and 10% fetal bovine serum). After the cells were grown, the medium was removed. Subsequently, media obtained by adding dimethyl sulfoxide (DMSO) solutions of the compounds to the same medium as described above to a concentration of 10 µM were individually added to the cells and allowed to stand for 24 hours. The compound-containing media were removed, and the plates were washed with phosphate buffered saline. Thereafter, the remaining cells were lysed and subjected to a reverse transcription polymerase chain reaction (RT-PCR reaction) to obtain cDNA. Primers specific to lipoprotein lipase (LPL) gene, a necessary enzyme, etc., were added to the obtained cDNA. The mixture was set in 7500 Fast Real Time PCR System produced by Applied Biosystem to perform a PCR reaction (20 cycles) and the amount of LPL mRNA amplified was quantified. The LPL mRNA elevating action of each compound in the test cells was indicated as the ratio relative to the amount of LPL mRNA in cells allowed to stand in a medium to which only DMSO was added, with the amount being defined as 1.

As Comparative Example 1, a test was performed in the same manner as above, using a compound disclosed as the compound of Example 57 in WO2010/090200. The results are shown in Table 6 below.

TABLE 6

| Example | Rate of increase in LPL mRNA |
|---|---|
| 1 | 2.97 |
| 3 | 2.48 |
| 6 | 4.44 |
| 12 | 2.23 |
| 13 | 2.31 |
| 14 | 5.42 |
| 15 | 4.27 |
| 16 | 3.14 |
| 17 | 3.2 |
| 18 | 1.05 |
| 19 | 1.7 |
| 20 | 2.78 |
| 21 | 1.99 |
| 22 | 2.22 |
| 23 | 2.94 |
| 24 | 2.94 |
| 25 | 2.68 |
| 27 | 2.45 |
| 32 | 2.58 |
| 33 | 2.92 |
| 34 | 2.22 |
| 36 | 2.4 |
| 38 | 2.25 |
| 39 | 2.7 |
| 40 | 0.93 |
| 42 | 2.27 |
| 43 | 3.48 |
| 44 | 1.14 |
| 45 | 1.09 |
| 46 | 2.49 |
| 47 | 3.26 |

TABLE 6-continued

| | Rate of increase in LPL mRNA |
|---|---|
| 48 | 3.02 |
| 49 | 3.46 |
| 55 | 4.24 |
| 56 | 2.57 |
| 57 | 3.72 |
| 65 | 2.89 |
| 68 | 2.45 |
| 71 | 2.37 |
| 72 | 2.75 |
| 73 | 4.07 |
| 77 | 3.11 |
| 79 | 1.42 |
| 80 | 2.01 |
| 89 | 1.69 |
| 100 | 3.05 |
| 103 | 2.36 |
| 104 | 2.27 |
| 106 | 2.66 |
| 107 | 2.68 |
| 108 | 3.03 |
| 109 | 1.76 |
| 111 | 2.46 |
| 112 | 2.39 |
| 117 | 3.38 |
| 118 | 2.91 |
| 121 | 3.38 |
| 122 | 1.7 |
| 123 | 3.22 |
| 124 | 2.28 |
| 128 | 2.28 |
| 131 | 3.66 |
| 132 | 2.77 |
| 133 | 2.43 |
| 134 | 2.85 |
| 135 | 3.14 |
| 136 | 2.71 |
| 138 | 2.97 |
| 141 | 2.33 |
| 142 | 2.27 |
| 152 | 3.3 |
| 153 | 4.61 |
| 154 | 5.78 |
| 155 | 3.06 |
| 156 | 3.27 |
| 157 | 4.05 |
| 158 | 2.77 |
| 161 | 3.06 |
| 165 | 3.34 |
| 167 | 2.23 |
| 169 | 3.12 |
| 170 | 3.36 |
| 171 | 2.89 |
| 172 | 3.12 |
| 175 | 3.94 |
| 176 | 2.83 |
| 178 | 3.58 |
| 179 | 2.66 |
| 181 | 4.53 |
| 182 | 3.41 |
| 183 | 4.26 |
| 185 | 2.41 |
| 188 | 2.95 |
| 189 | 3.51 |
| 190 | 3.58 |
| 191 | 4.06 |
| 193 | 4.32 |
| 194 | 3.92 |
| 195 | 3.34 |
| 198 | 6.36 |
| 199 | 5.05 |
| 200 | 4.73 |
| 201 | 2.45 |
| 202 | 3.15 |
| 203 | 5.47 |
| 204 | 5.07 |
| 205 | 5.41 |

TABLE 6-continued

| | Rate of increase in LPL mRNA |
|---|---|
| 206 | 2.75 |
| 207 | 2.5 |
| 208 | 4.72 |
| 209 | 5.34 |
| 210 | 5.69 |
| 211 | 2.55 |
| 212 | 2.22 |
| 213 | 2.04 |
| 214 | 3.66 |
| 216 | 2.62 |
| 218 | 1.21 |
| 219 | 2.42 |
| 220 | 2.69 |
| 221 | 3.47 |
| 222 | 2.89 |
| 224 | 2.29 |
| 225 | 2.8 |
| 227 | 5.08 |
| 229 | 2.62 |
| 230 | 1.58 |
| 233 | 3.87 |
| 234 | 3.06 |
| 235 | 2.78 |
| 237 | 2.82 |
| 238 | 2.42 |
| 239 | 2.39 |
| 241 | 2.45 |
| 242 | 2.38 |
| 247 | 2.25 |
| 248 | 2.36 |
| 249 | 2.5 |
| 252 | 2.58 |
| 253 | 2.62 |
| 254 | 2.71 |
| 255 | 3.14 |
| 256 | 3.12 |
| 258 | 2.91 |
| 259 | 2.93 |
| 260 | 2.95 |
| 261 | 4.08 |
| 262 | 3.61 |
| 263 | 3.18 |
| 264 | 2.99 |
| 265 | 3.36 |
| 266 | 2.38 |
| 267 | 2.66 |
| 268 | 2.53 |
| 270 | 3.81 |
| 271 | 3.39 |
| 273 | 2.5 |
| 274 | 3.41 |
| 276 | 2.36 |
| 277 | 2.66 |
| 278 | 2.95 |
| 279 | 3.63 |
| 280 | 2.91 |
| 281 | 3.36 |
| 285 | 3.01 |
| 287 | 3.53 |
| 290 | 2.64 |
| 292 | 2.81 |
| 293 | 5.05 |
| 294 | 2.42 |
| 295 | 4.06 |
| 296 | 3.48 |
| 297 | 2.76 |
| 299 | 2.97 |
| 300 | 2.84 |
| 301 | 2.99 |
| 302 | 2.44 |
| 303 | 3.29 |
| 308 | 4.07 |
| 309 | 2.37 |
| 313 | 1.33 |
| 314 | 1.66 |
| 315 | 2.70 |

TABLE 6-continued

| | Rate of increase in LPL mRNA |
|---|---|
| 316 | 2.53 |
| 317 | 2.90 |
| 318 | 3.15 |
| 319 | 3.74 |
| 321 | 1.82 |
| 322 | 1.55 |
| 323 | 1.72 |
| 324 | 1.95 |
| 325 | 2.44 |
| 326 | 2.63 |
| 327 | 3.06 |
| 328 | 2.41 |
| 329 | 2.96 |
| 330 | 1.88 |
| 331 | 2.17 |
| 332 | 1.91 |
| 333 | 1.22 |
| 334 | 1.78 |
| 335 | 2.37 |
| 336 | 3.23 |
| 337 | 3.07 |
| 338 | 1.32 |
| 339 | 1.32 |
| 340 | 2.26 |
| 341 | 1.75 |
| 342 | 2.44 |
| 343 | 1.42 |
| 344 | 1.83 |
| 345 | 2.39 |
| 346 | 3.18 |
| 347 | 3.28 |
| 348 | 1.76 |
| 349 | 2.20 |
| 350 | 1.38 |
| 351 | 4.12 |
| 352 | 5.48 |
| 353 | 4.08 |
| 354 | 4.44 |
| 355 | 3.59 |
| 356 | 2.06 |
| 357 | 3.59 |
| 358 | 4.18 |
| 359 | 1.75 |
| 360 | 3.93 |
| 361 | 5.51 |
| 362 | 2.89 |
| 363 | 2.78 |
| 364 | 2.65 |
| 365 | 3.02 |
| 366 | 1.95 |
| 367 | 2.54 |
| 368 | 2.62 |
| 369 | 1.26 |
| 370 | 3.31 |
| 371 | 3.57 |
| 372 | 1.95 |
| 373 | 3.03 |
| 374 | 2.60 |
| 375 | 1.83 |
| 376 | 1.18 |
| 377 | 1.88 |
| 378 | 1.24 |
| 379 | 2.87 |
| 380 | 1.18 |
| 381 | 2.19 |
| 382 | 1.41 |
| 383 | 2.16 |
| 384 | 1.84 |
| 385 | 3.18 |
| 386 | 2.77 |
| 387 | 2.41 |
| 388 | 2.13 |
| 389 | 1.63 |
| 390 | 2.09 |
| 391 | 1.58 |
| 392 | 1.73 |

TABLE 6-continued

| | Rate of increase in LPL mRNA |
|---|---|
| 393 | 1.26 |
| 394 | 2.39 |
| 395 | 2.61 |
| 396 | 2.93 |
| 397 | 4.58 |
| 398 | 2.22 |
| 399 | 4.68 |
| 400 | 4.49 |
| 401 | 2.9 |
| 402 | 2.37 |
| 403 | 2.09 |
| 404 | 3.26 |
| 405 | 2.78 |
| 406 | 2.62 |
| 407 | 1.68 |
| 408 | 1.24 |
| 409 | 1.34 |
| 410 | 0.42 |
| 411 | 1.62 |
| 412 | 1.41 |
| 413 | 2.06 |
| Comp. Ex. | |
| 1 | 1.32 |

Test Example 2

Solubility in Gastric Juice or Intestinal Juice Model Fluid

Measurement was performed by a precipitation method using DMSO. Specifically, each of the dimethyl sulfoxide (DMSO) solutions of the compounds was individually added to 1st fluid for Disintegration Test of Japanese Pharmacopoeia (pH: 1.2) or 2nd fluid for Disintegration Test of Japanese Pharmacopoeia (pH: 6.8), and the mixtures were stirred by shaking at room temperature for 24 hours. Subsequently, insoluble substances in each mixture were removed by filtration, and the UV absorption of each filtrate was measured. The obtained values were individually applied to the calibration curves of the compounds prepared in advance to calculate the concentrations of the compounds dissolved (μg/mL). The results are shown in Table 7 below.

TABLE 7

| | Solubility (μg/mL) | |
|---|---|---|
| | 1st fluid | 2nd fluid |
| Example | | |
| 1 | 20.7 | 1.7 |
| 2 | >88 | 25.1 |
| 3 | 87.5 | 1 |
| 4 | 86.6 | 0.9 |
| 5 | 90.1 | 1.1 |
| 6 | 91.5 | 47 |
| 7 | 84 | 40.2 |
| 8 | 83.6 | <0.3 |
| 9 | 87.7 | 1.8 |
| 10 | 89.5 | 17.3 |
| 11 | 80.1 | 5.4 |
| 12 | 15.6 | <1.7 |
| 13 | >81 | 74 |
| 14 | >99 | <0.4 |
| 15 | 7.8 | <8.1 |
| 16 | 90.8 | 13.4 |
| 17 | >93 | 3 |
| 18 | 43.5 | 3.7 |
| 19 | 76.7 | 2.2 |
| 21 | 3 | <1.8 |
| 22 | 7.5 | 1.6 |
| 23 | 13.1 | <1.6 |
| 24 | 53.6 | 1.8 |
| 25 | 83.1 | 1 |
| 26 | 8.7 | 1.3 |
| 27 | 5.9 | 0.5 |
| 29 | 3 | 0.6 |
| 30 | 24 | 0.6 |
| 31 | 7.7 | 1.6 |
| 34 | 17 | <0.3 |
| 37 | 5.6 | 0.6 |
| 38 | 60.5 | 0.9 |
| 39 | >99 | 5.2 |
| 40 | 6.9 | 2.8 |
| 41 | 23.3 | 1.3 |
| 42 | 8.6 | 2.3 |
| 43 | 16.2 | 3.4 |
| 44 | 11.9 | 0.7 |
| 45 | 27.8 | <0.3 |
| 46 | 22.9 | <9.1 |
| 47 | 5.1 | 0.3 |
| 48 | >89 | 80.8 |
| 49 | 8.7 | 0.9 |
| 51 | 90.2 | 9 |
| 53 | >86 | 4.6 |
| 55 | >78 | 2.3 |
| 56 | 4.8 | 0.8 |
| 57 | >99 | 0.8 |
| 58 | 94.4 | 16.5 |
| 60 | 8.8 | 1.1 |
| 61 | >101 | 1.6 |
| 62 | >101 | 1.3 |
| 63 | 82.2 | 12.5 |
| 64 | 56.2 | 2.6 |
| 65 | 77.3 | 1.3 |
| 66 | 56.9 | 0.9 |
| 67 | 93.5 | 0.4 |
| 68 | 104.1 | 2.3 |
| 69 | 5.3 | 1.3 |
| 72 | >116 | 1.8 |
| 73 | >108 | 5.3 |
| 74 | 53.6 | 1.8 |
| 75 | 83.1 | 1 |
| 76 | <8.5 | 1 |
| 77 | 8.7 | 1.3 |
| 78 | >83 | 20.6 |
| 79 | 10.6 | 1.2 |
| 80 | 84.9 | 0.4 |
| 81 | 78.7 | 5.8 |
| 82 | >78 | 41.1 |
| 83 | 27.8 | 2.9 |
| 85 | 85.4 | 1 |
| 86 | 73.5 | <0.3 |
| 87 | 39.4 | 0.7 |
| 88 | 54.1 | 0.5 |
| 89 | 85.4 | 1.8 |
| 91 | 42.8 | 0.6 |
| 93 | 10 | 0.9 |
| 94 | 8.7 | 0.9 |
| 97 | 15.2 | 2.2 |
| 98 | 37.1 | 1.3 |
| 100 | 15 | <0.3 |
| 102 | 92.5 | 8.9 |
| 103 | 36 | <0.3 |
| 104 | 20.6 | 0.7 |
| 105 | 27.6 | <0.3 |
| 106 | 31.2 | 6.3 |
| 107 | 11.2 | 9.6 |
| 108 | 4.1 | <0.3 |
| 109 | >57 | 40 |
| 110 | >57 | >57 |
| 111 | 9.4 | 1.2 |
| 112 | 12 | 2.1 |
| 113 | 21.1 | 0.5 |
| 114 | 11.3 | 2.7 |

TABLE 7-continued

|  | Solubility (µg/mL) | |
|---|---|---|
|  | 1st fluid | 2nd fluid |
| 115 | 15.5 | 2 |
| 116 | 24.1 | <1.6 |
| 117 | 80.2 | 2.6 |
| 118 | 80.2 | 2.1 |
| 119 | 44.7 | 5.2 |
| 120 | >73 | 4 |
| 121 | >89 | 1.8 |
| 122 | 71.8 | 2.9 |
| 124 | 18.7 | <1.6 |
| 125 | 23.1 | 0.5 |
| 126 | 7.1 | 5.6 |
| 127 | 17.1 | <0.3 |
| 128 | 94.9 | 4 |
| 129 | 13.6 | <0.3 |
| 131 | 87.4 | <0.3 |
| 132 | 5.9 | <0.3 |
| 133 | 29.3 | 2 |
| 135 | 6.8 | 2.2 |
| 136 | >89 | 2.2 |
| 137 | 39.9 | 36.1 |
| 139 | 5 | <0.3 |
| 140 | 7.8 | 4.8 |
| 141 | 10.1 | <0.3 |
| 145 | <0.3 | 4 |
| 146 | 9.9 | 1.2 |
| 147 | 12.4 | 3.6 |
| 148 | <0.3 | 5.3 |
| 149 | 19.6 | 3.9 |
| 150 | 2.4 | 0.3 |
| 151 | >92 | 0.9 |
| 152 | >98 | <0.3 |
| 153 | >98 | 1.7 |
| 154 | 103.5 | 2 |
| 155 | >106 | 3 |
| 156 | 104.1 | 3.6 |
| 157 | 105.5 | 1.9 |
| 158 | 93.2 | 15.9 |
| 159 | >94 | 4 |
| 160 | >94 | <0.3 |
| 161 | >94 | 3.9 |
| 162 | 94.3 | 0.7 |
| 163 | >92 | 1.4 |
| 164 | >98 | 1.2 |
| 165 | 96 | 2.1 |
| 166 | >98 | 0.6 |
| 167 | 100.3 | 0.4 |
| 168 | >95 | <0.3 |
| 169 | 96.3 | <0.4 |
| 170 | 104.6 | 1.3 |
| 171 | >109 | <1.9 |
| 175 | 10 | 2.5 |
| 178 | 98.5 | 1.7 |
| 179 | 25.8 | 2.3 |
| 180 | 89.1 | 0.4 |
| 181 | 93.4 | <0.3 |
| 182 | 95.5 | 1.9 |
| 183 | 99 | 1.1 |
| 184 | 96.3 | 5.8 |
| 185 | 87.4 | 23.1 |
| 186 | 23.2 | <0.3 |
| 187 | 75.6 | <0.4 |
| 188 | 86.4 | 1.9 |
| 189 | 89 | 11.6 |
| 190 | 92.5 | 2 |
| 191 | 25.9 | 1.7 |
| 192 | 22.6 | 0.6 |
| 193 | 86.4 | 0.8 |
| 194 | >90 | 0.5 |
| 195 | >100 | 0.6 |
| 196 | >85 | <7.5 |
| 197 | >88 | 25.7 |
| 198 | >109 | 17.4 |
| 199 | >115 | <10.2 |
| 200 | 98.4 | 2.4 |
| 201 | 90 | 2.6 |
| 202 | 8.8 | <1.8 |
| 203 | 63.8 | <1.8 |
| 204 | >100 | <8.9 |
| 205 | >106 | <9.5 |
| 206 | >88 | 7 |
| 207 | 83.4 | 0.4 |
| 208 | 24.9 | <0.4 |
| 209 | 99.4 | <0.4 |
| 210 | 95.6 | 1.5 |
| 211 | 84.7 | 2.2 |
| 212 | 76.9 | 0.5 |
| 213 | 79.7 | 2.1 |
| 214 | >96 | 7.1 |
| 216 | 84.3 | 1.8 |
| 218 | 0.4 | <9.6 |
| 219 | 7.5 | <1.6 |
| 220 | <0.3 | <7.9 |
| 221 | 66.5 | <8.8 |
| 223 | >105 | <0.4 |
| 225 | 5.5 | 0.9 |
| 226 | <8.5 | 3.4 |
| 228 | 9.7 | 2.6 |
| 230 | 7.2 | <0.3 |
| 233 | 9.9 | 1.1 |
| 234 | 92.8 | <0.3 |
| 236 | <0.3 | 29.9 |
| 237 | 7.1 | <1.8 |
| 238 | 7.5 | 5.6 |
| 239 | 8.8 | 15.6 |
| 240 | 12 | <0.4 |
| 245 | 90.2 | 11.7 |
| 246 | 15.6 | 5 |
| 247 | 8.4 | 5.3 |
| 253 | 5.9 | 1 |
| 255 | 17.5 | <0.4 |
| 256 | 11.4 | <0.4 |
| 265 | 2.2 | 5.8 |
| 266 | 64.3 | 4.6 |
| 267 | 17.7 | 0.4 |
| 268 | 13.8 | 6.6 |
| 270 | 9.1 | <0.4 |
| 274 | 6.7 | 0.4 |
| 275 | 96 | 4.2 |
| 276 | 66.5 | 6.7 |
| 279 | 4.1 | 0.5 |
| 281 | 9.7 | 9.3 |
| 288 | <0.3 | 23.4 |
| 289 | 10.8 | 2.2 |
| 290 | <0.3 | 27.6 |
| 291 | 9.9 | 3.5 |
| 292 | >111 | <9.9 |
| 293 | 91.5 | 0.4 |
| 294 | 103.8 | 2.4 |
| 295 | 18.3 | 1.1 |
| 296 | 73 | 2.3 |
| 297 | 89.8 | 7 |
| 298 | 108.5 | 1.6 |
| 300 | >111 | <0.4 |
| 301 | 15.1 | <0.4 |
| 302 | >107 | <0.4 |
| 303 | 84.3 | <0.4 |
| 304 | >48 | 0.5 |
| 305 | 24.7 | 0.4 |
| 306 | >102 | <0.4 |
| 308 | 101.2 | 0.4 |
| 309 | 14.8 | <0.4 |
| 310 | >99 | <1.8 |
| 311 | 5.6 | <0.4 |
| 312 | 23.6 | <0.4 |
| 313 | 62.3 | 5.0 |
| 314 | 50.2 | 0.9 |
| 315 | 1.8 | 2.7 |
| 316 | 94.4 | 4.9 |
| 317 | 69.1 | 9.3 |
| 318 | 100.4 | 8.7 |
| 319 | 4.7 | 0.5 |
| 321 | 69.4 | 1.9 |

TABLE 7-continued

| | Solubility (μg/mL) | |
|---|---|---|
| | 1st fluid | 2nd fluid |
| 322 | 72.0 | 1.3 |
| 323 | 78.3 | 17.0 |
| 324 | 20.2 | 0.8 |
| 325 | 4.7 | 1.3 |
| 326 | 63.7 | 0.7 |
| 327 | 109.6 | 0.7 |
| 328 | 44.2 | 0.4 |
| 329 | 5.8 | 13.6 |
| 330 | 6.5 | 0.9 |
| 331 | 94.6 | 8.0 |
| 332 | 77.7 | 3.3 |
| 333 | 59.0 | 5.2 |
| 334 | 76.6 | 7.8 |
| 335 | 93.4 | 6.6 |
| 336 | 89.3 | 0.4 |
| 337 | 110.3 | 0.5 |
| 338 | >62 | 59.7 |
| 339 | >62 | 58.9 |
| 340 | 93.8 | 8.1 |
| 341 | 91.7 | 15.8 |
| 342 | 32.7 | 1.4 |
| 343 | 50.0 | 39.2 |
| 344 | 85.9 | 4.6 |
| 345 | <0.4 | <0.4 |
| 346 | 99.1 | <0.4 |
| 347 | 83.2 | <0.4 |
| 348 | 89.6 | 22.4 |
| 349 | 83.6 | 10.8 |
| 350 | 53.3 | 51.0 |
| 351 | 85.9 | 7.0 |
| 352 | 9.8 | 6.0 |
| 353 | 85.4 | 0.5 |
| 354 | 38.8 | 1.1 |
| 355 | <0.3 | <0.3 |
| 357 | 7.8 | <0.3 |
| 358 | 1.6 | <0.4 |
| 359 | 57.3 | 52.8 |
| 360 | 90.7 | 0.6 |
| 361 | 3.4 | <0.4 |
| 362 | 95.5 | 5.0 |
| 363 | 103.6 | 6.9 |
| 364 | <0.4 | <0.4 |
| 365 | 77.9 | 31.2 |
| 366 | 79.2 | 24.7 |
| 367 | 82.1 | <0.3 |
| 368 | 82.9 | 0.5 |
| 369 | 35.9 | <0.3 |
| 370 | 1.6 | 1.8 |
| 371 | 84.0 | 42.9 |
| 372 | 80.4 | 33.5 |
| 373 | 88.3 | <0.3 |
| 374 | 88.3 | 1.2 |
| 375 | 73.9 | 72.5 |
| 376 | 75.2 | 79.4 |
| 377 | 84.6 | 0.7 |
| 378 | 81.6 | 7.5 |
| 379 | 79.9 | 72.9 |
| 380 | 81.2 | 63.7 |
| 381 | 78.2 | 66.9 |
| 382 | 74.8 | 62.1 |
| 383 | 85.1 | <0.3 |
| 384 | 86.4 | 1.2 |
| 385 | 84.7 | 2.1 |
| 386 | 82.7 | 0.9 |
| 387 | 4.8 | 0.8 |
| 388 | 0.8 | <0.4 |
| 389 | 96.0 | 1.8 |
| 390 | 49.5 | 21.6 |
| 391 | 1.1 | 7.1 |
| 392 | 60.8 | <0.3 |
| 393 | >85 | 1.9 |
| 394 | 96.3 | <0.4 |
| 395 | 3.8 | <0.4 |
| 396 | 28.0 | <0.4 |
| 397 | 15.9 | <0.3 |
| 398 | 79.2 | 39.7 |

TABLE 7-continued

| | Solubility (μg/mL) | |
|---|---|---|
| | 1st fluid | 2nd fluid |
| 399 | 54.1 | 3.4 |
| 400 | 97.1 | 0.6 |
| 406 | >90 | 12.4 |
| 407 | 2.7 | <0.3 |
| 408 | 1.9 | <0.4 |
| 409 | 1.3 | 1.9 |
| 410 | 1.1 | <0.3 |
| 411 | 3.1 | 3.0 |
| 412 | 0.6 | 1.5 |
| 413 | 37.0 | 2.9 |
| Comp. Ex. | | |
| 1 | <0.3 | <0.3 |

As is clear from the above results, it was confirmed that the compound of the present invention has excellent LPL activity and excellent solubility in gastric juice or intestinal juice model fluid. Thus, the compound of the present invention is useful for the prevention or treatment of hyperlipidemia, arteriosclerosis, or obesity.

The invention claimed is:

1. A phenylimidazole compound represented by the following formula (1) or a pharmaceutically acceptable salt thereof

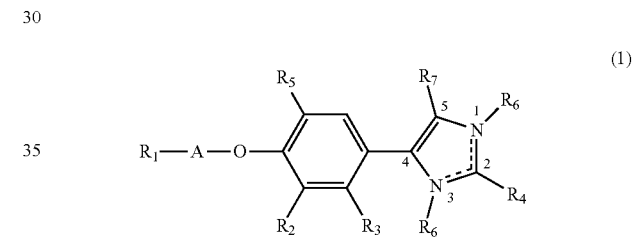

wherein $R_1$ is
(1-2) pyrazolyl,
(1-3) pyrimidinyl,
(1-4) pyridyl having one or two substituents each independently selected from the group consisting of halogen, cyano, C1-C6 alkyl, C1-C6 alkylsulfonyl, and halogen-substituted C1-C6 alkyl,
(1-5) oxazolyl having one or more C1-C6 alkyl groups,
(1-6) pyrazinyl optionally substituted with at least one group selected from the group consisting of halogen and C1-C6 alkyl,
(1-7) phenyl having one or two substituents each independently selected from the group consisting of halogen and halogen-substituted C1-C6 alkyl,
(1-8) (pyridine 1-oxide)yl having one or two substituents each independently selected from the group consisting of halogen and halogen-substituted C1-C6 alkyl,
(1-9) halogen-substituted thiazolyl,
(1-10) C1-C6 alkyl-substituted isoxazolyl,
(1-11) C3-C8 cycloalkyl-substituted 1,2,4-oxadiazolyl, or
(1-12) phenyl;
$R_2$ represents hydrogen or C1-C6 alkoxy;
$R_3$ is
(3-1) hydrogen,
(3-2) C1-C6 alkoxy,
(3-3) C1-C6 alkoxy C1-C6 alkoxy,
(3-4) C1-C6 alkyl, (3-5) halogen,
(3-6) benzyloxy, or
(3-7) hydroxy;
$R_4$ is
(4-1) pyridyl optionally having at least one substituent selected from the group consisting of halogen, cyano, hydroxy, pyrrolidinyl, C1-C6 alkyl, C1-C6 alkylthio, C1-C6 alkylsulfonyl, C1-C6 alkoxy, and halogen-substituted C1-C6 alkyl,
(4-2) C3-C10 cycloalkyl optionally having one or two substituents each independently selected from the group consisting of halogen and C1-C6 alkyl, or
(4-3) lower alkyl;
$R_5$ is
(5-1) hydrogen,
(5-2) C1-C6 alkyl, or
(5-3) C1-C6 alkoxy;
$R_6$ is
(6-1) hydrogen,
(6-2) C1-C6 alkoxy C1-C6 alkyl, or
(6-3) C1-C6 alkyl optionally substituted with one or more C3-C10 cycloalkyl groups,
wherein $R_6$ is attached to only one of N at the 1-position and N at the 3-position of the imidazole skeleton, $R_6$ is attached to N at the 1-position when the bond between N at the 3-position and C at the 2-position of the imidazole skeleton is a double bond, and $R_6$ is attached to N at the 3-position when the bond between N at the 3-position and C at the 2-position of the imidazole skeleton is a single bond;
$R_7$ is
(7-1) hydrogen,
(7-2) halogen,
(7-3) C1-C6 alkyl,
(7-4) hydroxymethyl,
(7-5) halogen-substituted C1-C6 alkyl, or
(7-6) cyano;
A is C1-C6 alkylene;
in the imidazole skeleton, the bond between C at the 2-position and N at the 1-position is a single bond when the bond between N at the 3-position and C at the 2-position is a double bond, and the bond between C at the 2-position and N at the 1-position is a double bond when the bond between N at the 3-position and C at the 2-position is a single bond;
with the proviso that the compound represented by formula (1) wherein $R_1$ is a group of (1-7) or (1-12) and $R_4$ is a group of (4-3) is excluded.

2. The phenylimidazole compound according to claim 1 or a pharmaceutically acceptable salt thereof, wherein $R_4$ is a group of (4-1).

3. The phenylimidazole compound according to claim 1 or a pharmaceutically acceptable salt thereof, wherein $R_4$ is pyridyl optionally having at least one substituent selected from the group consisting of halogen, cyano, hydroxy, pyrrolidinyl, C1-C6 alkyl, C1-C6 alkoxy, and halogen-substituted C1-C6 alkyl, or a group of (4-2).

4. The phenylimidazole compound according to claim 1 or a pharmaceutically acceptable salt thereof, wherein $R_1$ is a group of (1-4).

5. The phenylimidazole compound according to claim 1 or a pharmaceutically acceptable salt thereof, wherein $R_3$ is hydrogen or C1-C6 alkoxy, and $R_5$ is hydrogen or C1-C6 alkoxy.

6. The phenylimidazole compound according to claim 1 or a pharmaceutically acceptable salt thereof, wherein $R_4$ is halogen-substituted pyridyl.

7. The phenylimidazole compound according to claim 1 or a pharmaceutically acceptable salt thereof, wherein $R_1$ is pyridyl having one or two substituents each independently selected from the group consisting of halogen and halogen-substituted C1-C6 alkyl.

8. The phenylimidazole compound according to claim 1 or a pharmaceutically acceptable salt thereof, wherein $R_2$ and $R_5$ each represent hydrogen, and $R_3$ is C1-C6 alkoxy.

9. The phenylimidazole compound according to claim 1 or a pharmaceutically acceptable salt thereof, wherein $R_6$ is hydrogen, and $R_7$ is halogen.

10. The phenylimidazole compound according to claim 8 or a pharmaceutically acceptable salt thereof, selected from the following compounds:
5-[[4-(5-chloro-2-(6-fluoropyridin-3-yl)-1H-imidazol-4-yl)-3-methoxyphenoxy]methyl]-2-(trifluoromethyl)pyridine
2-[[4-(5-chloro-2-(6-fluoropyridin-3-yl)-1H-imidazol-4-yl)-3-methoxyphenoxy]methyl]-3-fluoro-5-(trifluoromethyl)pyridine
2-[[4-(5-bromo-2-(6-fluoropyridin-3-yl)-1H-imidazol-4-yl)-3-methoxyphenoxy]methyl]-3-fluoro-5-(trifluoromethyl)pyridine
3-chloro-2-[[4-(5-chloro-2-(6-fluoropyridin-3-yl)-1H-imidazol-4-yl)-3-methoxyphenoxy]methyl]-5-(trifluoromethyl)pyridine
2-[[4-(5-bromo-2-(6-chloropyridin-3-yl)-1H-imidazol-4-yl)-3-methoxyphenoxy]methyl]-5-(trifluoromethyl)pyridine
5-bromo-2-[[4-(4-chloro-2-(6-fluoropyridin-3-yl)-1H-imidazol-5-yl)-3-methoxyphenoxy]methyl]-3-fluoropyridine
5-[4-chloro-5-[2-methoxy-4-((6-(trifluoromethyl)pyridin-2-yl)methoxy)phenyl]-1H-imidazol-2-yl]-2-fluoropyridine.

11. A pharmaceutical composition comprising the compound according to claim 1 or a pharmaceutically acceptable salt thereof.

12. An LPL activator comprising the compound according to claim 1 or a pharmaceutically acceptable salt thereof.

13. The pharmaceutical composition according to claim 11 for use in the treatment of hyperlipidemia, arteriosclerosis, or obesity.

14. The phenylimidazole compound according to claim 10 or a pharmaceutically acceptable salt thereof, the compound being 5[[4-(5-chloro-2-(6-fluoropyridin-3-yl)-1H-imidazol-4-yl)-3-methoxyphenoxy]methyl]-2-(trifluoromethyl)pyridine.

15. The phenylimidazole compound according to claim 10 or a pharmaceutically acceptable salt thereof, the compound being 2[[4-(5-chloro-2-(6-fluoropyridin-3-yl)-1H-imidazol-4-yl)-3-methoxyphenoxy]methyl]-3-fluoro-5-(trifluoromethyl)pyridine.

16. The phenylimidazole compound according to claim 10 or a pharmaceutically acceptable salt thereof, the compound being 2[[4-(5-bromo-2-(6-fluoropyridin-3-yl)-1H-imidazol-4-yl)-3-methoxyphenoxy]methyl]-3-fluoro-5-(trifluoromethyl)pyridine.

17. A pharmaceutical composition comprising the compound according to claim 14 or a pharmaceutically acceptable salt thereof.

18. A pharmaceutical composition comprising the compound according to claim 15 or a pharmaceutically acceptable salt thereof.

19. A pharmaceutical composition comprising the compound according to claim 16 or a pharmaceutically acceptable salt thereof.

\* \* \* \* \*